United States Patent [19]
Lin et al.

[11] Patent Number: 5,750,735
[45] Date of Patent: May 12, 1998

[54] 2-THIOSUBSTITUTED CARBAPENEMS

[75] Inventors: Yang-I Lin, Tappan; Panayota Bitha, Nanuet; Subas Sakya, Pomona, all of N.Y.; Timothy W. Strohmeyer, Demarest; Karen Bush, Princeton, both of N.J.; Carl Bernard Ziegler, Pearl River; Gregg Brian Feigelson, Airmont, both of N.Y.

[73] Assignee: American Cyanamid Company, Madison, N.J.

[21] Appl. No.: 445,388

[22] Filed: May 19, 1995

Related U.S. Application Data

[60] Division of Ser. No. 182,781, Jan. 26, 1994, Pat. No. 5,602,112, which is a continuation-in-part of Ser. No. 33,684, Mar. 16, 1993, abandoned.

[51] Int. Cl.$^6$ .................................................. C07D 307/02
[52] U.S. Cl. ........................... 549/475; 549/476; 549/478; 544/379; 546/283; 548/517
[58] Field of Search ............................... 549/475, 476, 549/478; 544/379; 546/283; 548/517

[56] References Cited

U.S. PATENT DOCUMENTS

| | | |
|---|---|---|
| 4,119,737 | 10/1978 | Van Den Bosch et al. . |
| 4,232,036 | 11/1980 | Christensen . |
| 4,260,627 | 4/1981 | Christensen . |
| 4,341,706 | 7/1982 | Christensen . |
| 4,347,368 | 8/1982 | Christensen . |
| 4,380,655 | 4/1983 | Van Den Bosch et al. . |
| 4,477,662 | 10/1984 | Corbett et al. . |
| 4,477,678 | 10/1984 | Van Den Bosch et al. . |
| 4,745,188 | 5/1988 | Christensen . |
| 4,820,817 | 4/1989 | Christensen . |
| 4,997,829 | 3/1991 | Ishiguro et al. . |
| 5,102,997 | 4/1992 | Sugimura et al. . |
| 5,321,020 | 6/1994 | Jasys . |

FOREIGN PATENT DOCUMENTS

| | | |
|---|---|---|
| 1051441 | 3/1979 | Canada . |
| 176325 | 2/1979 | Czechoslovakia . |
| 010317 | 12/1983 | European Pat. Off. . |
| 126587 | 11/1984 | European Pat. Off. . |
| WO-11284 | 10/1990 | WIPO . |

OTHER PUBLICATIONS

CA62:9118d, Registry No. 89124-39-0, 1965.
CA92:128705, Van Den Bosch, 1975.
CA91:56820, Kahovcova, 1975.
CA108:38276, 1987.
L.T. Kaulinya and M.Y. Lidak, Khim. Geterotsikl. Soedin, 1, 94–99(1987) (translated).

*Primary Examiner*—Rebecca Cook
*Attorney, Agent, or Firm*—Michael R. Nagy

[57] ABSTRACT

Carbapenem antibiotic compounds of the general formula:

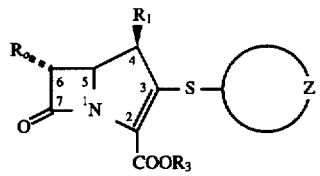

wherein the moiety

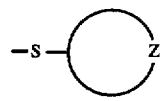

is a 4, 5 or 6 membered mono, di- or tri-substituted oxygen or sulfur containing ring; wherein Z is oxygen, sulfur, sulfoxide and sulfone, pharmaceutical compositions thereof useful for the treatment of bacterial infections, processes for preparing the compounds and new intermediates useful in the process.

29 Claims, No Drawings

2-THIOSUBSTITUTED CARBAPENEMS

This is a divisional of application(s) Ser. No. 08/182,781 filed on Jan. 26, 1994, now U.S. Pat. No. 5,602,112 which is a continuation-in-part of 08/033,684 filed Mar. 16, 1993 abandoned.

FIELD OF THE INVENTION

This invention relates to novel carbapenem antibiotics and non-toxic pharmaceutically acceptable salts thereof, which have antimicrobial activity.

Therefore, the present carbapenem antibiotics and pharmaceutical compositions thereof are useful in the treatment of bacterial infections in humans and animal, either alone or in combination with other antibiotics. The present invention also provides processes for the preparation of the carbapenem antibiotics and of certain novel intermediates.

SUMMARY OF THE INVENTION

This invention is concerned with novel carbapenems, represented by formula I, which have anti-bacterial activity; with methods of treating infectious disease in humans and other animals when administering these new compounds; with pharmaceutical preparations containing these compounds; with novel intermediate compounds and stereoselective processes for the production of compounds of formula IV; and with the production of compounds of formulae I.

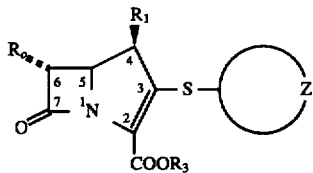

I wherein the moiety

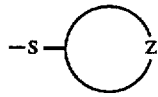

is a 4,5 or 6 membered mono-, di- or tri-substituted oxygen or sulfur containing ring.

For example, the moiety

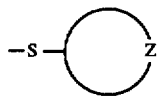

may be a 5 membered ring of the formula

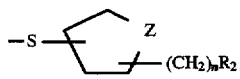

In such an instance, the following isomers are included:

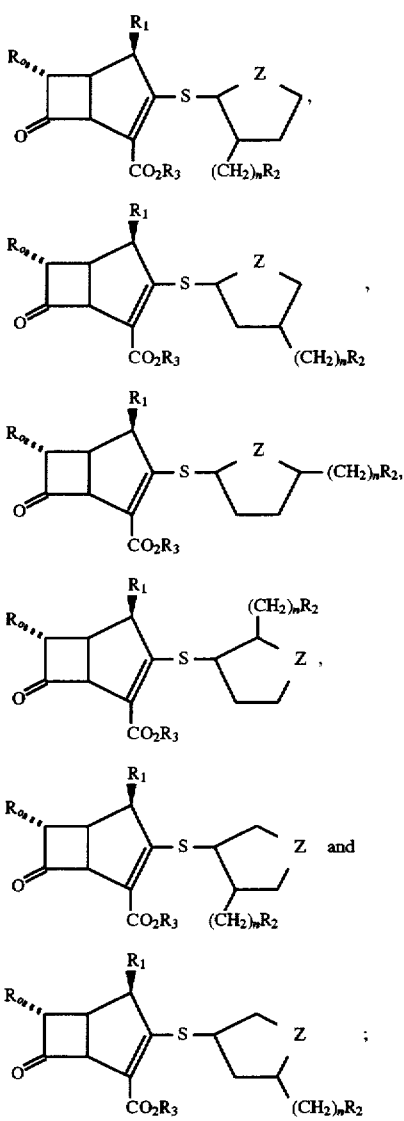

and the stereochemical assignment of each residue

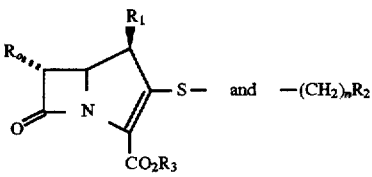

on the 4, 5 or 6-membered ring (containing the Z substituent) can be either R or S.

DETAILED DESCRIPTION

As stated, the invention relates to compounds of Formula I:

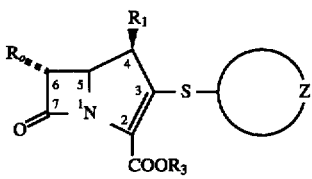

wherein the moiety:

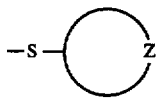

represents a 4,5 or 6 membered mono, di-or tri-substituted ring and (A) Z is selected from oxygen, sulfur, sulfoxide and sulfone; when Z is sulfoxide, the relative stereochemistry between the substituent and the sulfoxide can be cis or trans;

(B) $R_o$ is hydrogen, $(C_1-C_2)$alkyl, $CH_2OR_4$, $CH_2NHR_5$, $CH(OR_4)CH_3$, CHFCH$_3$ or $CH(NHR_5)CH_3$; wherein (i) $R_4$ is selected from hydrogen, and moieties of the formulae:

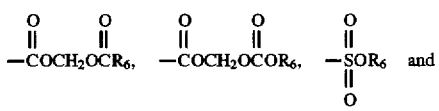

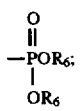

(ii) $R_5$ is selected from hydrogen, and moieties of the formulae:

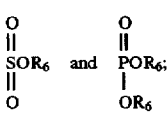

(iii) $R_6$ is selected from a straight, branched or substituted $(C_1-C_{18})$alkyl, $(C_2-C_{18})$ alkenyl, unsubstituted or substituted $(C_3-C_7)$monocyclo$(C_1-C_{10})$alkyl, unsubstituted or substituted $(C_5-C_{10})$bicyclo $(C_1-C_{10})$alkyl, aryl or substituted aryl, heteroaryl or substituted heteroaryl, heterocyclyl or substituted heterocyclyl; the substitution for the alkyl, monocycloalkyl and bicycloalkyl moieties are selected from trifluoromethyl, pentafluoroethyl, amino, mono $(C_1-C_6)$alkylamino, di$(C_1-C_6)$alkylamino, hydroxy, $(C_1-C_6)$ alkoxy, $(C_3-C_8)$cycloalkoxy, carboxy, $(C_2-C_{10})$carboalkoxy, cyano and $(C_1-C_{10})$ carboxamido; the substitution for the aryl, heteroaryl and heterocyclyl moieties is selected from $(C_1-C_6)$ alkyl, $(C_1-C_6)$mono-, di- or polyfluoroalkyl, hydroxy, $(C_1-C_6)$alkoxy, $(C_3-C_8)$cycloalkoxy, amino, mono$(C_1-C_6)$alkylamino, di$(C_1-C_6)$ alkylamino, carboxy, $(C_2-C_{10})$carboalkoxy, cyano and $(C_1-C_{10})$carboxamido;

(C) $R_1$ is straight or branched $(C_1-C_8)$alkyl, straight or branched $(C_2-C_8)$alkenyl, $(C_3-C_8)$cycloalkyl, or $(CH_2)_n$R;

wherein n' is an integer of from 1-6 and R is selected from $CF_3$, $C_2F_5$, fluorine, chlorine, bromine, hydroxy, alkoxy, nitrile, azido, a quaternary ammonio group, amidino, formamidino, guanidino and NR'R"; wherein (i) R' and R" are independently selected from hydrogen, straight or branched $(C_1-C_6)$alkyl, straight or branched $(C_1-C_6)$alkoxy, 2-hydroxyethyl, 2-azidoethyl and 2-aminoethyl;

(ii) and when R' is hydrogen or straight or branched $(C_1-C_6)$alkyl, R" may also be selected from amino, hydroxy, mono$(C_1-C_6)$ alkylamino, di $(C_1-C_6)$ alkylamino, acyl, benzoyl, dihydroxybenzoyl, an acyl residue of an amino acid or peptide, and straight or branched substituted $(C_1-C_6)$alkyl wherein said alkyl substituent is selected from hydroxy, $(C_1-C_6)$ alkoxy, azido, amino, mono$(C_1-C_6)$alkylamino, di$(C_1-C_6)$alkylamino, guanidino, nitrile, carboxy, formimidoyl and phenyl; or (iii) R' and R" taken together with the associated nitrogen may also be an unsubstituted or substituted monocyclic or bicyclic heterocyclic ring having up to four (4) heteroatoms in each ring independently selected from oxygen, nitrogen and sulfur, wherein said substituent is selected from straight or branched $(C_1-C_6)$alkyl, straight or branched $(C_1-C_6)$alkoxy, $(C_3-C_8)$ cycloalkyl, $(C_3-C_8)$cycloalkoxy, trifluoromethyl, hydroxy, halogen (selected from bromine, chlorine, fluorine and iodine), amino, nitrile, carboxy, carbamido, carbamoyl, straight or branched mono$(C_1-C_6)$alkylamino, straight or branched di$(C_1-C_6)$alkylamino, and amino$(C_1-C_6)$ alkyl.

The term "acyl residue of an amino acid or peptide" as used herein means the acyl residue of a naturally occurring amino acid, a racemic amino acid or a peptide derived therefrom. Suitable amino acids are those described herein and other known amino acids such as alanine, glycine, arginine, cysteine, isoleucine, leucine, lysine, methionine, phenylalanine, proline, aminopimelic acid, threonine and the like.

The substituent or substituents on the

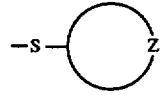

ring are independently selected from moieties of the formula $-(CH_2)_nR_2$ wherein:

(D) n is an integer from 0–4 and (E) $R_2$ is:

(i) methyl, fluorine, or any suitable leaving group such as but not limited to chlorine, bromine, iodine, $OCOCH_3$, $OCOCF_3$, $OSO_2CH_3$, $OSO_2Ph$, $NO_2$, cyano or azido;

(ii) $R_2$ may also be a moiety of the formula:

wherein n" is an integer from 0–2; and $R^a$ is (a) hydrogen or (b) an organic group bonded via a carbon atom selected from (C₁–C₆)alkyl, (C₃–C₇) cycloalkyl, (C₂–C₆)alkenyl, (C₂–C₆)alkynyl, aryl, heteroaryl, aryl(C₁–C₆)alkyl, heteroaryl (C₁–C₆) alkyl, (C₁–C₆)alkanoyl, arylcarbonyl, heteroarylcarbonyl, heterocyclyl, heterocyclyl (C₁–C₆)alkyl, heterocyclyl(C₁–C₆)thioalkyl, any of such groups being optionally substituted. Preferably, the heteroatom or heteroatoms in the above-named heterocyclyl and heteroaryl moieties are nitrogen atoms and may be quaternized and carry a positive charge and be associated with a physiologically acceptable counterion. As used herein, a physiologically acceptable counterion is selected from anions such as Cl⁻, OH⁻, HCO₃⁻, CH₃CO₂⁻, Br⁻, I⁻, H₂PO₄⁻, carboxylate and the like.

Optional substituents on the group Rᵃ include (C₁–C₆) alkyl, hydroxy, (C₁–C₆)alkoxy, phenyl, heterocyclyl, amino, amidino, guanidino, carboxamido, carbamoyl, (C₁–C₆) alkanoylamino, mono- and di(C₁–C₆)alkylamino, an acyclic quaternary ammonio moiety of the formula:

—NR₇R₈R₉ wherein R₇, R₈ and R₉ are the same or different and are selected from hydrogen, a straight or branched (C₁–C₆) alkyl, (C₂–C₆)alkenyl and substituted (C₁–C₆)alkyl, wherein the substitution is selected from hydroxy, (C₁–C₆)alkoxy, azido, amino, (C₁–C₆)alkylamino, di(C₁–C₆)alkylamino, guanidino, nitrile, carboxy, formimidoyl, phenyl, an amidino or guanidino moiety of the formula:

—N=CR₁₀—NR₁₁R₁₂ wherein R₁₀ is hydrogen, straight or branched (C₁–C₆)alkyl, amino, (C₁–C₆)alkylamino or di(C₁–C₆)alkylamino; and R₁₁ and R₁₂ are independently selected from hydrogen and straight or branched (C₁–C₆)alkyl.

Suitably, Rᵃ is (C₁–C₆)alkyl for example methyl, ethyl or isopropyl, optionally substituted by amino, (C₁–C₆) alkanoylamino, carboxy, mono- and di(C₁–C₆)alkylamino, hydroxy, amidino or (C₁–C₆)alkoxy. Preferably, Rᵃ is ethyl substituted by (C₁–C₆)alkanoylamino, for example Rᵃ is acetamidoethyl.

Suitably, Rᵃ is (C₂–C₆)alkenyl and, in particular, optionally substituted vinyl wherein the substituents are selected from those described hereinabove. Preference for substituents is given to (C₁–C₆)alkanoylamino such as acetamido; carbamoyl groups including mono- and di(C₁–C₆) alkylcarbamoyl, such as phenylcarbamoyl and NH₂CO—; a carboxy group where the carboxy group is esterified with an alkyl ester such as methyl or as its aralkyl ester such as 4-nitrobenzyl ester or the carboxy group is salified as its sodium or potassium salt.

Suitably, Rᵃ is aryl such as phenyl; aralkyl wherein the aryl moiety is phenyl and the alkyl moiety is 1 to 6 carbon atoms such as benzyl or phenethyl. In particular Rᵃ may be optionally substituted aralkyl wherein the substituents for the (C₁–C₆)alkyl portion is as hereinabove defined and optional substitution for the phenyl ring consists of one or more of the following substituents: amino, (C₁–C₆) alkanoylamino, mono- and di(C₁–C₆)alkylamino, hydroxy, amidino, (C₁–C₆)alkoxy, sulphanoyl, carbamoyl, nitro, chloro, fluoro, bromo, carboxy and salts and esters thereof. Suitable examples of the above-named list are:

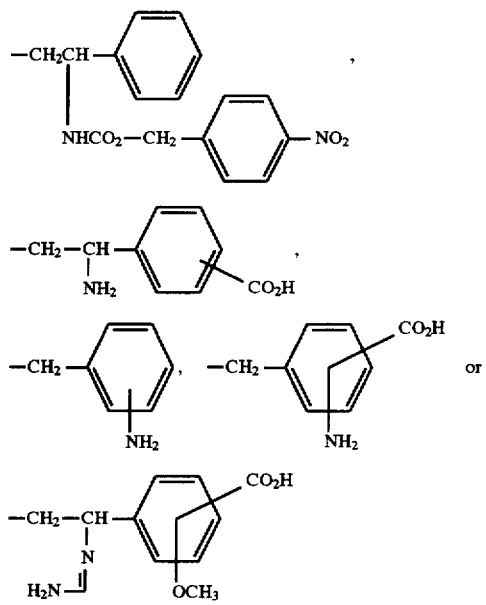

Suitably, Rᵃ is a heteroaryl wherein the heteroatom or heteroatoms of the heteroaryl ring are selected from 1–4 oxygen, nitrogen or sulfur atoms such as 1,2-dihydro-2-methyl-5,6-dioxo-1,2,4-triazin-3-yl, thienyl, pyrazolyl, pyridyl, pyrazinyl, pyrimidiniyl, triazinyl, benzofuranyl, benzothienyl, furanyl, imidazolyl, thiazolyl, triazolyl; a heteroaryl(C₁–C₆)alkyl such as:

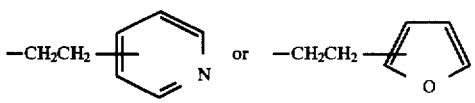

wherein the alkyl portion is optionally substituted as hereinabove described and the heteroaryl portion is optionally substituted with substituents hereinabove defined. Suitable examples are:

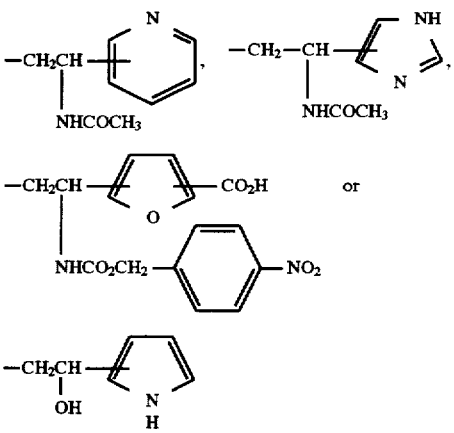

Suitably, Rᵃ is a bicyclic fused heteroaryl wherein the heteroatoms or heteroatoms of the heteroaryl ring are selected from 1–4 oxygen, nitrogen or sulfur atoms and optionally substituted as hereinabove defined. Preferably, examples are the [3.3.0] and (3.4.0] fused bicyclic heteroaryl ring system generically shown:

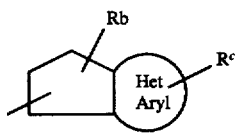

wherein the definitions of $R^b$ and $R^c$ may be selected from any of the above referenced substituents for $R^a$.

Suitably, $R^a$ is a quaternized fused heteroaryl wherein the heteroatoms of the heteroaryl ring are selected from 1 to 4 nitrogens and optionally substituted as hereinabove defined. Preferably, examples are the [3.3.0], [3.4.0], [4.3.0] and [4.4.0] quaternized fused heteroaryl rings, optionally substituted with an acidic substituent. Suitable examples are shown:

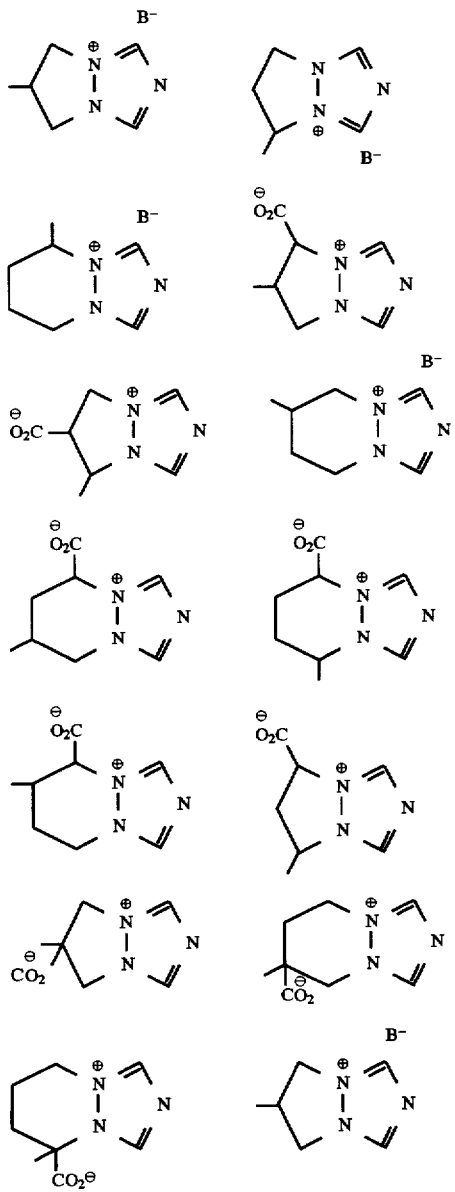

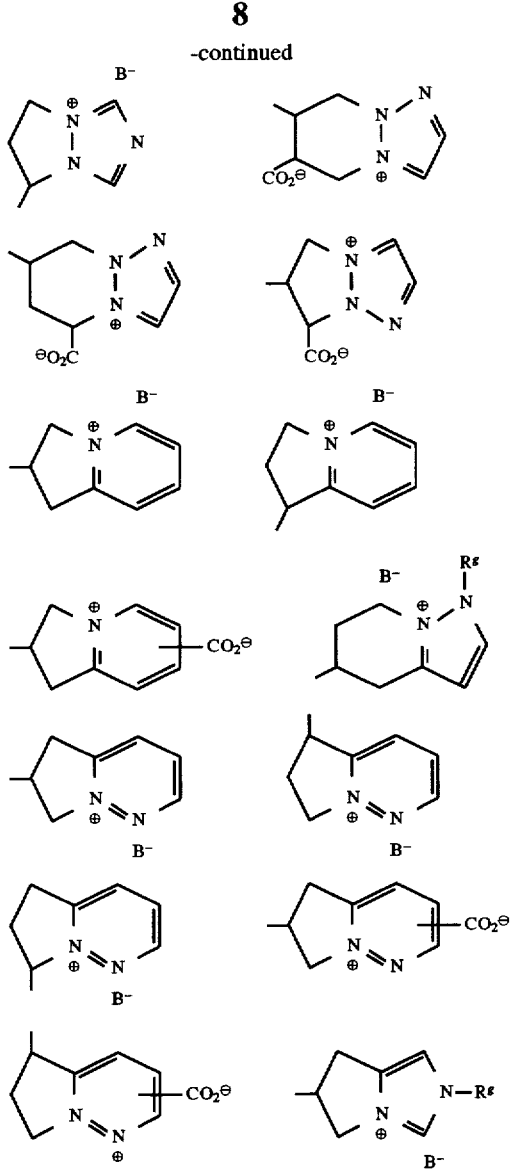

where $R^g$ is hereinafter defined and $B^-$ is a physiologically acceptable anion.

Suitably $R^a$ is a quaternized heteroaryl($C_1$–$C_6$)alkyl group of the formula:

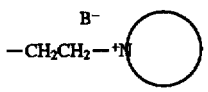

wherein the definition of the heteroaryl moiety

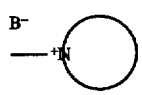

is as referenced above. Contemplated equivalents are disclosed in U.S. Pat. No. 4,952,397.

Suitably $R^a$ is a quaternized heteroaryl($C_1$–$C_6$)thioalkyl group such as:

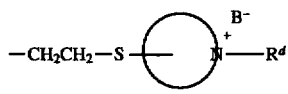

wherein $R^d$ is $(C_1-C_6)$alkyl and the definition of the heteroaryl ring

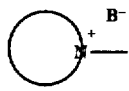

is as defined above. Contemplated equivalents of the heteroaryl ring and the alkyl group $R^d$ are disclosed in U.S. Pat. No. 4,880,922.

Suitably, $R^a$ is a heterocyclyl wherein the heteroatom or heteroatoms in the heterocycle are selected from 1 to 4 oxygen, nitrogen or sulfur atoms. Additionally, the above mentioned heterocyclyl moiety is optionally substituted with one or more of the substituents hereinabove defined. Preferred examples of the above-mentioned list are substituted pyrrolidinyl groups of the formula:

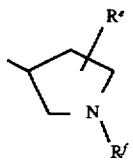

wherein the definitions of $R^e$ and $R^f$ are any of the above referenced substituents for $R^a$. Contemplated equivalents are found in U.S. Pat. No. 4,921,852; U.S. Pat. No. 4,963,543; U.S. Pat. No. 4,463,544 and U.S. Pat. No. 4,740,507; or pyrazolidinyl substituents preferably:

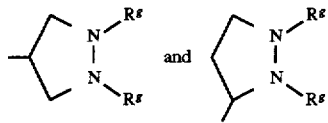

wherein $R^g$ is hydrogen, tert-butyldimethylsilyl or other suitable tri-substituted silyl groups, —CO$_2$CH$_2$—(4-nitrophenyl), or —CO$_2$ CH$_2$CH=CH$_2$.

(iii) $R_2$ may also be hydroxy, —OR$^a$, —OC(O)R$^a$, —OC(O)OR$^a$, —OC(O)NR$^a$R$^a$,

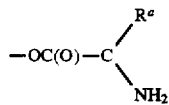

wherein $R^a$ is independently selected and is as hereinabove defined or

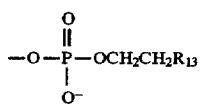

wherein $R_{13}$ is a moiety selected from those of the formulae:

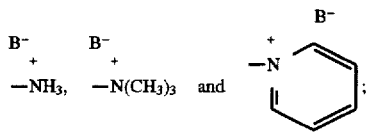

wherein B$^-$ is a physiologically acceptable anion;

(iv) $R_2$ may also be an organic residue bonded via a nitrogen atom, such as: (a) NO, NO$_2$, NO$_3$, NC, NCO, NHCN, NR$^h$R$^j$ wherein R$^h$ and R$^j$ are independently selected from hydrogen; substituted or unsubstituted amino, substituted or unsubstituted (C$_1$–C$_8$)alkyl and (C$_3$–C$_8$)cycloalkyl(C$_1$–C$_8$)alkyl, aryl, aralkyl, heterocyclyl, heterocyclyl(C$_1$–C$_4$)alkyl, heteroaryl and heteroaryl(C$_1$–C$_4$)alkyl wherein the heteroatom or heteroatoms are selected from oxygen, nitrogen and sulfur, and a cyclic group wherein R$^h$ and R$^j$ taken together with the associated nitrogen is an unsubstituted or substituted mono- or bicyclic heterocyclic ring having up to four (4) heteroatoms in each ring independently selected from oxygen, nitrogen and sulfur wherein the substituents in the aforementioned substituted alkyl, amino and heterocyclic groups consist of amino, mono-, di- and tri(C$_1$–C$_6$)alkylamino, hydroxyl, oxo, carboxyl, alkoxyl, chloro, fluoro, bromo, nitro, —SO$_2$NH$_2$, phenyl, benzyl, acyloxy, alkoxylcarbonyl, alkoxycarbonyloxy cycloalkoxycarbonyloxy and carboxamido. Relative to the above defined NR$^h$R$^j$, representative examples are:

—NH$_2$, —NHCH$_3$, —NHCH$_2$CH$_3$, —NHCH(CH$_3$)$_2$, —N(CH$_3$)$_2$, —N(CH$_2$CH$_3$)$_2$, —N[CH(CH$_3$)$_2$]$_2$, —NHCH$_2$CH$_2$OH, —NHCH$_2$CH$_2$CH$_2$OH, —N(CH$_2$CH$_2$OH)$_2$, —N[CH(CH$_3$)CH$_2$OH]$_2$, —NH(CH$_2$CO$_2$CH$_3$), —NH(CH$_2$CH$_2$CO$_2$CH$_3$), —NHCH$_2$CF$_3$, —NHCH$_2$CH$_2$NHCO$_2$C(CH$_3$)$_3$, —NHCH(CH$_3$)CH$_2$CO$_2$C(CH$_3$)$_3$, —NHCH$_2$CH$_2$NH$_2$, —NHCH$_2$CH$_2$N(CH$_3$)$_2$, —NHCH(CH$_3$)CH$_2$N(CH$_3$)$_2$,

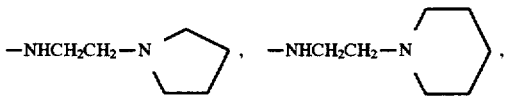

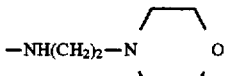

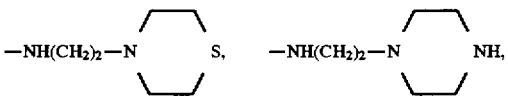

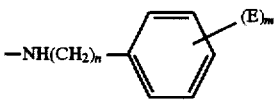

n = 1, 2   m = 1, 2   E = CH$_3$, OCH$_3$, Cl, Br, F, I, NO$_2$, OH  SO$_2$NH$_2$,  CO$_2$H,  CONH$_2$

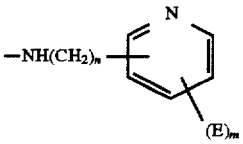

n = 1, 2   m = 1, 2   E = same as above

-continued

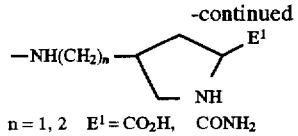
n = 1, 2    E¹ = CO₂H, CONH₂

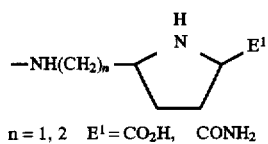
n = 1, 2    E¹ = CO₂H, CONH₂

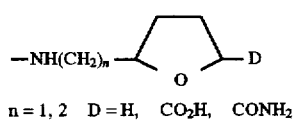
n = 1, 2    D = H, CO₂H, CONH₂

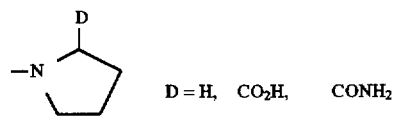
D = H, CO₂H, CONH₂

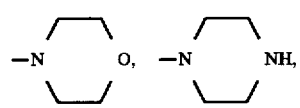

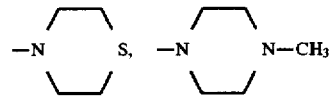

$R_2$, as an organic residue bonded through nitrogen, may also be; (b) hydroxylamino, hydrazinyl, iminyl and hydroxamic acid derivatives of the formulae:

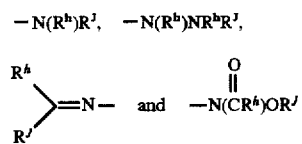

respectively; wherein $R^h$ and $R^j$ are as hereinabove defined; (c) moieties of the formulae

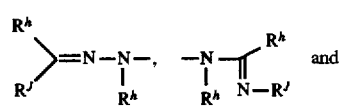

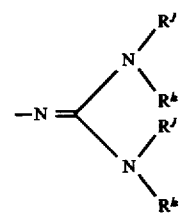

wherein $R^h$ and $R^j$ are as hereinabove defined; (d) acylamino moieties of the formulae

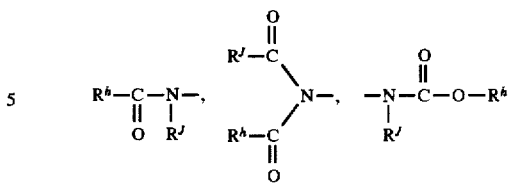

wherein $R^h$ and $R^j$ are as hereinabove defined; (e) moieties represented by the formulae

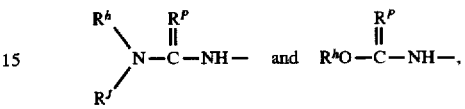

wherein $R^h$ and $R^j$ are as hereinabove defined and $R^p$ is selected from oxygen and sulfur; (f) moieties of the formulae

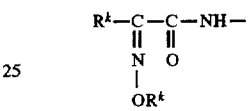

wherein $R^k$ represents hydrogen, substituted or unsubstituted ($C_1$–$C_3$)alkyl* (in the description of respective groups in the present specification, moieties marked with an asterisk (*) may have a substituent as assigned hereinabove for $R^h$ and $R^j$), ($C_2$–$C_6$)alkenyl*, ($C_2$–$C_6$)alkynyl*, heterocyclyl* and heteroaryl* wherein the heteroatom or heteroatoms are selected from 1–4 oxygen, nitrogen or sulfur and the cyclic portion has 5 or 6 ring atoms; (g) moieties of the formulae

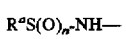
$R^a S(O)_n$-NH— wherein $n^a$ and $R^a$ are as hereinabove defined; (h) moieties represented by the formulae:

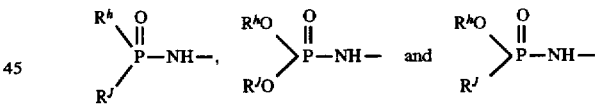

wherein $R^h$ and $R^j$ are as hereinabove defined.

$R_2$, as an organic residue bonded through nitrogen, may also be (i) an amino moiety containing an acyl residue of an amino acid or peptide represented by the formula:

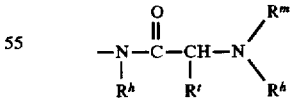

wherein $R^h$ is as hereinabove defined; $R^m$ is hydrogen or an acyl residue of an amino acid or peptide; and $R^t$ is hydrogen, benzyl, straight or branched ($C_1$–$C_6$)alkyl optionally substituted with halo, hydroxy, amino, guanidinyl, carboxy, phenyl, aminocarbonyl, alkylthio, hydroxyphenyl or heterocyclyl.

Representative examples of an acylamino moiety of the formulae:

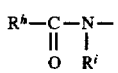

from the above-mentioned groups are formylamino, acetylamino, isobutyrylamino, benzyloxycarbonylamino, 1-aminocyclohexylcarbonylamino, 2-(2-amino-4-thiazolyl)-2-ethylideneacetylamino, 4-bromobenzoylamino, nicotinoylamino, 3-phenyl-5-methylisoxazol-4-yl-carbonylamino, pyrrolidinone, succinimidoyl and maleimidoyl.

Representative examples of a moiety of the formulae:

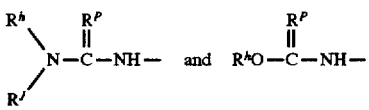

from the above-mentioned groups are:

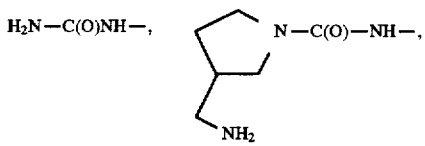

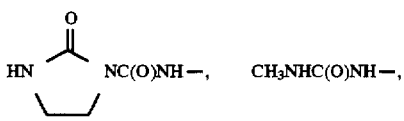

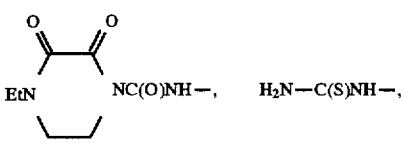

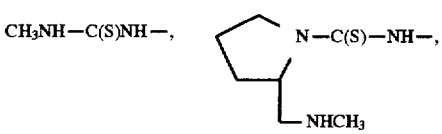

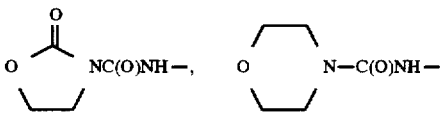

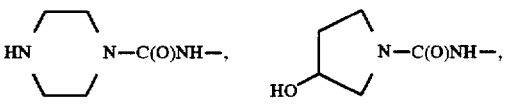

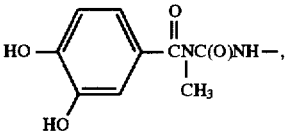

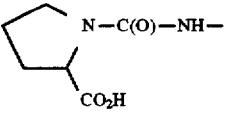

-continued

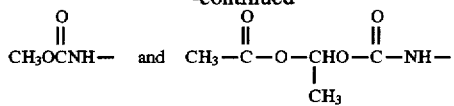

Representative examples of an acylamino moiety of the formulae:

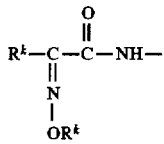

from the above-mentioned groups are

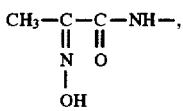

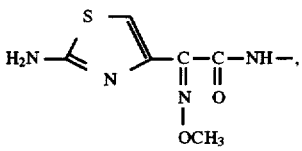

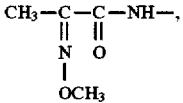

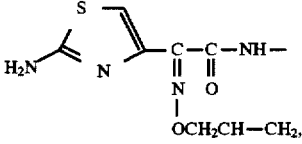

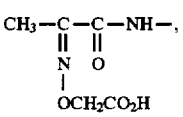

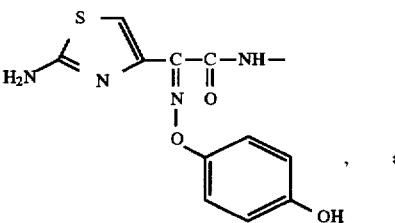

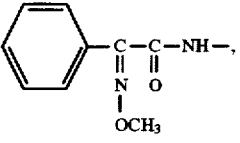

Representative examples of moieties of the formulae:

$R^a S(O)_n$-NH— from the above-mentioned listings are

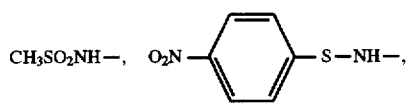

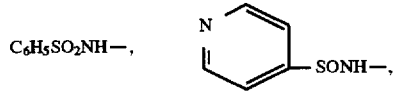

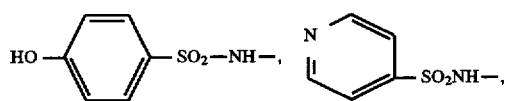

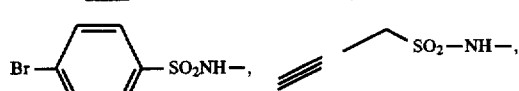

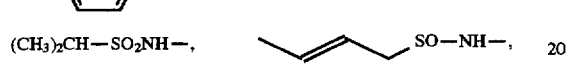

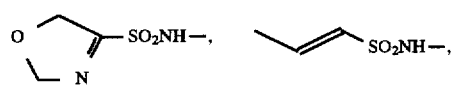

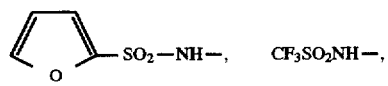

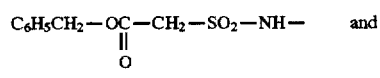

Representative examples of moieties of the formulae:

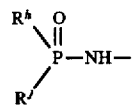

from the above-mentioned listings are (dimethoxyphosphinyl)amino, (diethoxyphosphinyl)amino, (diisopropoxyphosphinyl)amino, (diphenoxyphosphinyl)amino, and bis(phenylmethoxy)phosphinylamino, Representative examples of the formulae:

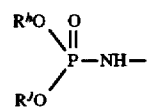

from the above-mentioned listings are:

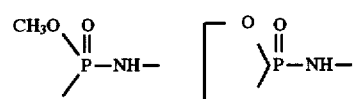

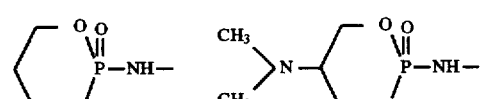

Representative examples of the formulae:

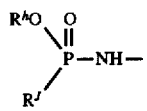

from the above-mentioned listings are

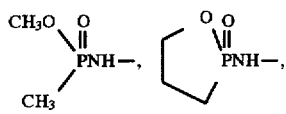

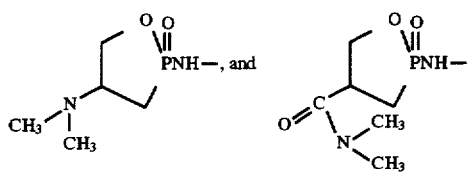

Representative examples of moieties the formulae:

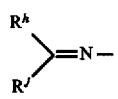

from the above-mentioned listings are

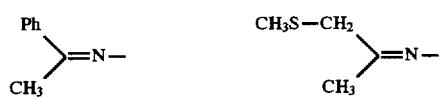

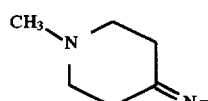

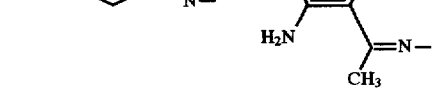

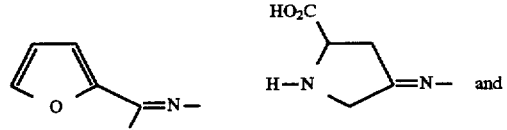

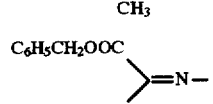

Representative examples of moieties with the formulae:

from the above-mentioned listings are

—NHOH, —N(CH₃)OH, —N(CH₃)OCH₃, —N(CH₂CH₃)OH, —N(CH₂CH₃)OCH₃, —N(CH₃) OCH₂CO₂H, —N(CH₃) OCH₂CO₂CH₂C₆H₅, —N(CH₃)OC₆H₅,

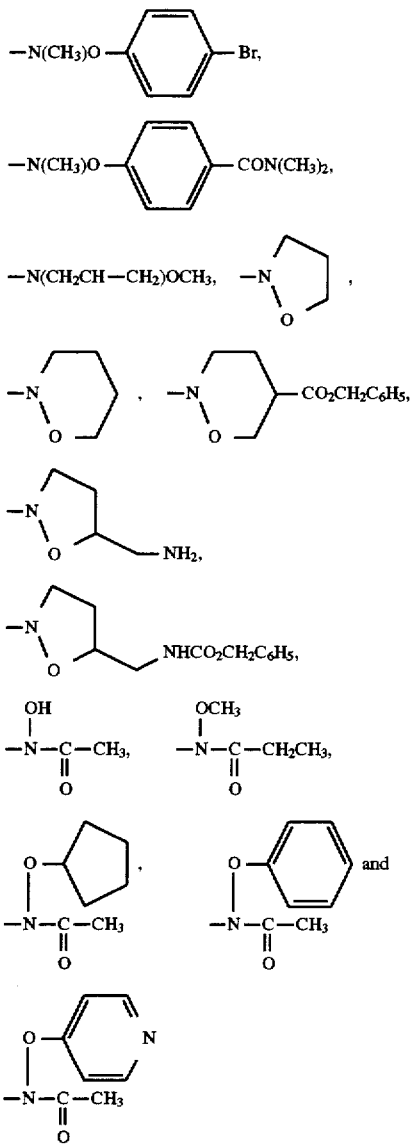

Representative examples of moieties with the formulae:

—N(Rʰ)NRʰRʲ from the above-mentioned listings are:

—NHNH₂, —N(CH₃)NH₂, —N(CH₃)NHCH₃, —NHN(CH₃)₂, —N(CH₃)N(CH₃)₂, —NHNHCO₂CH₂C₆H₅, —NHNHC₆H₅, —NHNHCH₂C₆H₅,

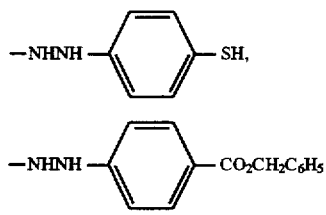

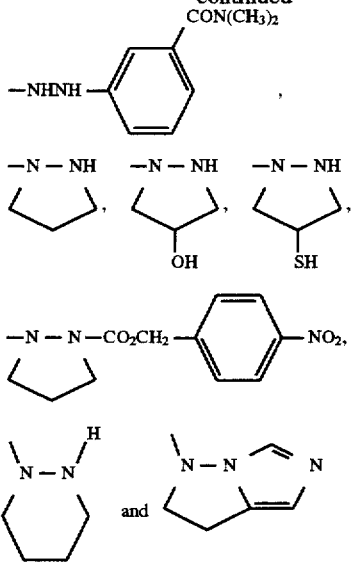

Representative examples of moieties with the formulae:

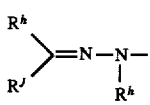

from the above-mentioned listings are

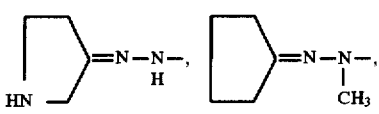

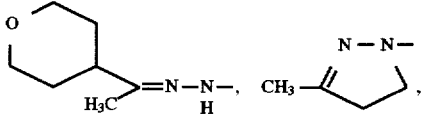

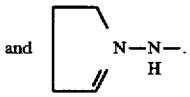

Representative examples of moieties with the formulae:

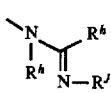

from the above-mentioned listings are

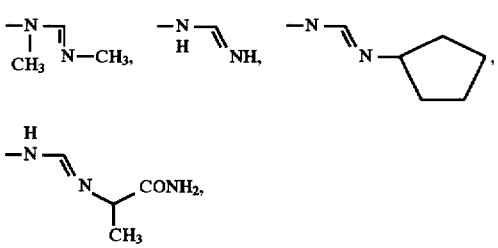

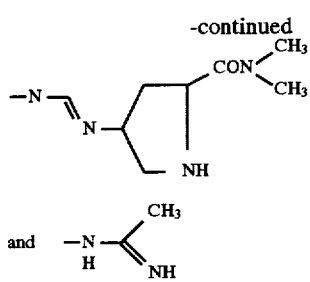

Representative listings of moieties with the formulae:

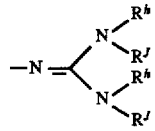

from the above-mentioned listings are

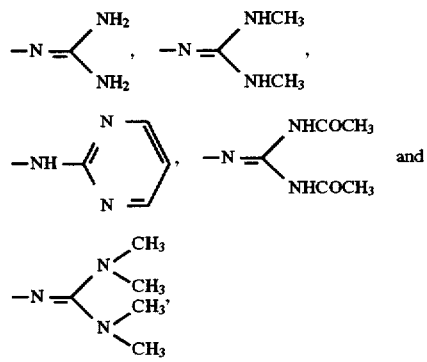

Representative listings of moieties with the formulae:

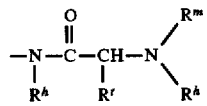

from the above-mentioned listings are

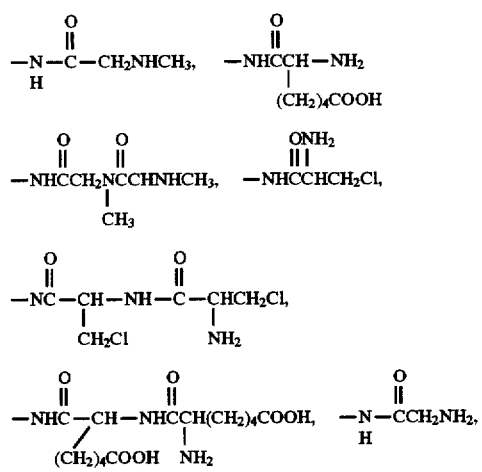

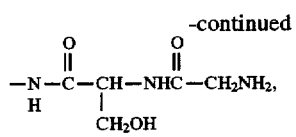

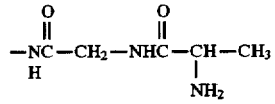

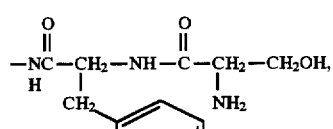

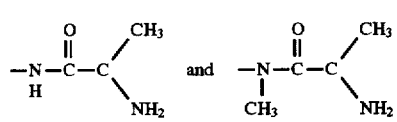

$R_2$, as an organic residue bonded through nitrogen, may also be an (j) acyclic quaternary ammonio moiety of the formula:

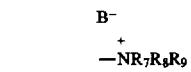

wherein $R_7$, $R_8$ and $R_9$ are the same or different and are selected from hydrogen, a straight or branched ($C_1$–$C_6$) alkyl, ($C_2$–$C_6$)alkenyl and substituted ($C_1$–$C_6$)alkyl, wherein the substitution is selected from hydroxy, ($C_1$–$C_6$)alkoxy, azido, amino, ($C_1$–$C_6$)alkylamino, di($C_1$–$C_6$) alkylamino, guanidino, nitrile, carboxy, formimidoyl and phenyl. Alternatively, $R_7$ and $R_8$ taken together may be —(CH$_2$)$_2$X (CH$_2$)$_2$—, wherein X is (CH$_2$)$_w$ (w is an integer from 0 to 2), oxygen, sulfur, NH, NR$^h$, NOH and NOR$^h$. Suitable examples are:

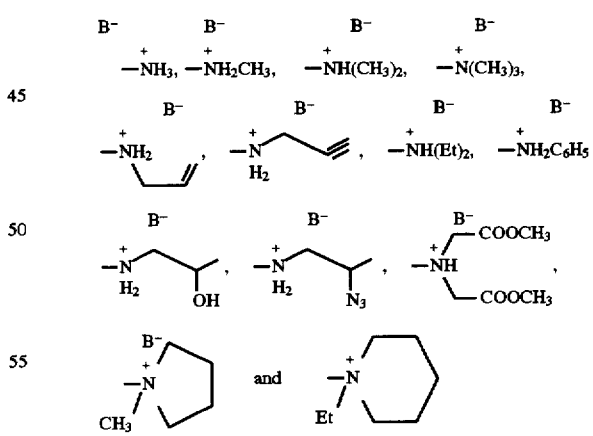

where B$^-$ is a physiologically acceptable anion.

$R_2$, as an organic residue bonded through nitrogen, may also be (k) a quaternized heteroaryl wherein the heteroatoms are selected from 1–4 oxygen, nitrogen and sulfur atoms and must contain at least one positively charged nitrogen atom in association with a physiologically acceptable anion wherein the quaternized heteroaryl is optionally substituted by R$^a$ as hereinabove defined; preferably, the quaternized heteroaryl moiety is a quarternized bicyclic heteroaryl ring. Representative examples of quaternized heteroaryl groups are:

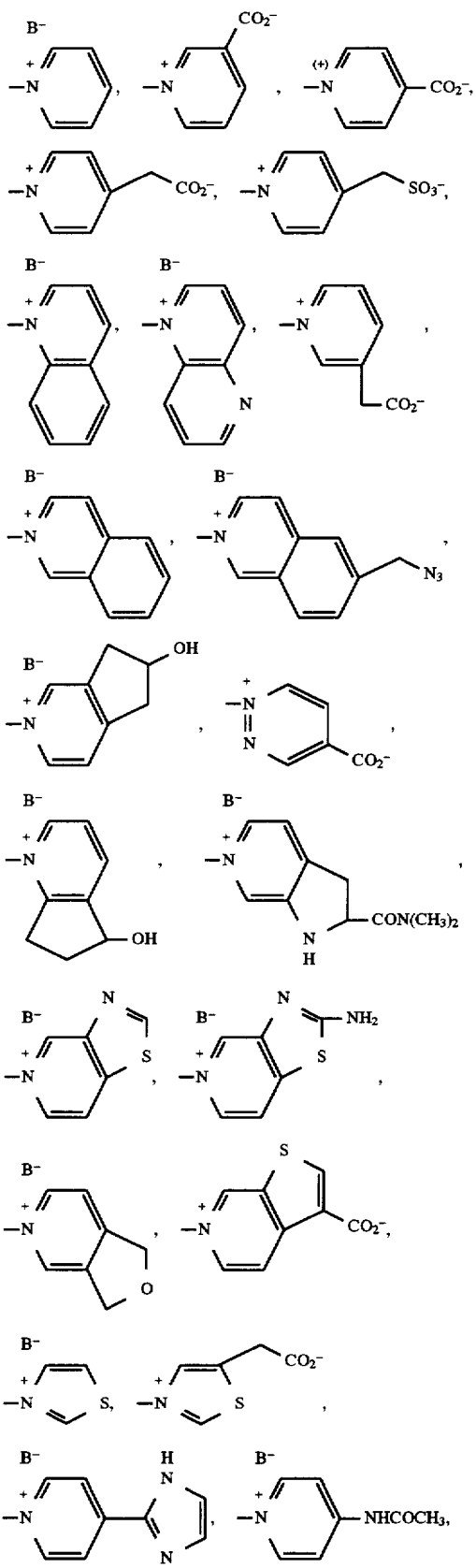

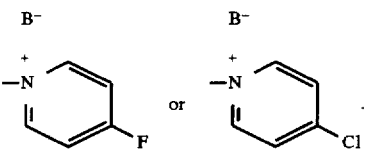

(v) $R_2$ may also be an organic residue bonded via a carbon atom. Suitably, the organic residue is bonded to either a sp-, $sp^2$- or $sp^3$-hybridized carbon as follows:

(a) Suitably, an organic residue bonded via an sp-hybridized carbon can be a nitrile,

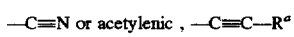

wherein $R^a$ is as hereinabove defined (b) An organic residue bonded via an $sp^2$-hybridized carbon can be moieties of the formulae:

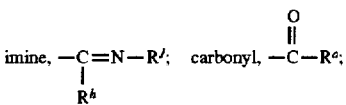

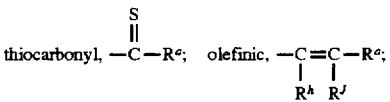

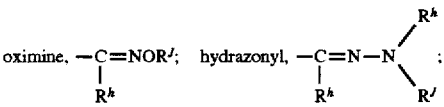

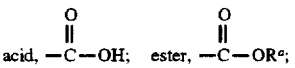

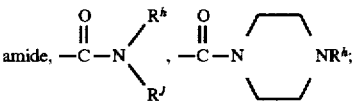

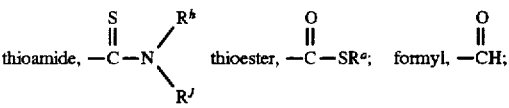

functional groups of the formulae:

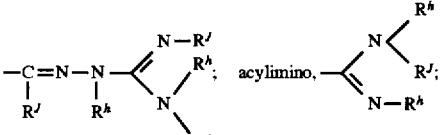

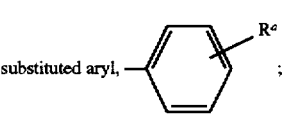

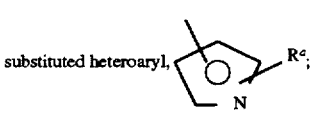

wherein $R^a$, $R^h$ and $R^j$ are as hereinabove defined.

(c) an organic residue bonded via an $sp^3$-hybridized carbon can be —$CHF_2$, —$CHCl_2$, —$CH(OCH_3)_2$, $CF_3$, $CF_2CF_3$ or $CHR^h R^j$.

Representative examples of an organic residue bonded via an sp-hybridized carbon are:

[chemical structures]

Representative examples of an organic residue bonded via an sp²-hybridized carbon are:

[chemical structures]

(F) $R_3$ is selected from hydrogen; a straight or branched $(C_1-C_4)$alkyl group such as methyl, ethyl, n-propyl, isopropyl, n-butyl, isobutyl, or tert-butyl; a $(C_1-C_4)$ alkoxymethyl group such as methoxymethyl, ethoxymethyl, n-propoxymethyl, isopropoxymethyl, n-butoxymethyl or isobutoxymethyl; a straight or branched 1-$(C_1-C_5)$aliphatic acyloxy-ethyl or methyl group such as acetoxymethyl, 1-propionyloxyethyl, n-butyryloxymethyl, isobutyryloxymethyl or pivaloyloxymethyl; a straight, branched or cyclic 1-$(C_1-C_6)$alkoxycarbonyloxy-ethyl or methyl group such as ethoxycarbonyloxymethyl, 1-isopropoxycarbonyloxyethyl, 1-n-butoxycarbonyloxyethyl, 1-cyclohexyloxycarbonyloxyethyl or 1-isobutoxycarbonyloxyethyl; a phthalidyl group; and water soluble cations such as lithium, sodium, potassium, ammonium or tetra$(C_1-C_4)$alkyl ammonium.

Preferred compounds are those of formula I wherein:

(A) Z is selected from oxygen; and (B) $R_o$ is —CH(OR$_4$)CH$_3$; wherein $R_4$ is selected from hydrogen and groups of formulae:

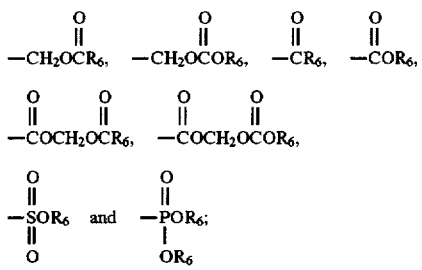

wherein $R_6$ is selected from a straight, branched or substituted $(C_1-C_{18})$ alkyl, $(C_2-C_{18})$alkenyl, unsubstituted or substituted $(C_3-C_7)$monocyclo$(C_1-C_{10})$alkyl, unsubstituted or substituted $(C_5-C_{10})$bicyclo$(C_1-C_{10})$alkyl, aryl or substituted aryl, heteroaryl or substituted heteroaryl, heterocyclyl or substituted heterocyclyl; wherein the substitution for the alkyl, monocycloalkyl and bicycloalkyl moieties are selected from trifluoromethyl, pentafluoroethyl, amino, mono$(C_1-C_6)$alkylamino, di$(C_1-C_6)$alkylamino, hydroxy, $(C_1-C_6)$alkoxy, $(C_3-C_8)$ cycloalkoxy, carboxy, $(C_2-C_{10})$ carboalkoxy, cyano, and $(C_1-C_{10})$carboxamido; and the substitution for the aryl, heteroaryl and heterocyclyl is selected from $(C_1-C_6)$alkyl, $(C_1-C_6)$mono-, di- or polyfluoroalkyl, hydroxy, $(C_1-C_6)$alkoxy, $(C_3-C_8)$ cycloalkoxy, amino, mono$(C_1-C_6)$alkylamino, di$(C_1-C_6)$ alkylamino, carboxy, $(C_2-C_{10})$carboalkoxy, cyano and $(C_1-C_{10})$carboxamido;

(C) $R_1$ is straight or branched $(C_1-C_4)$alkyl, straight or branched $(C_2-C_4)$alkenyl, $(C_3-C_6)$cycloalkyl, or $(CH_2)_{n'}R$; wherein n' is an integer of from 1–4; R is selected from $CF_3$, $C_2F_5$, fluorine, chlorine, bromine, hydroxy, alkoxy, nitrile, azido, a quaternary ammonio group, amidino, formamidino, guanidino and NR'R"; wherein (i) R' and R" are independently selected from hydrogen, straight or branched $(C_1-C_4)$alkyl, and straight or branched $(C_1-C_4)$alkoxy;

(ii) when R' is hydrogen or straight or branched $(C_1-C_4)$alkyl, R" may also be selected from amino, hydroxy, mono$(C_1-C_4)$alkylamino, di$(C_1-C_4)$ alkylamino, acyl, benzoyl, dihydroxybenzoyl, and an acyl residue of an amino acid or peptide, or (iii) R' and R" taken together with the associated nitrogen is an unsubstituted or substituted monocyclic or bicyclic heterocyclic ring having up to four (4) heteroatoms in each ring independently selected from oxygen, nitrogen and sulfur, wherein said substituent is selected from straight or branched $(C_1-C_4)$ alkyl, straight or branched $(C_1-C_4)$alkoxy, $(C_3-C_6)$ cycloalkyl, $(C_3-C_6)$cycloalkoxy, trifluoromethyl, hydroxy, halogen (selected from bromine, chlorine, fluorine and iodine), amino, nitrile, carboxy, carbamido, carbamoyl, straight or branched mono $(C_1-C_4)$alkylamino, straight or branched di$(C_1-C_4)$ alkylamino, and amino$(C_1-C_4)$alkyl;

(D) n is an integer from 0–4;

(E) $R_2$ is:

(i) methyl, fluorine, chlorine, bromine, iodine, —OCOCH$_3$, —OCOCF$_3$, —OSO$_2$CH$_3$, —OSO$_2$Ph, azido, (ii) a moiety of the formula:

wherein n" is an integer from 0–2; and $R^a$ is (a) hydrogen or (b) an organic group bonded via a carbon atom selected from substituted or unsubstituted $(C_1-C_4)$alkyl, substituted or unsubstituted $(C_3-C_6)$ cycloalkyl, substituted or unsubstituted $(C_2-C_4)$ alkenyl, substituted or unsubstituted $(C_2-C_4)$alkynyl, substituted or unsubstituted aryl, substituted or unsubstituted heteroaryl, substituted or unsubstituted aryl $(C_1-C_6)$alkyl, substituted or unsubstituted heterocyclyl; said substitution is selected from $(C_1-C_4)$alkyl, hydroxy, $(C_1-C_4)$alkoxy, phenyl, heterocyclyl, amino, amidino, guanidino, carboxamido, carbamoyl and quaternary ammonio. Preferably, the above referenced heteroaryl or heterocyclyl moiety is monocyclic or bicyclic and each ring is comprised of 5 or 6 atoms. Preferably, at least one of the heteroatoms is nitrogen and is quarternized.

(iii) or $R_2$ is hydroxy, —OR$^a$, —OC(O)R$^a$, —OC(O) OR$^a$, —OC(O)NR$^a$R$^a$ or —OC(O)—C(NH$_2$)R$^a$ wherein R$^a$ is independently selected and is as hereinabove defined or

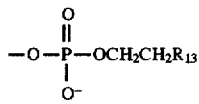

wherein $R_{13}$ is a moiety selected from those of the formulae:

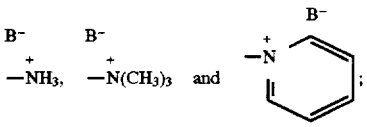

(iv) or $R_2$ is an organic residue bonded via a nitrogen atom, selected from (a) NO, NO$_2$, NO$_3$, NC, NCO, NHCN, and NR$^h$R$^J$ wherein R$^h$ and R$^J$ are independently selected from hydrogen; substituted or unsubstituted amino, substituted or unsubstituted $(C_1-C_4)$alkyl and $(C_3-C_6)$cycloalkyl$(C_1-C_4)$alkyl, aryl, aralkyl, heterocyclyl, heterocyclyl$(C_1-C_4)$alkyl, heteroaryl and heteroaryl$(C_1-C_4)$alkyl wherein the heteroatom or heteroatoms are selected from oxygen, nitrogen and sulfur, and a cyclic group wherein R$^h$ and R$^J$ taken together with the associated nitrogen is an unsubstituted or substituted mono- or bicyclic heterocyclic ring having up to four heteroatoms in each ring independently selected from oxygen, nitrogen and sulfur wherein the substituents in the aforementioned substituted alkyl, amino and heterocyclic groups consist of amino, mono-, di- and tri$(C_1-C_4)$alkylamino, hydroxyl, oxo, carboxyl, alkoxyl, chloro, fluoro, bromo, nitro, —SO$_2$NH$_2$, phenyl, benzyl, acyloxy, alkoxylcarbonyl, cycloalkoxycarbonyloxy alkoxycarbonyloxy, and carboxamido;

or $R_2$, as an organic residue bonded through nitrogen, is (b) a hydroxylamino, hydrazinyl, and hydroxamic acid derivative:

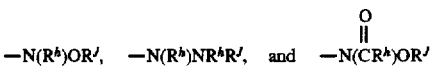

respectively; wherein R$^h$ and R$^J$ are as hereinabove defined;

(c) moieties of the formulae:

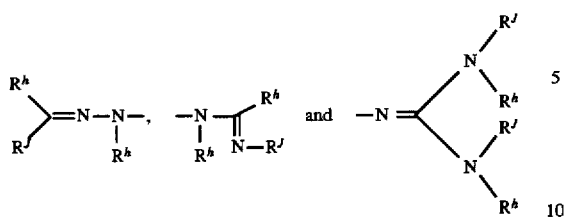

wherein $R^h$ and $R^j$ are as hereinabove defined;

(d) acylamino moiety of the formula:

wherein $R^h$ and $R^j$ are as hereinabove defined;

(e) moieties represented by the formulae:

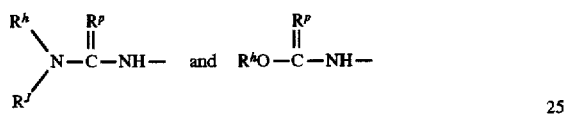

wherein $R^h$ and $R^j$ are as hereinabove defined and $R^p$ is oxygen or sulfur;

(f) moieties of the formula:

wherein $R^k$ represents hydrogen, substituted or unsubstituted $(C_1-C_3)$alkyl* (in the description of respective groups in the present specification, groups marked with an asterisk (*) may have a substituent as assigned hereinabove for $R^h$ and $R^j$), $(C_2-C_4)$alkenyl*, $(C_2-C_4)$alkynyl*, heterocyclyl* and heteroaryl* wherein the heteroatom or heteroatoms are selected from 1–4 oxygen, nitrogen or sulfur and the cyclic portion has 5 or 6 ring atoms;

(g) moieties of the formula:

wherein $n^u$ and $R^a$ are as hereinabove defined; or $R_2$, as an organic residue bonded through nitrogen, is (h) an amino moiety containing an acyl residue of an amino acid or peptide represented by the formula:

wherein $R^h$ is as hereinabove defined; $R^m$ is hydrogen or an acyl residue of an amino acid or peptide; and $R^r$ is hydrogen, benzyl, straight or branched $(C_1-C_4)$alkyl optionally substituted with halo, hydroxy, amino, guanidinyl, carboxy, phenyl, aminocarbonyl, alkylthio, hydroxyphenyl or heterocyclyl; $R_2$, as an organic residue bonded through nitrogen, may also be (i) an acyclic quaternary ammonio moiety of the formula:

wherein $B^-$ is a physiologically acceptable anion and $R_7$, $R_8$ and $R_9$ are the same or different and are selected from hydrogen, a straight or branched $(C_1-C_4)$alkyl, $(C_2-C_4)$alkenyl and substituted $(C_1-C_4)$alkyl, wherein the substitution is selected from hydroxy, $(C_1-C_4)$alkoxy, azido, amino, $(C_1-C_4)$ alkyl- amino, di$(C_1-C_4)$alkylamino, guanidino, nitrile, carboxy, formimidoyl and phenyl; alternatively, $R_7$ and $R_8$ taken together are —$(CH_2)_2X(CH_2)_2$—, wherein X is $(CH_2)_w$ (w is an integer from 0 to 2), oxygen, sulfur, NH, $NR^h$, NOH and $NOR^h$; or $R_2$, as an organic residue bonded through nitrogen, is (j) a quaternized heteroaryl wherein the heteroatoms are selected from 1–4 oxygen, nitrogen and sulfur atoms with the proviso that the heteroaryl moiety must contain at least one positively charged nitrogen atom in association with a physiologically. acceptable anion wherein the quaternized heteroaryl is optionally substituted by $R^a$ as hereinabove defined; quaternized fused bicyclic heteroaryl rings wherein the heteroatom or heteroatoms of the quaternized fused heteroaryl ring are selected from 1–3 oxygens, nitrogens and sulfurs; wherein the quaternized fused heteroaryl is optionally substituted by $R^a$ as hereinabove defined;

(v) or R2 is an organic residue bonded via a carbon atom; suitably, the organic residue is bonded to either a sp-, $sp^2$- or $sp^3$-hybridized carbon; wherein (a) an organic residue bonded via an sp-hybridized carbon is a nitrile.

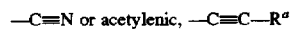

wherein $R^a$ is as hereinabove defined;

(b) an organic residue bonded via an $sp^2$-hybridized carbon is selected from those of the formulae:

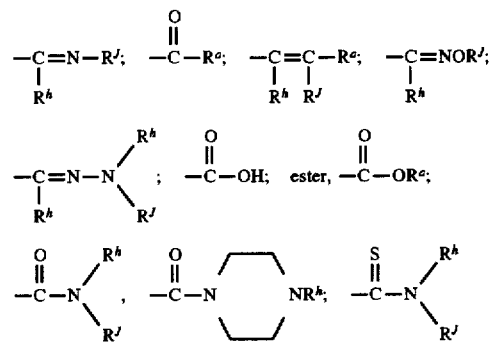

-continued

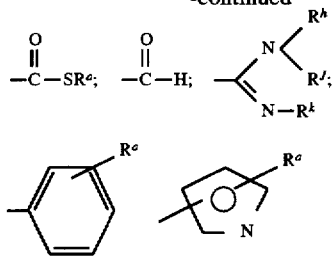

(c) an organic residue bonded via an sp³-hybridized carbon is —CHF$_2$, CF$_3$, —CF$_2$CF$_3$, —CH(OCH$_3$)$_2$, —CHCl$_2$ or CHR$^h$R$^J$;

(F) R$_3$ is hydrogen; a straight or branched (C$_1$–C$_4$)alkyl group such as methyl, ethyl, n-propyl, isopropyl, n-butyl, isobutyl, or tert-butyl; a (C$_1$–C$_4$)alkoxymethyl group such as methoxymethyl, ethoxymethyl, n-propoxymethyl, n-butoxymethyl or isobutoxymethyl; a straight or branched 1-(C$_1$–C$_5$)aliphatic acyloxy-ethyl or methyl group such as acetoxymethyl, 1-propionyloxyethyl, n-butyryloxymethyl, isobutyryloxymethyl or pivaloyloxymethyl; a straight, branched or cyclic 1-(C$_1$–C$_6$)alkoxycarbonyloxy-ethyl or methyl group such as, ethoxycarbonyloxymethyl, 1-isopropoxycarbonyloxyethyl, 1-n-butoxycarbonyloxyethyl, 1-cyclohexyloxycarbonyloxyethyl or 1-isobutoxycarbonyloxyethyl; a phthalidyl group; or water soluble cations selected from lithium, sodium, potassium, ammonium or tetra(C$_1$–C$_4$)alkyl ammonium.

Most preferred compounds are those of formula I wherein:

n is an integer from 0–4;
Z is selected from oxygen;
R$_o$ is —CH(OR$_4$)CH$_3$;
R$_4$ is selected from hydrogen,

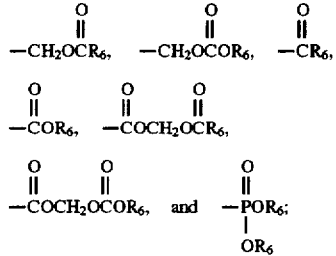

R$_6$ is selected from a straight, branched or substituted (C$_1$–C$_{18}$) alkyl, (C$_2$–C$_{18}$)alkenyl, unsubstituted or substituted (C$_3$–C$_7$)monocyclo(C$_1$–C$_{10}$)alkyl, unsubstituted or substituted (C$_5$–C$_{10}$)bicyclo(C$_1$–C$_{10}$)alkyl, phenyl or substituted phenyl; the substitution for the alkyl, monocycloalkyl and bicycloalkyl are selected from trifluoromethyl, pentafluoroethyl, amino, mono (C$_1$–C$_6$)alkylamino, di(C$_1$–C$_6$)alkylamino, hydroxy, (C$_1$–C$_6$) alkoxy, (C$_3$–C$_8$) cycloalkoxy, carboxy, (C$_2$–C$_{10}$)carboalkoxy, cyano, and (C$_1$–C$_{10}$) carboxamido; the substitution for the phenyl group is selected from (C$_1$–C$_6$)alkyl, (C$_1$–C$_6$)mono-, di- or polyfluoroalkyl, hydroxy, (C$_1$–C$_6$) alkoxy, (C$_3$–C$_8$) cycloalkoxy, amino, mono(C$_1$–C$_6$)alkylamino, di (C$_1$–C$_6$)alkylamino, carboxy, (C$_2$–C$_{10}$)carboalkoxy, cyano and (C$_1$–C$_{10}$)carboxamido;

R$_1$ is straight or branched (C$_1$–C$_4$)alkyl, straight or branched (C$_2$–C$_4$)alkenyl, or (CH$_2$)$_n$R; n' is an integer of from 1–4; R is selected from CF$_3$, C$_2$F$_5$, fluorine, chlorine, bromine, hydroxy, alkoxy, nitrile, azido, a quaternary ammonio group, amidino, formamidino, guanidino and NR'R"; wherein R' and R" are independently selected from hydrogen, straight or branched (C$_1$–C$_4$)alkyl, and straight or branched (C$_1$–C$_4$)alkoxy;

and when R' is hydrogen or straight or branched (C$_1$–C$_4$) alkyl, R" may also be selected from amino, hydroxy, mono(C$_1$–C$_4$)alkylamino, di(C$_1$–C$_4$)alkylamino, acyl, benzoyl and dihydroxybenzoyl;

R$_2$ is selected from methyl, fluorine, chlorine, bromine, iodine, —OCOCH$_3$, —OCOCF$_3$, —OSO$_2$CH$_3$, —OSO$_2$Ph, azido, a moiety of the formula:

—S(O)$_{n''}$R$^a$ wherein n" is an integer from 0–2;

and R$^a$ is hydrogen, substituted or unsubstituted (C$_1$–C$_4$) alkyl, substituted or unsubstituted (C$_3$–C$_6$)cycloalkyl, substituted or unsubstituted (C$_2$–C$_4$)alkenyl, substituted or unsubstituted (C$_2$–C$_4$)alkynyl, substituted or unsubstituted phenyl; said substitution is selected from (C$_1$–C$_4$)alkyl, hydroxy, (C$_1$–C$_4$)alkoxy, phenyl, amino, amidino, guanidino, carboxamido, carbamoyl and quaternary ammonio;

or R$_2$ is hydroxy, —OR$^a$, —OC(O)R$^a$, —OC(O)OR$^a$, —OC(O)NR$^a$R$^a$, —OC(O)—C(NH$_2$)R$^a$ wherein R$^a$ is independently selected and is as hereinabove defined or

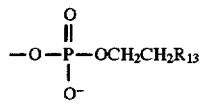

wherein R$_{13}$ is a moiety selected from those of the formulae:

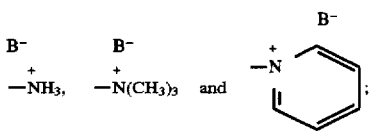

where B$^-$ is a physiologically acceptable anion, or R$_2$ is an organic residue bonded via a nitrogen, atom, selected from —NR$^h$R$^J$.

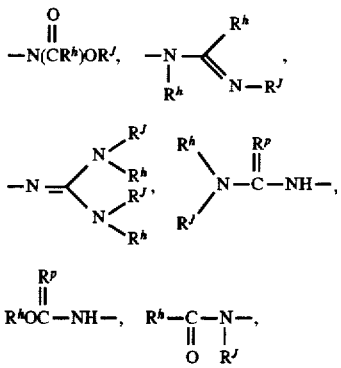

-continued

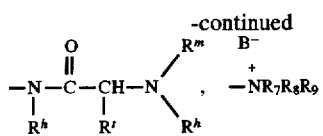

wherein $R^h$ and $R^j$ are independently selected from hydrogen; substituted or unsubstituted $(C_1-C_4)$alkyl and $(C_3-C_6)$cycloalkyl $(C_1-C_4)$alkyl, and substituted or unsubstituted phenyl, and with respect to the $NR^hR^j$ moiety, $R^h$ and $R^j$ taken together with the associated nitrogen may be unsubstituted or substituted mono- or bicyclic heterocyclic ring having from 5–7 atoms in each ring and up to four (4) heteroatoms in each ring independently selected from oxygen, nitrogen and sulfur wherein the substituents consist of amino, mono-, di- and tri$(C_1-C_4)$alkylamino, hydroxyl, oxo, carboxyl, alkoxyl, chloro, fluoro, bromo, nitro, $-SO_2NH_2$, phenyl, benzyl, acyloxy, alkoxycarbonyloxy, cycloalkoxycarbonyloxy, alkoxylcarbonyl and carboxamido; $R^p$ is oxygen or sulfur; $R^m$ is hydrogen or an acyl residue of an amino acid or peptide; and $R^r$ is hydrogen, benzyl, straight or branched $(C_1-C_4)$alkyl optionally substituted with halo, hydroxy, amino, guanidinyl, carboxy, phenyl, aminocarbonyl, alkylthio or hydroxyphenyl;

and $R_7$, $R_8$ and $R_9$ are the same or different and are selected from hydrogen, a straight or branched $(C_1-C_4)$ alkyl, $(C_2-C_4)$alkenyl and substituted $(C_1-C_4)$alkyl, wherein the substitution is selected from hydroxy, $(C_1-C_4)$alkoxy, azido, amino, $(C_1-C_4)$alkylamino, di$(C_1-C_4)$alkylamino, guanidino, nitrile, carboxy, formimidoyl and phenyl; alternatively, $R_7$ and $R_8$ taken together are $-(CH_2)_2X(CH_2)_2-$, wherein X is $(CH_2)_w$ (w is an is integer from 0 to 2), oxygen, sulfur, NH, $NR^h$, NOH and $NOR^h$;

or $R_2$ is an organic residue bonded via a carbon atom; suitably, the organic residue is bonded to either an sp-, $sp^2$- or $sp^3$-hybridized carbon; wherein an sp-hybridized carbon is a nitrile moiety, an acetylene moiety or a moiety of the formula:

wherein $R^a$ is as hereinabove defined; an $sp^2$-hybridized carbon is,

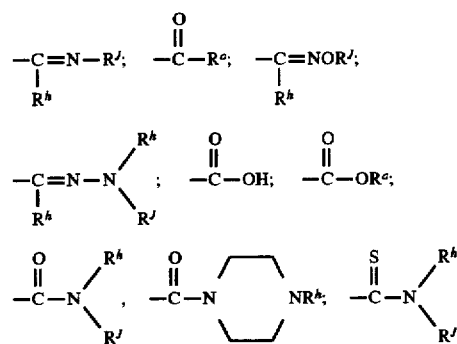

-continued

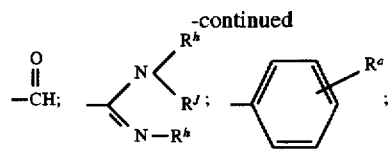

wherein $R^a$, $R^h$ and $R^j$ are as hereinabove defined; an $sp^3$-hybridized carbon is $-CHF_2$, $CF_3$, $-CF_2CF_3$, $-CH(OCH_3)_2$, $-CHCl_2$, or $-CHR^hR^j$;

$R_3$ is hydrogen; a straight or branched $(C_1-C_4)$alkyl group such as methyl, ethyl, n-propyl, isopropyl, n-butyl, isobutyl, or tert-butyl; a $(C_1-C_4)$alkoxymethyl group such as methoxymethyl, ethoxymethyl, n-propoxymethyl, isopropoxymethyl, n-butyoxymethyl or isobutoxymethyl; a straight or branched 1-$(C_1-C_5)$aliphatic acyloxy-ethyl or methyl group such as acetoxymethyl, 1-propionyloxyethyl, n-butyryloxymethyl, isobutyryloxymethyl or pivaloyloxymethyl; a straight, branched or cyclic 1-$(C_1-C_6)$ alkoxycarbonyloxy-ethyl or methyl group such as ethoxycarbonyloxymethyl, 1-isopropoxycarbonyloxyethyl, 1-n-butoxycarbonyloxyethyl, 1-cyclohexyloxycarbonyloxyethyl or 1-isobutoxycarbonyloxyethyl; a phthalidyl group; or water soluble cations such as lithium, sodium, potassium ammonium or tetra$(C_1-C_4)$alkyl ammonium.

Most particularly preferred compounds are those selected from formula I wherein:

n is an integer from 0–4;

Z is selected from oxygen;

$R_o$ is $-CH(OR_4)CH_3$;

$R_4$ is selected from hydrogen.

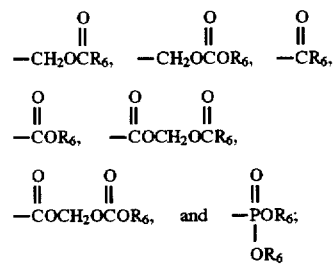

$R_6$ is selected from a straight, branched or substituted $(C_1-C_{18})$alkyl, $(C_2-C_{18})$alkenyl, unsubstituted or substituted $(C_3-C_7)$monocyclo$(C_1-C_{10})$alkyl, unsubstituted or substituted $(C_5-C_{10})$bicyclo$(C_1-C_{10})$alkyl, phenyl and substituted phenyl; the substitution for the alkyl, monocycloalkyl and bicycloalkyl are selected from trifluoromethyl, pentafluoroethyl, amino, mono $(C_1-C_6)$alkylamino, di $(C_1-C_6)$alkylamino, hydroxy, $(C_1-C_6)$alkoxy, $(C_3-C_8)$cycloalkoxy, carboxy, $(C_2-C_{10})$carboalkoxy, cyano and $(C_1-C_{10})$ carboxamido; the substitution for the phenyl group is selected from $(C_1-C_6)$alkyl, $(C_1-C_6)$mono-, di- or polyfluoroalkyl, hydroxy, $(C_1-C_6)$alkoxy, $(C_3-C_8)$ cycloalkoxy, amino, mono$(C_1-C_6)$alkylamino, di$(C_1-C_6)$alkylamino, carboxy, $(C_2-C_{10})$carboalkoxy, cyano and $(C_1-C_{10})$carboxamido; $R_1$ is straight $(C_1-C_3)$alkyl, $CH_2CF_3$ and $CH_2CF_2CF_3$; $R_2$ is selected from:

(a) methyl, fluorine, chlorine, bromine, iodine, $-OCOCH_3$, $-OCOCF_3$, $-OSO_2CH_3$, $-OSO_2Ph$, azido;

(b) a moiety of the formula:

—S(O)$_{n''}$-R$^a$ wherein n" is an integer from 0–2; and R$^a$ is hydrogen, substituted or unsubstituted (C$_1$–C$_4$)alkyl, substituted or unsubstituted phenyl wherein the substituents are selected from (C$_1$–C$_4$)alkyl, hydroxy, (C$_1$–C$_4$)alkoxy, amino, amidino, guanidino, carboxamido, carbamoyl and quaternary ammonio;

(c) or R$_2$ is hydroxy, —OR$^a$, —OC(O)NR$^a$R$^a$ or —OC(O)—C(NH$_2$)R$^a$ wherein R$^a$ is independently selected and is as hereinabove defined or $$-O-\overset{\overset{O}{\|}}{\underset{O^-}{P}}-OCH_2CH_2R_{13}$$

wherein R$_{13}$ is a moiety selected from those of the formulae:

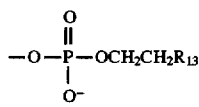

(d) or R$_2$ is an organic residue bonded via a nitrogen atom, selected from —NR$^h$R$^J$,

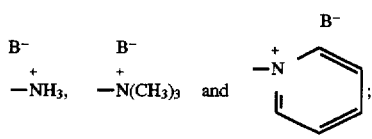

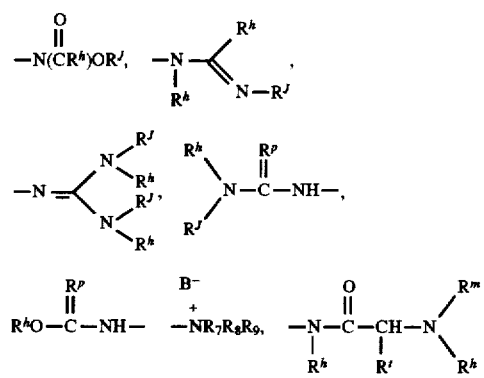

wherein R$^h$ and R$^J$ are independently selected from hydrogen; substituted or unsubstituted (C$_1$–C$_4$)alkyl and (C$_3$–C$_6$)cycloalkyl(C$_1$–C$_4$)alkyl, and substituted or unsubstituted phenyl, wherein the substituents consist of amino, mono-, di- and tri(C$_1$–C$_4$) alkylamino, hydroxyl, oxo, carboxyl, alkoxyl, chloro, fluoro, bromo, nitro, —SO$_2$NH$_2$, phenyl, benzyl, acyloxy, alkoxylcarbonyloxy, cycloalkoxycarbonyloxy and carboxamido; R$^P$ is oxygen or sulfur; R$^m$ is hydrogen or an acyl residue of an amino acid or peptide, R$^l$ is hydrogen or (C$_1$–C$_4$)alkyl, and R$_7$, R$_8$ and R$_9$ are the same or different and are selected from hydrogen, a straight or branched (C$_1$–C$_4$)alkyl, (C$_2$–C$_4$)alkenyl and substituted (C$_1$–C$_4$)alkyl, wherein the substitution is selected from hydroxy, (C$_1$–C$_4$)alkoxy, azido, amino, (C$_1$–C$_4$)alkylamino, di(C$_1$–C$_4$)alkylamino, guanidino, nitrile, carboxy, formimidoyl and phenyl; alternatively, R$_7$ and R$_8$ taken together are —(CH$_2$)$_2$X(CH$_2$)$_2$—, wherein X is (CH$_2$)$_w$ (w is an integer from 0 to 2), oxygen, sulfur, NH, NR$^h$, NOH and NOR$^h$;

(e) or R$_2$ is an organic residue bonded via a carbon atom; suitably, the organic residue is bonded to either an sp-, sp$^2$- or sp$^3$-hybridized carbon; wherein an sp-hybridized carbon is a nitrile,

—C≡N;

an sp$^2$-hybridized carbon is a moiety of the formulae:

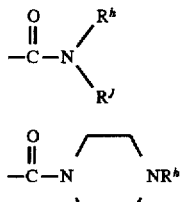

wherein, R$^h$ and R$^J$ are as hereinabove defined; an sp$^3$-hybridized carbon is —CHF$_2$, CF$_3$, —CF$_2$CF$_3$, —CH(OCH$_3$)$_2$, —CHCl$_2$, or —CHR$^h$R$^J$;

R$_3$ is hydrogen; a straight or branched (C$_1$–C$_4$)alkyl group such as methyl, ethyl, n-propyl, isopropyl, n-butyl, isobutyl, or tert-butyl; a (C$_1$–C$_4$)alkoxymethyl group such as methoxymethyl, ethoxymethyl, n-propoxymethyl, isopropoxymethyl, n-butoxymethyl or isobutoxymethyl; a straight or branched 1-(C$_1$–C$_5$) aliphatic acyloxy-ethyl or methyl group such as acetoxymethyl, 1-propionyloxyethyl, n-butyryloxymethyl, isobutyryloxymethyl or pivaloyloxymethyl; a straight, branched or cyclic 1-(C$_1$–C$_6$) alkoxycarbonyloxy-ethyl or methyl group such as ethoxycarbonyloxymethyl, 1-isopropoxycarbonyloxyethyl, 1-n-butoxycarbonyloxyethyl, 1-cyclohexyloxycarbonyloxyethyl, or 1-isobutoxycarbonyloxyethyl; a phthalidyl group; or water soluble cations such as lithium, sodium, potassium ammonium or tetra (C$_1$–C$_4$)-alkyl ammonium.

Unless otherwise specified herein, the particulars of the various definitions mentioned above and specific examples falling within such definitions are as follows:

(a) the aryl group is an aromatic monocyclic or bicyclic hydrocarbon group having from 6 to 15 carbon atoms such as a phenyl group, a biphenyl group, a 1-naphthyl group or a 2-naphthyl group;

(b) the aralkyl or arylalkyl group is an aromatically substituted alkyl group having from 7 to 15 carbon atoms such as a benzyl group, a 1-naphthylmethyl group, a 2-naphthylmethyl group, a 5,6,7,8-tetrahydro-1-naphthyl group, a 5,6,7,8-tetrahydro-2-naphthyl group, a phenylethyl group, a 3-phenylpropyl group or a 4-phenylpropyl group;

(c) the heteroaryl group is an aromatic monocyclic or bicyclic heterocyclic group of 5 to 12 atoms wherein each ring is comprised of 5 to 6 atoms wherein the heteroatom or heteroatoms are selected from 1–4 oxygen, nitrogen or sulfur atoms such as thienyl, pyrazolyl, pyridyl, pyrazinyl, pyrimidinyl, triazinyl, furanyl, imidazolyl, thiazolyl and triazolyl;

(d) the heterocyclyl group is a monocyclic or bicyclic heterocyclic group having from 1 to 10 carbon atoms and 1 to 4 heteroatoms selected from oxygen, nitrogen or sulfur atoms and each ring of the heterocycle is comprised of 4 to 7 atoms, preferably 5 to 6 atoms such as pyrrolidinyl group, a pyrazolidinyl group, an imidazolidinyl group, a piperidinyl group, a piperazinyl group or a morpholinyl group.

It is understood that any quaternized, positively charged nitrogen containing moiety used herein such as trialkylamino, will be associated with a physioloically acceptable counterion as previously defined.

Pharmaceutically suitable salts include both the metallic (inorganic) salts and organic salts; a list of which is given in *Remington's Pharmaceutical Sciences*, 17th Edition, page 1418 (1985). It is well known to one skilled in the art that an appropriate salt form is chosen based on physical and chemical stability, flowability, hygroscopicity and solubility. Preferred salts of this invention for the reasons cited above include potassium, sodium, calcium, magnesium and ammonium salts.

Also included in the present invention are compounds that are useful as intermediates for making the above compounds of formula I. Such intermediate compounds include those of formula IV(1-6) and IX(1-6):

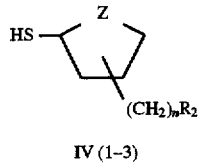

IV (1-3)

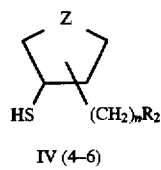

IV (4-6)

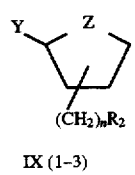

IX (1-3)

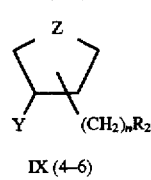

IX (4-6)

wherein

Y is selected from chloro, bromo, iodo, methanesulfonate and trifluoromethanesulfonate; and n, Z, and $R_2$ are as hereinabove described.

Preferred intermediate compounds are those chosen from formula IV(1-6) or IX(1-6) wherein:

$R_2$ is methyl, fluorine, chlorine, bromine, iodine, —OCOCH$_3$, —OCOCF$_3$, —OSO$_2$CH$_3$, —OSO$_2$Ph, azido, a moiety of the formula:

$S(O)_{n'}$-$R^a$ wherein n" is an integer from 0–2;
and $R^a$ is hydrogen or an organic group bonded via a carbon atom selected from substituted or unsubstituted ($C_1$–$C_4$)alkyl, substituted or unsubstituted ($C_3$–$C_6$) cycloalkyl, substituted or unsubstituted ($C_2$–$C_4$) alkenyl, substituted or unsubstituted ($C_2$–$C_4$)alkynyl, substituted or unsubstituted aryl, substituted or unsubstituted heteroaryl, substituted or unsubstituted aryl ($C_1$–$C_6$)alkyl, substituted or unsubstituted heterocyclyl, any of such groups being optionally substituted; said substitution is selected from ($C_1$–$C_4$) alkyl, hydroxy, ($C_1$–$C_4$)alkoxy, phenyl, heterocyclyl, amino, amidino, guanidino, carboxamido, carbamoyl and quaternary ammonio;

or $R_2$ is hydroxy, —OR$^a$, —OC(O)R$^a$, —OC(O)OR$^a$, —OC(O)NR$^a$R$^a$ or

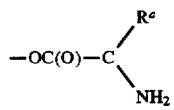

wherein $R^a$ is independently selected and is as hereinabove defined or

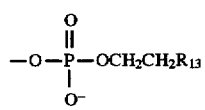

wherein $R_{13}$ is a moiety selected from those of the formulae:

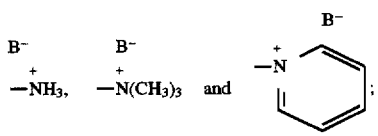

or $R_2$ is an organic residue bonded via a nitrogen atom, selected from NO, NO$_2$, NO$_3$, NC, NCO, NHCN, and NR$^h$R$^j$ wherein R$^h$ and R$^j$ are independently selected from hydrogen; substituted or unsubstituted amino, substituted or unsubstituted ($C_1$–$C_4$)alkyl and ($C_3$–$C_6$) cycloalkyl ($C_1$–$C_4$)alkyl, aryl, aralkyl, heterocyclyl, heterocyclyl($C_1$–$C_4$)alkyl, heteroaryl and heteroaryl ($C_1$–$C_4$)alkyl wherein the heteroatom or heteroatoms are selected from oxygen, nitrogen and sulfur, and a cyclic group wherein R$^h$ and R$^j$ taken together with the associated nitrogen is an unsubstituted or substituted mono- or bicyclic heterocyclic ring having up to four (4) heteroatoms in each ring independently selected from oxygen, nitrogen and sulfur wherein the substituents in the aforementioned substituted alkyl, amino and heterocyclic groups consist of amino, mono-, di- and tri($C_1$–$C_4$)alkylamino, hydroxyl, oxo, carboxyl, alkoxyl, chloro, fluoro, bromo, nitro, —SO$_2$NH$_2$, phenyl, benzyl, acyloxy, alkoxylcarbonyl, alkoxycarbonyloxy, cycloalkoxycarbonyloxy and carboxamido;

or $R_2$, as an organic residue bonded through nitrogen, is a hydroxylamino, hydrazinyl, and hydroxamic acid derivatives:

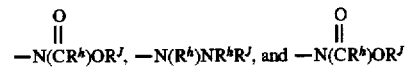

respectively; wherein R$^h$ and R$^j$ are as hereinabove defined;

moieties of the formulae:

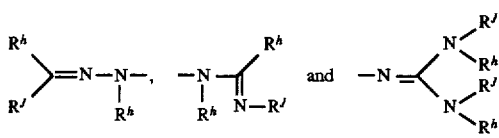

wherein $R^h$ and $R^J$ are as hereinabove defined; acylamino moieties of the formula:

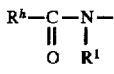

wherein $R^h$ and $R^J$ are as hereinabove defined; moieties represented by the formulae:

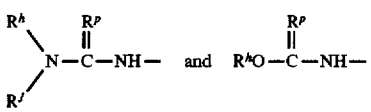

wherein $R^h$ and $R^J$ are as hereinabove defined and $R^e$ is oxygen and sulfur; moieties of the formulae:

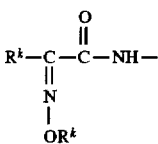

wherein $R^k$ represents hydrogen, substituted or unsubstituted $(C_1-C_3)$alkyl* (in the description of respective groups in the present specification, groups marked with an asterisk (*) may have a substituent as assigned hereinabove for $R^h$ and $R^J$), $(C_2-C_4)$alkenyl*, $(C_2-C_4)$alkynyl*, heterocyclyl* and heteroaryl* wherein the heteroatom or heteroatoms are selected from 1–4 oxygen, nitrogen or sulfur and the cyclic portion has 5 or 6 ring atoms; moieties of the formula:

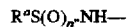

wherein n" and $R^a$ are as hereinbefore defined; or $R^2$ may be a moiety of the formula:

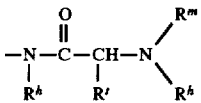

wherein $R^h$ is as hereinabove defined; $R^m$ is hydrogen or an acyl residue of an amino acid or peptide; and $R^r$ is hydrogen, benzyl, straight or branched $(C_1-C_6)$alkyl optionally substituted with halo, hydroxy, amino, guanidinyl, carboxy, phenyl, aminocarbonyl, alkylthio, hydroxyphenyl or heterocyclyl;

or $R_2$ is an organic residue bonded via a carbon atom; suitably, the organic residue is bonded to either a sp-, $sp^2$- or $sp^3$-hybridized carbon;

an sp-hybridized carbon is a nitrile,

wherein $R^a$ is as hereinabove defined; an $sp^2$-hybridized carbon is,

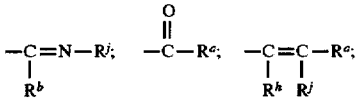

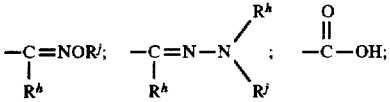

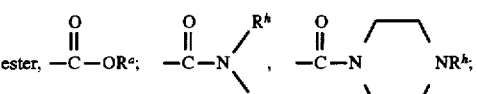

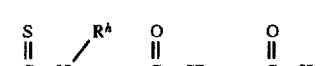

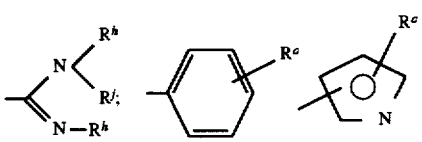

an $sp^3$-hybridized carbon is —$CHF_2$, $CF_3$, —$CF_2CF_3$, —$CH(OCH_3)_2$, —$CHCl_2$, or —$CHR^hR^J$.

Most particularly preferred intermediate compounds are those chosen from formula IV(1-6) or IX(1-6) wherein:

$R_2$ is (a) hydrogen, fluorine, chlorine, bromine, iodine, —$OCOCH_3$, —$OCOCF_3$, —$OSO_2CH_3$, —$OSO_2Ph$, azido, (b) a moiety of the formula:

wherein n" is an integer from 0–2;

and $R^a$ is hydrogen or an organic group bonded via a carbon atom selected from substituted or unsubstituted $(C_1-C_4)$alkyl, substituted or unsubstituted phenyl, any of such groups being optionally substituted; said substitution is selected from $(C_1-C_4)$alkyl, hydroxy, $(C_1-C_4)$alkoxy, amino, amidino, guanidino, carboxamido, carbamoyl and quaternary ammonio;

(c) or $R_2$ is hydroxy, —$OR^a$ or —$OC(O)NR^aR^a$ wherein $R^a$ is independently selected and is as hereinabove defined or

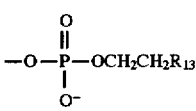

wherein $R_{13}$ is a moiety selected from those of the formulae:

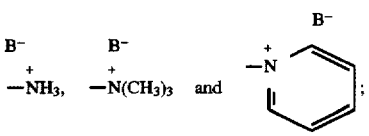

or (d) $R_2$ is an organic residue bonded via a nitrogen atom, selected from —$NR^hR^J$,

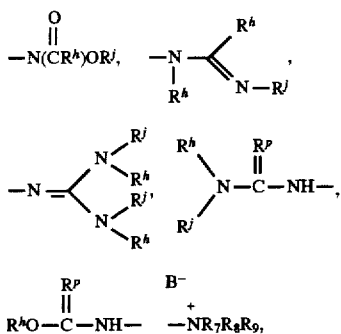

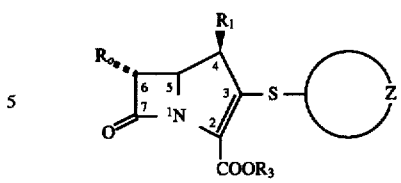

wherein $R^h$ and $R^j$ are independently selected from hydrogen; amino $(C_1-C_4)$alkyl, $(C_3-C_6)$cycloalkyl$(C_1-C_4)$alkyl, and phenyl; $R^p$ is oxygen or sulfur;

and $R_7$, $R_8$ and $R_9$ are the same or different and are selected from hydrogen, a straight or branched $(C_1-C_4)$ alkyl, $(C_2-C_4)$alkenyl and substituted $(C_1-C_4)$alkyl, wherein the substitution is selected from hydroxy, $(C_1-C_4)$alkoxy, azido, amino, $(C_1-C_4)$ alkylamino, di$(C_1-C_4)$alkylamino, guanidino, nitrile, carboxy, formimidoyl and phenyl; alternatively, $R_7$ and $R_8$ taken together are $-(CH_2)_2X(CH_2)_2-$, wherein X is $(CH_2)_w$ (w is an integer from 0 to 2), oxygen, sulfur, NH, $NR^h$, NOH and $NOR^h$;

(e) or $R_2$ is moiety of the formula:

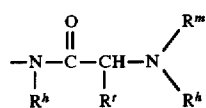

wherein $R^h$ is as hereinabove defined; $R^m$ is hydrogen or an acyl residue of an amino acid or peptide and $R'$ is hydrogen, benzyl, straight or branched $(C_1-C_6)$alkyl optionally substituted with halo, hydroxy, amino, guanidinyl, carboxy, phenyl, aminocarbonyl, alkylthio, hydroxyphenyl or heterocyclyl;

(f) or $R_2$ is an organic residue bonded via a carbon atom; suitably, the organic residue is bonded to either an sp-, $sp^2$- or $sp^3$-hybridized carbon; wherein an sp-hybridized carbon is a nitrile, an $sp^2$-hybridized carbon is

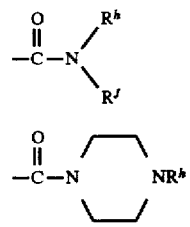

wherein, $R^h$ and $R^j$ are as hereinabove defined; and an $sp^3$-hybridized carbon is $-CHF_{21}$, $CF_3$, $-CF_2CF_3$, $-CH$ $(OCH_3)_2$, $CHR^hR^j$ or $-CHCl_2$.

It will be appreciated that certain products within the scope of Formula I:

may be formed as optical isomers as well as epimeric mixtures thereof. It is intended that the present invention include within its scope all such optical isomers and epimeric mixtures. For example, when the 6-substituent in I is 1-hydroxyethyl, such substituents may be either R or S configuration with the R configuration being preferred. Likewise, the configuration of the carbapenem nucleus may be 5R or 5S and 6R or 6S with 5R, 6S being the preferred configuration.

BIOLOGICAL ACTIVITY

Method for in vitro Antibacterial Evaluations (Table 1)

The minimal inhibitory concentration (MIC), the lowest concentration of the antibiotic which inhibits growth of the test organism, is determined by the agar dilution method using Mueller Hinton II agar following the recommendations of the National Commitee for Clinical Laboratory Standards [Methods for dilution antimicrobial susceptibility tests for bacteria that grow aerobically. Approved standard M7-A2. National Committee for Clinical Laboratory Standards, Villanova, Pa.].

An inoculum of $10^7$ cfu/ml is applied using a Steers replicator, yielding a final density of $10^4$ cfu/spot, to the surface of the agar containing two fold serial dilutions of the antibacterial agent. The plates are incubated at 35° C. for 18 hours.

The organisms tested for susceptibility to the antibacterial agents comprise a spectrum of Gram-positive and Gram-negative, recent clinical isolates, including those sensitive to various β-lactam antibiotics as well as those producing specific β-lactamases and thereby resistant to many β-lactams.

In Vivo Antibacterial Evaluation Determination of Effective Therapeutic Dose ($ED_{50}$) (Table 2 )

In Vivo Antibacterial Evaluation

The therapeutic effects of the carbapenems are determined against various models of acute lethal infections (*E. coli* #311, *S. aureus* Smith, P. aeruginosa PA-7). Female mice, strain CD-1 (Charles River Laboratories), 20±2 grams, are challenged by an intraperitoneal injection of a bacterial suspension in broth or hog mucin at a bacterial density to kill non-treated controls within 24–48 hours. The antibacterial agent(s) [carbapenem (s)] contained in 0.5 ml of 0.2% aqueous agar is administered subcutaneously, intravenously or orally 30 minutes after infection. When an oral dosing schedule is used, the animals are deprived of food for 5 hours before and 2 hours after infection. Five mice are treated at each dose level. The 7 day survival ratios from three separate tests are pooled for calculation of the median effective dose (ED50).

Penicillin-Binding Protein Assay (Table 3 and 4)

Binding of the test compounds to penicillin-binding proteins (PBPs) is determined using methods described by B. G. Spratt, Properties of the penicillin-binding proteins of *Escherichia coli* K12, Eur. J. Biochem., 72:341-352(1977) and N. H. Georgopapadakou, S. A. Smith, C. M. Cimarusti, and R. B. Sykes, Binding of monobactams to penicillin-binding proteins of *Escherichia coli* and *Staphylococcus*

*aureus*: Relation to antibacterial activity, Antimicrob. Agents Chemother., 23:98–104(1983). Membranes containing the PBPs are prepared from *E. coli* ATCC 25922 and *S. aureus* ATCC 29213. These membranes are incubated with the test compound at selected concentrations and are then challenged with $^{14}$C-benzylpenicillin. Following polyacryamide gel electrophoresis and fluorography, IC$_{50}$ values are estimated using densitometry.

Stability to Hydrolysis by Renal Dehydropeptidase (DHP) (Table 5)

Compounds are also tested for stability to renal dehydropeptidase (DHP) prepared from mouse and hog kidneys using butanol extraction procedures similar to those described by B. J. Campbell et al., β-Lactamase Activity of Purified and Partially Characterized Human Renal Dipeptidase, J. Bio. Chem., 259:14586–14590(1984).

Assays are performed spectrophotometrically at 25° C. in 10 mM HEPES buffer, pH 7.2 at a wavelength of 295 nm. Extinction coefficients were determined for the carbapenems using a metallo-β-lactamase. Hydrolysis rates are obtained using a stock concentration of 50 μl/ml of the antibiotic and 10–50 μl DHP in a volume of 1.0 ml. At least two concentrations of DHP are used for hydrolysis. The rate of hydrolysis (n moles/min) is determined per μl DHP added to the reaction. Relative hydrolysis rates are calculated by setting the rate of hydrolysis of imipenem as 100 and normalizing the carbapenems to imipenem.

Testing Results

The claimed compounds exhibit activity against a spectrum of Gram-positive and Gram-negative bacteria, including those producing specific β-lactamases. Potent activity comparable to that noted with imipenem, biapenem and meropenem is noted with Examples 18, 21, 46, 47, 48, 49, 52, 54A, 64, 65, 79, 114, 120, 129, 162, 192 and 193 against strains of *E. coli*, Klebsiella, Enterobacter and most other Gram-negative bacteria. Examples 46, 47, 48, 49, 52, 54A, 64, 65, 114, 120, 129, 136, 161, 162, 174, 192 and 193 are also active against *Pseudomonas aeruginosa* but at a higher concentration than imipenem, biapenem and meropenem. None of the carbapenems is active against the *Xanthomonas maltophilia* isolate tested. All of these compounds exhibit potent activity against the methicillin-sensitive *Staphlococcus aureus* isolates and the *Enterococcus faecalis* isolate at a comparable concentration as the reference carbapenems. None of the carbapenems exhibited good activity against the methicillin-resistant *S. aureus* (MRSA) or the *Enterococcus faecium* isolates. Examples 46, 47, 48, 49, 64, 65, 129, 136 and 161 are a mixture of two diastereoisomers. Example 114, Example 120 and Example 162, are optically pure compounds and have similar potency as their corresponding mixtures of diastereoisomers. Example 46 and Example 64, against all of the organisms.

Example 51A, Example 52 and Example 54A, acyl derivatives of amino acids of Example 46, also exhibit potent activity against both Gram-negative and Gram-positive bacteria but slightly less than Example 46, especially against *Pseudomonas aeruginosa*. Example 51B and Example 54B, the di-amino acid analogues are less active than the corresponding mono-amino acid analogues against the organisms tested.

Example 59, which contains a methyl group in place of the aminomethyl group of Example 46, while active against a variety of organisms, demonstrates no activity against *Pseudomonas aeruginosa* and exhibits less activity against Gram-negative and Gram-positive bacteria than Example 46.

Example 174, the tetrahydrothiophene analogue, is slightly less active than the corresponding tetrahydrofuran analogue, Example 46.

Example 186, an isobutyl carbonate prodrug of Example 46, exhibited very poor activity on its own. However, when incubated for 1 hour in the presence of mouse serum the antibacterial activity is partially restored to that of Example 46. A similar response is obtained with Example 195, the isobutyl carbonate prodrug of Example 64, after incubation in the presence of mouse serum.

Example 160, exhibits activity against the spectrum of organisms tested but is less active than Example 46.

Example 79 and Example 18, containing a cis configuration, and Example 21, containing a trans configuration, have similar potent activity against the majority of the isolates tested. These compounds are all less active against *Pseudomonas aeruginosa* than Example 64.

Example 26, Example 42, Example 69, Example 34 and Example 38 are less active against the Gram-negative bacteria but have similar activity as the reference carbapenems against the Gram-positive bacteria.

Example 144, Example 148A and Example 148B are active against Gram-positive and most Gram-negative bacteria, except *P. aeruginosa* and *X. maltoihilia*. Example 144 is less active than Example 148A and Example 148B against the Gram-negative bacteria tested, but have comparable activity against the Gram-positive bacteria.

Example 87, a triazine thio analogue, is slightly less active than Example 46 and is especially poor against *P. aeruginosa*.

Comparable activity against Gram-negative and Gram-positive bacteria is obtained with optically pure positional isomers depicted by Example 192 (1,2-positional isomer) and Example 120 (1,3-positional isomer). The substitution of a formamidine moiety—Example 193, in place of the amino group—Example 192, results in a slight decrease in activity against some organisms.

Example 46, Example 114, Example 120 and Example 162 have a similar binding profile to the essential penicillin binding proteins (PBPs) of *E. coli* and *S. aureus* (Table 3 and 4). *E. coli* PBP 2, as noted with the reference carbapenems, is the primary target for these compounds. Tight binding to PBP 4 is also observed for all of the carbapenems. In *S. aureus*, PBP 1 is the major target for Example 46, Example 114, Example 120, Example 162 and meropenem. Imipenem and biapenem bind tighter to the other PBPs as well. However, all of the compounds have very low MICs for this strain.

Example 46 and Example 64 exhibit increased stability to mammalian dehydropeptidase than imipenem and meropenem. (Table 5).

The potent in vitro antibacterial activity of Example 46, 64 and 192 is also demonstrated by their in vivo efficacy against an acute lethal infection of *S. aureus* Smith and *E. coli* 311 in mice when dosed by the subcutaneous route (Table 2). These compounds show good efficacy relative to the reference carbapenems: meropenem, biapenem and imipenem. These compound also demonstrate good oral activity against both organism: *S. aureus* Smith and *E. coli* 311. L-amino acid derivatives of Example 192 as examplified by Example 261, 391, 265, 266, 257, 344 and 345 demonstrate substantially improved oral activity based on their ED$_{50}$'s and comparative SOD/SSC ratios (SOD=single oral dose; SSC=single subcutaneous dose). In particular, the improved oral activity is seen in Examples 261, 344 and 345.

TABLE 1

| | Antibacterial Activity, MIC (μg/ml) | | | | | | |
|---|---|---|---|---|---|---|---|
| | Controls | | | | Example No. | | |
| ORGANISM | Piperacillin | Imipenem | Biapenem | Meropenem | 18 | 21 | 26 |
| E. coli (25922) | 2.00 | <=0.06 | <=0.06 | <=0.06 | <=0.06 | <=0.06 | 2.00 |
| E. coli (IVES 912) | >128.00 | <=0.06 | <=0.06 | <=0.06 | <=0.06 | <=0.06 | 2.00 |
| E. coli (300) | <=0.06 | <=0.06 | <=0.06 | <=0.06 | <=0.06 | <=0.06 | |
| E. coli (35218) | >128.00 | <=0.06 | <=0.06 | <=0.06 | <=0.06 | <=0.06 | 0.50 |
| E. coli (MEDEIROS 4) | >128.00 | <=0.06 | <=0.06 | <=0.06 | <=0.06 | <=0.06 | 4.00 |
| E. coli (MEDEIROS 14) | 64.00 | <=0.06 | <=0.06 | <=0.06 | <=0.06 | <=0.06 | 8.00 |
| E. coli (BUSH 91-39) | >128.00 | <=0.06 | <=0.06 | <=0.06 | 0.12 | <=0.06 | 8.00 |
| K. pneumo (IVES 688) | 128.00 | 12.00 | 0.12 | <=0.06 | <=0.06 | <=0.06 | 8.00 |
| K. oxytoca (CUHN 88-11) | >128.00 | 12.00 | <=0.06 | <0.06 | <=0.06 | <=0.06 | 8.00 |
| E. aerogenes (IVES 1500) | >128.00 | 12.00 | <=0.06 | <=0.06 | 0.25 | 0.12 | 9.00 |
| E. cloacae (Richmond 1) | 128.00 | <=0.06 | <=0.06 | <=0.06 | 0.50 | 0.50 | 1.00 |
| C. diversus (IVES 1680) | 16.00 | <=0.06 | <=0.06 | <=0.06 | <=0.06 | <=0.06 | 8.00 |
| C. Freundii (IVES 953) | >128.00 | 0.25 | <=0.06 | <=0.06 | 1.00 | 1.00 | 16.00 |
| S. marcescens (IVES 3062) | 32.00 | 0.25 | 0.50 | <=0.06 | 0.25 | 0.12 | 16.00 |
| M. morganii (IVES 335) | >128.00 | 1.00 | 0.50 | <=0.06 | 0.25 | 0.12 | 2.00 |
| Salmonella sp. (CHBM 88-58) | >128.00 | <=0.06 | <=0.06 | <=0.06 | | | 2.00 |
| P. stuartii (CUHN 88-7) | >128.00 | 0.50 | 0.50 | <=0.06 | 0.50 | 0.25 | 8.00 |
| P. aerug. (27853) | 2.00 | 1.00 | 0.50 | 0.25 | 128.00 | 64.00 | >128.00 |
| P. aerug. (IVES 5250) | 2.00 | 0.25 | <=0.06 | 0.12 | 128.00 | 64.00 | >128.00 |
| P. aerug. (MEDEIROS-7) | 128.00 | 0.50 | 0.25 | 0.50 | 128.00 | 128.00 | >128.00 |
| P. aerug. (BUSH 91-73) | 4.00 | 16.00 | 8.00 | 4.00 | 128.00 | 128.00 | >128.00 |
| X. malto. (NEMC 87-210) | >128.00 | >128.00 | >128.00 | >128.00 | >128.00 | >128.00 | 128.00 |
| A. calco. (BMMR 88-2) | 128.00 | 0.25 | 0.25 | 0.50 | 4.00 | 4.00 | 8.00 |
| S. aureus (29213) | 0.25 | <=0.06 | <=0.06 | <=0.06 | <=0.06 | <=0.06 | <0.06 |
| S. aureus (25923) | 0.25 | <=0.06 | <=0.06 | <=0.06 | <=0.06 | <=0.06 | <0.06 |
| S. aureus (IVES 1097) | 2.00 | <=0.06 | <=0.06 | 0.12 | 0.12 | 0.12 | <0.06 |
| S. aureus (IVES 1545) | 64.00 | <=0.06 | <=0.06 | 0.12 | 0.25 | 0.25 | <0.06 |
| S. aureus (IVES 2837) | >128.00 | 1.00 | 4.00 | 8.00 | 32.00 | 16.00 | 4.00 |
| CNS (IVES 191) | 0.50 | <=0.06 | <=0.06 | 0.12 | 0.25 | 0.25 | <0.06 |
| CNS (IVES 1754) | >128.00 | 64.00 | 64.00 | 64.00 | >128.00 | 128.00 | 64.00 |
| E. faecalis (CHBM 88-60) | 4.00 | 0.50 | 2.00 | 4.00 | 4.00 | 4.00 | 2.00 |
| E. faecium (DLMC 89-1) | >128.00 | 128.00 | >128.00 | >128.00 | >128.00 | >128.00 | 128.00 |

| | Example No. | | | | | | |
|---|---|---|---|---|---|---|---|
| ORGANISM | 34 | 38 | 42 | 46 | 47 | 48 | 49 |
| E. coli (25922) | 2.00 | 4.00 | 8.00 | <=0.06 | <=0.06 | <=0.06 | <=0.06 |
| E. coli (IVES 912) | 2.00 | 2.00 | 4.00 | <=0.06 | <=0.06 | <=0.06 | <=0.06 |
| E. coli (300) | <0.06 | <0.06 | <0.06 | <=0.06 | <=0.06 | 0.12 | 0.12 |
| E. coli (35218) | 4.00 | 4.00 | 2.00 | <=0.06 | <=0.06 | <=0.06 | <=0.06 |
| E. coli (MEDEIROS 4) | 4.00 | 4.00 | 16.00 | <=0.06 | <=0.06 | <=0.06 | <=0.06 |
| E. coli (MEDEIROS 14) | 4.00 | 4.00 | 16.00 | <=0.06 | <=0.06 | <=0.06 | <=0.06 |
| E. coli (BUSH 91-39) | 4.00 | 4.00 | 16.00 | <=0.06 | <=0.06 | <=0.06 | <=0.06 |
| K. pneumo (IVES 688) | 4.00 | 4.00 | 32.00 | <=0.06 | <=0.06 | 0.12 | <=0.06 |
| K. oxytoca (CUHN 88-11) | 4.00 | 8.00 | 16.00 | <0.06 | <=0.06 | 0.12 | <=0.06 |
| E. aerogenes (IVES 1500) | 4.00 | 8.00 | 8.00 | <=0.06 | <=0.06 | <=0.06 | <=0.06 |
| E. cloacae (Richmond 1) | 2.00 | 1.00 | 2.00 | <=0.06 | <=0.06 | <=0.06 | <=0.06 |
| C. diversus (IVES 1680) | 4.00 | 8.00 | 32.00 | <=0.06 | <=0.06 | <=0.06 | <=0.06 |
| C. Freundii (IVES 953) | 8.00 | 16.00 | 32.00 | <=0.06 | <=0.06 | 0.12 | 0.12 |
| S. marcescens (IVES 3062) | 16.00 | 16.00 | 16.00 | 0.12 | 0.12 | 0.12 | 0.25 |
| M. morganii (IVES 335) | 2.00 | 2.00 | 4.00 | 0.25 | 0.50 | 0.05 | 0.50 |
| Salmonella sp. (CHBM 88-58) | 2.00 | 2.00 | 4.00 | <=0.06 | <=0.06 | <=0.06 | <=0.06 |
| P. stuartii (CUHN 88-7) | 8.00 | 8.00 | 16.00 | 0.50 | 0.50 | 0.25 | 0.50 |
| P. aerug. (27853) | >128.00 | >127.00 | >128.00 | 4.00 | 8.00 | 8.00 | 16.00 |
| P. aerug. (IVES 5250) | >128.00 | 128.00 | 128.00 | 4.00 | 2.00 | 4.00 | 8.00 |
| P. aerug. (MEDEIROS-7) | <128.00 | <128.00 | <128.00 | 4.00 | 8.00 | 8.00 | 8.00 |
| P. aerug. (BUSH 91-73) | <128.00 | 128.00 | 128.00 | 8.00 | 16.00 | 16.00 | 32.00 |
| X. malto. (NEMC 87-210) | >128.00 | 128.00 | 128.00 | >128.00 | >128.00 | >128.00 | >128.00 |
| A. calco. (BMMR 88-2) | 16.00 | 4.00 | 8.00 | 1.00 | 2.00 | 2.00 | 2.00 |
| S. aureus (29213) | <0.06 | | <0.06 | <=0.06 | <=0.06 | <=0.06 | <=0.06 |
| S. aureus (25923) | <0.06 | <0.06 | <0.06 | <=0.06 | <=0.06 | <=0.06 | <=0.06 |
| S. aureus (IVES 1097) | <0.06 | <0.06 | <0.06 | <=0.06 | 0.12 | 0.12 | 0.12 |
| S. aureus (IVES 1545) | 0.25 | <0.06 | <0.06 | 0.12 | 0.12 | 0.12 | 0.25 |
| S. aureus (IVES 2837) | 16.00 | 1.00 | 4.00 | 8.00 | 8.00 | 8.00 | 16.00 |
| CNS (IVES 191) | <0.06 | <0.06 | <0.06 | <=0.06 | <=0.06 | <=0.06 | 0.12 |
| CNS (IVES 1754) | >128.00 | 32.00 | 64.00 | 64.00 | 64.00 | 64.00 | 64.00 |
| E. faecalis (CHBM 88-60) | 4.00 | 0.50 | 2.00 | 2.00 | 2.00 | 4.00 | 4.00 |
| E. faecium (DLMC 89-1) | >128.00 | 64.00 | 128.00 | 128.00 | 128.00 | 128.00 | >128.00 |

TABLE 1-continued

Antibacterial Activity, MIC (µg/ml)

| ORGANISM | Example No. | | | | | | |
|---|---|---|---|---|---|---|---|
| | 51A | 51B | 52 | 54A | 54B | 59 | 64 |
| E. coli (25922) | <0.06 | 0.50 | <0.06 | <0.06 | <0.06 | 0.12 | <=0.06 |
| E. coli (IVES 912) | <0.06 | 1.00 | <0.06 | <0.06 | <0.06 | 0.12 | <=0.06 |
| E. coli (300) | <0.06 | 2.00 | <0.06 | <0.06 | <0.06 | <=6.00 | <=0.06 |
| E. coli (35218) | <0.06 | 1.00 | <0.06 | <0.06 | <0.06 | <=0.06 | <=0.06 |
| E. coli (MEDEIROS 4) | 0.12 | 4.00 | <0.06 | <0.06 | 0.12 | 0.25 | <=0.06 |
| E. coli (MEDEIROS 14) | 0.25 | 4.00 | <0.06 | <0.06 | 0.25 | 0.50 | <=0.06 |
| E. coli (BUSH 91-39) | 0.50 | 8.00 | <0.06 | <0.06 | 0.25 | 0.50 | <=0.06 |
| K. pneumo (IVES 688) | <0.06 | 2.00 | <0.06 | <0.06 | 0.12 | 0.25 | <=0.06 |
| K oxytoca (CUHN 88-11) | 0.25 | 8.00 | <0.06 | 0.12 | 0.25 | 0.50 | <=0.06 |
| E. aerogenes (IVES 1500) | 1.00 | 16.00 | <0.06 | 0.12 | 1.00 | 0.50 | <=0.06 |
| E. cloacae (Richmond 1) | 0.50 | 8.00 | <0.06 | <0.06 | 1.00 | 0.50 | <=0.06 |
| C. diversus (IVES 1680) | <0.06 | 1.00 | <0.06 | <0.06 | <0.06 | 0.25 | <=0.06 |
| C. Freundii (IVES 953) | 2.00 | 32.00 | 0.25 | 0.25 | 4.00 | 4.00 | <=0.06 |
| S. marcescens (IVES 3062) | 0.50 | 16.00 | 0.12 | 0.25 | 1.00 | 2.00 | 0.25 |
| M. morganii (IVES 335) | 0.50 | 16.00 | 0.25 | 0.25 | 1.00 | 0.25 | 0.50 |
| Salmonella sp. (CHBM 88-58) | <0.06 | 1.00 | <0.06 | <0.06 | <0.06 | <=0.06 | <=0.06 |
| P stuartii (CUHN 88-7) | 1.00 | 16.00 | 0.25 | 0.25 | 1.00 | 1.00 | 0.25 |
| P. aerug. (27853) | >128.00 | >128.00 | 32.00 | 16.00 | >128.00 | 128.00 | 8.00 |
| P. aerug. (IVES 5250) | >128.00 | >128.00 | 32.00 | 16.00 | >128.00 | 128.00 | 2.00 |
| P. aerug. (MEDEIROS-7) | 128.00 | >128.00 | 32.00 | 32.00 | >128.00 | 128.00 | 2.00 |
| P. aerug. (BUSH 91-73) | >128.00 | >128.00 | 32.00 | 32.00 | >128.00 | 128.00 | 16.00 |
| X. malto. (NEMC 87-210) | >128.00 | >128.00 | >128.00 | >128.00 | >128.00 | >128.00 | >128.00 |
| A. calco. (BMMR 88-2) | 16.00 | >128.00 | 2.00 | 2.00 | 16.00 | 16.00 | 2.00 |
| S. aureus (29213) | 0.12 | 2.00 | <0.06 | <0.06 | <0.06 | <=0.06 | <=0.06 |
| S. aureus (25923) | 0.50 | 4.00 | <0.06 | <0.06 | 0.25 | 0.12 | <=0.06 |
| S. aureus (IVES 1097) | 1.00 | 8.00 | 0.12 | 0.12 | 0.50 | 0.25 | <=0.06 |
| S. aureus (IVES 1545) | 1.00 | 8.00 | 0.25 | 0.25 | 1.00 | 1.00 | 0.12 |
| S. aureus (IVES 2837) | 128.00 | >128.00 | 16.00 | 16.00 | 64.00 | 16.00 | 4.00 |
| CNS (IVES 191) | 2.00 | 32.00 | 0.12 | 0.12 | 1.00 | 0.25 | <=0.06 |
| CNS (IVES 1754) | >128.00 | >128.00 | 64.00 | 64.00 | >128.00 | 128.00 | 64.00 |
| E. faecalis (CHBM 88-60) | 8.00 | >128.00 | 4.00 | 2.00 | 16.00 | 8.00 | 2.00 |
| E. faecium (DLMC 89-1) | >128.00 | >128.00 | >128.00 | >128.00 | >128.00 | >128.00 | 128.00 |

| ORGANISM | Example No. | | | | | | |
|---|---|---|---|---|---|---|---|
| | 65 | 69 | 79 | 87 | 114 | 120 | 129 |
| E. coli (25922) | <=0.06 | 32.00 | <=0.06 | <0.06 | <=0.06 | <=0.06 | <=0.06 |
| E. coli (IVES 912) | <=0.06 | 16.00 | <=0.06 | <0.06 | <=0.06 | <=0.06 | <=0.06 |
| E. coli (300) | 0.12 | <0.06 | <=0.06 | <0.06 | <=0.06 | <=0.06 | <=0.06 |
| E. coli (35218) | <=0.06 | 4.00 | <=0.06 | <0.06 | <=0.06 | <=0.06 | <=0.06 |
| E. coli (MEDEIROS 4) | <=0.06 | 32.00 | <=0.06 | 0.12 | <=0.06 | <=0.06 | <=0.06 |
| E. coli MEDEIROS 14) | <=0.06 | 32.00 | <=0.06 | 0.25 | <=0.06 | <=0.06 | <=0.06 |
| E. coli (BUSH 91-39) | <=0.06 | 64.00 | <=0.06 | 0.25 | <=0.06 | <=0.06 | <=0.06 |
| K. pneumo (IVES 688) | 0.12 | 64.00 | <=0.06 | 0.12 | <=0.06 | <=0.06 | <=0.06 |
| K oxytoca (CUHN 88-11) | 0.12 | 64.00 | <=0.06 | 0.12 | <=0.06 | <=0.06 | <=0.06 |
| E. aerogenes (IVES 1500) | <=0.06 | 32.00 | <=0.06 | 1.00 | <=0.06 | <=0.06 | <=0.06 |
| E. cloacae (Richmond 1) | <=0.06 | 8.00 | <=0.06 | 0.12 | <=0.06 | <=0.06 | <=0.06 |
| C. diversus (IVES 1680) | <=0.06 | 64.00 | <=0.06 | <0.06 | <=0.06 | <=0.06 | <=0.06 |
| C. Freundii (IVES 953) | 0.12 | 128.00 | 0.25 | 5.00 | <=0.06 | 0.12 | <=0.06 |
| S. marcescens (IVES 3062) | 0.50 | 64.00 | 0.12 | 1.00 | <=0.06 | 0.12 | 0.25 |
| M. morganii (IVES 335) | 0.50 | 32.00 | <=0.06 | 0.50 | 0.25 | 0.50 | 1.00 |
| Salmonella sp. (CHBM 88-58) | <=0.06 | 32.00 | | <0.06 | <=0.06 | <=0.06 | <=0.06 |
| P stuartii (CUHN 88-7) | 0.50 | 64.00 | <=0.06 | 0.12 | 0.25 | 0.25 | 0.25 |
| P. aerug. (27853) | 16.00 | >128.00 | 64.00 | >128.00 | 2.00 | 16.00 | 16.00 |
| P. aerug. (IVES 5250) | 16.00 | >128.00 | 64.00 | >128.00 | 2.00 | 8.00 | 8.00 |
| P. aerug. (MEDEIROS-7) | 16.00 | >128.00 | 64.00 | >128.00 | 4.00 | 8.00 | 8.00 |
| P. aerug. (BUSH 91-73) | 32.00 | >128.00 | 64.00 | >128.00 | 8.00 | 32.00 | 32.00 |
| X. malto. (NEMC 87-210) | >128.00 | 128.00 | >128.00 | >128.00 | >128.00 | >128.00 | >128.00 |
| A. calco. (BMMR 88-2) | 4.00 | 16.00 | 2.00 | 16.00 | 1.00 | 2.00 | 2.00 |
| S. aureus (29213) | <=0.06 | <0.06 | <=0.06 | <0.06 | <=0.06 | <=0.06 | <=0.06 |
| S. aureus (25923) | <=0.06 | <0.06 | <=0.06 | 0.12 | <=0.06 | <=0.06 | <=0.06 |
| S. aureus (IVES 1097) | <=0.06 | <0.06 | 0.12 | 0.25 | <=0.06 | <=0.06 | <=0.06 |
| S. aureus (IVES 1545) | 0.12 | <0.06 | 0.25 | 0.50 | 0.12 | 0.12 | <=0.06 |
| S. aureus (IVES 2837) | 4.00 | 2.00 | >128.00 | 32.00 | 8.00 | 8.00 | 4.00 |
| CNS (IVES 191) | <=0.06 | <0.06 | 0.25 | 0.50 | <=0.06 | <=0.06 | <=0.06 |
| CNS (IVES 1754) | 32.00 | 128.00 | 64.00 | >128.00 | 64.00 | 64.00 | 64.00 |
| E. faecalis (CHBM 88-60) | 2.00 | 2.00 | >4.00 | 8.00 | 2.00 | 4.00 | 4.00 |
| E. faecium (DLMC 89-1) | 128.00 | 128.00 | >128.00 | >128.00 | >128.00 | >128.00 | 128.00 |

TABLE 1-continued

Antibacterial Activity, MIC (μg/ml)

| | Example No. | | | | | | |
|---|---|---|---|---|---|---|---|
| ORGANISM | 136 | 141 | 148A | 148B | 160 | 161 | 162 |
| E. coli (25922) | 0.12 | 2.00 | <=0.06 | <0.06 | 0.25 | 0.25 | <=0.06 |
| E. coli (IVES 912) | <=0.06 | 1.00 | <=0.06 | <0.06 | 0.25 | 0.12 | <=0.06 |
| E. coli (300) | 0.25 | <0.06 | <=0.06 | <0.06 | 0.50 | 0.50 | <=0.06 |
| E. coli (35218) | <=0.06 | 0.50 | 0.12 | <0.06 | 0.24 | 0.12 | <=0.06 |
| E. coli (MEDEIROS 4) | <=0.06 | 2.00 | 0.25 | 0.12 | 0.50 | 0.25 | <=0.06 |
| E. coli (MEDEIROS 14) | 0.12 | 2.00 | 0.25 | 0.25 | 0.50 | 0.25 | <=0.06 |
| E. coli (BUSH 91-39) | 0.12 | 2.00 | 0.12 | 0.25 | 0.50 | 0.25 | <=0.06 |
| K. pneumo (IVES 688) | 0.12 | 2.00 | 0.12 | 0.12 | 0.50 | 0.25 | <=0.06 |
| K oxytoca (CUHN 88-11) | 0.25 | 2.00 | 0.50 | 0.12 | 1.00 | 0.25 | <=0.06 |
| E. aerogenes (IVES 1500) | 0.12 | 2.00 | 1.00 | 0.50 | 0.50 | 0.25 | <=0.06 |
| E. cloacae (Richmond 1) | 0.12 | 4.00 | <=0.06 | 1.00 | 0.50 | 0.12 | <=0.06 |
| C. diversus (IVES 1680) | <=0.06 | 1.00 | <=0.06 | 0.12 | 0.12 | <=0.06 | <=0.06 |
| C. Freundii (IVES 953) | 0.25 | 8.00 | 1.00 | 1.00 | 2.00 | 0.50 | 0.12 |
| S. marcescens (IVES 3062) | 0.25 | 4.00 | 0.50 | 0.50 | 1.00 | 1.00 | 0.12 |
| M. morganii (IVES 335) | 1.00 | 4.00 | 1.00 | 0.50 | 2.00 | 1.00 | 0.50 |
| Salmonella sp. (CHBM 88-58) | <=0.06 | 2.00 | <=0.06 | <0.06 | 0.50 | 0.12 | <=0.06 |
| P stuartii (CUHN 88-7) | 1.00 | 8.00 | 0.50 | 0.50 | 2.00 | 2.00 | 0.25 |
| P. aerug. (27853) | 16.00 | 128.00 | 64.00 | 64.00 | 128.00 | 32.00 | 16.00 |
| P. aerug. (IVES 5250) | 8.00 | 128.00 | 128.00 | 128.00 | 64.00 | 16.00 | 8.00 |
| P. aerug. (MEDEIROS-7) | 16.00 | >128.00 | 128.00 | 128.00 | 64.00 | 16.00 | 8.00 |
| P. aerug. (BUSH 91-73) | | 128.00 | 128.00 | 128.00 | >128.00 | 64.00 | 32.00 |
| X. malto. (NEMC 87-210) | >128.00 | >128.00 | >128.00 | >128.00 | >128.00 | >128.00 | >128.00 |
| A. calco. (BMMR 88-2) | 4.00 | 32.00 | 4.00 | 8.00 | 32.00 | 8.00 | 2.00 |
| S. aureus (29213) | <=0.06 | <=0.06 | <=0.06 | <=0.06 | 0.50 | 0.12 | <=0.06 |
| S. aureus (25923) | 0.12 | <=0.06 | <=0.06 | <=0.06 | 1.00 | 0.12 | <=0.06 |
| S. aureus (IVES 1097) | 0.25 | 0.25 | 0.12 | 0.12 | 2.00 | 0.50 | <=0.06 |
| S. aureus (IVES 1545) | 0.50 | 0.25 | 0.25 | 0.25 | 2.00 | 1.00 | 0.12 |
| S. aureus (IVES 2837) | 8.00 | 16.00 | 32.00 | 32.00 | 64.00 | 32.00 | 8.00 |
| CNS (IVES 191) | 0.25 | 0.25 | 0.25 | 0.25 | 2.00 | 0.50 | <=0.06 |
| CNS (IVES 1754) | 128.00 | <=0.06 | 128.00 | 128.00 | >128.00 | >128.00 | 64.00 |
| E. faecalis (CHBM 88-60) | 8.00 | 4.00 | 4.00 | 8.00 | 32.00 | 8.00 | 2.00 |
| E. faecium (DLMC 89-1) | >128.00 | >128.00 | >128.00 | >128.00 | >128.00 | >128.00 | >128.00 |

| | Example No. | | | | | | |
|---|---|---|---|---|---|---|---|
| ORGANISM | 174 | 186 | 186* | 192 | 193 | 195 | 195* |
| E. coli (25922) | 0.12 | 32.00 | 0.25 | <=0.06 | <=0.06 | 64.00 | 0.50 |
| E. coli (IVES 912) | 0.12 | 32.00 | 0.12 | <=0.06 | <=0.06 | 64.00 | 0.50 |
| E. coli (300) | 0.25 | 4.00 | 0.50 | <=0.06 | 0.12 | 2.00 | 1.00 |
| E. coli (35218) | 0.25 | 32.00 | 0.25 | <=0.06 | <=0.06 | 64.00 | 0.50 |
| E. coli (MEDEIROS 4) | 0.12 | 32.00 | 0.25 | <=0.06 | <=0.06 | 128.00 | 0.50 |
| E. coli MEDEIROS 14) | 0.12 | 64.00 | 0.25 | <=0.06 | <=0.06 | 128.00 | 0.50 |
| E. coli (BUSH 91-39) | 0.25 | 64.00 | 0.25 | <=0.06 | <=0.06 | 128.00 | 1.00 |
| K. pneumo (IVES 688) | 0.25 | 64.00 | 1.00 | <=0.06 | <=0.06 | 128.00 | 2.00 |
| K oxytoca (CUHN 88-11) | 0.50 | 128.00 | 1.00 | <=0.06 | 0.12 | 128.00 | 1.00 |
| E. aerogenes (IVES 1500) | 0.25 | 64.00 | 0.50 | <=0.06 | <=0.06 | >128.00 | 1.00 |
| E. cloacae (Richmond 1) | 0.12 | 32.00 | 0.12 | <=0.06 | <=0.06 | 64.00 | 1.00 |
| C. diversus (IVES 1680) | 0.12 | 32.00 | 0.12 | | | 64.00 | 0.25 |
| C. Freundii (IVES 953) | 0.25 | 64.00 | 0.50 | 0.12 | 0.50 | >128.00 | 2.00 |
| S. marcescens (IVES 3062) | 0.50 | 128.00 | 2.00 | 0.50 | 1.00 | >128.00 | 4.00 |
| M. morganii (IVES 335) | 2.00 | 128.00 | 4.00 | 0.50 | 1.00 | >128.00 | 8.00 |
| Salmonella sp. (CHBM 88-58) | 0.25 | 32.00 | 0.50 | <=0.06 | <=0.06 | 128.00 | 1.00 |
| P stuartii (CUHN 88-7) | 1.00 | 128.00 | 2.00 | 0.50 | 1.00 | >128.00 | 4.00 |
| P. aerug. (27853) | 16.00 | >128.00 | 32.00 | 8.00 | 16.00 | >128.00 | 128.00 |
| P. aerug. (IVES 5250) | 8.00 | >128.00 | 32.00 | 4.00 | 8.00 | >128.00 | 128.00 |
| P. aerug. (MEDEIROS-7) | 16.00 | >128.00 | 32.00 | 8.00 | 16.00 | >128.00 | 128.00 |
| P. aerug. (BUSH 91-73) | 32.00 | >128.00 | 64.00 | 16.00 | 32.00 | >128.00 | 128.00 |
| X. malto. (NEMC 87-210) | >128.00 | >128.00 | >128.00 | >128.00 | >128.00 | >128.00 | >128.00 |
| A. calco. (BMMR 88-2) | 4.00 | >128.00 | 8.00 | 2.00 | 8.00 | >128.00 | 32.00 |
| S. aureus (29213) | <=0.06 | 0.50 | 0.12 | <=0.06 | <=0.06 | 0.25 | 0.12 |
| S. aureus (25923) | <=0.06 | 2.00 | 0.25 | | | 0.50 | 0.25 |
| S. aureus (IVES 1097) | 0.12 | 4.00 | 1.00 | <=0.06 | <=0.06 | 4.00 | 1.00 |
| S. aureus (IVES 1545) | 0.25 | 4.00 | 1.00 | 0.12 | 0.25 | 4.00 | 1.00 |
| S. aureus (IVES 2837) | 16.00 | 128.00 | 32.00 | 2.00 | 4.00 | 128.00 | 32.00 |
| CNS (IVES 191) | 0.25 | 2.00 | 0.50 | <=0.06 | 0.12 | 1.00 | 0.50 |
| CNS (IVES 1754) | 64.00 | 128.00 | 128.00 | 64.00 | 128.00 | 128.00 | 128.00 |
| E. faecalis (CHBM 88-60) | 4.00 | 64.00 | 32.00 | 0.50 | 2.00 | 64.00 | 64.00 |
| E. faecium (DLMC 89-1) | >128.00 | >128.00 | >128.00 | 64.00 | 128.00 | >128.00 | >128.00 |

*Preincubated for one hour in the presence of serum.

TABLE 2

In Vivo Efficacy of Carbapenems in Mice When Dosed by Oral and Subcutaneous Routes

| | S. aureus Smith $ED_{50}$ (mg/kg) | | | E. coli 311 $ED_{50}$ (mg/kg) | | |
|---|---|---|---|---|---|---|
| Compound | SOD | SSC | SOD/SSC | SOD | SSC | SOD/SSC |
| Example 46 | 1.8 | 0.11 | 16 | 1.7 | 0.68 | 2.5 |
| Example 64 | 1.3 | 0.05 | 26 | 1.1 | 0.42 | 2.6 |
| Example 192 | 0.85 | 0.05 | 17 | 3.8 | 0.34 | 11 |
| Example 261 | 0.21 | 0.06 | 3.5 | 0.95 | 0.54 | 1.8 |
| Example 391 | 0.30 | 0.06 | 5 | 1.10 | 0.74 | 1.4 |
| Example 265(A) | 0.40 | 0.08 | 5 | 1.59 | 0.67 | 2.4 |
| Example 265(B) | 0.61 | 0.10 | 6 | 5.10 | 0.86 | 5.9 |
| Example 266(A) | 0.67 | 0.08 | 8.4 | — | — | — |
| Example 266(B) | 1.00 | 0.11 | 9.1 | — | — | — |
| Example 257 | 0.48 | 0.18 | 3.3 | 1.6 | 0.66 | 2.4 |
| Example 344 | 0.25 | 0.19 | 1.3 | 0.79 | 0.80 | 0.99 |
| Example 345 | 0.28 | 0.30 | 0.93 | 0.77 | 1.4 | 0.55 |
| Biapenem | 1.4 | 0.04 | 35 | 8.6 | 0.58 | 15 |
| Primaxin | 3.30 | 0.03 | 110 | ND | 1.1 | |
| Meropenem | 19.90 | 0.52 | 38.3 | ND | 0.30 | |

TABLE 3

Binding to Penicillin Binding Proteins of
E. coli ATCC 25922
Approximate IC50 (ug/ml)

| | Controls | | Example No. | | | |
|---|---|---|---|---|---|---|
| PBP | IMIPENEM | BIAPENEM | 46 | 114 | 120 | 162 |
| 1a/1b | <0.1/0.47 | <0.1/0.55 | >1 | >1 | >1 | >1 |
| 2 | <0.1 | ≦0.1 | 0.04 | 0.05 | 0.05 | 0.05 |
| 3 | 1.8 | 0.32 | 0.6 | 3 | 2 | 2 |
| 4 | <0.1 | 0.03 | 0.05 | 0.09 | 0.09 | 0.08 |
| 5/6 | >100 | >100 | >100 | >100 | >100 | >100 |
| MIC E. coli | ≦0.06 | ≦0.06 | ≦0.06 | ≦0.06 | ≦0.06 | ≦0.06 |

TABLE 4

Binding to Penicillin Binding Proteins
of S. aureus ATCC 29213
Approximate IC50 (ug/ml)

| | Controls | | | Example No. | | | |
|---|---|---|---|---|---|---|---|
| PBP | IMIPENEM | MEROPENEM | BIAPENEM | 46 | 114 | 120 | 162 |
| 1 | 0.01 | 0.04 | 0.01 | 0.03 | 0.03 | 0.06 | <0.01 |
| 2 | 0.05 | 0.18 | 0.02 | 0.58 | 0.55 | 0.35 | 0.50 |
| 3 | 0.1 | 0.35 | 0.02 | 1.2 | 0.80 | 0.65 | 0.55 |
| 4 | ND* | ND | ND | 0.56 | 0.78 | <1 | <0.01 |
| MIC | <0.06 | <0.06 | <0.06 | <0.06 | <0.06 | <0.06 | <0.06 |

*PBP 4 not detected in these assays.

TABLE 5

Hydrolysis of Carbapenems
by Dehydropeptidases

| Antibiotic | Relative Hydrolysis Rates | |
|---|---|---|
| (50 mg/ml) | Mouse | Swine |
| Imipenem | 100 | 100 |
| Meropenem | 320 ± 5 | 28 ± 6 |
| Biapenem | <1 | <1 |
| Example 46 | 107 | 19 |
| Example 64 | 30 | 10 |

When the compounds are employed as antibacterials, they can be combined with one or more pharmaceutically acceptable carriers, for example, solvents, diluents and the like, and may be administered orally in such forms as tablets, capsules, dispersible powders, granules, or suspensions containing, for example, from about 0.05 to 5% of suspending agent, syrups containing, for example, from about 10 to 50% of sugar, and elixirs containing for example, from about 20 to 50% ethanol and the like, or parenterally in the form of sterile injectable solutions or suspensions containing from about 0.05 to 5% suspending agent in an isotonic medium. Such pharmaceutical preparations may contain, for example, from about 25 to about 90% of the active ingredient in combination with the carrier, more usually between about 5% and 60% by weight.

An effective amount of compound from 2.0 mg/kg of body weight to 100.0 mg/kg of body weight should be administered one to five times per day via any typical route of administration including but not limited to oral, parenteral (including subcutaneous, intravenous, intramuscular, intrasternal injection or infusion techniques), topical or rectal, in dosage unit formulations containing conventional non-toxic pharmaceutically acceptable carriers, adjuvants and vehicles. It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition of the host undergoing therapy.

These active compounds may be administered orally as well as by intravenous, intramuscular, or subcutaneous routes. Solid carriers include starch, lactose, dicalcium phosphate, microcrystalline cellulose, sucrose and kaolin, while liquid carriers include sterile water, polyethylene glycols, non-ionic surfactants and edible oils such as corn, peanut and sesame oils, as are appropriate to the nature of the active ingredient and the particular form of administration desired. Adjuvants customarily employed in the preparation of pharmaceutical compositions may be advantageously included, such as flavoring agents, coloring agents, preserving agents, and antioxidants, for example, vitamin E, ascorbic acid, BHT and BHA.

These active compounds may also be administered parenterally or intraperitoneally. Solutions or suspensions of these active compounds as a free base or pharmacologically acceptable salt can be prepared in glycerol, liquid, polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacterial and fungi. The carrier can be a solvent or dispersion medium containing, for example, water, ethanol, polyol (e.g., glycerol, propylene glycol and liquid polyethylene glycol), suitable mixtures thereof, and vegetable oil.

The invention will be more fully described in conjunction with the following specific examples which are not to be construed as limiting the scope of the invention.

In another aspect of the present invention, it is contemplated that the active compounds may be administered in combination with a substance capable of inhibiting the β-lactam hydrolase enzyme, dehydropeptidase. Such dipeptidase inhibitors are know in the art, as disclosed for example in U.S. Pat. No. 4,539,208 and European Patent Application 0497353, and include such compounds as cilastatin, glutathione and N-acetyl-L-cysteine. The dipeptidase inhibitor may be used to inhibit the renal or gastrointestinal metabolism of the carbapenems of the present invention and may be used to enhance the gastrointestinal absorption of the active carbapenem compounds. When combined in such a manner, the carbapenem antibiotic and the peptidase inhibitor can be administered either in a pharmaceutical composition containing the two substances in combination or can be separately administered. Administration separately or combined can be oral, intramuscularly or intravenously.

PREPARATION OF THE COMPOUNDS

Three distinct processes for producing carbapenems of formula I according to the present invention are described.

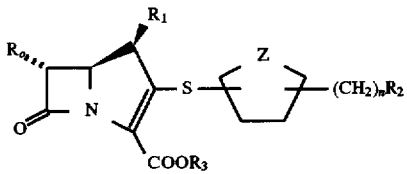

One method of preparation utilizes an addition-elimination reaction sequence by contacting the carbapenem of formula III with the appropriate thiol IV and base, Step 1—Scheme I, in an inert solvent and atmosphere at low temperature. Suitable solvents include dioxane, tetrahydrofuran, dimethylformamide, acetonitrile and mixtures thereof; with acetonitrile and dimethylformamide being preferred. Suitable bases include, but are not limited to, sodium or potassium carbonate, triethylamine, diisopropylethylamine, 4-(dimethylamino)pyridine and 2,6-lutidine; with diisopropylethylamine being preferred. A suitable temperature ranges from –40° C. to 30° C.; with –5° C. being used most often with argon as the inert atmosphere.

It is understood that the thiol of formula IV is a representation of the regioisomeric possibilities IV-1 to IV-6.

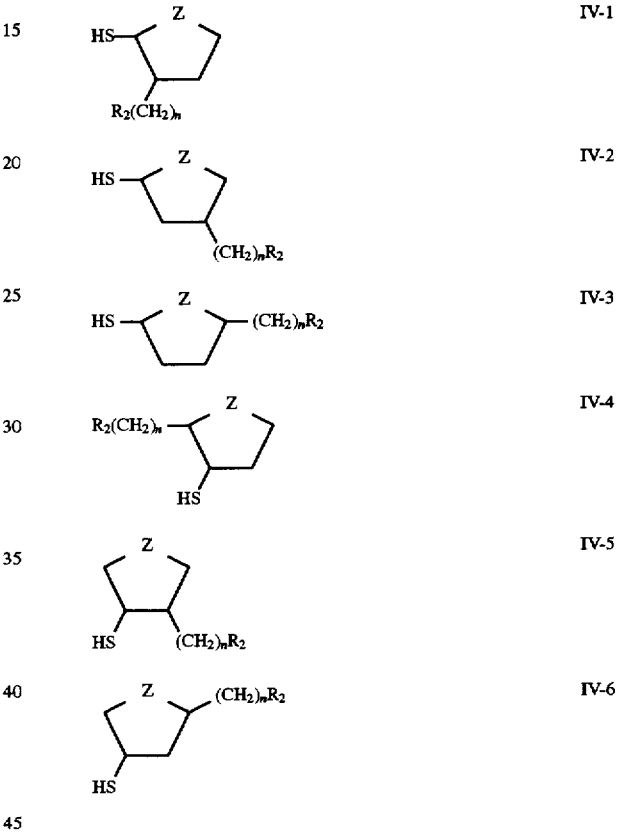

In addition, the asymmetric ring carbons bearing the thiol fragment, —SH and the alkyl fragment —$(CH_2)_nR_2$, may independently have the R or S stereochemical assignment. The nature of $R_o$, $R_1$, $R_2$, $R_3$, $R_{15}$, Z and n are as defined hereinbefore.

SCHEME 1

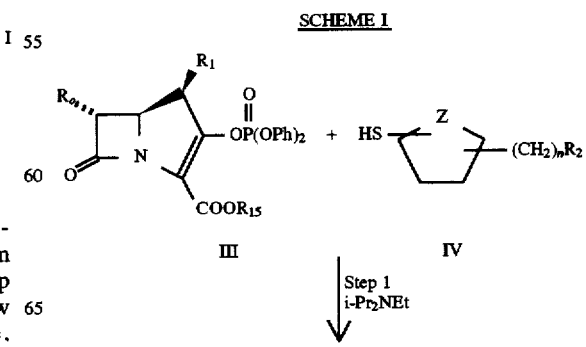

-continued
SCHEME I

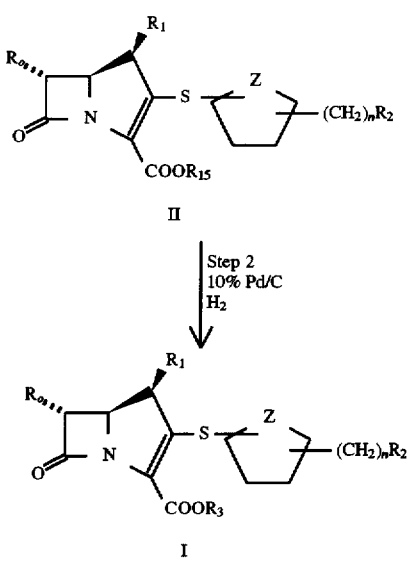

Following the formation of the desired carbapenems of general formula II, the carboxyl protecting group $R_{15}$ of these intermediates may be optionally removed in Step 2 by conventional procedures such as solvolysis, chemical reduction or hydrogenation. Protecting groups such as p-nitrobenzyl, benzyl or benzhydryl can be removed by catalytic hydrogenation. Intermediates II, in a suitable solvent such as dioxane-water-ethanol, tetrahydrofuran-diethyl ether-buffer, tetrahydrofuran-aqueous dipotassium hydrogen phosphate-isopropanol or the like, may be treated under a hydrogen pressure of from 1 to 4 atmospheres in the presence of hydrogenation catalyst such as palladium on charcoal, palladium hydroxide, platinum oxide or the like, at a temperature from 20° to 40° C., for 0.2 to 4 hours. Protecting groups such as 2,2,2-trichloroethyl may be removed by mild zinc reduction. The allyl protecting group may be removed by using a catalyst comprising a mixture of a zero valent palladium compound and triarylphosphine in a suitable aprotic solvent such as tetrahydrofuran, methylene chloride or diethyl ether. Similarly, other conventional carboxyl protecting groups may be removed by methods known to those skilled in the art.

Thus, in Step 2, carbapenem esters of general formula II are deblocked according to the nature and chemical reactivity of their ester group to form the carbapenem of general formula I, wherein $R_o$, $R_1$, $R_2$, $R_3$, Z and n are as defined hereinbefore. The method of product isolation in Step 2 will vary on the method of deblocking used. But all methods used in the transformation follow conventional techniques in the art including chromatography and lyophilization.

It is usual to isolate carbapenems of general formula I as an alkali metal salt wherein $R_3$ is a lithium, sodium or a potassium ion or as a water soluble zwitterionic species, whereby $R_3$ represents a proton or the cationic component of an internal salt pair dependent on the nature of the $R_2$ substituent.

Compounds of formula I wherein $R_3$ is a physiologically hydrolyzable ester such as acetoxymethyl, pivaloyloxymethyl, methoxymethyl, etc., may be administered directly to the host without deblocking since these esters are hydrolyzed in vivo under physiological conditions.

A second method of producing carbapenems of formula I utilizes an acid mediated ring closure as the key step in the sequence outlined in Scheme II.

In Step 1—Scheme II, the 3-bromo-2-ketoester of formula V is contacted with the thiol IV in a suitable solvent and temperature range (as described in (U.S. Pat. No. 5,189,158). The product azetidinone of formula VI thus formed is a result of a nucleophilic displacement of the bromide of formula V by the conjugate base (thiolate species) of the thiol IV that is formed in situ, wherein $R_o$, $R_1$, $R_2$, $R_{15}$, Z and n are as defined hereinbefore. Suitable solvents are anhydrous and include tetrahydrofuran, dimethoxyethane, acetonitrile, dimethylformamide and methylene chloride. The following bases are representative: triethylamine, diisopropylethylamine, lithium bis (trimethylsilyl)amide or 1,8-diazabicyclo[5.4.0]undec-7-ene. The reaction temperature for transformation can range from −70° to +30° C.

In Step 2—Scheme II, the preferred 1-(tert-butyldimethyl)siloxyethyl group of $R_o$ and the tert-butyldimethylsilyl protecting group for the azetidinone nitrogen of the compound of formula VI are hydrolyzed to the 1-hydroxyethyl and N—H respectively via standard procedures in the art. A representative procedure entails contacting keto ester VI with hydrogen fluoride in acetonitrile-water solvent according to R. F. Newton et al, *Tetrahedron Letters* (1979), No. 41, pp 4381–82.

SCHEME II

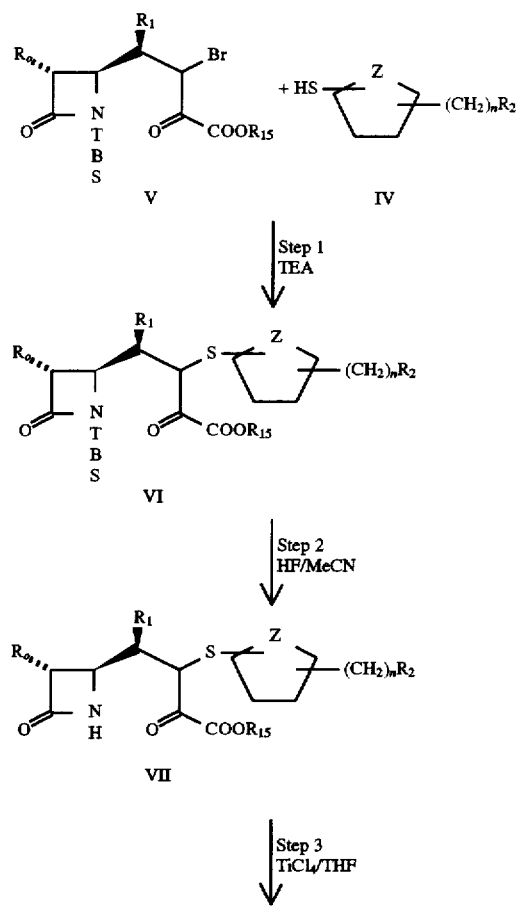

-continued
SCHEME II

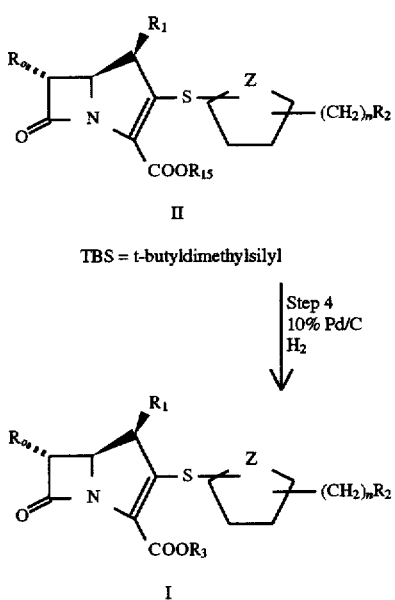

TBS = t-butyldimethylsilyl

Step 4
10% Pd/C
H₂

In Step 3—Scheme II, the compounds of formula VII are contacted with an appropriate acid in a suitable solvent at temperatures in the range of −20° to +20° C. Suitable acids that can be employed for this step include, but are not limited to, titanium tetrachloride or hydrochloric acid. Suitable solvents and solvent combinations can be anhydrous or at least in part, aqueous ones. Tetrahydrofuran (THF), THF/water, dimethoxyethane (DME), DME/water, dioxane, acetonitrile, acetonitrile/water and dimethylformamide all serve as suitable solvents with THF being preferred. The product carbapenem II is isolated after a sequence of quenching the reaction with excess base such as aqueous sodium bicarbonate followed by conventional techniques in the art including dissolution in an organic solvent, aqueous washing and chromatography.

Following formation of the carbapenem of formula II the carboxyl protecting group, $R_{15}$, of these intermediates may be optionally removed in Step 4 by conventional procedures such as solvolysis, chemical reduction or hydrogenation. Protecting groups such as p-nitrobenzyl, benzyl, or benzhydryl can be removed by catalytic hydrogenation. In the catalytic hydrogenation procedure intermediates II, in a suitable solvent mixture such as dioxane-water-ethanol, tetrahydrofuran-diethyl ether-buffer, tetrahydrofuran-aqueous dipotassium hydrogen phosphate-isopropanol or the like are treated under a hydrogen pressure of from 1 to 4 atmospheres in the presence of a hydrogenation catalyst such as palladium on charcoal, palladium hydroxide, platinum oxide or the like, at a temperature from 20° to 40° C., for 0.2 to 4 hours. Protecting groups such as 2,2,2-trichloroethyl may be removed by mild zinc reduction. The allyl protecting group may be removed by using a catalyst comprising a mixture of a zero valent palladium compound and triarylphosphine in a suitable aprotic solvent such as tetrahydrofuran, methylene chloride or diethyl ether. Similarly, other conventional carboxyl protecting groups may be removed by method known to those skilled in the art.

Thus, in Step 4, carbapenem esters of general formula II are deblocked according to the nature and chemical reactivity of their ester group to form the carbapenem of general formula I, wherein $R_o$, $R_1$, $R_2$, $R_3$, Z and n are as defined hereinbefore. The method of product isolation in Step 4 will vary on the method of deblocking used. But all methods used in the transformation follow conventional techniques in the art including chromatography and lyophilization.

It is usual to isolate carbapenem I as an alkali metal salt wherein $R_3$ is a lithium, sodium or potassium ion or as a water soluble zwitterionic species, whereby $R_3$ represents a proton or the cationic component of an internal salt pair dependent on the nature of the $R_2$ substituent.

Compounds of formula I wherein $R_3$ is a physiologically hydrolyzable ester such as acetoxymethyl, pivaloyloxymethyl, methoxymethyl, etc., may be administered directly to the host without deblocking since such esters are hydrolyzed in vivo under physiological conditions.

A third method of producing carbapenems of formula I in this invention utilizes the synthetic route of Scheme III.

In Step 1—Scheme III, carbapenems of formula II are formed by the nucleophilic substitution of the silver thiolate carbapenem of formula VIII with the requisite halo-substituted heterocycle of formula IX. In this transformation $R_o$, $R_1$, $R_2$, $R_{15}$, Z and n are as defined hereinbefore and Y is chloro, bromo, iodo, methanesulfonate or trifluoromethanesulfonate.

SCHEME III

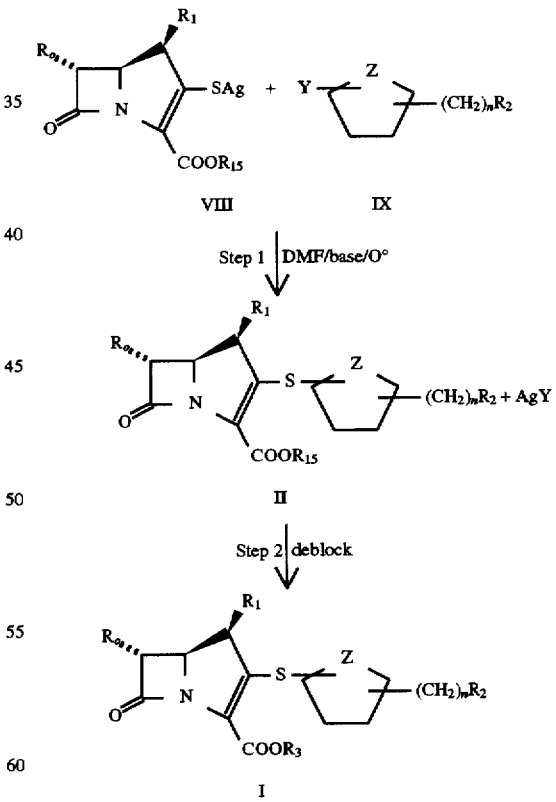

It is understood that the halo-substituted heterocycle of formula IX is a representation of the regioisomeric possibilities IX-1 to IX-6 with IX-1 to IX-3 being the preferred entities for use as reactant in Step 1—Scheme III.

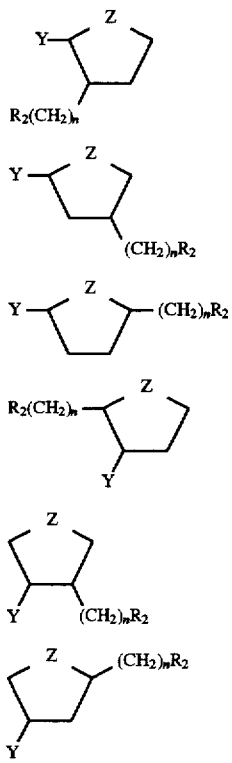

IX-1

IX-2

IX-3

IX-4

IX-5

IX-6

In addition, the asymmetric ring carbons bearing the halide Y, and the alkyl fragment, —(CH$_2$)—R$_2$, may independently have the R or S stereochemical assignment.

The transformation in Step 1—Scheme III is usually conducted by contacting the carbapenem silver thiolate VIII with the halo-substituted heterocycle IX in a suitable solvent such as dimethylformamide or acetonitrile and an iodide source such as lithium iodide or equivalent metal iodide in a temperature range of 0°–60° C. The carbapenem product of formula II is isolated after a sequence of dissolution in an organic solvent such as ethyl acetate, washing with water and chromatography.

Following formation of the carbapenem of formula II the carboxyl protecting group, R$_{15}$, of these intermediates may be optionally removed in Step 2 by conventional procedures such as solvolysis, chemical reduction or hydrogenation. Protecting groups such as p-nitrobenzyl, benzyl, or benhydryl can be removed by catalytic hydrogenation. In this procedure intermediates II, in a suitable solvent such as dioxane-water-ethanol, tetrahydrofuran-diethyl ether-buffer, tetrahydrofuran-aqueous dipotassium hydrogen phosphate-isopropanol or the like, are treated under a hydrogen pressure of from 1 to 4 atmospheres in the presence of hydrogenation catalyst such as palladium on charcoal, palladium hydroxide, platinum oxide or the like, at a temperature from 20° to 40° C., for 0.2 to 4 hours. Protecting groups such as 2,2,2-trichloroethyl may be removed by mild zinc reduction. The allyl protecting group may be removed by using a catalyst comprising a mixture of a zero valent palladium compound and triarylphosphine in a suitable aprotic solvent such as tetrahydrofuran, methylene chloride or diethyl ether. Similarly, other conventional carboxyl protecting groups may be removed by methods known to those skilled in the art.

Thus, in Step 2, carbapenem esters of general formula II are deblocked according to the nature and chemical reactivity of their ester group to form the carbapenem of general formula I, wherein R$_o$, R$_1$, R$_2$, R$_3$, Z and n are as defined hereinbefore. The method of product isolation in Step 2 will vary on the method of deblocking used. But all methods used in the transformation follow conventional techniques in the art including chromatography and lyophilization.

It is usual to isolate carbapenems of formula I as an alkali metal salt wherein R$_3$ is a lithium, sodium or potassium ion or as a water soluble zwitterionic species, whereby R$_3$ represents a proton or the cationic component of an internal salt pair dependent on the nature of the R$_2$ substituent.

Compounds of formula I wherein R$_3$ is a physiologically hydrolyzable ester such as acetoxymethyl, pivaloyloxymethyl, methoxymethyl, etc., may be administered directly to the host without deblocking since such esters are hydrolyzed in vivo under physiological conditions.

Several synthetic routes are employed to prepare the various isomeric thiol entities of general formula IV and halo-substituted heterocycles of general formula IX which are utilized in Step 1 of Schemes I, II, and III. The following synthetic schemes demonstrate preferred synthesis of compounds IV and IX.

SCHEME IV

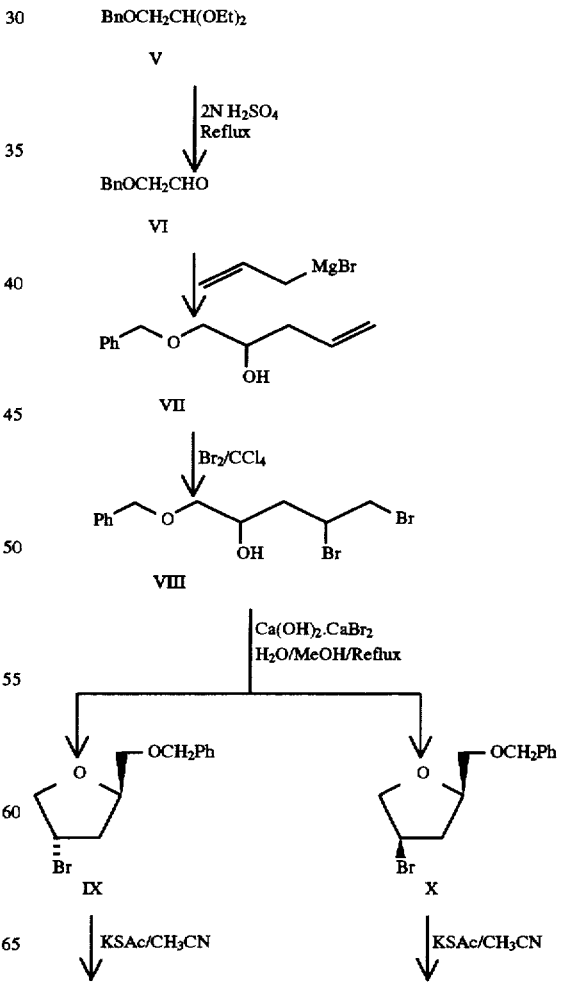

-continued
SCHEME IV

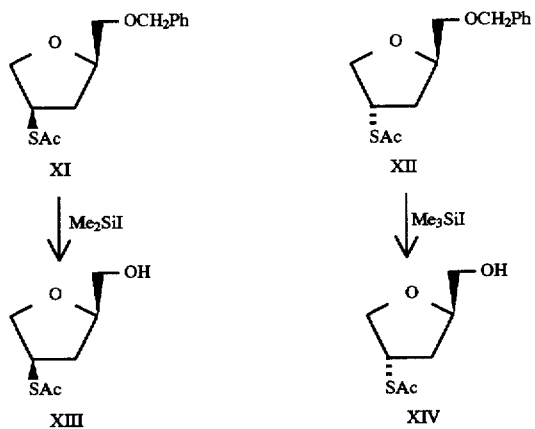

In accordance with Scheme IV, benzyloxyacetaldehyde diethyl acetal is hydrolyzed with dilute sulfuric acid giving benzyloxyacetaldehyde, which is then reacted with allyl magnesium bromide to give 1-phenylmethoxy-4-penten-2-ol. This alcohol, is brominated with bromine in carbon tetrachloride or dichloromethane at −20° C. to 0° C. to give 4,5-dibromo-1-(phenylmethoxy)-2-pentanol. This dibromo alcohol, in aqueous methanol, is cyclized with calcium hydroxide in the presence of calcium bromide, to give a racemic mixture of trans and cis-4-bromo-2-[(phenylmethoxy)methyl]tetrahydrofuran, IX and X respectively, which is separated by flash column chromatography using silica gel. The trans bromide, IX, is reacted with potassium thioacetate, in a dipolar aprotic solvent, to give cis-[5-[(phenylmethoxy)methyl]-3-tetrahydrofuranyl] ethanethioate, XI. The thioacetate, XI, is reacted with iodotrimethylsilane to give cis-[5-(hydroxymethyl)-3-tetrahydrofuranyl]ethanethioate, XIII. In the same manner, the cis bromide, X, is converted to the trans-[5-(hydroxymethyl)-3-tetrahydrofuranyl]ethanethioate, XIV.

In accordance with Scheme V, the cyclization of 1-phenylmethoxy-4-penten-2-ol with iodine in the presence of sodium bicarbonate gives a racemic mixture of cis and trans-5-(iodomethyl)-3-tetrahydrofuranols, XV and XVI, which is separated by flash column chromatography using silica gel.

The optically active tetrahydrofuran derivatives are prepared according to Scheme V. Benzyloxyacetaldehyde is reacted with optically active 2-allyl-1,3,2-dioxaborolane-4, 5-dicarboxylic acid ester, XVII, to give optically pure (S)-1-phenylmethoxy-4-penten-2-ol, XVIII. Cyclization of alcohol, XVIII, with iodine in the presence of sodium bicarbonate gives a mixture of optically pure 2,5-anhydro-1,3-dideoxy-1-iodo-D-threopentitol, XIX.

SCHEME V

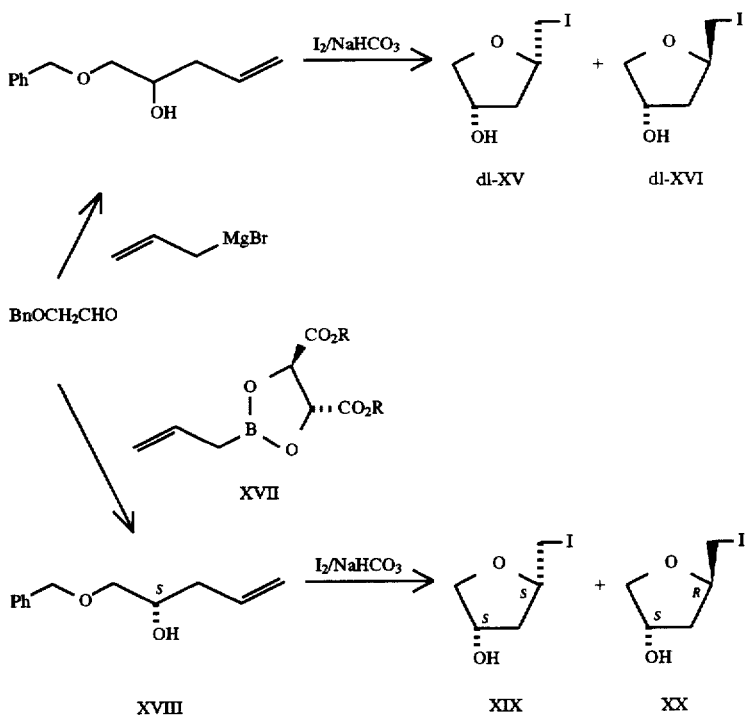

and 2,5-anhydro-1,3-dideoxy-1-iodo-D-erythro-pentitol, XX, which is separated by flash chromatography using silica gel.

anhydro-3-deoxy-4-thio-L-threo-pentonoyl)-1-piperazinecarboxylic acid ester, XXIV.

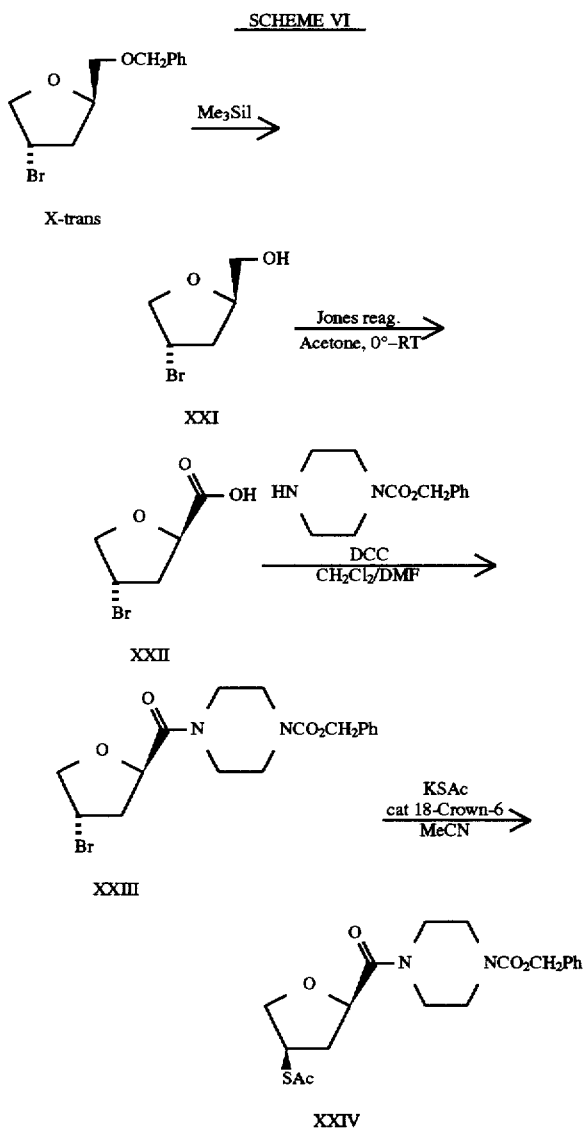

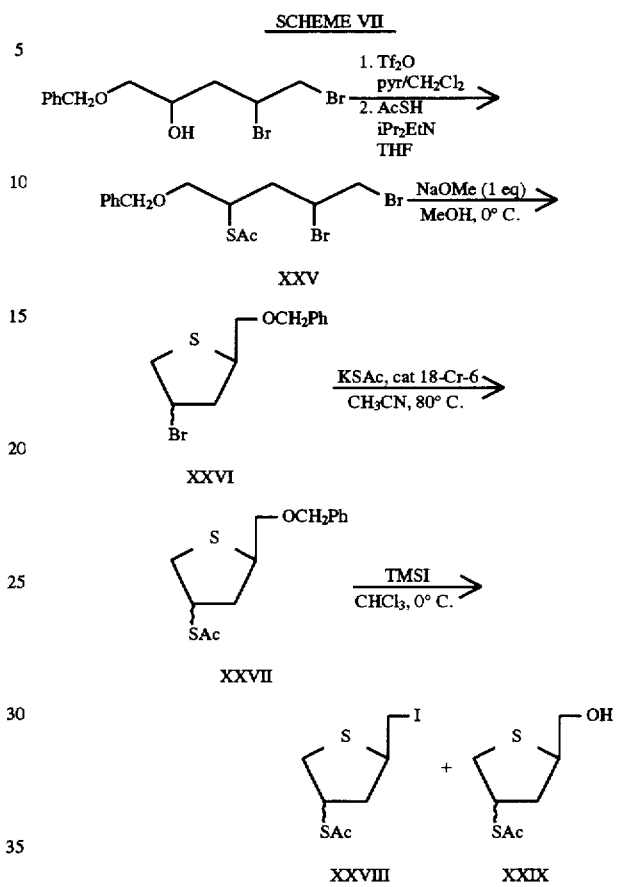

In accordance with Scheme VI, the bromide, X-trans, is reacted with iodotrimethylsilane to give (±)-4-bromo-2-tetrahydrofuranmethanol, XXI, which is oxidized with Jones reagent to give 2,5-anhydro-4-bromo-3,4-dideoxy-D-erythro-pentonic acid, XXII. The bromide, XXII, is reacted with phenylmethyl 1-piperazinecarboxylate, in the presence of 1,3-dicyclohexylcarbodiimide, to give phenylmethyl 4-(2,5-anhydro-4-bromo-3,4-dideoxy-D-erythro-pentonoyl)-1-piperazinecarboxylic acid ester, XXIII, which is then reacted with potassium thioacetate, in a dipolar aprotic solvent, to give phenylmethyl 4-(4-S-acetyl-2,5-

In accordance with Scheme VII, 4,5-dibromo-1-phenylmethoxy-2-pentanol is reacted with triflic anhydride, in the presence of pyridine, to give the desired triflate which is then reacted with thio acetic acid, in the presence of diisopropylethylamine, to give S-[3,4-dibromo-1-[(phenylmethoxy)methyl]butyl]ethanethioic acid ester, XXV. The dibromo thioacetate, XXV, is treated with one equivalent of sodium methoxide, in methyl alcohol, to give 4-bromotetrahydro-2-[(phenylmethoxy)methyl]thiophene, XXVI, which is reacted with potassium thioacetate, in a dipolar aprotic solvent, to give tetrahydro-5-[[(phenylmethoxy)methyl]-3-thienyl]-ethanethioic acid ester, XXVII. The thioacetate, XXVII, is reacted with iodotrimethylsilane, in chloroform, to give a mixture of tetrahydro-5-(iodomethyl)-3-thienyl ethanethioic acid ester, XXVIII, and tetrahydro-5-(hydroxymethyl)-3-thienyl ethanethioic acid ester, XXIX, which is separated by flash column chromatography using silica gel.

In Scheme VIII, the thioacetate, XIII from Scheme IV, and the alcohol, XVI from Scheme V, are converted to the azido derivative, XXXIII.

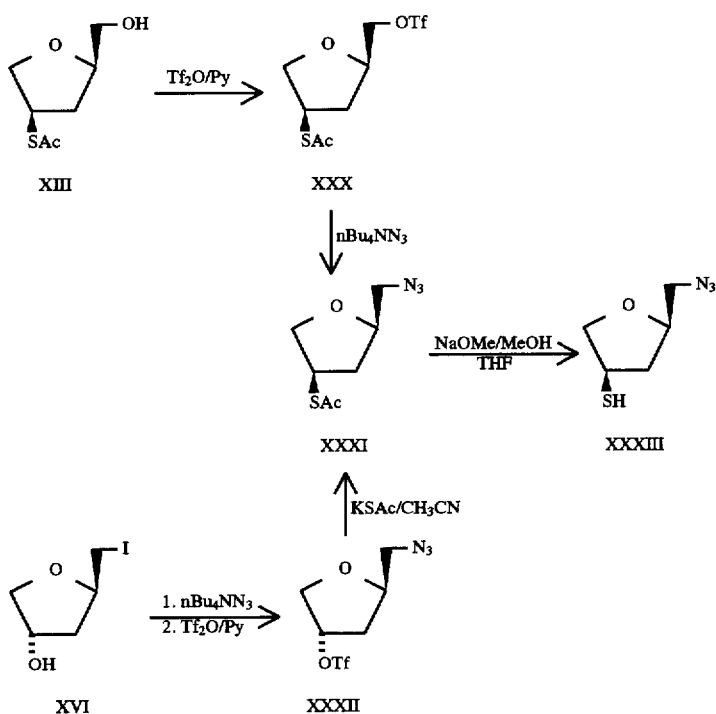

The thioacetate, XIII, is reacted with triflic anhydride, in the presence of pyridine, to give the desired triflate, XXX, which is then reacted with tetrabutylammonium azide to give cis(±)-S-[5-(azidomethyl)-3-tetrahydrofuranyl] ethanethioic acid ester, XXXI.

Alternatively, the alcohol, XVI, is reacted with tetrabutylammonium azide to give the desired azide which is then reacted with triflic anhydride, in the presence of pyridine, to give the desired triflate, XXXII. The triflate, XXXII, is reacted with potassium thioacetate in acetonitrile to give the thioacetate, XXXI. The thioacetate, XXXI, is then reacted with sodium methoxide, in a mixture of methanol and tetrahydrofuran, to give cis-(±)-5-azidomethyl)-3-tetrahydrofuranthiol, XXXIII.

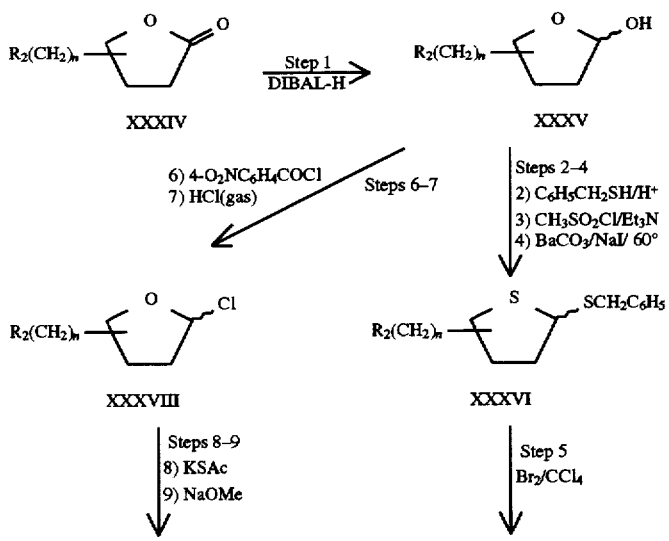

-continued
SCHEME IX

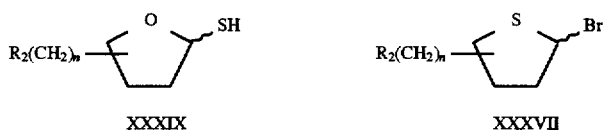

Scheme IX outlines synthetic methods common in the art that ensure access to other thiol congeners with the general formula IV-1 to IV-3 and halo-substituted heterocycles of general formula IX-1 to IX-3.

The mono-substituted lactone, XXXIV, serves as the starting point for the above-mentioned compound classes. It will be appreciated that XXXIV is a representation of the following regioisomers:

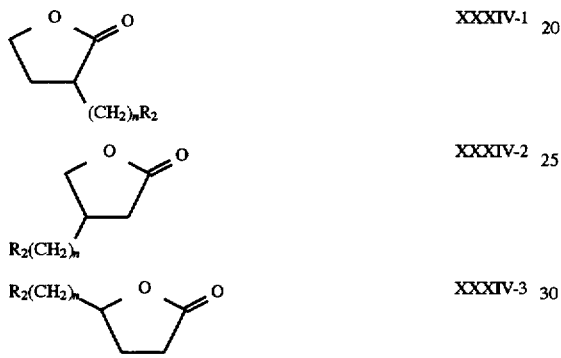

In addition, the asymmetric ring carbon bearing the $R_2$—$(CH_2)_n$— fragment may have the R or S stereochemistry, wherein n and $R_2$ are as defined hereinbefore. The preparation of lactones with general formula XXXIV utilizes basic synthetic techniques that are common in the art.

In Step 1—Scheme IX, the lactone, XXXIV, is reduced via a standard diisobutylaluminum hydride or equivalent reduction in the art to the corresponding lactol, XXXV. This lactol, in turn can be treated with the sequence of reagents in Steps 2–4 as per the example of M. R. Dyson et al., *Carbohydrate Research*, Vol. 216, pp237–48 (1991) to form the dithioglycoside XXXVI. In Step 5, this dithioglycoside is converted to the 2-bromo-thioglycoside, XXXVII by bromine and carbon tetrachloride according to the method of M. R. Dyson et al, *J. Med. Chem.*, Vol 34, pp2782–86 (1991). The 2-bromo-thioglycoside, XXXVII, thus formed (representative of the halo-substituted heterocycles of general formula IX-1 to IX-3) can be utilized in the carbapenem synthesis outlined in Scheme III. In steps 6 and 7 of Scheme IX, the lactol of general formula XXXV is converted to the 2-chlorotetrahydrofuranyl derivative of formula XXXVIII by stepwise treatment with 4-nitrobenzoyl chloride and hydrogen chloride gas. Both procedures are common in the art and are described in detail by Baker and Fletcher in *J. Org. Chem.*, Vol. 24, 4605 (1961) and Stevens, Ness and Fletcher in *J. Org. Chem.*, Vol 33, 1806–09 (1968) respectively. The 2-chlorotetrahydrofuran of formula XXXVIII is sequentially treated with potassium thioacetate and then by sodium methoxide in steps 8 and 9. The tetrahydrofuran thiol product XXXIX, representative of the thiols of general formula IV-1 to IV-3, can be utilized in the carbapenem synthesis outlined in Schemes I and II.

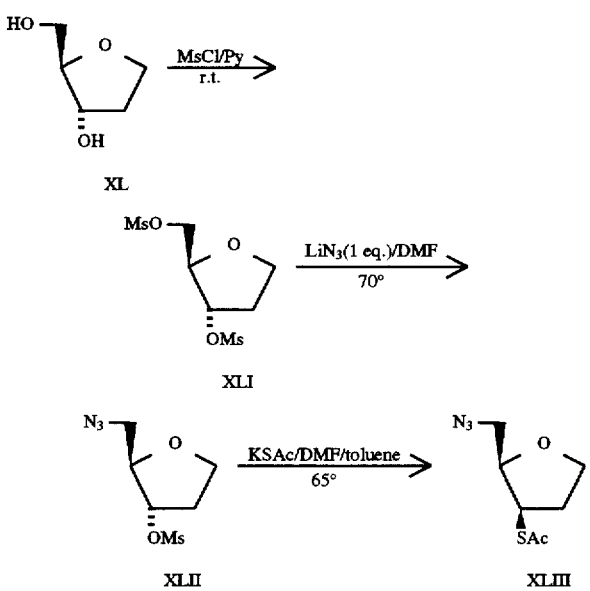

1,2-Dideoxy-D-ribose, XL, is prepared according to M. Takeshita et al, *J. Biol. Chem.* (1987), 262(21), 10171.

In accordance with Scheme X, 1,2-dideoxy-D-ribose is reacted with excess methanesulfonyl chloride in pyridine to give dimesylate XLI, which is reacted with one equivalent of lithium azide in dimethylformamide to give azido derivative XLII. The azido derivative XLII is then reacted with potassium thioacetate in a mixture of dimethylformamide and toluene to give the desired thioacetate XLIII.

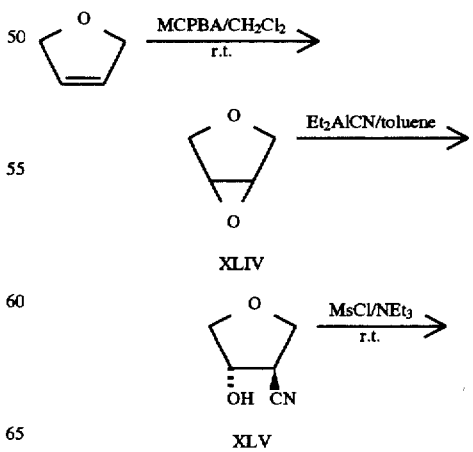

SCHEME XI -continued

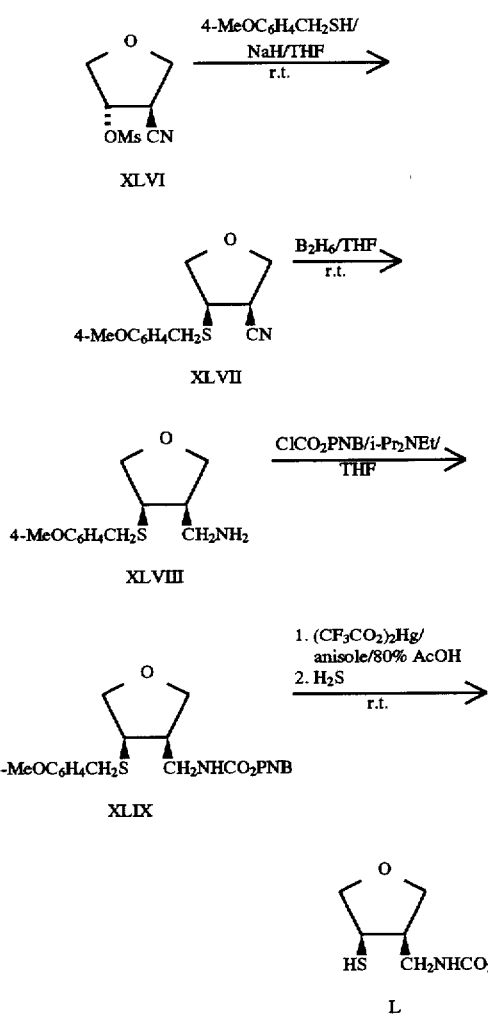

In accordance with Scheme XI, 2,5-dihydrofuran is reacted with m-chloroperbenzoic acid in methylene chloride to give epoxide XLIV, which is then reacted with diethyla- luminium cyanide in toluene to give the cyanoalcohol XLV. The cyanoalcohol XLV is mesylated with methanesulfonyl chloride in the presence of triethylamine to give cyanome- sylate XLVI, which is then reacted with 4-methoxybenzyl mercaptan and sodium hydride in tetrahydrofuran to give the cyanothioether XLVII. Reduction of the cyanothioether with diborane in tetrahydrofuran gives aminomethylthioether XLVIII, which is then reacted with 4-nitrobenzyl chlorofor- mate in the presence of diisopropylethylamine in tetrahy- drofuran to give protected aminomethylthioether XLIX. Treatment of the protected aminomethylthioether XLIX with mercuric trifluoroacetate and anisole in 80% aqueous acetic acid, followed by treatment with hydrogen sulfide gives the desired thiol L.

SCHEME XII

As an alternate synthetic route to Scheme IX, Scheme XII outlines complimentary methods common in the art to access thiol congeners with general formula IV-1 to IV-3 and halo-substituted heterocycles of general formula IX-1 to IX-3. In step 1 of Scheme XII, the thiolactol LI is prepared from the lactone XXXIV using the synthetic sequence of J. A. Secrist et al. in *J. Med. Chem.*, Vol 35, pp 533–538 (1992). Treatment of the thiolactol LI with anhydrous hydro- chloric acid in step 2 represents one way to access the requisite 2-chlorotetrahydrothiophene LII, representative of the halo-substituted heterocycles of general formula IX-1 to IX-3, which can, in turn, be utilized in the carbapenem synthesis outlined in Scheme III.

The lactone XXXIV can also be converted to the thiolac- tone LIII using Lawessons' reagent in step 3 of Scheme XII. The procedure found to be most useful in this step is that of S. Scheibye et al., *Tetrahedron*, Vol 35, pp 1339–43 (1979). In step 4 of Scheme XII, the thiolactone LIII is reduced with lithium triethylborohydride using the procedure of A. G. M. Barrett et al, *J. Org. Chem.*, Vol 54, pp 2275–2277 (1989). The thiolactol LIV thus formed representative of the thiols of general formula IV-1 to IV-3, can be utilized in the carbapenem syntheses outlined in Schemes I and II.

SCHEME XIII

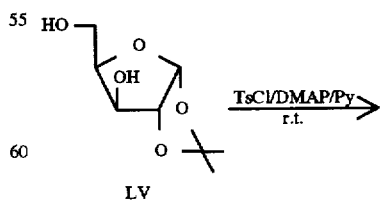

-continued
SCHEME XIII

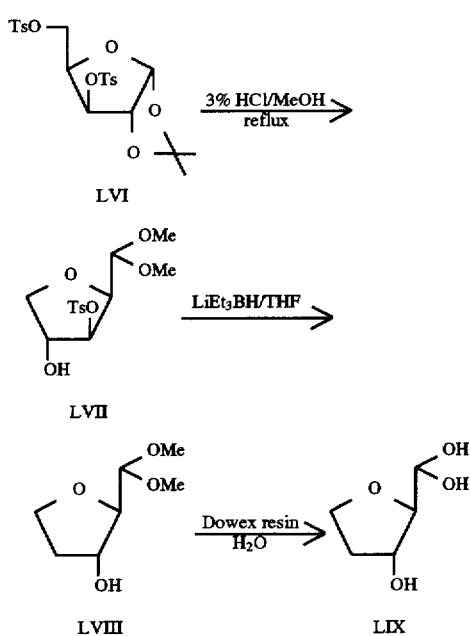

In accordance with Scheme XIII, 1,2O-isopropylidene-D-xylofuranose LV is reacted with excess p-toluenesulfonyl chloride in the presence of a catalytic amount of 4-dimethylaminopyridine in pyridine to give ditosylate LVI, which is treated with 3% hydrochloric acid in methanol under reflux to give p-toluenesulfonyl dimethyl acetal LVII. The p-toluenesulfonyl dimethyl acetal LVII is reduced with 10 equivalent of lithium triethylborohydride in tetrahydrofuran to give dimethyl acetal LVIII, which is hydrolyzed with Dowex resin in water to give aldehyde hydrate LIX.

In the foregoing word description of the above schematic reaction diagrams for the synthesis of (3-tetrahydrofuranyl) carbapenem and (3-tetrahydrothienyl)carbapenem antibacterials, it is understood that there is latitude in selection of precise reaction parameters. Suggestion of this latitude and its breadth is generally indicated by the enumeration of equivalent solvent systems, temperature ranges, protecting groups, bases (organic and inorganic), and range of identities of involved reagents.

EXAMPLE 1

(Phenylmethoxy)acetaldehyde

A stirring mixture of 100 g of benzyloxyacetaldehyde diethyl acetal, 500 ml of tetrahydrofuran and 400 ml of 2N sulfuric acid is heated at reflux temperature for 45 minutes. The resulting solution is cooled to room temperature, concentrated in vacuo to 400 ml volume and diluted with 1000 ml of chloroform. The organic layer is washed with water, cold saturated sodium bicarbonate, saturated sodium chloride and dried. The filtrate is evaporated in vacuo to give the product as an oil. The crude oil is purified by Kugelrohr distillation (bath temperature 100° C.) to give 59.0 g of the desired product as a colorless oil.

$^1$H NMR(CDCl$_3$):δ 9.73(t,1H); 7.36(m,5H); 4.63(s,2H); 4.11(d,2H).

IR (neat): 1736 cm$^{-1}$.

EXAMPLE 2

1-(Phenylmethoxy)-4-penten-2-ol

To a stirring 0° C. solution of 59.0 g of product from Example 1 in 375 ml of diethyl ether is added, dropwise, 432.24 ml of 1M allylmagnesium bromide in ether. The reaction is stirred at 0° C. for 1 hour, followed by overnight stirring at room temperature. The reaction is cooled to 0° C., hydrolyzed with saturated ammonium chloride, and the layers are separated. The organic layer is washed with saturated sodium chloride, dried and concentrated in vacuo to give the product as an oil. The crude oil is purified by Kugelrohr distillation (bath temperature 100° C.) to give 61.5 g of the desired product as a colorless oil.

$^1$H NMR(CDCl$_3$) : δ 7.34(m,5H); 5.82(m,1H); 5.08(m,, 2H); 4.56(s,2H); 3.88(m,1H); 3.44(ABq,2H); 2.27(t,2H); 1.7(bs,1H).

EXAMPLE 3

4,5-Dibromo-1-(phenylmethoxy)-2-pentanol

Using anhydrous conditions, 28.0 g of product from Example 2 in 40 ml of carbon tetrachloride, is cooled to −20° C. A solution of 7.88 ml of bromine in 10 ml of carbon tetrachloride is added, dropwise, over 50 minutes while maintaining the temperature at −20° C. Vigorous stirring is required through out the addition to avoid local overheating of the reaction mixture. At the end of the addition, the reaction mixture turns red and the reaction is complete. The mixture is concentrated in vacuo to give an oily residue. The oil is purified by chromatography (Silica Gel: 10% ethyl acetate/hexane to 20% ethyl acetate/hexane) to give 31 g of the desired product as a light yellow oil, which is a mixture of 2 isomers.

$^1$H NMR(CDCl$_3$): Isomer I:δ 7.35(m,5H); 4.55(s,2H); 4.5(m,1H); 4.1(m,1H); 3.88(dd,1H); 3.65(dd,1H); 3.5(dd, 1H); 3.38(dd,1H); 2.6(bs,1H, OH); 2.25(m,1H); 1.7(m,1H);

Isomer II:δ 7.4(m,5H); 4.52(m,2.5H); 4.26(m,0.5H); 4.05 (m,1H); 3.7(m,2H); 3.5(dd,1H); 3.38(dd,1H); 2.75(s,1H, OH); 2.22(m,1H); 2.1(m,1H).

EXAMPLE 4

Trans-(±)-4-Bromotetrahydro-2-[(phenylmethoxy) methyl]furan and cis-(±)-4-Bromotetrahydro-2-[(phenylmethoxy) methyl]furan A solution of 10.0 g of product from Example 3 in 25 ml of methyl alcohol is diluted with 50 ml of distilled water. To this heterogeneous mixture is added 1.6 g of calcium hydroxide followed by 16.95 g of calcium bromide. The reaction is stirred vigorously while heating in an oil bath, at 100° C., for 24 hours. The internal temperature is maintained at 85° C. The reaction is cooled, extracted with methylene chloride, filtered thru diatomaceous earth and the layers partitioned. The organic layer is washed with water and saturated sodium chloride, dried and concentrated in vacuo to give 7.18 g of an oil. The oil is purified by chromatography (Silica Gel: 5% ethyl acetate/hexane) to give 2.82 g of the trans-isomer and 2.89 g of the cis-isomer.

$^1$H NMR(CDCl$_3$) trans-Isomer:δ 7.35(s,5H); 4.6(s,2H); 4.48(m,2H); 4.3(dd,1H); 4.04–4.1(dd,1H); 3.6–3.65(dd, 1H); 3.5–3.57(dd,1H); 2.3(m,2H);

cis-Isomer:δ 7.36(m,5H); 4.6(d,2H); 4.3–4.42(m,1H); 4.12–4.25(m,1H); 4.0–4.12(m,2H); 3.55–3.7(m,2H); 2.55–2.7(m,1H); 2.08–2.2(m,1H).

EXAMPLE 5

Ethanethioic acid trans-(±)-S-[tetrahydro-5-[(phenylmethoxy)methyl]-3-furanyl]ester To an argon purged solution of 2.17 g of the cis-isomer from Example 4 in 25 ml of dry acetonitrile is added 0.96 g of potassium thioacetate. The reaction is heated at reflux temperature for 16 hours, cooled, filtered and diluted with ethyl acetate. The solution is washed with saturated sodium chloride, dried and concentrated in vacuo to give 2.16 g of a yellow oil. The crude oil is purified by chromatography (Silica Gel: 5–10% ethyl acetate/hexane) to give 1.72 g of the desired product.

$^1$H NMR(CDCl$_3$):δ 7.35(s,5H); 4.6(s,2H); 4.28–4.32(dd, 1H); 4.18–4.25(m,1H); 3.98–4.08(m,1H); 3.6–3.68(dd,1H); 3.52(m,3H); 2.32(s,3H,Ac); 2.16–2.27(m,1H); 1.89–1.98 (m,1H).

EXAMPLE 6

Ethanethioic acid trans-(±)-S-[tetrahydro-5-(hydroxymethyl)-3-furanyl]ester

Using anhydrous conditions and under an argon flush, 0.80 g of product from Example 5 is dissolved in 11 ml of chloroform. The reaction mixture is cooled to 2° C. and 0.47 ml of iodotrimethylsilane is added, via syringe. The reaction is stirred overnight at 2° C. Upon completion of the reaction, 0.49 ml of methyl alcohol is added, the reaction is stirred for 15 minutes longer and concentrated in vacuo. The residue is purified by chromatography (Silica Gel: 20–50% ethyl acetate/hexane) to give 0.406 g of the desired product as a colorless oil.

$^1$H NMR(CDCl$_3$):δ 4.26–4.31(dd,1H); 4.15(m,1H); 4.0 (m,1H); 3.7–3.78(dd,1H); 3.6–3.68(dd,1H); 3.5–3.58(dd, 1H); 2.32(s,3H,Ac); 2.19–2.29(m,1H); 1.86–1.96(m,1H); 1.75(bs,1H,OH).

EXAMPLE 7

Ethanethioic acid trans-(±)-S-[5-[[(aminocarbonyl)oxy]methyl]tetrahydro-3-furanyl]ester To a −20° C. solution, under argon, of 0.406 g of product from Example 6 in 30 ml of methylene chloride is added 0.3 ml of trichloroacetyl isocyanate. The reaction is followed by thin layer chromatography (tlc). When reaction is complete, 1.16 ml of acetic acid, 0.54 ml of water and 9.84 ml of 1M tetrabutylammonium fluoride in tetrahydrofuran is added. The mixture is stirred at room temperature overnight followed by concentration in vacuo. The residue is purified by chromatography (Silica Gel: 50% ethyl acetate/hexane) to give 0.430 g of the desired product.

$^1$H NMR(CDCl$_3$):δ 4.8(bs,2H,NH$_2$); 4.2–4.32(m,3H); 4.05(m,2H); 3.62(dd,1H); 2.32(s,3H,Ac); 2.25(m,1H); 2.0 (m,1H).

Ref.: Journal of Labelled Compounds and Radiopharmaceuticals, Vol. XXIV, No. 1, p. 41, 1987. IR(KBR); 1686 cm$^{-1}$ (broad).

EXAMPLE 8

Ethanethioic acid cis-(±)-S-tetrahydro-5-[(phenylmethoxy)methyl]-3-furanyl]ester The title compound is prepared by the procedure of Example 5 using 2.17 g of trans-isomer product from Example 4, 0.96 g of potassium thioacetate and 25 ml of acetonitrile to give 1.86 g of the desired product.

$^1$H NMR(CDCl$_3$):δ 7.38(s,5H); 4.6(s,2H); 4.15(m,2H); 4.0(m,1H); 3.74(dd,1H); 3.53(d,2H), 2.45(m,1H); 2.32(s, 3H,Ac); 1.65(m,1H).

EXAMPLE 9

Ethanethioic acid cis(±)-S-[tetrahydro-5-(hydroxymethyl)-3-furanyl]ester

The title compound is prepared by the procedure of Example 6 using 0.600 g of product from Example 8, 0.35 g of iodotrimethylsilane, 8 ml of chloroform and 0.37 ml of methyl alcohol to give 0.310 g of the desired product.

$^1$H NMR(CDCl$_3$):δ 4.13–4.2(dd,1H); 3.98–4.12(m,2H); 3.7–3.8(m,2H); 3.52–3.61(dd,1H); 2.38–2.48(m,1H); 2.38 (s,3H,Ac); 1.9(bs,1H,OH); 1.65–1.78(m,1H).

EXAMPLE 10

Ethanethioic acid cis-(±)-S-[5-[[(aminocarbonyl)oxy]methyl]tetrahydro-3-furanyl]ester The title compound is prepared by the procedure of Example 7 using 0.28 g of product from Example 9 in 20 ml of methylene chloride, 0.208 ml of trichloroacetyl isocyanate, 0.80 ml of acetic acid, 6.79 ml of 1M tetrabutylammonium fluoride in tetrahydrofuran and 0.37 ml of water to give 0.320 g of the desired product.

$^1$H NMR(CDCl$_3$):δ 4.6–4.85(bs,2H,NH$_2$); 4.12–4.28(m, 3H); 3.98–4.1(m,2H); 3.7–3.8(dd,1H); 2.43–2.56(m,1H); 2.32(s,3H,Ac); 1.55–1.7(m,1H).

Ref.: Journal of Labelled Compounds and Radiopharmaceuticals, Vol. XXIV, No. 1, p. 41, 1987.

EXAMPLE 11

[2R-[2alpha(R*),3beta(R*)]]-3-[1-[[(1,1-Dimethylethyl)dimethylsilyl]oxy]ethyl]-gamma-methyl-beta,4-dioxo-2-azetidinebutanoic acid (4-nitrophenyl)methyl ester Nine grams of [2S-[2alpha(S*),3beta(S*)]]-3-[1-[[(1,1-dimethylethyl)dimethylsilyl]oxy]ethyl]-alpha-methyl-4-oxo-2-azetidineacetic acid is suspended at room temperature, under argon flush, in 266 ml of dry acetonitrile. To this suspension is added 5.79 g of carbonyldiimidazole and the resulting clear solution is stirred for 30 minutes. Twenty-eight grams of p-nitrobenzylmalonate magnesium salt (dried in vacuo over P$_2$O$_5$ for 1 week) is added and the reaction is heated at 65° C. for 3 hours. The reaction is concentrated in vacuo, diluted with methylene chloride and filtered. The filtrate is washed with saturated sodium chloride, dried and concentrated in vacuo to give 9.7 g of a yellow oil. The residue is purified by chromatography (Silica Gel: 25–45% ethyl acetate/hexane) to give 5.2 g of a crystalline solid.

$^1$H NMR indicates 35% in the enol form.

$^1$H NMR(CDCl$_3$):δ 11.93(d,minor isomer); 8.24(d,2H); 7.53(d,2H); 5.97(d,1H); 5.27(s,2H); 3.7–4.25(m,2H); 3.64 (s,ca. 2H major isomer); 2.95(m,1H); 1.13–1.28(m,6H); 0.87(d,9H); 0.06(m,6H).

EXAMPLE 12

[2R-[2alpha(R*),3beta(R*)]]-3-(1-Hydroxyethyl)-gamma-methyl-beta,4-dioxo-2-azetidinebutanoic acid (4-nitrophenyl)methyl ester To a stirring 0° C. solution, under argon, of 3.7 g of product from Example 11 in 40 ml of methyl alcohol is added 2.5 ml of concentrated hydrochloric acid. The reaction is stirred for 3 hours as the temperature rises to room temperature. The mixture is concentrated to ⅓ volume, diluted with ethyl acetate, poured into cold saturated sodium bicarbonate solution and extracted. The organic layer is washed with saturated sodium chloride, dried and concentrated in vacuo to give 2.61 g of a sticky solid. The residue is purified by chromatography (Silica Gel: ethyl acetate) to give 1.91 g of the desired product as a colorless oil which solidifies on standing.

¹H NMR(CDCl₃):δ 8.25(d,2H); 7.55(d,2H); 5.88(bs,1H); 5.28(s,2H); 4.15(m,1H); 3.81(m,1H); 3.65(d,2H); 2.90(m, 2H); 1.31(d,3H); 1.26(d,3H).

EXAMPLE 13

4-Dodecylbenzenesulfonyl azide

To a stirring solution of 0.38 g of 4-docecylbenzenesulfonyl chloride in 1.9 ml of acetone is added 0.09 g of sodium azide. The resulting suspension is stirred at room temperature for 2 hours, followed by carefully concentrating the mixture in vacuo. The resulting orange oil is purified by chromatography (Silica Gel: hexane-20% methylene chloride/hexane) to give 0.22 g of pure product as a colorless oil.

Ref.: Synthetic Comm., 11(12), 947 (1981).

¹H NMR(CDCl₃):δ 7.87(d,2H); 7.56(d,2H); 0.6–1.7(m, 25H).

IR(neat): 2125 cm⁻¹.

EXAMPLE 14

[2R-[2alpha(R*),3beta(R*)]]-alpha-Diazo-3-(1-hydroxyethyl)-gamma-methyl-beta,4-dioxo-2-azetidinebutanoic acid (4-nitrophenyl)methyl ester To a stirring room temperature solution, under argon, of 0.270 g of product from Example 12 in 3.2 ml of dry acetonitrile is added 0.327 g of triethylamine and 0.427 g of product from Example 13. The reaction is stirred for 45 minutes, diluted with ethyl acetate, washed with water, saturated sodium chloride, dried and filtered to give an oil. The oil is purified by chromatography (Silica Gel: 5–10% acetone/chloroform) to give 0.230 g of the desired product.

¹H NMR(CDCl₃):δ 8.26(d,2H); 7.55(d,2H); 5.95(bs,1H); 5.37(s,2H); 4.14(m,1H); 3.55–3.9(m,2H); 2.91(m,1H); 2.45 (bs,1H); 1.31(d,3H); 1.22(d,3H).

EXAMPLE 15

[4R-[4alpha,5beta,6beta(R*)]]-3-[(Diphenoxyphosphinyl)oxy]-6-(1-(hydroxyethyl)-4-methyl-7-oxo-1-azabicyclo[3.2.0]hept-2-ene-2-carboxylic acid (4-nitropheny)methyl ester For 10 minutes, argon is bubbled through a suspension of 0.10 g of product from Example 14, 6 ml of dry cyclohexane and a catalytic amount of rhodium diacetate. The reaction is then heated at 80° C., under argon for 30 minutes, 1 ml of ethyl acetate is added and the heating continued for an additional hour. The suspension is cooled to room temperature, diluted with ethyl acetate and filtered through a pad of hydrous magnesium silicate. The filtrate is concentrated in vacuo and the residue is dissolved in 1 ml of dry acetonitrile and is called intermediate 15A. The solution (15A), under argon, is cooled to 0° C. and 51 microliter of diphenylphosphoric chloride and 43 microliter of N,N-diisopropylethylamine, herein after called Hunig's base, is added. The reaction is stirred at 0° C. for 1 hour and then concentrated in vacuo to give 0.185 g of the product as an orange oil. The residue is purified by chromatography (Silica Gel: 5–10% acetone/chloroform) to give 0.045 g of the desired product as a white solid.

¹H NMR(CDCl₃):δ 8.18(d,2H); 7.58(d,2H); 7.29(m, 10H); 5.2 and 5.35(q,2H); 4.1–4.4(m,2H); 3.5(m,1H); 3.3 (m,1H); 1.34(d,3H); 1.24(d,3H).

EXAMPLE 16 cis-(±)-Tetrahydro-4-mercapto-2-furanmethanol 2-carbamate

Under anhydrous conditions, 0.109 g of product from Example 10 dissolved in 1.75 ml of tetrahydrofuran, cooled in an ice bath, is treated, via syringe, with 120 microliter of sodium methoxide/methanol (25 wt % in methanol). The progress of the reaction is monitored by thin layer chromatography. After 20 minutes, 280 microliter of 1.86N hydrochloric acid/isopropyl alcohol is added and the reaction is stirred for 5 minutes. The reaction is concentrated in vacuo to give the desired product as a white solid which is used as is in the following reaction.

EXAMPLE 17

[4R-[3(3R*,5R* and 3S*,5S*)4alpha,5beta,6beta (R*)]]-3-[[5[[(Aminocarbonyl)oxy]methyl] tetrahydro-3-furanyl]thio]-6-(1-hydroxyethyl)-4-methyl-7-oxo-1-azabicyclo[3.2.0]hept-2-ene-2-carboxylic acid (4-nitrophenyl)methyl ester To a –20° C. solution, under argon, of 0.297 g of product from Example 15 in 2.5 ml of acetonitrile, is added 61 microliter of Hunig's base, and 0.089 g of product from Example 16 suspended in 2.5 ml of acetonitrile. The reaction is stirred overnight and allowed to warm to room temperature. The mixture is concentrated in vacuo and purified by chromatography (Silica Gel: 80% ethyl acetate/acetone) to give 0.135 g of the desired product.

¹H NMR(CDCl₃):δ 8.3(d,2H); 7.7(d,2H); 5.5(d,1H); 5.25 (d,1H); 5.1(bs,2H,NH₂); 4.0–4.5(m,7H); 3.8(m,2H); 3.3(m, 1H); 2.5(m,1H); 2.4(bs,1H,OH); 1.8(m,0.5H); 1.7(m,0.5H); 1.38(d,3H,Me); 1.25(d,3H,Me).

EXAMPLE 18

[4R-[3(3R*,5R* and 3S*,5S*)4alpha,5beta,6beta (R*)]]-3-[[5-[[(Aminocarbonyl)oxy]methyl] tetrahydro-3-furanyl]thio]-6-(1-hydroxyethyl)-4-methyl-7-oxo-1-azabicyclo[3.2.0]hept-2-ene-2-carboxylic acid monosodium salt A mixture of 0.181 g of product from Example 17, 0.032 g of sodium bicarbonate, 2 ml of water, 11 ml of dioxane and 0.100 g of 10% palladium/carbon is reduced in a Parr apparatus at 42 psi of hydrogen for 3 hours. The reaction mixture is filtered through a pad of diatomaceous earth, washed with water and concentrated to ½ volume. The solution is extracted with ethyl acetate and the aqueous layer is freeze-dried. The product is purified using C₁₈ reverse phase chromatography (95/5 water/ethyl alcohol) to give 0.095 g of the desired product as a yellow solid.

¹H NMR(CDCl₃):δ 3.45–4.15(m,9H); 3.2–3.3(m,2H); 2.32–2.48(m,1H); 1.57–1.64(m,0.5H); 1.4–1.5(m,0.5H); 1.1 (d,3H,Me); 1.03(dd,3H,Me).

IR(KBr): 1729 and 1606 cm⁻¹.

EXAMPLE 19 trans-(±)-Tetrahydro-4-mercapto-2-furanmethanol 2-carbamate

The title compound is prepared by the procedure of Example 16 using 0.109 g of product from Example 7, 120 microliter of 25% methoxide/methyl alcohol, 1.75 ml of tetrahydrofuran, 280 microliter of 1.86N hydrochloric acid/ isopropyl alcohol to give the desired product as a white solid.

EXAMPLE 20

[4R-[3(3R*,5S* and 3S*,5R*)4alpha,5beta,6beta (R*)]]-3-[[5-[[(Aminocarbonyl)oxy]methyl] tetrahydro-3-furanyl]thiol-6-(1-hydroxyethyl)-4-methyl-7-oxo-1-azabicyclo[3.2.0]hept-2-ene-2-carboxylic acid (4-nitrophenyl)methyl ester The title compound is prepared by the procedure of Example 17 using 0.089 g of product from Example 19 in 2.5 ml of acetonitrile, 0.297 g of product from Example 15 in 2.5 ml of acetonitrile, and 61 microliter of Hunig's base to give 0.126 g of the desired product as a white solid.

$^1$H NMR(CDCl$_3$):δ 8.3(d,2H); 7.7(d,2H); 5.5(d,1H); 5.25 (d,1H); 5.1(bs,2H,NH$_2$); 4.0–4.3(m,7H); 3.8(m,2H); 3.3(m, 1H); 2.5(m,1H); 2.4(bs,1H,OH); 1.8(m,0.5H); 1.7(m,0.5H); 1.38(d,3H,Me); 1.25(d,3H,Me).

EXAMPLE 21

[4R-[3(3R*,5S* and 3S*,5R*)4alpha,5beta,6beta (R*)]]-3-[[(Aminocarbonyl)oxy]methyl]tetrahydro-3-furanyl]thiol-6-(1-hydroxyethyl)-4-methyl-7-oxo-1-azabicyclo[3.2.0]hept-2-ene-2-carboxylic acid monosodium salt The title compound is prepared by the procedure of Example 18 using 0.126 g of product from Example 20, 0.0223 g of sodium bicarbonate, 1.4 ml of water, 7.8 ml of dioxane, and 0.070 g of 10% palladium/carbon to give 0.055 g of the desired product as a yellow solid.

$^1$H NMR(CDCl$_3$):δ 3.9–4.2(m,6H); 3.6–3.8(m,2H); 3.25 (m,2H); 2.35–2.49(m,1H); 1.59–1.69(m,0.5H); 1.42–1.52 (m,0.5H); 1.12(d,3H,Me); 1.04(dd,3H,Me).

EXAMPLE 22

Ethanethioic acid trans(±)-S-[tetrahydro-5-[[[(trifluoromethyl)sulfonyl]oxy]methyl]-3-furanyl]ester To a 0° C. solution of 0.535 ml of trifluoromethane-sulfonic anhydride in 3.75 ml of methylene chloride is added, via a syringe, a 0° C. solution of 0.529 g of product from Example 6 in 0.75 ml of methylene chloride and 0.243 ml of pyridine. The reaction is stirred in an ice bath for 45 minutes; during which time the progress of reaction is checked by thin layer chromatography. The mixture is concentrated in vacuo, slurried with ethyl acetate and filtered. The filtrate is purified by chromatography (Silica Gel: 50% ethyl acetate/hexane) to give 0.799 g of the desired product.

$^1$H NMR(CDCl$_3$):δ 4.54–4.61(dd,1H); 4.41–4.49(dd,1H); 4.32–4.4(m,1H); 4.26–4.31(dd,1H); 4.0–4.1(m,1H); 3.67–3.75(dd,1H); 2.35(s,3H); 2.18–2.32(m,1H); 2.03–2.12 (m,1H).

EXAMPLE 23

Ethanethioic acid trans-(±)-S-[tetrahydro-5-(phenoxymethyl)-3-furanyl]-ester

To a 0° C. solution of 0.326 g of phenol, 1.8 ml of Hunig's base, and 2.5 ml of methylene chloride is added, via syringe, 1.07 g of product from Example 22 in 0.50 ml of methylene chloride. The reaction is stirred in an ice bath for 50 minutes; during which time the progress of reaction is checked by thin layer chromatography. The mixture is concentrated in vacuo, dissolved in ethyl acetate and washed with sodium bicarbonate. The organic layer is dried, concentrated in vacuo, and purified by chromatography (Silica Gel: 30% ethyl acetate/hexane) to give 0.532 g of the desired product.

$^1$H NMR(CDCl$_3$):δ 7.25(m,2H); 6.9(m,3H); 4.4(m,1H); 4.35(dd,1H); 4.1(m,1H); 3.95(dd,2H); 3.7(dd,1H); 2.33(s, 3H,Ac); 2.25(m,1H); 2.0(m,1H).

EXAMPLE 24 trans-(±)-Tetrahydro-5-(phenoxymethyl)-3-furanthiol

The title compound is prepared by the procedure of Example 16 using 0.532 g of product from Example 23, 506 microliter of 25% sodium methoxide/methyl alcohol, 7.5 ml of tetrahydrofuran, and 1.18 ml of 1.86N hydrochloric acid/isopropyl alcohol to give 0.311 g of the desired product.

$^1$H NMR(CDCl$_3$):δ 7.25(m,2H); 6.9(m,3H); 4.5(m,1H); 4.2(dd,1H); 3.95(m,2H); 3.6(dd,1H); 3.5(m,1H); 2.3(m,1H); 1.95(m,1H); 1.75(d,1H,SH).

EXAMPLE 25

[4R-[3(3R*,5S* and 3S*,5R*)4alpha,5beta,6beta (R*)]]-6-(1-Hydroxyethyl)-4-methyl-7-oxo-3-[[tetrahydro-5-(phenoxymethyl)-3-furanyl]thio]-1-azabicyclo[3.2.0]hept-2-ene-2-carboxylic acid (4-nitrophenyl)methyl ester The title compound is prepared by the procedure of Example 17 using 0.311 g of product from Example 24 in 7.5 ml of acetonitrile, 0.879 g of product from Example 15 in 7.5 ml of acetonitrile and 0.18 ml of Hunig's base to give 0.349 g of the desired product.

$^1$H NMR(CDCl$_3$):δ 8.23(d,2H); 7.65(d,2H); 7.3(m,2H); 6.92(m,3H); 5.5(d,1H); 5.26(d,1H); 4.5(m,1H); 4.3(m,3H); 4.06(m,2H); 3.9(m,1H); 3.72(m,1H); 3.4(m,1H); 3.3(dd, 1H); 2.38(m,1H); 2.09(m,1H); 1.32(d,3H,Me); 1.29(t,3H, Me).

EXAMPLE 26

[4R-[3(3R*,5S* and 3S*,5R*)4alpha,5beta,6beta (R*)]]-6-(1-Hydroxyethyl)-4-methyl-7-oxo-3-[[tetrahydro-5-(phenoxymethyl)-3-furanyl]thio]-1-azabicyclo[3.2.0]hept-2-ene-2-carboxylic acid monosodium salt The title compound is prepared by the procedure of Example 18 using 0.320 g of product from Example 25, 0.054 g of sodium bicarbonate, 3.5 ml of water, 8.3 ml of dioxane and 0.166 g of 10% palladium/carbon to give 0.052 g of the desired product.

$^1$H NMR(CDCl$_3$):δ 7.39(m,2H); 7.07(m,3H); 4.6(m,2H); 4.25(m,4H); 4.20(m,1H); 4.0(m,1H); 3.8(m,1H); 3.43(m, 1H); 2.25(m,1H); 2.18(m,1H); 1.3(d,3H,Me); 1.23(m,3H, Me).

EXAMPLE 27 cis-(±)-4-Bromotetrahydro-2-furanmethanol

The title compound is prepared by the procedure of Example 6 using 5.42 g of product from Example 4, 3.13 ml of iodotrimethylsilane, 117 ml of chloroform and 5.3 ml of methyl alcohol to give 3.17 g of the desired product.

$^1$H NMR(CDCl$_3$):δ 4.3–4.5(m,1H); 4.0–4.2(m,3H); 3.6–3.8(m,2H); 2.1–2.2(m,1H); 1.94(br s,1H).

EXAMPLE 28

Trifluoromethanesulfonic acid cis-(±)-(4-bromotetrahydro-2-furanyl)methyl ester

The title compound is prepared by the procedure of Example 22 using 3.1 g of product from Example 27 in 4.5 ml of methylene chloride, 3.05 ml of trifluoromethane-sulfonic anhydride in 21.5 ml of methylene chloride, and 1.38 ml of pyridine to give 4.76 g of the desired product.

$^1$H NMR(CDCl$_3$):δ 4.55–4.7(m,2H); 4.35–4.46(m,2H); 4.05–4.2(m,2H);2.7–2.8(m,1H); 2.1–2.2(m,1H).

EXAMPLE 29 cis-(±)-4-Bromo-2-[[(4-fluorophenyl)thio]methyl]tetrahydrofuran

The title compound is prepared by the procedure of Example 23 using 4.7 g of product from Example 28 in 15 ml of methylene chloride, 1.61 ml of 4-fluorothiophenol in 15 ml of methylene chloride, and 2.61 ml of Hunig's base to give 3.96 g of the desired product as a light yellow oil.

¹H NMR(CDCl₃):δ 7.35–7.48(m,2H); 6.9–7.1(m,2H); 4.32–4.5(m,1H); 4.0–4.15(m,3H); 3.2–3.32(m,1H); 3.05–3.15(m,1H); 2.62–2.78(m,1H); 2.1–2.25(m,1H).

EXAMPLE 30 cis-(±)-4-Bromo-2-[[(4-fluorophenyl)sulfonyl]methyl]tetrahydrofuran

A mixture of 3.3 g of product from Example 29, 174 ml of glacial acetic acid and 46.5 ml of 30% hydrogen peroxide is heated at 100° C. for 0.5 hour. The reaction mixture is concentrated in vacuo and purified by chromatography (Silica Gel: 50% ethyl acetate/hexane) to give 3.4 g of the desired product as a white solid.

¹H NMR(CDCl₃):δ 7.93–8.0(m,2H); 7.21–7.28(m,2H); 4.42–4.56(m,1H); 4.37–4.41(m,1H); 3.97–4.05(m,2H); 3.64–3.71(dd,1H); 3.41–3.47(dd,1H); 2.75–2.85(m,1H); 2.20–2.3(m,1H).

EXAMPLE 31

Ethanethioic acid trans-(±)-S-[5-[[(4-fluorophenyl)sulfonyl]methyl]tetrahydro-3-furanyl]ester The title compound is prepared by the procedure of Example 5 using 0.969 g of product from Example 30, 0.360 g of potassium thioacetate, and 9 ml of acetonitrile to give 0.533 g of the desired product.

¹H NMR(CDCl₃):δ 7.93–8.0(m,2H); 7.2–7.3(m,2H); 4.38–4.5(m,1H); 4.13–4.21(dd,1H); 3.9–4.01(m,1H); 3.5–3.56(dd,1H); 3.4–3.48(dd,1H); 3.2–3.3(dd,1H); 2.33(s, 3H); 2.16–2.22(m,2H).

EXAMPLE 32 trans-(±)-5-[[(4-Fluorophenyl)sulfonyl]methyl]tetrahydro-3-furanthiol

The title compound is prepared by the procedure of Example 16 using 0.955 g of product from Example 31, 0.72 ml of 25% sodium methoxide/methyl alcohol and 10 ml of tetrahydrofuran to give 0.523 g of the desired product.

¹H NMR(CDCl₃):δ 8.0(m,2H); 7.4(m,2H); 4.3–4.6(m, 1H); 3.9–4.2(m,1H); 3.2–3.6(m,4H); 2.6(m,0.5H); 2.2(m, 1H); 1.75(d,1H,SH); 1.65(m,0.5H).

EXAMPLE 33

[4R-[3(3R*,5S* and 3S*,5R*)4alpha,5beta,6beta(R*)]]-3-[[5-[[(4-Fluorophenyl)sulfonyl]methyl]tetrahydro-3-furanyl]thio]-6-(1-hydroxyethyl)-4-methyl-7-oxo-1-azabicyclo[3.2.0]hept-2-ene-2-carboxylic acid (4-nitrophenyl)methyl ester The title compound is prepared by the procedure of Example 17 using 0.523 g of product from Example 32 in 12 ml of acetonitrile, 1.13 g of product from Example 15 in 12 ml of acetonitrile and 0.23 ml of Hunig's base to give 0.726 g of the desired product.

¹H NMR(CDCl₃):δ 8.23(m,2H); 7.95(m,2H); 7.65(m, 2H); 7.25(m,2H); 5.48–5.53(m,1H); 5.2–5.28(m,1H); 3.2–4.5(m,10H); 2.58(m,1H); 2.2(m,0.5H); 1.9(m,0.5H); 1.37(m,3H,Me); 1.27(m,3H,Me).

EXAMPLE 34

[4R-[3(3R*,5S* and 3S*,5R*)4alpha,5beta,6beta(R*)]]-3-[[5-[[(4-Fluorophenyl)sulfonyl]methyl]tetrahydro-3-furanyl]thio]-6-(1-hydroxyethyl)-4-methyl-7-oxo-1-azabicyclo[3.2.0]hept-2-ene-2-carboxylic acid monosodium salt The title compound is prepared by the procedure of Example 18 using 0.821 g of product from Example 33, 0.124 g of sodium bicarbonate, 8 ml of water, 20 ml of dioxane, and 0.380 g of 10% palladium/carbon to give 0.135 g of the desired product.

¹H NMR(D₂O):δ 7.96–8.06(m,2H); 7.37–7.47(m,2H); 3.2–4.65(m,10H); 2.55(m,1H); 2.1(m,0.5H); 1.6(m,0.5H); 1.25(d,3H,Me); 1.15(t,3H,Me).

MS(FAB):m/z 530(M+Na) and 508(M+H).

EXAMPLE 35

Ethanethioic acid trans-(±)-S-[5-[(4-fluorophenoxy)methyl]tetrahydro-3-furanyl]ester The title compound is prepared by the procedure of Example 23 using 1.49 g of product from Example 22 in 1 ml of methylene chloride, 0.542 g of 4-fluorophenol, 2.5 ml of Hunig's base and 3 ml of methylene chloride to give 0.963 g of the desired compound.

¹H NMR(CDCl₃):δ 6.74–7.0(m,4H); 4.26–4.47-(m,2H); 4.05–4.13(m,1H); 3.96–4.00(dd,2H); 3.67–3.72(m,1H); 2.35(s,3H,Ac); 2.24(m,1H); 2.0–2.1(m,1H).

EXAMPLE 36

5-[(4-Fluorophenoxy)methyl]tetrahydro-3-furanthiol

The title compound is prepared by the procedure of Example 16 using 0.943 g of product from Example 35, 0.86 ml of 25% sodium methoxide/methyl alcohol and 12 ml of tetrahydrofuran to give 0.417 g of the desired product.

¹H NMR(CDCl₃):δ 6.75–7.05(m,4H); 4.5(m,1H); 4.3(dd, 1H); 3.95(m,2H); 3.6(dd,1H); 3.5(m,1H); 2.3(m,1H); 2.05 (m,1H); 1.75(d,1H,SH).

EXAMPLE 37

[4R-[3(3R*,5S* and 3S*,5R*)4alpha,5beta,6beta(R*)]]-3-[[5-[[4-Fluorophenoxy)methyl]tetrahydro-3-furanyl]thiol-6-(1-hydroxyethyl)-4-methyl-7-oxo-1-azabicyclo[3.2.0]hept-2-ene-2-carboxylic acid (4-nitrophenyl)methyl ester The title compound is prepared by the procedure of Example 17 using 0.417 g of product from Example 36 in 9 ml of acetonitrile, 1.09 g of product from Example 15 in 9 ml of acetonitrile, and 220 microliter of Hunig's base to give 0.473 g of the desired product.

¹H NMR(CDCl₃):δ 8.22(d,2H); 7.65(d,2H); 6.95(m,2H); 6.85(m,2H); 5.5(d,1H); 5.25(d,1H); 4.48(m,1H); 4.2–4.4(m, 3H); 3.8–4.08(m,3H); 3.72(m,1H); 3.4(m,1H); 3.3(m,1H); 2.3–2.43(m,1H); 2.0–2.20(m,1H); 1.37(d,3H,Me); 1.31(t, 3H,Me).

EXAMPLE 38

[4R-[3(3R*,5S* and 3S*,5R*)4alpha,5beta,6beta(R*)]]-3-[[5-[[(4-Fluorophenoxy)methyl]tetrahydro-3-furanyl]thio]-6-(1-hydroxyethyl)-4-methyl-7-oxo-1-azabicyclo[3.2.0]hept-2-ene-2-carboxylic acid monosodium salt The title compound is prepared by the procedure of Example 18 using 0.450 g of product from Example 37, 0.074 g of sodium bicarbonate, 5 ml of water, 12 ml of dioxane and 0.226 g of 10% palladium/carbon to give 0.147 g of the desired compound.

¹H NMR(D₂O):δ 7.0–7.1(m,4H); 4.6(m,2H) 4.10–4.3(m, 3.5H); 3.9–4.1(m,2H); 3.78(m,1H); 3.3–3.43(m,1.5H); 2.22–2.39(m,1H); 2.05–2.2(m,1H); 1.29–1.31(d,3H,Me); 1.20–1.23(dd,3H,Me).

EXAMPLE 39

Ethanethioic acid trans-(±)-S-[5-[[(4-fluorophenyl)thio]methyl]tetrahydro-3-furanyl]ester The title compound is prepared by the procedure of Example 23 using 0.308 g of product from Example 22 in 1 ml of methylene chloride, 107 microliter of 4-fluorothiophenol, and 174 microliter of Hunig's base to give 0.236 g of the desired product.

$^1$H NMR(CDCl$_3$):δ 7.4(m,2H); 7.0(m,2H); 4.3(dd,1H); 4.1–4.2(m,1H); 3.98–4.08(m,1H); 3.6–3.65(dd,1H); 3.08–3.15(m,1H); 2.98–3.05(dd,1H); 2.32(s,3H,Ac); 2.1–2.23(m,1H); 1.98–2.08(m,1H).

EXAMPLE 40 trans-(±)-5-[[4-(Fluorophenyl)thio]methyl]tetrahydro-3-furanethiol

The title compound is prepared by the procedure of Example 16 using 0.206 g of product from Example 39, 173 microliter of 25% sodium methoxide/methyl alcohol, 2.5 ml of tetrahydrofuran, and 403 microliter of 1.86N hydrochloric acid/isopropyl alcohol to give 0.0405 g of the desired product.

$^1$H NMR(CDCl$_3$):δ 7.4(m,2H); 7.0(m,2H); 4.3(m,2H); 3.55(m,1H); 3.48(m,1H); 3.1(m,1H); 2.9(m,1H); 2.2(m,1H); 2.0(m,1H); 1.78(d,1H,SH).

EXAMPLE 41

[4R-[3(3R*,5S* and 3S*,5R*)5beta,6beta(R*)]]-3-[[5-[[(4-Fluorophenyl)thio]methyl]tetrahydro-3-furanyl]thio]-6-(1-hydroxyethyl)-4-methyl-7-oxo-1-azabicyclo[3.2.0]hept-2-ene-2-carboxylic acid (4-nitrophenyl)methyl ester The title compound is prepared by the procedure of Example 17 using 0.110 g of product from Example 40 in 2 ml of acetonitrile, 0.268 g of product from Example 15 in 2 ml of acetonitrile and 55 microliter of Hunig's base to give 0.230 g of the desired product.

$^1$H NMR(CDCl$_3$):δ 8.3(d,2H); 7.7(d,2H); 7.4(m,2H); 7.0 (m,2H); 5.5(d,1H); 5.25(d,1H); 4.3(m,4H); 3.85(m,1H); 3.7 (m,1H); 3.4(m,1H); 3.3(d,1H); 3.1(m,2H); 2.4(bs,1H,OH); 2.2(m,2H); 1.4(d,3H,Me); 1.3(m,3H,Me).

EXAMPLE 42

[4R-[3(3R*,5S* and 3S*,5R*)5beta,6beta(R*)]]-3-[[5-[[(4-Fluorophenyl)thio]methyl]tetrahydro-3-furanyl]thio]-6-(1-hydroxyethyl)-4-methyl-7-oxo-1-azabicyclo[3.2.0]hept-2-ene-2-carboxylic acid monosodium salt The title compound is prepared by the procedure of Example 18 using 0.230 g of product from Example 41, 0.118 g of 10% palladium/carbon, 0.038 g of sodium bicarbonate, 2.5 ml of water and 6.0 ml of dioxane to give 0.062 g of the desired product.

$^1$H NNR(D$_2$O):δ 7.25(bs,2H); 6.8(bs,2H); 2.35–4.4(m,10H); 2.88(m,2H); 1.1(bs,3H,Me); 0.96.(bs,3H,Me).

EXAMPLE 43

Ethanethioic acid trans-(±)S-[5-(azidomethyl)tetrahydro-3-furanyl]ester

To a 0° C. solution of 5.768 g of product from Example 22 in 16 ml of methylene chloride, under argon, is added, via syringe, a 0° C. solution of 5.86 g of tetrabutylammonium azide in 16 ml of methylene chloride. The reaction is stirred in an ice bath for 30 minutes and then concentrated in vacuo. The residue is purified by chromatography (Silica Gel: 50% ethyl acetate/hexane) to give 3.418 g of the desired product.

$^1$H NMR(CDCl$_3$):δ 4.28–4.33(dd,1H, CH$_2$O); 4.15–4.17 (m,1H,CHO); 4.0–4.12(m,1H,CHS); 3.63–3.38(dd,1H, CHN); 3.4–3.49(dd,1H,CHN); 3.24–3.68(dd,1H,CH$_2$O); 2.34(s,3H,Ac); 2.16–2.26(m,1H); 1.93–2.01(m,1H).

IR(neat): 2101 and 1693 cm$^{-1}$.

EXAMPLE 44 trans-(±)-5-(Azidomethyl)tetrahydro-3-furanthiol

The title compound is prepared by the procedure of Example 16 using 3.35 g of product from Example 43, 3.8 ml of 25% sodium methoxide/methyl alcohol and 59 ml of tetrahydrofuran to give 1.995 g of the desired product.

$^1$H NMR(CDCl$_3$):δ 4.3–4.4(m,1H); 4.2–4.26(m,1H); 3.8–3.86(m,0.5H); 3.56–3.65(m,1H); 3.43–3.52(m,1.5H); 3.2–3.3(m,1H); 2.14–2.31(m,1H); 1.9–1.98(m,1H); 1.78(d,1H,SH).

IR(neat): 2099 cm$^{-1}$.

EXAMPLE 45

[4R-[3(3R*,5S* and 3S *5R*)4alpha,5beta,6beta(R*)]]-3-[[5-(Azidomethyl)tetrahydro-3-furanyl]thio]-6-(1-hydroxyethyl)-4-methyl-7-oxo-1-azabicyclo[3.2.0]hept-2-ene-2-carboxylic acid (4-nitrophenyl)methyl ester The title compound is prepared by the procedure of Example 17 using 1.995 g of product from Example 44 in 35 ml of acetonitrile, 7.45 g of product from Example 15, and 1.7 ml of Hunig's base to give 2.83 g of the desired product.

$^1$H NMR(CDCl$_3$):δ 8.3(d,2H); 7.7(d,2H); 5.5(d,1H); 5.25 (d,1H); 4.35(m,4H); 3.8(m,1H); 3.7(m,1H); 3.5(m,1H); 3.4 (m,1H); 3.3(m,2H); 2.3(m,1H); 1.98(m,1H); 1.4(d,3H,Me); 1.3(m,3H,Me).

IR(neat): 2101 and 1769 cm$^{-1}$.

EXAMPLE 46

[4R-[3(3R*,5S* and 3S*,5R*)4alpha,5beta,6beta(R*)]]-3-[[5-(Aminomethyl)tetrahydro-3-furanyl]thio]-6-(1-hydroxyethyl)-4-methyl-7-oxo-1-azabicyclo[3.2.0]hept-2-ene-2-carboxylic acid The title compound is prepared by the procedure of Example 18 using 2.8 g of product from Example 45, 0.60 g of 10% palladium/carbon, 27 ml of sodium phosphate buffer (pH 7) and 82 ml of dioxane to give 0.562 g of the desired product.

$^1$H NMR(D$_2$O):δ 4.4(m,1H); 4.2(m,2.5H); 3.95(m,1H); 3.75(m,1.5H); 3.4(m,2H); 3.2(m,1H); 3.1(m,1H); 2.2(m,2H); 1.35(d,3H,Me); 1.30(d,3H,Me).

EXAMPLE 47

[4R-[3(3R*,5S* and 3S*,5R*)4alpha,5beta,6beta(R*)]]-6-(1-Hydroxyethyl)-3-[[tetrahydro-5-(iminomethyl)amino]methyl]-3-furanyl]thio]-4-methyl-7-oxo-1-aza-bicyclo[3.2.0]-hept-2-ene-2-carboxylic acid Five ml of phosphate buffer (pH 7) is cooled to 0° C. and the pH is adjusted with 1N sodium hydroxide to pH 8.5. This solution is added to 0.052 g of product from Example 46, followed by the addition of 0.0832 g of ethyl methanimidate hydrochloride. The pH is maintained at pH 8.5 and the temperature at 0° C. during the reaction. After 35 minutes, the pH is adjusted to pH 7 with 5% hydrochloric acid and the mixture is concentrated in vacuo. The residue is purified by chromatography ($C_{18}$ reverse phase plates: 5% aqueous ethyl alcohol) to give 0.038 g of the desired product.

$^1$H NMR($D_2O$):δ 7.68(t,1H,CH=N); 4.27(m,1H); 4.05 (m,3H); 3.79(m,1H); 3.6(m,1H); 3.38(m,1H); 3.28(m,3H); 1.97(m,2H); 1.12(d,3H,Me); 1.03(d,3H,Me).

Reference: The Journal of Antibiotics, 36, No. 8, p1034, 1983.

EXAMPLE 48

[4R-[3(3R*,5S* and 3S*,5R*)4alpha,5beta,6beta (R*)]]-6-(1-Hydroxyethyl)-4-methyl-7-oxo-3-[[tetrahydro-5-[[(1-iminoethyl)amino]methyl]-3-furanyl]thio]-1-azabicyclo[3.2.0]-hept-2-ene-2-carboxylic acid The title compound is prepared by the procedure of Example 47 using 0.052 g of product from Example 46, 5 ml of sodium phosphate buffer (pH 7) adjusted to pH 8.5 and 0.097 g of ethyl acetimidate hydrochloride to give 0.045 g of the desired product.

$^1$H NMR($D_2O$):δ 4.24(m,1H); 4.04(m,3H); 3.8(m,1H); 3.58(m,1H); 3.25(m,4H); 1.96(d,3H,Me—C=); 1.93(m,2H); 1.11(d,3H,Me); 1.02(d,3H,Me).

EXAMPLE 49

[4R-[3(2R*,4S* and 2S*,4R*)4alpha,5beta,6beta (R*)]]-4-[[2-Carboxy-6-(1-hydroxyethyl)-4-methyl-7-oxo-1-azabicyclo[3.2.0]hept-2-en-3-yl]thio] tetrahydro-N,N,N-trimethyl-2-furanmethanaminium hydroxide, inner salt The title compound is prepared by the procedure of Example 47 using 0.0514 g of product from Example 46, 3 ml of sodium phosphate buffer (pH 8.6), 0.26 ml of dimethyl sulfate, 1.5 ml of acetonitrile and 1.9 ml of dioxane to give 0.0073 g of the desired product.

$^1$H NMR($D_2O$):δ 4.08(m,3H); 3.6–3.89(m,3H); 3.2–3.4 (m,4H); 3.02(s,9H,3-Me); 2.05(m,1H); 1.96(m,1H); 1.12(d, 3H,Me); 1.04(d,3H,Me).

EXAMPLE 50

2,5-Dioxo-4-oxazolidinepentanoic acid

A suspension of 1.752 g of DL-2-aminopimelic acid, 55 ml of tetrahydrofuran and 16 ml of 1.93M phosgene in toluene is heated, in an oil bath, at 50° C. for 1 hour. Argon is bubbled through the reaction to remove the excess phosgene and the solvents are removed under house vacuum. The resulting oil is dissolved in 14 ml of ethyl alcohol, diluted with 14 ml of petroleum ether and the solution stored overnight at room temperature. The formed crystals are collected and dried to give 1.6 g of the desired product.

mp 102°–104° C.

$^1$H NMR(DMSO-$d_6$):δ 12.1(bs,1H); 9.14(s,1H); 4.44(t, 1H); 2.21(t,2H); 1.68(m,2H); 1.5(m,2H); 1.34(m,2H).

Reference: J. Med. Chem., (1986), 22,89–95.

EXAMPLE 51

[4R-[3(3R*,5S* and 3S*,5R*)4alpha,5beta,6beta (R*)]]-3-[[5-[[(2-Amino-6-carboxy-1-oxohexyl) amino]methyl]tetrahydro-3-furanyl]thio]-6-(1-hydroxyethyl)-4-methyl-7-oxo-1-azabicyclo[3.2.0] hept-2-ene-2-carboxylic acid monosodium salt (A)

The title compound is prepared by the procedure of Example 47 using 0.0514 g of product from Example 46 in 1.5 ml of sodium phosphate buffer (pH 8.5), 0.0302 g of product from Example 50 in 0.5 ml of dioxane, adjusting reaction pH to 9, to give 0.0173 g the desired product.

$^1$H NMR($D_2O$):δ 4.06(m,3H); 3.78(m,2H); 3.57(m,1H); 3.25(m,4H); 2.02(t,3H); 1.92(m,2H); 1.68(m,2H); 1.42(m, 2H); 1.20(m,2H); 1.12(d,3H,Me); 1.03(d,3H,Me).

MS(FAB): m/z 544(M+Na), 522(M+H).

[4R-[3(3R*,5S* and 3S*,5R*)4alpha,5beta,6beta(R*)]]-3-[[5-[[[2-[(2-Amino-6-carboxy-1-oxohexyl)amino]-6-carboxy-1-oxohexyl]amino]methyl]tetrahydro-3-furanylthio-6-(1-hydroxyethyl)-4-methyl-7-oxo-1-azabicyclo-[3.2.0]hept-2-ene-2-carboxylic acid disodium salt (B) (0.0263 g) is also isolated from the reaction as a by-product.

$^1$H NMR($D_2O$):δ 3.2–4.25(10H in 4 multiplets); 1.02–2.06(26H, 2–Me, CCH$_2$C from THF ring and 18H from side chain in 2 doublets and many multiplets).

MS(FAB): m/z 723(M+Na), 701(M+H).

EXAMPLE 52

[4R-[3(3R*,5S* and 3S*,5R*)4alpha,5beta,6beta (R*)]]-6-(1-Hydroxyethyl)-4-methyl-7-oxo-3-[[tetrahydro-5-[[[(methylamino)acetyl]amino]-methyl]-3-furanyl]thio]-1-azabicyclo[3.2.0]hept-2-ene-2-carboxylic acid The title compound is prepared by the procedure of Example 47 using 0.068 g of product from Example 46 in 2.0 ml of sodium phosphate buffer (pH 8.5) and 0.029 g of 3-methyl-2,5-oxazolidinedione, prepared by the procedure described in J. Org. Chem., 34, No. 1, 243(1969), in 1 ml of dioxane to give 0.036 g of the desired product.

$^1$H NMR($D_2O$):δ 3.1–4.2(12H in multiplet); 2.58(s,3H, Me); 1.82(m,2H); 1.12(d,3H,Me); 1.05(dd,3H,Me).

EXAMPLE 53

4-(Chloromethyl)-2,5-oxazolidinedione

The title compound is prepared by the procedure of Example 50 using 1.24 g of 2-chloro-L-alanine, 16 ml of 1.93M phosgene in toluene and 55 ml of tetrahydrofuran to give 0.150 g of the desired product.

$^1$H NMR(DMSO-$d_6$):δ 9.26(br s,1H,NH); 4.97(t,1H,CH); 3.99(dd,1H,CH$_2$); 3.87(dd,1H,CH$_2$).

EXAMPLE 54

[4R-[3(3R*,5S* and 3S*,5R*)4alpha,5beta,6beta (R*)]]-3-[[5-[[(2-Amino-3-chloro-[-oxopropyl) amino]methyl]tetrahydro-3-furanyl]thio]-6-(1-hydroxyethyl)-4-methyl-7-oxo-1-azabicyclo[3.2.0] hept-2-ene-2-carboxylic acid (A)

The title compound is prepared by the procedure of Example 47 using 0.0685 g of product from Example 46 in 1.5 ml of sodium phosphate buffer (pH 8.5) and 0.0299 g of product from Example 53 to give 0.0347 g of the desired product.

$^1$H NMR($D_2O$):δ 2.8–4.4(13H in multiplets); 1.96(m,2H) 1.12(d,3H,Me); 1.04(d,3H,Me).

[4R-[3(2R*,4S* and 2S*,4R*)4alpha,5beta,6beta(R*)]]-3-chloro-L-alanyl-N-[[4-[[2-carboxy-6-(1-hydroxyethyl)-4-methyl-7-oxo-1-azabicyclo[3.2.0]hept-2-en-3-yl]thio] tetrahydro-2-furanyl]methyl-3-chloro-L-alaninamide (B) (0.0152 g) is isolated as a by-product.

$^1$H NMR($D_2O$):δ 3.2–4.7(16H in multiplets); 1.93(m,2H) 1.12(d,3H,Me); 1.05(d,3H,Me).

EXAMPLE 55 trans-(±)-Tetrahydro-4-mercapto-2-furanmethanol

The title compound is prepared by the procedure of Example 16 using 1.06 g of product from Example 6, 20 ml of tetrahydrofuran, 1.43 ml of 25% sodium methoxide/methyl alcohol, and 3.35 ml of 1.86N hydrochloric acid/isopropanol to give 0.687 g of the desired product.

$^1$H NMR($CDCl_3$):δ 4.25(m,1H); 4.2(dd,1H); 3.74(dd, 1H); 3.4–3.6(m,3H); 2.98(s,1H,OH); 2.2(m,1H); 1.9(m,1H); 1.78(d,1H,SH).

EXAMPLE 56

[4R-[3(3R*,5S* and 3S*,5R*)4alpha,5beta,6beta (R*)]]-6-(1-Hydroxyethyl)-4-methyl-7-oxo-3-[[tetrahydro-5-(hydroxymethyl)-3-furanyl]thio]-1-azabicyclo[3.2.0]hept-2-ene-2-carboxylic acid (4-nitrophenyl)methyl ester The title compound is prepared by the procedure of Example 17 using 3.55 g of product from Example 15 in 25 ml of acetonitrile, 0.687 g of product from Example 55 in 25 ml of acetonitrile and 0.625 g of Hunig's base to give 1.66 g of the desired product.

$^1$H NMR($CDCl_3$):δ 8.22(d,2H); 7.67(d,2H); 5.5(d,1H); 5.22(d,1H); 4.28(m,4H); 3.8(m,2H); 3.7(m,1H); 3.55(m, 1H); 3.32–4.1(m,1H); 3.3(m,1H); 2.3(m,1H); 2.18(bs,2H, OH); 1.98(m,1H); 1.36(d,3H,Me); 1.28(d,3H,Me).

EXAMPLE 57

[4R-[3(3R*,5S* and 3S*,5R*)4alpha,5beta,6beta (R*)]]-6-(1-Hydroxyethyl)-4-methyl-7-oxo-3-[[tetrahydro-5-[[(methylsulfonyl)oxy]methyl]-3-furanyl]thio]-1-azabicyclo[3.2.0]hept-2-ene-2-carboxylic acid (4-nitrophenyl)methyl ester To a 0° C. solution, under argon, of 0.821 g of product from Example 56 and 3.4 ml of pyridine is added 148 microliter of methanesulfonyl chloride. The reaction is stirred at 0° C. for 2 hours, diluted with water and extracted with chloroform. The organic layer washed with water and saturated sodium chloride, dried and concentrated in vacuo. The residue is purified by chromatography (Silica Gel; 80% ethyl acetate/hexane) to give 0.632 g of the desired product.

$^1$H NMR($CDCl_3$):δ 8.22(d,2H); 7.64(d,2H); 5.53(d,1H); 5.25(d,1H); 4.2–4.45(m,6H); 3.78–3.88(m,1H); 3.72(dd, 1H); 3.32–3.48(m,1H); 3.3(m,1H); 3.07(s,3H,Me); 2.28(m, 1H); 2.08(m,1H); 1.7(bs,1H,OH); 1.38(d,3H,Me); 1.29(m, 3H,Me).

EXAMPLE 58

[4R-[3(3R*,5S* and 3S*,5R*)4alpha,5beta,6beta (R*)]]-6-(1-Hydroxyethyl)-4-methyl-7-oxo-3-[[tetrahydro-5-(iodomethyl)-3-furanyl]thio]-1-azabicyclo[3.2.0]hept-2-ene-2-carboxylic acid (4-nitrophenyl)methyl ester A mixture of 0.80 g of product from Example 57, 0.431 g of sodium iodide and 20 ml of acetone is heated at reflux temperature for 5 days. The reaction is concentrated in vacuo and the residue purified by chromatography (silica Gel: 80% ethyl acetate/hexane) to give 0.472 g of the desired product.

$^1$H NMR($CDCl_3$):δ 8.22(d,2H); 7.68(d,2H); 5.49(d,1H); 5.25(d,1H); 3.28–4.4(m,1OH); 2.14(m,2H); 1.38(m,3H, Me), 1.26(m,3H,Me).

EXAMPLE 59

[4R-[3(3R*,5S* and 3S*,5R*)4alpha,5beta,6beta (R*)]]-6-(1-Hydroxyethyl)-4-methyl-7-oxo-3-[(tetrahydro-5-methyl-3-furanyl)thio]-1-azabicyclo [3.2.0]hept-2-ene-2-carboxylic acid monosodium salt The title compound is prepared by the procedure of Example 18 using 0.450 g of product from Example 58, 0.230 g of 10% palladium/carbon, 0.161 g of sodium bicarbonate, 5 ml of water, and 12 ml of dioxane to give 0.0967 g of the desired product.

$^1$H NMR($CDCl_3$):δ 3.3–4.6(m,8H); 2.0(m,2H); 1.2(m, 9H,3×Me).

EXAMPLE 60

Ethanethioic acid cis-(±)-S-[tetrahydro-5-[[[(trifluoromethyl)sulfonyl]oxy]methyl]-3-furanyl] ester The title compound is prepared by the procedure of Example 22 using 0.529 g of product from Example 9 in 0.75 ml of methylene chloride, 0.54 ml of trifluoromethanesulfonic anhydride in 3.75 ml of methylene chloride, and 0.243 ml of pyridine to give 0.560 g of the desired product.

$^1$H NMR($CDCl_3$):δ 4.55(m,2H); 4.35(m,1H); 4.2(dd,1H); 4.05(m,1H); 3.75(dd,1H); 2.65(m,1H); 2.35(s,3H,Me); 1.7 (m,1H).

EXAMPLE 61

Ethanethioic acid cis-(±)-S-[5-(Azidomethyl) tetrahydro-3-furanyl]ester

The title compound is prepared by the procedure of Example 43 using 0.560 g of product from Example 60 in 2 ml of methylene chloride, 0.569 g of tetrabutylammonium azide in 2 ml of methylene chloride to give 0.321 g of the desired product.

$^1$H NMR($CDCl_3$):δ 4.15(m,2H); 4.05(m,1H); 3.75(dd, 1H); 3.45(dd,1H); 3.3(dd,1H); 2.49(m,1H); 2.34(s,3H,Me): 1.7(m,1H).

IR(NEAT): 2100 and 1692 $cm^{-1}$.

EXAMPLE 62 cis-(±)-5-(Azidomethyl)tetrahydro-3-furanthiol

The title compound is prepared by the procedure of Example 16 using 0.310 g of product from Example 61 in 4.5 ml of tetrahydrofuran and 0.30 ml of 25% sodium methoxide/methyl alcohol to give 0.159 g of the desired product.

$^1$H NMR($CDCl_3$):δ 4.2(m,2H); 3.7(m,1H); 3.3–3.5(m, 3H); 2.5(m,1H); 1.8(d,1H,SH); 1.7(m,1H).

IR(neat): 2099 $cm^{-1}$.

EXAMPLE 63

[4R-[3(3R*,5S* and 3S*,5R*)4alpha,5beta,6beta (R*)]]-3-[[5-(Azidomethyl)tetrahydro-3-furanyl] thio]-6-(1-hydroxyethyl)-4-methyl-7-oxo-1-azabicyclo[3.2.0]hept-2-ene-2-carboxylic acid (4-nitrophenyl)methyl ester The title compound is prepared by the procedure of Example 17 using 0.159 g of product from Example 62 in 3.5 ml of acetonitrile, 0.693 g of product from Example 15 in 3.5 ml of acetonitrile and 134 microliter of Hunig's base to give 0.340 g of the desired product.

¹H NMR(CDCl₃):δ 8.23(d,2H); 7.66(d,2H); 5.5(d,1H); 5.24(d,1H); 4.1–4.3(m,4H); 3.82(m,2H); 3.28–3.38(m, 4H); 2.5(m,1H); 1.85(m,1H); 1.73(bs,1H,OH); 1.37(d,3H, Me); 1.29(m,3H,Me).

EXAMPLE 64

[4R-[3(3R*,5S* and 3S*,5R*)4alpha,5beta,6beta (R*)]]-3-[[5-(Aminomethyl)tetrahydro-3-furanyl] thio]-6-(1-hydroxyethyl)-4-methyl-7-oxo-1-azabicyclo[3.2.0]hept-2-ene-2-carboxylic acid The title compound is prepared by the procedure of Example 18 using 0.320 g of product from Example 63, 0.220 g of 10% palladium/carbon, 12 ml of 0.05M sodium phosphate buffer (pH 7) and 32 ml of dioxane to give 0.112 g of the desired product.

¹H NMR(D₂O):δ 4.2(m,4H); 3.8(m,3H); 3.4(m,3H); 3.2 (m,2H); 2.78(m,1H); 1.8(m,0.5H); 1.6(m,0.5H); 1.25(d,3H, Me); 1.20(m,3H,Me).

EXAMPLE 65

[4R-[3(3R*,5S* and 3S*,5R*)4alpha,5beta,6beta (R*)]]-6-(1-Hydroxyethyl)-3-[[5-(iminomethyl) amino]methyl]tetrahydro-3-furanyl]thio]-4-methyl-7-oxo-1-azabicyclo[3.2.0]-hept-2-ene-2-carboxylic acid The title compound is prepared by the procedure of Example 47 using 0.0615 g of product from Example 64, 0.0984 g of ethyl methanimidate hydrochloride, and 4 ml of sodium phosphate buffer (pH 7) to give 0.0379 g of the desired product.

¹H NMR(D₂O):δ 7.8(m,1H,CH=); 4.25(m,3H); 4.1(m, 1H); 3.8(m,2H); 3.6(m,2H); 3.4(m,2H); 2.1(m,1H); 1.7(m, 0.5H); 1.52(m,0.5H); 1.3(d,3H,Me); 1.2(d,3H,Me).

EXAMPLE 66

Ethanethioic acid trans-(±)-S-[tetrahydro-5-[(2-naphthalenyloxy)methyl]3-furanyl]ester The title compound is prepared by the procedure of Example 23 using 0.813 g of product from Example 22 in 2 ml of methylene chloride, 0.380 g of 2-naphthol in 2 ml of methylene chloride, and 1.38 ml of Hunig's base to give 0.673 g of the desired product.

¹H NMR(CDCl₃):δ 7.05–7.75(m,7H); 4.35–4.45(m,1H); 4.28–4.35(dd,1H); 4.05–4.15(m,1H); 4.02(m,2H); 3.65–3.75(dd,1H); 2.28(s,3H,Me); 2.24–2.34(m,1H);, 1.95–2.05(m,1H).

EXAMPLE 67 trans-(±)-Tetrahydro-5-[(2-naphthalenyloxy)methyl]-3-furanthiol

The title compound is prepared by the procedure of Example 16 using 0.673 g of product from Example 66, 0.53 ml of 25% sodium methoxide/methyl alcohol and 8 ml of tetrahydrofuran to give 0.099 g of the desired product.

¹H NMR(CDCl₃):δ 7.05–7.75(m,7H); 4.55(m,1H); 4.25 (dd,1H); 4.02(m,2H); 3.6(dd,1H); 3.5(m,1H); 2.35(m,1H); 2.0(m,1H); 1.78(d,1H,SH).

EXAMPLE 68

[4R-[3(3R*,5S* and 3S*,5R*)4alpha,5beta,6beta (R*)]]-6-(1-Hydroxyethyl)-4-methyl-7-oxo-3-[[tetrahydro-5-[(2-naphthalenyloxy)methyl]3-furanyl] thio]-1-azabicyclo[3.2.0]hept-2-ene-2-carboxylic acid (4-nitrophenyl) methyl ester The title compound is prepared by the procedure of Example 17 using 0.099 g of the product from Example 67 in 2 ml of acetonitrile, 0.226 g of product from Example 15 in 2 ml of acetonitrile and 93 microliter of Hunig's base to give 0.158 g of the desired product.

¹H NMR(CDCl₃):δ 7.05–8.2(4m and 2d,11H); 5.5(d,1H); 5.2(d,1H); 3.3–4.6(8m,10 H); 2.5(m,1H); 2.2(m,1H); 1.4(d, 3H,Me); 1.3(d,3H,Me).

EXAMPLE 69

[4R-[3(3R*,5S* and 3S*,5R*)4alpha,5beta,6beta (R*)]]-6-(1-Hydroxyethyl)-4-methyl-7-oxo-3-[[tetrahydro-5-[(2-naphthalenyloxy)methyl]3-furanyl] thio]-1-azabicyclo[3.2.0.]hept-2-ene-2-carboxylic acid monosodium salt The title compound is prepared by the procedure of Example 18 using 0.158 g of product from Example 68, 0.075 g of 10% palladium/carbon, 0.025 g of sodium bicarbonate, 1.5 ml of water, and 3.8 ml of dioxane to give 0.0307 g of the desired product.

¹H NMR(CDCl₃):δ 6.4–7.4(m,7H); 3.0–4.5(m,10H); 2.0 (m,2H); 1.4(m,3H,Me); 1.1(m,3H,Me).

EXAMPLE 70

(Phenylmethoxy)carbamic acid 2,2,2-trichloroethyl ester

Under anhydrous conditions, 50 g of O-benzylhydroxylamine hydrochloride is suspended in 783 ml of acetonitrile. To the suspension is added 50.6 ml of pyridine followed by dropwise addition of 43.15 ml trichloroethyl chloroformate in 235 ml of acetonitrile. The reaction is allowed to stir overnight at room temperature. The mixture is concentrated in vacuo and diluted with ethyl acetate. The organic layer is washed with 0.5N citric acid, water, saturated sodium bicarbonate, saturated sodium chloride, dried and concentrated in vacuo. The residue is purified by Kugelrohr distillation (bp 150° C. at 0.5 mmHg.) to give 70 g of the desired product.

¹H NMR(CDCl₃):δ 7.52(s,1H); 7.4(m,5H); 4.93(s,2H); 4.80(s,2H).

CI-MS:m/z 315(M+NH₄)⁺.

EXAMPLE 71

Ethanethioic acid trans-(±)-S-[tetrahydro-5-[[(phenylmethoxy)[(2,2,2-trichloroethoxy)carbonyl] amino]methyl]-3-furanyl]ester To a 0° C. solution, under argon, of 1.0 g of product from Example 6, 1.69 g of product from Example 70, 1.49 g of triphenylphosphine and 5.4 ml of tetrahydrofuran is added 0.988 g of diethyl azodicarboxylate in 1.4 ml of tetrahydrofuran. The reaction is stirred at room temperature for 48 hours, filtered and the filtrate concentrated in vacuo to give 5.18 g of thick oil. The oil is purified by chromatography (Silica Gel: 15–25% ethyl acetate/hexane) to give 0.805 g of the desired product.

¹H NMR(CDCl₃):δ 7.4(m,5H); 4.8–5.05(m,4H); 4.29(m, 2H); 4.03(m,1H); 3.5–3.75(m,3H); 2.32(s,3H); 2.1(m,1H); 1.95(m,1H).

IR(neat): 1719 and 1693 cm⁻¹.

EXAMPLE 72

Ethanethioic acid trans-(±)-S-[5-[[Acetyl (phenylmethoxy)amino]methyl]tetrahydro-3-furanyl] ester To a room temperature solution, under argon, of 0.188 g of product from Example 71 in 2.3 ml of glacial acetic acid is added 0.269 g of zinc dust. The reaction is stirred 10 minutes and 155 microliter of acetic anhydride is added. The reaction is stirred at room temperature overnight, diluted with ethyl acetate and filtered. The filtrate is concentrated in vacuo to give 0.110 g of the desired product.

$^1$H NMR(CDCl$_3$):δ 7.39(s,5H); 4.89(d,2H); 4.31(m,2H); 4.05(m,1H); 3.78(m,1H); 3.64(m,1H); 2.32(s,3H); 2.13(s,3H); 2.1(m,1H); 2.0(m,1H).

IR(neat): 1684 and 1667 cm$^{-1}$.

CI-MS: m/z 324(MH$^+$), 341(M+NH$_4$)$^+$.

EXAMPLE 73 trans-(±)-N-[(Tetrahydro-4-mercapto-2-furanyl)methyl]-N-(phenylmethoxy)acetamide The title compound is prepared by the procedure of Example 16 using 0.390 g of product from Example 72, 0.580 ml of 25% sodium methoxide/methyl alcohol, 0.850 ml of tetrahydrofuran and 1.26 ml of 2N hydrochloric acid/isopropyl alcohol to give 0.205 g of the desired product.

$^1$H NMR(CDCl$_3$):δ 7.38(s,5H); 4.88(s,2H); 4.42(m,1H); 4.2(m,1H); 3.74(m,2H); 3.58(m,1H); 3.48(m,1H); 2.11(m,4H); 1.98(m,1H); 1.73(d,1H).

IR(neat): 1664 cm$^{-1}$.

CI-MS:m/z 282(MH$^+$).

EXAMPLE 74

[4R-[3(3R*,5S* and 3S*,5R*)4alpha,5beta,6beta(R*)]]-3-[[5-[[Acetyl(phenylmethoxy)amino]methyl]tetrahydro-3-furanyl]thio]-6-(1-hydroxyethyl)-4-methyl-7-oxo-1-azabicyclo[3.2.0]hept-2-ene-2-carboxylic acid (4-nitrophenyl)methyl ester The title compound is prepared by the procedure of Example 17 using 0.190 g of product from Example 73, 0.401 g of product from Example 15, 5 ml of acetonitrile and 117.6 microliter of Hunig's base to give 0.286 g of the desired product.

$^1$H NMR(CDCl$_3$):δ 8.22(d,2H); 7.65(d,2H); 7.38(s,5H); 5.5(m,1H); 5.22(m,1H); 4.87(d,2H); 4.2–4.45(m,4H); 3.62–3.88(m,5H); 3.28(m,2H); 1.95–2.15(m,5H); 1.37(m,3H); 1.26(d,3H).

IR(KBr): 3444, 1769 and 1706 cm$^{-1}$.

EXAMPLE 75

[4R-[3(3R*,5S* and 3S*,5R*)4alpha,5beta,6beta(R*)]]-3-[[5-[[Acetyl(phenylmethoxy)amino]methyl]tetrahydro-3-furanyl]thio]-6-(1-hydroxyethyl)-4-methyl-7-oxo-1-azabicyclo[3.2.0]hept-2-ene-2-carboxylic acid monosodium salt The title compound is prepared by the procedure of Example 18 using 0.272 g of product from Example 74, 0.0402 g of sodium bicarbonate, 2 ml of water, 11.3 ml of dioxane, and 0.110 g of 10% palladium/carbon to give 0.059 g of the desired product.

$^1$H NMR(D$_2$O):δ 7.34(d,5H); 4.85(m,2H); 4.15–3.3(m,2H); 3.35–3.83(m,10H); 2.95–3.25(m,3H); 1.72–1.92(m,6H); 1.04(d,3H); 0.9(d,3H).

EXAMPLE 76

[4R-[3(3R*,5S* and 3S*,5R*)4alpha,5beta,6beta(R*)]]-3-[[5-[(Acetylhydroxyamino)methyl]tetrahydro-3-furanyl]thio]-6-(1-hydroxyethyl)-4-methyl-7-oxo-1-azabicyclo[3.2.0]hept-2-ene-2-carboxylic acid monosodium salt A mixture of 0.010 g of product from Example 75, 0.014 g of 10% palladium/carbon, and 1 ml of deuterium oxide is reduced in a Parr apparatus for 2 hours at 30 psi. The reaction solution is filtered and lyophilyzed to give 0.007 g of the desired product.

$^1$H NMR(D$_2$O):δ 4.0–4.2(m,3H); 3.08–3.84(m,13H); 1.9–2.04(m,6H); 1.07(d,3H); 1.02(d,3H).

EXAMPLE 77 cis-(±)-Tetrahydro-4-mercapto-2-furanmethanol

The title compound is prepared by the procedure of Example 16 using 0.370 g of product from Example 9, 505 microliter of 25% sodium methoxide/methyl alcohol, 850 microliter of tetrahydrofuran and 1.1 ml of 2N hydrochloric acid/isopropanol to give 0.209 g of the desired product.

$^1$H NMR(CDCl$_3$):δ 3.55–4.1(m,5H); 3.23(m,1H); 2.23 (m,1H); 1.64(m,1H); 1.3(m,1H); 0.9(d,1H).

EXAMPLE 78

[4R-[3(3R*,5R* and 3S*,5S*)4alpha,5beta,6beta(R*)]]-6-(1-Hydroxyethyl)-4-methyl-7-oxo-3-[[tetrahydro-5-(hydroxymethyl)-3-furanyl]thio]-1-azabicyclo[3.2.0]hept-2-ene-2-carboxylic acid (4-nitrophenyl)methyl ester The title compound is prepared by the procedure of Example 17 using 0.080 g of the product from Example 77, 0.355 g of product from Example 15, 5 ml of acetonitrile and 7.3 microliter of Hunig's base to give 0.180 g of the desired product.

$^1$H NMR(CDCl$_3$):δ 8.23(d,2H); 7.66(d,2H); 5.51(d,1H); 5.24(d,2H); 4.37(m,2H); 4.13(m,2H); 3.75(m,3H); 3.6(m,2H); 3.29(m,2H); 2.44(m,2H); 2.17(m,1H); 1.26–1.4(m,6H).

EXAMPLE 79

[4R-[3(3R*,5S* and 3S*,5R*)4alpha,5beta,6beta(R*)]]-6-(1-Hydroxyethyl)-4-methyl-7-oxo-3-[[tetrahydro-5-(hydroxymethyl)-3-furanyl]thio]-1-azabicyclo[3.2.0]hept-2-ene-2-carboxylic acid monosodium salt The title compound is prepared by the procedure of Example 18 using 0.170 g of product from Example 78, 0.0328 g of sodium bicarbonate, 2 ml of water, 11.3 ml of dioxane, and 0.070 g of 10% palladium/carbon to give 0.060 g of the desired compound.

$^1$H NMR(D$_2$O):δ 3.3–4.0(m,11H); 3.18(m,1H); 2.25(m,1H); 1.22–1.5(m,1H); 0.94(m,6H).

EXAMPLE 80 cis(±)-Tetrahydro-5-[(phenylmethoxy)methyl-3-furanthiol

The title compound is prepared by the procedure of Example 16 using 1.89 g of product of Example 8, 0.392 g of sodium methoxide, 38.7 ml of methyl alcohol, and 38.7 ml of tetrahydrofuran to give 1.03 g of the desired product.

$^1$H NMR(CDCl$_3$):δ 7.28(m,5H); 4.55(m,2H); 4.12(m,1H); 4.02(m,1H); 3.59(m,1H); 3.51(d,2H); 3.31(m,1H); 1.74(d,1H); 1.59(m,1H).

IR(neat): 2859, 1496 and 1452 cm$^{-1}$.

EXAMPLE 81

[4R-[3(3R*,5S* and 3S*,5R*)4alpha,5beta,6beta(R*)]]-6-(1-Hydroxyethyl)-4-methyl-7-oxo-3-[[tetrahydro-5-[(phenylmethoxy)methyl]-3-furanyl]thio]-1-azabicyclo[3.2.0]hept-2-ene-2-carboxylic acid (4-nitrophenyl)methyl ester The title compound is prepared by the procedure of Example 17 using 0.921 g of product from Example 15, 0.347 g of product from Example 80, 271 microliter of Hunig's base and 200 microliter of acetonitrile to give 0.340 g of the desired product.

$^1$H NMR(CDCl$_3$): δ 8.2(m,2H); 7.62(d,2H); 7.25(m,5H); 5.2–5.5(m,2H); 2.58(m,2H); 4.2(m,4H); 3.84(s,1H); 3.78 (m,2H); 3.55(m,2H); 3.24–3.42(m,2H); 2.62(s,1H); 2.43–2.58(m,2H); 1.6–1.85(m,2H); 1.26(m,6H).

EXAMPLE 82

[4R-[3(3R*,5S* and 3S*,5R*)4alpha,5beta,6beta (R*)]]-6-(1-Hydroxyethyl)-4-methyl-7-oxo-3-[[tetrahydro-5-[(phenylmethoxy)methyl]-3-furanyl]thio]-1-azabicyclo[3.2.0]hept-2-ene-2-carboxylic acid monosodium salt The title compound is prepared by the procedure of Example 18 using 0.170 g of product from Example 81, 0.0277 g of sodium bicarbonate, 1.2 ml of water, 6.8 ml of dioxane, and 0.055 g of 10% palladium/carbon to give 0.045 g of desired product.

$^1$H NMR(D$_2$O):δ 7.28(m,5H); 4.95(s,2H); 3.49–4.15(m, 7H); 3.45(m,2H); 1.4–1.55(m,1H); 1.1(m,6H).

EXAMPLE 83

1,2,3,4-Tetrahydro-2-methyl-3-thioxo-1,2,4-triazine-5,6-dione

Under anhydrous condition, 35 g of diethyloxalate is added, dropwise, to a vigorously stirred solution of 21 g of 2-methyl-3-thiosemicarbazide, 32.4 g of fresh sodium methoxide, and 750 ml of methyl alcohol. The resulting suspension is heated at 60° C. for 4 hours, stirred overnight at room temperature, and heated at 70° C. for 15 hours. The white suspension is cooled to room temperature, 200 ml of ice water is added and the reaction concentrated in vacuo. The residue is cooled to 0° C. and made acidic with 2N hydrochloric acid. The reaction mixture is concentrated, ethyl alcohol is added and the suspension is heated to boiling. The white precipitate is collected, washed with hexane and dried to give 11 g of the crude product. Eight grams of the crude product is heated in methylene chloride and filtered while hot. The collected solid is resuspended in methyl alcohol and a solution of 4N potassium-2-ethyl hexanoate is added. The mixture is cooled to 0° C. and the precipitate collected. The solid is dissolved in water, filtered, and 2N hydrochloric acid is added to the clear 0° C. solution. The resulting precipitate is collected and dried to give 4.1 g of the pure product.

$^{13}$C NMR(CDCl$_3$):δ 44.145, 150.115, 152.559, 169.786.

$^1$H NMR(CDCl$_3$):δ 13.11(s,1H); 12.5(br s,1H); 3.66(s, 3H).

CI-MS:m/z 160(MH$^+$).

EXAMPLE 84

Ethanethioic acid trans-(±)-S-[5-[[(hexahydro-2-methyl-5,6-dioxo-1,2,4-triazin-3-yl)thio]methyl]tetrahydro-3-furanyl]ester The title compound is prepared by the procedure of Example 23 using 0.551 g of product from Example 83 in 1 ml of tetrahydrofuran, 1.07 g of product from Example 22 in 1 ml of tetrahydrofuran, 3 ml of dimethylformamide, and 605 microliter of Hunig's base to give 0.357 g of the desired product.

$^1$H NMR(CDCl$_3$):δ 13.17(s,1H); 3.98–4.33(m,8H); 3.69 (s,3H); 3.55(m,1H); 2.33(s,3H); 2.22(m,1H); 1.96(t,1H).

IR(KBr): 1721 and 1672 cm$^{-1}$.

EXAMPLE 85 trans-(±)-Tetrahydro-2-methyl-3[[(tetrahydro-4-mercapto-2-furanyl)methyl]thio]-1,2,4-triazine-5,6-dione The title compound is prepared by the procedure of Example 16 using 0.357 g of product from Example 84, 281 microliter of 25% sodium methoxide/methyl alcohol and 500 microliter of tetrahydrofuran to give 0.148 g of the desired product.

$^1$H NMR(CDCl$_3$):δ 9.37(bs,1H); 4.55(s,1H); 4.26(m,3H); 3.83(s,3H); 3.6(m,2H); 2.34(m,2H); 2.06(m,2H); 1.76(d, 1H).

IR(KBr): 1722 and 1604 cm$^{-1}$.

EXAMPLE 86

[4R-[3(3R*,5S* and 3S*,5R*)4alpha,5beta,6beta (R*)]]-3-[[5-[[(Hexahydro-2-methyl-5,6-dioxo-1,2,4-triazin-3-yl)thio]methyl]tetrahydro-3-furanyl]-thio]-6-(1-hydroxyethyl)-4-methyl-7-oxo-1-azabicyclo[3.2.0]hept-2-ene-2-carboxylic acid (4-nitrophenyl) methyl ester The title compound is prepared by the procedure of Example 17 using 0.207 g of product from Example 85, 0.0965 g of product from Example 15, 0.045 g of Hunig's base and 500 microliter of dimethylformamide to give 0.109 g of the desired product.

$^1$H NMR(CDCl$_3$):δ 10.3(bs,1H); 8.21(d,2H); 7.65(d,2H); 5.36(dd,2H); 4.47(m,1H); 4.2–4.4(m,4H); 4.15(m,1H); 3.99 (m,1H); 3.81(s,3H); 3.71(m,1H); 3.48(m,1H); 3.35(m,1H); 2.6(bs,1H); 2.38(m,1H); 2.13(m,1H); 1.3(m,7H); 0.86(m, 1H).

EXAMPLE 87

[4R-[3(3R*,5S* and 3S*,5R*)4alpha,5beta,6beta (R*)]]-3-[[5-[[(Hexahydro-2-methyl-5,6-dioxo-1,2,4-triazin-3-yl)thio]methyl]tetrahydro-3-furanyl]-thio]-6-(1-hydroxyethyl)-4-methyl-7-oxo-1-azabicyclo[3.2.0]hept-2-ene-2-carboxylic acid monosodium salt The title compound is prepared by the procedure of Example 18 using 0.10 g of product from Example 86, 0.0135 g of sodium bicarbonate, 2 ml of water, 10 ml of dioxane, and 0.030 g of 10% palladium/carbon to give 0.038 g of the desired product.

$^1$H NMR(D$_2$O):δ 3.85–4.5(m,8H); 3.75(m,1H); 3.6(s, 3H); 3.2(m,2H); 1.8–2.2(m,3H); 1.0(m,7H).

EXAMPLE 88

[4R-[4alpha,5beta,6beta(R*)]]-6-(1-Hydroxyethyl)-4-methyl-7-oxo-3-[[tetrahydro-5-(hydroxymethyl)-3-furanyl]thio]-1-azabicyclo[3.2.0]hept-2-ene-2-carboxylic acid monosodium salt The title compound is prepared by the procedure of Example 18 using 0.050 g of product from Example 56, 0.0096 g of sodium bicarbonate, 600 microliter of water, 3.4 ml of dioxane, and 0.030 g of 10% palladium/carbon to give 0.028 g of the desired product.

$^1$H NMR(D$_2$O):δ 3.3–4.3(m,12H); 2.13(m,2H); 1.24(d, 3H); 1.16(d,3H).

EXAMPLE 89

Ethanethioic acid (3R-cis)-S-[5-[[[(2-bromoethoxy) hydroxyphosphinyl]oxy]methyl]tetrahydro-3-furanyl]ester A 0° C. solution, under argon, of 0.520 g of product from Example 9, 0.53 ml of triethylamine, and 10 ml of carbon tetrachloride is treated with 0.50 ml of 2-bromoethylphosphorodichloridate. The reaction is stirred at room temperature for 1 hour, filtered, and concentrated in vacuo. The residue is slurried in 0.5M sodium acetate and tetrahydrofuran (1:1) at room temperature for 4 hours. The mixture is concentrated in vacuo, the aqueous layer is acidified and extracted with 30% isopropyl alcohol and chloroform. The organic layers are combined, dried, concentrated in vacuo, and chromatographed (Silica Gel: ethyl acetate, 5–30% methyl alcohol/chloroform) to give 0.617 g of the desired product.

$^1$H NMR(MeOH-d$_4$):δ 4.26(m,1H); 4.21–3.96(m,6H); 3.67(dd,1H,J=5.8 Hz); 3.61(t,2H,J=5.8 Hz); 2.51(m,1H); 2.31(s,3H.COCH$_3$); 1.72(m,1H).

MS(FAB): m/z 363(M$^+$), 321(M+H—COCH$_3$).

EXAMPLE 90

(2R-cis)-2-[[[[(4-Acetylthio)tetrahydro-2-furanyl] methoxy]hydroxyphosphinyl]oxy]-N,N,N-trimethylethanaminium hydroxide inner salt To a 0° C. solution, under argon, of 0.508 g of product Example 89 in 15 ml of acetonitrile and 15 ml of chloroform is added 20 ml of anhydrous trimethylamine. The mixture is warmed at 70° C. for 2.5 hours, under dry ice/acetone condenser, concentrated in vacuo, and slurried in 20 ml of methyl alcohol and 2.0 g of Amberlyst A-21 for 0.5 hour. The suspension is filtered and the filtrate concentrated in vacuo. The residue is purified by chromatography (Silica Gel: 15–80% methyl alcohol/chloroform; 7:3:1 to 2:8:2 chloroform:methyl alcohol:water) to give 0.260 g of the desired product.

$^1$H NMR(MeOH-d$_4$):δ 4.28(br s,2H); 4.12(m,2H); 4.00–3.8(m,3H); 3.65(m,3H); 3.22(s,9H,CH$_2$N(CH$_3$)$_3$); 2.46(m,1H); 2.3(s,3H,COCH$_3$); 1.7(m,1H).

MS(FAB):m/z 364(M+Na—H), 342(M$^+$), 332(M+Na—HCOCH$_3$).

EXAMPLE 91

[4R-[3(2R*,4R*)4alpha,5beta,6beta(R*)]]-2-[[Hydroxy[[4-[[6-(1-hydroxyethyl)-4-methyl-2-[[(4-nitrophenyl)methoxy]carbonyl]-7-oxo-1-azabicyclo [3.2.0]hept-2-en-3-yl]thio]tetrahydro-2-furanyl] methoxy]phosphinyl]oxy-N,N,N-trimethylethanaminium hydroxide, inner salt A solution of 0.190 g of Example 90 dissolved in 1.8 ml of anhydrous methyl alcohol at 0° C. is treated with 130 microliters of 4.37M solution of sodium methoxide. The reaction is stirred at 0° C. for 1 hour and then concentrated in vacuo to give the crude thiol which is used in the next step.

The crude thiol is mixed at −30° C. with 0.393 g of product from Example 15A, dissolved in a 1:1 mixture of acetonitrile:dimethylformamide, and 90 microliters of Hunig's base. The resulting solution is stirred at room temperature for 6 hours. The reaction solution is diluted with ethyl acetate to provide a foamy precipitate which is collected after trituration with ethyl acetate to give 0.387 g of the product mixture. A portion is purified to analytical purity using C$_{18}$ reverse-phase chromatography.

$^1$H NMR(MeOH-d$_4$):δ 8.21(d,2H); 7.70(d,2H); 5.40(d, 1H,J=13.9 Hz); 5.28(d,1H,J=13.9 Hz); 4.4–3.6(m,15H); 3.21(s,9H,N(CH$_3$)$_3$); 2.54(m,1H); 1.90–1.65(m,1H); 1.30 (m,6H).

EXAMPLE 92

[4R-[3(2R 4R*)4alpha,5beta,6beta(R*)]]-2-[[[[4-[[2-Carboxy-6-(1-hydroxyethyl)-4-methyl-7-oxo-1-azabicyclo[3.2.0]hept-2-en-3-yl]thio]tetrahydro-2-furanyl]methoxy]hydroxyphosphinyl]oxy]-N,N,N-trimethylethanaminium hydroxide inner salt monosodium salt The title compound is prepared by the procedure of Example 18 using 0.387 g of product from Example 91, 0.046 g of sodium bicarbonate, 4 ml of water, 19 ml of dioxane, and 0.050 g of 10% palladium/carbon to give 0.031 g of the desired product.

$^1$H NMR(D$_2$O):δ 4.35–3.75(m,13H); 3.63(br s,2H); 3.39 (m,1H); 3.19(d,9H,N(CH$_3$)$_3$); 2.52(m,1H); 1.8–1.52(m,1H); 1.25(d,3H,CH$_3$); 1.18(t,3H,CH$_3$).

MS(FAB):m/z 553(M+Na), 531(M+H).

EXAMPLE 93

Ethanethioic acid (3S-trans)-S-[5-[[[(2-bromoethoxy)hydroxyphosphinyl]oxy]methyl]-tetrahydro-3-furanyl]ester The title compound is prepared by the procedure of Example 89 using 1.0 g of product from Example 6, 19 ml of carbon tetrachloride, 1.03 ml of triethylamine, and 0.97 ml of 2-bromoethylphosphorodichloridate to give 0.896 g of the desired product.

$^1$H NMR(CDCl$_3$):δ 4.35(m,4H); 4.2–4.0(m,4H); 3.7(m, 1H); 3.58(m,2H); 2.35(s,3H,COCH$_3$); 2.28(m,1H); 2.0(m, 1H).

MS(FAB):m/z 363(M$^+$).

EXAMPLE 94

(2R-trans)-1-[2-[[[[4-(Acetylthio)tetrahydro-2-furanyl]methoxy]hydroxyphosphinyl]oxy]ethyl] pyridinium hydroxide inner salt The title compound is prepared by the procedure of Example 90 using 0.50 g of product from Example 93, 3 ml of pyridine, 4 g of Amberlyst-21, and 10 ml of methyl alcohol to give 0.233 g of the desired product.

$^1$H NMR(DMSO-d$_6$):δ 8.18(dd,2H,J=6.7 and 1.2 Hz); 7.80(tt,1H,J=6.7 and 1.2 Hz); 7.31(t,2H,J=6.7 Hz); 3.78(br s,2H); 3.5(m,2H); 3.38(dd,1H,J=9.1 and 6.2 Hz); 3.30(m, 1H); 3.17(m,1H); 2.93(m,2H); 2.74(dd,1H,J=9.1 and 6.2 Hz); 1.5(s,3H,COCH$_3$); 1.40(m,1H); 1.10(m,1H).

MS(FAB): 362(M+H).

EXAMPLE 95

[4R-[3(2R*,4S*)4alpha,5beta,6beta(R*)]]-1-[2-[[Hydroxy[[tetrahydro-4-[[6-(1-hydroxyethyl)-4-methyl-2-[[(4-nitrophenyl)methoxy]carbonyl]-7-oxo-1-azabicyclo[3.2.0]hept-2-en-3-yl]thio]-2-furanyl]methoxy]phosphinyl]oxy]ethyl]pyridinium hydroxide inner salt The title compound is prepared by the procedure of Example 91 using 0.209 g of product from Example 94, 130 microliter of 4.37M sodium methoxide, 2.06 ml of methyl alcohol, 0.406 g of product from Example 15A, 0.10 ml of Hunig's base to give 0.150 g of the desired product.

$^1$H NMR(MeOH-d$_6$):δ 9.0(d,2H); 8.60(t,1H); 8.24(d,2H); 8.11(t,2H); 7.69(d,2H); 5.38(q,2H,CH$_2$Ar); 4.30(br s,3H); 4.18(m,3H); 3.92(m,1H); 3.8–3.6(m,6H); 3.20(m,1H); 2.95 (m,1H); 2.18(m,1H); 1.19(d,3H); 1.12(m,3H).

EXAMPLE 96

[4R-[3(2R*,4S*)4alpha,5beta,6beta(R*)]]-1-[2-[[[[4-[[2-Carboxy-6-(1-hydroxyethyl)-4-methyl-7-oxo-1-azabicyclo[3.2.0]hept-2-en-3-yl]thio]tetrahydro-2-furanyl]methoxy]hydroxyphosphinyl]oxy]ethyl] pyridinium hydroxide inner salt monosodium salt The title compound is prepared by the procedure of Example 18 using 0.150 g of product from Example 95, 0.025 g of sodium bicarbonate, 3 ml of water, 9 ml of dioxane and 0.030 g of 10% palladium/carbon to give 0.0786 g of the desired product.

$^1$H NMR(D$_2$O):δ 8.98(d,2H,J=5.6 Hz); 8.69(m,1h); 8.2 (t,2H,J=6.5 Hz); 4.42(br s,2H); 4.37–4.22(m,5H); 4.00(m, 1H); 3.82–3.7(m,4H); 3.53(br m,1H); 3.45(t,1H), 2.19(m, 1H); 2.05(m,1H), 1.38(d,3H); 1.29(d,3H).

MS(FAB): 551(M+H).

EXAMPLE 97

(Dimethoxyphosphinyl)hydroxyacetic Acid (4-nitrophenyl)methyl ester

To a mixture of 4.32 g of p-nitrobenzyl glyoxalate and 2.0 ml of dimethylphosphite in 25 ml of benzene is added a catalytic amount of p-toluenesulfonic acid. The reaction is heated at reflux temperature for 1.5 hours. The formed water is removed using a Dean-Stark trap. After cooling, the solvent is removed in vacuo and the resulting crystals are slurried in ethyl acetate and collected to give 3.48 g of the desired product.

$^1$H NMR(CDCl$_3$):δ 8.3(d,2H); 7.73(d,2H); 5.42(AB q,2H); 4.91(d,1H); 3.75(dd,6H).

Ref.: E. Nakamura, Tet. Let., vol. 22, p 663 (1981).

EXAMPLE 98

(Dimethoxyphosphinyl)[[(1,1-dimethylethyl) dimethylsilyl]oxy]acetic acid (4-nitrophenyl)methyl ester To a mixture of 3.48 g of product from Example 97 and 12 ml of dimethylformamide is added 1.86 g of t-butyldimethylsilyl chloride and 1.86 g of imidazole. After stirring the reaction at room temperature for 2 hours, the mixture is diluted with 50% ethyl acetate/diethyl ether, washed 5 times with water, once with saturated sodium bicarbonate and once with saturated sodium chloride. The organic layer is dried, filtered and concentrated in vacuo to give 3.90 g of the desired silylated product.

$^1$H NMR(CDCl$_3$):δ 8.23(d,2H); 7.59(d,2H); 5.35(AB q,2H);4.71(d,1H); 3.84(d,3H); 3.61(d,3H); 0.91(s,9H); 0.11 (s,3H); 0.09(s,3H).

EXAMPLE 99

[2S-[2α(S*),3β(S*)]]-1-[(1,1-Dimethylethyl) dimethylsilyl]-3-[1-[[(1,1-dimethylethyl) dimethylsilyl]oxy]ethyl]-α-methyl-4-oxo-2-azetidineacetic acid Ten grams of (3S,4S)-3[(R)-1-(t-butyldimethylsilyloxy) ethyl]-4-[(R)-1-carboxyethyl]-2-azetidinone is dissolved, under argon, in 100 ml of anhydrous dimethylacetamide and treated with 10.46 g of t-butyldimethylsilyl chloride and 14.14 g of triethylamine. The reaction is stirred overnight at room temperature followed by dilution with hexane. The organic layer is washed with water and saturated sodium chloride, dried and concentrated in vacuo. The residue is treated with 100 ml of tetrahydrofuran and 100 ml of saturated sodium bicarbonate. The mixture is stirred at room temperature for 2.5 hours, diluted with 200 ml of diethyl ether and the layers separated. The organic layer is washed with saturated sodium chloride, dried and concentrated in vacuo to give 19 g of product as a yellow oil.

$^1$H NMR(CDCl$_3$):δ 6.62(bs,1H); 4.0(m,1H); 3.54(t,1H); 3.27(dd,1H); 2.83(m,1H); 1.18(d,3H); 1.14(d,3H); 0.85(m, 18H); 0.09(m,12H).

EXAMPLE 100

[3S-[3α(S*),4β(S*)]]-[(1,1-Dimethylethyl) dimethylsilyl]-3-[1[[(1,1-dimethylethyl) dimethylsilyl]oxy]ethyl]-4-(2-Hydroxy-1-methylethyl)-2-azetidinone To a 0° C. solution, under argon, of 25 g of product from Example 99 dissolved in 150 ml of anhydrous tetrahydrofuran is added 6.31 ml of borane-methyl sulfide complex. The reaction mixture is heated at reflux temperature for 1 hour, cooled to room temperature and concentrated in vacuo. The residue is purified by chromatography (silica gel: 20% ethyl acetate/hexane) to give 20.45 g of the desired product as a colorless oil.

$^1$H NMR(CDCl$_3$):δ 3.05(m,1H); 3.75(m,1H); 3.55(m, 1H); 3.46(m,1H); 3.06(dd,1H); 1.99(m,1H); 1.85(m,1H); 1.27(d,3H); 0.95(d,3H); 0.88(m,18H); 0.097(m,12H).

EXAMPLE 101

[2R-[2α(R*),3β(R*)]]-1-[(1,1-Dimethylethyl) dimethylsilyl]-3-[1-[[(1,1-dimethylethyl) dimethylsilyl]oxy]ethyl]-α-methyl-4-oxo-2-azetidineacetaldehyde A mixture of 14.3 g of product from Example 100 dissolved in 75 ml of methylene chloride is treated with 8.47 g of pyridinium chlorochromate, 3.5 g of sodium acetate and 5 g of diatomaceous earth. The reaction is heated at reflux for 30 minutes, diluted with 400 ml of diethyl ether and filtered through a pad of hydrous magnesium silicate. The solid residue is triturated with diethyl ether and diethyl ether passed through a pad of hydrous magnesium silicate. The combined filtrates are concentrated in vacuo, the residue is purified by chromatography (silica gel: 15 to 25% ethyl acetate/hexane) to give 8.95 g of the desired product as a tan solid.

$^1$H NMR(CDCl$_3$):δ 9.88(s,1H); 4.09(m,1H); 3.82(t,1H); 2.96(m,1H); 2.79(m,1H); 1.25(d,3H); 1.14(d,3H); 0.91(s, 9H); 0.89(s,9H); 0.09(d,12H).

EXAMPLE 102

[2S-[2α(S*-E),3β(S*)]]-4-[1-[(1,1-Dimethylethyl) dimethylsilyl]-3-[1-[[(1,1-dimethylethyl) dimethylsilyl]oxy]ethyl]-4-oxo-2-azetidinyl]-[[(1,1-dimethylethyl)dimethylsilyl]oxy]-2-pentenoic acid (4-nitrophenyl)methyl ester and

[2S-[2α(S*-Z),3β(S*)]]-4-[1-[(1,1-Dimethylethyl) dimethylsilyl]-3-[1-[[(1,1-dimethylethyl) dimethylsilyl]oxy]ethyl]-4-oxo-2-azetidinyl]-[[(1,1-dimethylethyl)dimethylsilyl]oxy]-2-pentenoic acid (4-nitrophenyl)methyl ester A mixture of 4.76 g of product from Example 98 in 30 ml of dry tetrahydrofuran, cooled to −40° C., under argon, is treated with 12 ml of 1M solution of lithium bis (trimethylsilyl)amide. After 5 minutes, 4.08 g of product from Example 101 in 5 ml of tetrahydrofuran is added dropwise and the temperature of the cooling bath is allowed to warm gradually (30 minutes) to 0° C. The reaction is diluted with diethyl ether and quenched with water. The organic layer is washed with water and saturated sodium chloride, dried and concentrated in vacuo. The residue is purified by filtration through silica gel eluting with 10% ethyl acetate/hexane to give 3.97 g of the product as a 88:12 mixture of E:Z isomers.

$^1$H NMR(CDCl$_3$):E isomer δ 8.2(d,2H); 7.6(d,2H); 5.5 (d,1H); 5.27(s,2H); 4.07(m,1H); 3.64(m,1H); 3.52(m,1H); 2.88(m,1H); 1.27(d,3H); 1.06(d,3H); 0.92(s,9H); 0.91(s, 9H); 0.89(s,9H); 0.21(s,3H); 0.1(s,3H); 0.09(s,3H); 0.087(s, 3H); 0.07(s,3H); 0.06(s,3H).

Z isomer δ 8.2(d,2H); 7.49(d,2H); 6.07(d,1H); 5.28(q, 2H); 4.09(m,1H); 3.56(m,1H); 3.18(m,1H); 2.93(dd,1H); 2.5(d,3H); 1.08(d,3H); 0.95(s,9H); 0.92(s,9H); 0.89(s,9H); 0.17(s,3H); 0.165(s,3H); 0.16(s,3H); 0.14(s,3H); 0.09(s, 3H); 0.06(s,3H).

EXAMPLE 103

[2S-[2α[S*(R*) and S*(S*)]3β(S*)]]-β-Bromo-1-[(1,1-Dimethylethyl)dimethylsilyl]-3-[1-[[(1,1-dimethylethyl)dimethylsilyl]oxy]ethyl]-gamma-methyl-α,4-dioxo-2-azetidinebutanoic acid (4-nitrophenyl)methyl ester To a cooled solution, under argon, of 0.0381 g of product from Example 102 in 0.5 ml of tetrahydrofuran is added 0.004 ml of bromine. The reaction is stirred for 15 minutes, quenched with 10% sodium thiosulfate and diluted with ethyl acetate. The organic layer is washed with saturated sodium chloride, dried and concentrated in vacuo. The residue is purified by flash chromatography (silica gel: 20% ethyl acetate/hexane). The pure bromide, as a mixture of diastereomers, 4:1, is obtained in quantitative yield.

$^1$H NMR(CDCl$_3$):δ 8.26(d,2H); 7.59(d,2H); 5.48–5.36 (AB q and d,3H); 5.05(d, minor isomer); 4.12–4.02(m,1H); 3.67(t,1H); 3.43(m,1H); 2.87(m, minor isomer); 2.58(m, 1H); 1.25(d,3H); 1.18(d,3H); 1.08(d, minor isomer); 0.98(s, minor isomer); 0.91(s,9H); 0.89(s,9H); 0.88(s, minor isomer); 0.33, 0.26, 0.07(3s, minor isomer); 0.21(s,3H); 0.13(s,3H); 0.1(s,3H); 0.06(s,3H).

EXAMPLE 104

(also Example 56)

[4R-[3(3R*,5S* and 3S*,5R*)4α,5β,6β(R*)]]-6-(1-Hydroxyethyl)-4-methyl-7-oxo-3-[[tetrahydro-5-(hydroxymethyl)-3-furanyl]thio]-1-azabicyclo[3.2.0]hept-2-ene-2-carboxylic acid (4-nitrophenyl)methyl ester A solution, under argon, of 0.5 g of product from Example 103, 0.119 g of product from Example 55 and 7 ml of dry tetrahydrofuran is treated with 0.124 ml of triethylamine. The reaction is stirred for 30 minutes, quenched and diluted with ethyl acetate. The organic layer is washed with water and saturated sodium chloride, dried and concentrated in vacuo. The residue is dissolved in 5 ml of acetonitrile and treated with 10 ml of 10% aqueous hydrofluoric acid. After 30 minutes, the reaction is quenched by pouring into rapidly stirring saturated sodium bicarbonate/ethyl acetate. The organic layer is washed with saturated sodium chloride, dried and concentrated in vacuo to give the crude deprotected β-lactam, which is used in the cyclization step without further purification.

The crude β-lactam, under argon, is dissolved in 5 ml of dry tetrahydrofuran and treated with 4.46 ml of 1M solution in methylene chloride of titanium tetrachloride. The reaction is stirred at room temperature for 2 hours and poured into rapidly stirring saturated sodium bicarbonate/ethyl acetate. The organic layers is washed once with water and twice with saturated sodium chloride, dried and concentrated in vacuo. The residue is purified by chromatography (silica gel: 20% ethyl acetate/hexane) to give 0.142 g of the desired product as a white solid.

$^1$H NMR(CDCl$_3$):δ 8.22(d,2H); 7.67(d,2H); 5.5(d,1H); 5.22(d,1H); 4.28(m,4H); 3.8(m,2H); 3.7(m,1H); 3.55(m, 1H); 3.32–4.1(m,1H); 3.3(m,1H); 2.3(m,1H); 2.18(bs,2H); 1.98(m,1H); 1.36(d,3H); 1.28(d,3H).

EXAMPLE 105

(also Example 78)

[4R-[3(3R*,5R* and 3S*,5S*)4α,5β,6β(R*)]]-6-(1-Hydroxyethyl)-4-methyl-7-oxo-3-[[tetrahydro-5-(hydroxymethyl)-3-furanyl]thio]-1-azabicyclo[3.2.0]hept-2-ene-2-carboxylic acid (4-nitrophenyl)methyl ester The title compound is prepared by the procedure of Example 104 using 0.166 g of product from Example 103, 0.0396 g of product from Example 77, 2.3 ml of dry tetrahydrofuran and 0.0413 ml of triethylamine to obtain the crude β-lactam. The subsequent cyclization uses the above product, 1.48 ml of 1M solution in methylene chloride of titanium tetrachloride and 1.6 ml of dry tetrahydrofuran to give 0.053 g of the desired product as a white solid.

$^1$H NMR(CDCl$_3$):δ 8.23(d,2H); 7.66(d,2H); 5.51(d,1H); 5.24(d,1H); 4.37(m,2H); 4.13(m,2H); 3.75(m,3H); 3.6(m, 2H); 3.29(m,2H); 2.44(m,2H); 2.17(m,1H); 1.2–1.4(m,6H).

EXAMPLE 106

(4R-trans)-2-(2-Propenyl)-1,3,2-dioxoaborolane-4,5-dicarboxylic acid bis(1-methylethyl)ester To 400 ml of diethyl ether, under anhydrous conditions at −78° C., is added simultaneously, with vigorous stirring, 475 ml of 1M in diethyl ether allylmagnesium bromide and 60 ml of triethyl borate in 400 ml of diethyl ether. The reaction is stirred at −78° C. for 3 hours; followed by the removal of the cooling bath and dropwise addition (over 2.5 hours) of 450 ml of 2N hydrochloric acid. The layers are separated and the aqueous layer is extracted 4 times with a mixture of diethyl ether:methylene chloride (5:1). The organic layers are combined, dried and concentrated in vacuo to approximately 100 ml. The residue is redissolved in 400 ml of diethyl ether, treated with 77.8 g of (−)-diisopropyl L-tartrate, and stirred overnight at room temperature under argon. Ten grams of magnesium sulfate is added and the mixture stirred for 20 minutes. The reaction is concentrated in vacuo to give 90 g of crude product. The residue is purified by Kugelrohr distillation (100° C. to 110° C.) to give 39.35 g of product.

$^1$H NMR(CDCl$_3$):δ 5.82–5.96(m,1H); 4.97–5.16(m,4H); 4.78(s,2H); 1.92(d,2H); 1.3(d,12H).

EXAMPLE 107

(S)-1-Phenylmethoxy-4-penten-2-ol

To a mixture of 40.0 g of product from Example 106 in 560 ml of dry methylene chloride with 30 g of 4A° molecular sieves, under anhydrous conditions at −78° C., is added 11.2 g of product from Example 1 in 9.6 ml of methylene chloride. The reaction is stirred vigorously while maintaining the temperature at −78° C. for 16 hours. The reaction is filtered, the molecular sieves are washed with methylene chloride and the aqueous layer is extracted with methylene chloride. The combined organic layers are concentrated in vacuo and the residue dissolved in 400 ml of diethyl ether. The diethyl ether layer is stirred for 24 hours with 600 ml of 1M potassium hydroxide. The aqueous layer is extracted with diethyl ether. The combined organic layers are washed with saturated sodium bicarbonate and concentrated in vacuo. The crude residue is purified by Kugelrohr distillation (100° C. to 110° C.) to give 13.4 g of the desired product.

$^1$H NMR(CDCl$_3$):δ 7.35(s,5H); 5.8(m,1H); 5.1(m,2H); 4.55(s,2H); 3.85(m,1H); 3.48(dd,1H); 3.35(dd,1H); 2.68(bs, 1H); 2.25(t,2H).

EXAMPLE 108

2,5-Anhydro-1,3-dideoxy-1-iodo-D-threo-pentitol and 2,5-Anhydro-1,3-dideoxy-1-iodo-D-erythro-pentitol To a 3° C. vigorously stirring solution of 13.4 g of product from Example 107 dissolved in 262 ml of diethyl ether and 89 ml of water is added, in one portion, 8.73 g of sodium bicarbonate followed by 26.21 g of iodine. The reaction is stirred at room temperature for 1.5 hours. Saturated sodium sulfite is added slowly with vigorous stirring. The layers are separated and the organic layer is dried and concentrated in vacuo. The residue is purified by chromatography (silica gel: 20 to 50% ethyl acetate/hexane) to give 1.3 g of the cis-isomer (A) and 4.7 g of the trans-isomer (B).

$^1$H NMR(CDCl$_3$): cis-isomer δ 4.51–4.55(m,1H); 4.04–4.13(m,1H); 3.91–3.96(dd,1H); 3.78–3.83(dd,1H); 3.33–3.43(m,2H); 3.05(bs,1H,OH); 2.3–2.39(m,1H); 1.89 (m,0.5H); 1.79(m,0.5H).

$^1$H NMR(CDCl$_3$): trans-isomer δ 4.54–4.57(m,1H); 4.17–4.26(m,1H); 4.04–4.08(m,1H); 3.80–3.85(m,1H); 3.27–3.31(m,2H); 2.68(bs,1H,OH); 2.21–2.2(m,1H); 1.74–1.84(m,1H).

EXAMPLE 109

2,5-Anhydro-1-azido-1,3-dideoxy-D-threo-pentitol

To a mixture of 1.25 g of product from Example 108(cis-isomer) in 5 ml of dry dimethylformamide is added 0.537 g of lithium azide. The reaction is heated at 70° C. for 2 hours and then concentrated in vacuo. The residue is purified by chromatography (silica gel: diethyl ether) to give 0.642 g of the desired product.

IR(neat): 2100 cm$^{-1}$.

$^1$H NMR(CDCl$_3$):δ 4.4–4.5(bs,1H); 4.1–4.2(m,1H); 3.73–3.91(m,3H); 3.45(m,2H); 2.23–2.36(m,1H); 1.71–1.76 (m,0.5H); 1.66–1.71(m,0.5H).

EXAMPLE 110

2,5-Anhydro-1-azido-1,3-dideoxy-D-threo-pentitol 4-(trifluoromethanesulfonate)

The title compound is prepared by the procedure of Example 22 using 0.642 g of product from Example 109, 0.8 ml of trifluoromethanesulfonic anhydride and 0.38 ml of pyridine to give 0.890 g of pure product after chromatography (silica gel: diethyl ether).

IR(neat): 2104 cm$^{-1}$.

$^1$H NMR(CDCl$_3$):δ 5.5(m,1H); 4.3(m,2H); 3.9(m,1H); 3.4(m,2H); 2.6(m,1H); 2.2(m,1H).

EXAMPLE 111

1,4-Anhydro-5-azido-3,5-dideoxy-2-thio-D-erythropentitol 2-acetate

To an argon purged solution, cooled to 0° C., of 0.89 g of product from Example 110 dissolved in 10 ml of acetonitrile is added, in one portion, 0.406 g of potassium thioacetate. The reaction is stirred at 0° C. for 10 minutes and then allowed to warm to room temperature, slowly over 1.5 hours. The mixture is concentrated in vacuo and the residue purified by chromatography (silica gel: 30% ethyl acetate/hexane) to give 0.422 g of the desired product.

$^1$H NMR(CDCl$_3$):δ 4.25–4.35(dd,1H); 4.35–4.25(m,1H); 4.0–4.07(m,1H); 3.6–3.69(dd,1H); 3.47–3.40(dd,1H); 3.30–3.22(dd,1H); 2.34(s,3H,Me); 2.25–2.15(m,1H); 2.1–1.92(m,1H).

IR(neat): 2100(N$_3$) and 1692(SAc)cm$^{-1}$.

EXAMPLE 112

1,4-Anhydro-5-azido-3,5-dideoxy-2-thio-D-erythropentitol

The title compound is prepared by the procedure of Example 16 using 0.420 g of product from Example 111, 0.48 ml of 25 wt % sodium methoxide/methyl alcohol to give 0.216 g of the desired product after chromatography (silica gel: 30% ethyl acetate/hexane).

$^1$H NMR(CDCl$_3$):δ 4.25–4.4(m,1H); 4.18–4.24(dd,1H); 3.78–3.86(dd,0.5H); 3.54–3.66(m,1H); 3.4–3.54(m,1.5H); 3.18–3.29(m,1H); 2.15–2.25(m,1H); 1.88–1.98(m,1H); 1.78 (d,1H,SH).

EXAMPLE 113

2-[4R-[4α,5β,6β(R*)]]-1,4-Anhydro-5-azido-3,5-dideoxy-2-S-[6-(1-hydroxyethyl)-4-methyl-2-[[(4-nitrophenyl)methoxy]carbonyl]-7-oxo-1-azabicyclo[3.2.0]-hept-2-en-3-yl]-2-thio-D-erythro-pentitol The title compound is prepared by the procedure of Example 17 using 0.215 g of product from Example 112, 0.883 g of product from Example 15 and 198 microliter of Hunig's base to give 0.288 g of the desired product after chromatography (silica gel: 75% ethyl acetate/hexane).

IR(neat): 2101, 1769 and 1709 cm$^{-1}$.

$^1$H NMR(CDCl$_3$):δ 8.25(d,2H); 7.7(d,2H); 5.5(d,1H); 5.3 (d,1H); 4.15–4.3(m,4H); 3.7–3.85(m,1H); 3.57–3.66(m, 1H); 3.26–3.5(m,2H); 3.15–3.26(m,2H); 2.57(bs,1H,OH); 2.08–2.25(m,1H); 1.85–2.05(m,1H); 1.28(d,3H,Me); 1.21 (d,3H,Me).

EXAMPLE 114

2-[4R-[4α,5β,6β(R*)]]-5-Amino-1,4-anhydro-2-S-(2-carboxy-6-(1-hydroxyethyl)-4-methyl-7-oxo-1-azabicyclo[3.2.0]hept-2-en-3-yl)-3,5-dideoxy-2-thio-D-erthro-pentitol The title compound is prepared by the procedure of Example 18 using 0.288 g of product from Example 113, 0.198 g of 10% palladium/carbon, 12 ml of phosphate buffer (pH 7), and 35 ml of dioxane to give 0.070 g of the desired product after chromatography (C$_{18}$ reverse phase silica gel plates: 95/5 water/ethyl alcohol).

¹H NMR(D₂O):δ 4.45–4.59(m,1H); 4.22–4.38(m,3H); 3.98–4.11(m,1H); 3.82–3.9(m,1H); 3.4–3.58(m,2H); 3.2–3.3(m,1H); 3.08–3.18(m,1H); 2.12–2.35(m,2H); 1.36 (d,3H,Me); 1.27(d,3H,Me).

EXAMPLE 115

2,5-Anhydro-1-azido-1,3-dideoxy-D-erythro-pentitol

The title compound is prepared by the procedure of Example 109 using 2.3 g of product from Example 108 (trans-isomer), 0.988 g of lithium azide and 4 ml of dimethylformamide to give 1.42 g of the desired product after chromatography (silica gel: diethyl ether).

IR(neat): 2100 cm⁻¹.

¹H NMR(CDCl₃):δ 4.56(m,1H); 4.35–4.45(m,1H); 3.98–4.12(dd,1H); 3.78–3.87(dd,1H); 3.47–3.55(dd,1H); 3.2–3.3(dd,1H); 2.65(bs,1H,OH); 1.95–2.05(m,1H); 1.83–1.95(m,1H).

EXAMPLE 116

2,5-Anhydro-1-azido-1,3-dideoxy-D-erythro-pentitol 4-(trifluoromethanesulfonate

The title compound is prepared by the procedure of Example 22 using 1.42 g of product from Example 115, 1.8 ml of trifluoromethanesulfonic anhydride and 0.85 ml of pyridine to give 22.2 g of the desired product after chromatography (silica gel: 75% ethyl acetate/hexane).

IR(neat): 2104 cm⁻¹.

¹H NMR(CDCl₃):δ 5.58(m,1H); 4.38–4.48(m,1H); 4.1–4.27(m,2H); 3.58–3.68(dd,1H); 3.22–3.32(dd,1H); 2.3–2.4(m,1H); 2.16–2.26(m,2H).

EXAMPLE 117

2,5-Anhydro-1-azido-1,3-dideoxy-4-thio-L-threo-pentitol

The title compound is prepared by the procedure of Example 111 using 2.22 g of product from Example 116, 1.01 g of potassium thioacetate and 25 ml of acetonitrile to give 0.90 g of the desired product after chromatography (silica gel: 30% ethyl acetate/hexane).

IR(neat): 2100 and 1692 cm⁻¹.

¹H NMR(CDCl₃):δ 4.1–4.2(m,2H); 3.95–4.08(m,1H); 3.7–3.78(dd,1H); 3.4–3.50(dd,1H); 3.25–3.35(dd,1H); 2.42–2.53(m,1H); 2.34(s,3H,Me); 1.63–1.74(m,1H).

EXAMPLE 118

2,5-Anhydro-1-azido-1,3-dideoxy-4-thio-L-threo-pentitol

The title compound is prepared by the procedure of Example 16 using 0.90 g of product from Example 117, 1.1 ml of 25 wt. % sodium methoxide/methyl alcohol and 15 ml of tetrahydrofuran to give 0.441 g of the desired product after chromatography (silica gel: 30% ethyl acetate/hexane).

IR(neat): 2570 and 2099 cm⁻¹.

¹H NMR(CDCl₃):δ 4.0–4.25(m,2H); 3.57–3.67(m,1H); 3.25–3.5(m,3H); 2.4–2.55(m,1H); 1.82(d,1H,SH); 1.6–1.75 (m,1H).

EXAMPLE 119

2-[4R-[4α,5β,6β(R*)]]-2,5-Anhydro-1-azido-1,3-dideoxy-4-S-[6-(1-hydroxyethyl)-4-methyl-2-[[(4-nitrophenyl methoxy]carbonyl]-7-oxo-1-azabicyclo[3.2.0]hept-2-en-3-yl]-4-thio-L-threo-pentitol The title compound is prepared by the procedure of Example 17 using 0.441 g of product from Example 118 in 10 ml of acetonitrile, 1.8 g of product from Example 15 in 10 ml of acetonitrile and 0.41 ml of Hunig's base to give 0.747 g of the desired product after chromatography (silica gel: 75% ethyl acetate/hexane).

IR(KBr): 2101, 1769 and 1708 cm⁻¹.

¹H NMR(CDCl₃):δ 8.25(d,2H); 7.7(d,2H); 5.55(d,1H); 5.28(d,1H); 4.12–4.4(m,4H); 3.8–3.95(m,2H); 3.32–3.58 (m,4H); 3.03(bs,1H,OH); 2.48–2.65(m,1H); 1.85–1.96(m, 0.5H); 1.68–1.78(m,0.5H); 1.42(d,3H,Me); 1.35(m,3H,Me).

EXAMPLE 120

2-[4R-[4α,5β,6β(R*)]]-1-Amino-2,5-anhydro-4-S-(2-carboxy-6-(1-hydroxyethyl)-4-methyl-7-oxo-1-azabicyclo[3.2.0]hept-2-en-3-yl)-1,3-dideoxy-4-thio-L-threo-pentitol The title compound is prepared by the procedure of Example 18 using 0.747 g of product from Example 119, 0.513 g of 10% palladium/carbon, 30 ml of sodium phosphate buffer (pH 7) and 90 ml of dioxane to give 0.153 g of the desired product after chromatography (C₁₈ reverse phase silica gel plates: 95% aqueous ethyl alcohol).

¹H NMR(D₂O):δ 4.02–4.35(m,4H); 3.72–3.94(m,2H); 3.26–3.43(m,2H); 3.05–3.94(m,2H); 2.5–2.7(m,1H); 1.7–1.8(m,0.5H); 1.5–1.6(m,0.5H); 1.2–1.25(d,3H,Me); 1.10–1.17(q,3H,Me).

EXAMPLE 121 cis and trans-(±)-Tetrahydro-5-(iodomethyl)-3-furanol

The title compound is prepared by the procedure of Example 108 using 19.2 g of product from Example 2 in 385 ml of diethyl ether and 128 ml of water, 12.52 g of sodium bicarbonate and 37.56 g of iodine to give 13.16 g of the product as a mixture of isomers.

EXAMPLE 122 cis-(±)-Tetrahydro-5-(iodomethyl)-3-furanol trans-(±)-Tetrahydro5-(iodomethyl)-3-furanol A 1.6 g portion of the mixed isomer product of Example 121 is purified by chromatography (silica gel: 30% ethyl acetate/hexane) to give 0.341 g of Isomer A and 0.994 g of Isomer B.

Isomer A(cis) CI-MS: m/z 246 (M+NH₄)⁺.

Isomer β(trans) CI-MS: m/z 246 (M+NH₄)⁺.

EXAMPLE 123 trans-(±)-5-[(Ethylamino)methyl]tetrahydro-3-furanol

A solution of 4.0 g of product from Example 121, Isomer B, and 20 ml of 70% aqueous ethylamine is stirred at room temperature, in a pressure bottle, for 60 hours. The reaction is concentrated in vacuo and the residue purified by chromatography (silica gel: 30% methyl alcohol/chloroform) to give 3.2 g of the desired product.

¹H NMR(CDCl₃):δ 5.1(bs,H₂O, NH+OH); 4.58–4.75(m, 2H); 4.2–4.26(dd,1H); 3.39–3.99(m,1H); 3.1–3.5(m,4H); 2.25–2.35(m,1H); 2.0–2.1(m,1H); 1.55(3H,Me). CI-MS: m/z 146 (MH⁺).

EXAMPLE 124 trans-(±)-Ethyl[(tetrahydro-4-hydroxy-2-furanyl) methyl]carbamic acid (4-nitropheny)methyl ester Under anhydrous conditions with an argon purge, a solution of 3.2 g of product from Example 123 in 10 ml of dry tetrahydrofuran and 2.7 ml of Huning's base is cooled to −5° C. The mixture is treated with 4.75 g of 4-nitrobenzyl chloroformate in 20 ml of methylene chloride while maintaining the temperature at −5° C. The reaction is stirred at −5° C. for 2 hours; followed by concentration in vacuo. The residue is purified by chromatography (silica gel: 75% ethyl acetate/hexane) to give 2.63 g of the desired product.

¹H NMR(CDCl₃):δ 8.2(d,2H); 7.6(d,2H); 5.3(s,2H); 4.6 (m,1H); 4.28–4.42(m,1H); 3.92–4.02(dd,1H); 3.7–3.78(d, 1H); 3.5–3.6(dd,1H); 3.38–3.49(m,2H); 3.2–3.3(dd,1H); 2.08(bs,1H,OH); 1.92–2.05(m,1H); 1.6–1.77(m,1H); 1.16(t, 3H).

EXAMPLE 125 trans-(±)-Methanesulfonic acid 5-[[Ethyl[[(4-nitrophenyl)methoxy]carbonyl]amino]methyl] tetrahydro-3-furanyl ester To a −5° C. solution, under argon, of 2.63 g of product from Example 124, 1.7 ml of triethylamine and 18 ml of methylene chloride is added, dropwise, 0.94 ml of methanesulfonyl chloride. The reaction is stirred at −5° C. for one hour, washed successively with saturated sodium chloride, 5% sodium bicarbonate and saturated sodium chloride, dried and concentrated in vacuo. The residue is purified by chromatography (silica gel: 75% ethyl acetate/hexane) to give 3.18 g of the desired product.

¹H NMR(CDCl₃):δ 8.2(d,2H); 7.6(d,2H); 5.3(m,1H); 5.25(s,2H); 4.23–4.40(m,1H); 4.08–4.19(m,1H); 3.34–4.02 (m,1H); 3.22–3.62(m,4H); 3.05(s,3H,Me); 2.28–2.38(dd, 1H); 1.75–1.95(m,1H); 1.16(t,3H,Me).

EXAMPLE 126 cis-(±)-Ethanethioic acid S-[5-[[ethyl[[(4-nitrophenyl)methoxy]carbonyl]amino]methyl] tetrahydro-3-furanyl]ester A solution of 3.18 g of product from Example 125 in 10 ml of toluene and 10 ml of dimethylformamide is purged with argon. To this solution is added 1.36 g of potassium thioacetate and the reaction mixture is heated overnight at 65° C. in an oil bath with continuous stirring. The reaction mixture is cooled and diluted with 70 ml of water and 80 ml of toluene. The organic phase is washed with water, dried and concentrated in vacuo to give a dark yellow oil. The residue is purified by chromatography (silica gel: 50% ethyl acetate/hexane) to give 2.283 g of the desired product.

IR(neat): 1698 cm⁻¹.

¹H NMR(CDCl₃):δ 8.2(d,2H); 7.6(d,2H); 5.25(s,2H) 4.02–4.18(m,2H); 3.9–4.02(m,1H); 3.65–3.75(m,1H); 3.5–3.6(dd,1H); 3.38–3.5(m,4H); 3.2–3.3(dd,1H); 2.37–2.52(m,1H); 2.32(s,3H,Me); 1.45–1.6(m,1H); 1.16(t, 3H,Me).

EXAMPLE 127 cis-(±)-Ethyl[(tetrahydro-4-mercapto-2-furanyl) methyl]carbamic acid (4-nitrophenyl)methyl ester A 0°–5° C. solution, purged with argon, of 0.737 g of product from Example 126 in 5 ml of methyl alcohol is treated with 0.525 ml of 4N sodium hydroxide. The reaction is stirred for 10 minutes, acidified with 2.17 ml of 0.968N hydrochloric acid and diluted with 20 ml of ethyl acetate. The organic layer is washed with saturated sodium chloride, dried and concentrated in vacuo. The residue is purified by is chromatography (silica gel: 50% ethyl acetate/hexane) to give 0.483 g of the desired product.

¹H NMR(CDCl₃):δ 8.2(d,2H); 7.6(d,2H); 5.3(s,2H); 4.02–4.23(m,2H); 3.25–3.65(m,6H); 2.4–2.55(m,1H); 1.75–1.8(d,1H); 1.45–1.6(m,1H); 1.16(t,3H).

EXAMPLE 128

[4R-[3(3R*,5R* and 3S*,5S*),4α,5β,6β(R*)]]-3-[[5-[[Ethyl[[(4-nitrophenyl)methoxy]carbonyl]amino] methyl]tetrahydro-3-furanyl]thio]-6-(1-hydroxyethyl)-4-methyl-7-oxo-1-azabicyclo[3.2.0] hept-2-ene-carboxylic acid (4-nitrophenyl)methyl ester The title compound is prepared by the procedure of Example 17 using 0.483 g of product from Example 127 in 5 ml of acetonitrile, 0.923 g of product from Example 15 in 5 ml of acetonitrile and 0.21 ml of Hunig's base to give 0.63 g of the desired product after chromatography (silica gel: 75% to 80% ethyl acetate/hexane).

¹H NMR(CDCl₃):δ 8.2(d,4H); 7.68(d,2H); 7.52(dd,2H); 5.5(dd,1H); 5.3(dd+s,3H); 4.0–4.35(m,4H); 3.7–3.85(m, 2H); 3.25–3.65(m,6H); 2.4–2.55(m,1H); 1.5–1.8(m,1H+1 OH); 1.37(d,3H,Me); 1.27(t,3H,Me); 1.6(t,3H,Me of Et).

EXAMPLE 129

[4R-[3(3R*,5R* and 3S*,5S*),4α,5β,6β(R*)]]-3-[(5-[[Ethylamino)methyl]tetrahydro-3-furanyl]thio]-6-(1-hydroxyethyl)-4-methyl-7-oxo-1-azabicyclo [3.2.0]hept-2-ene-carboxylic acid The title compound is prepared by the procedure of Example 18 using 0.755 g of product from Example 128, 0.345 g of 10% palladium/carbon, 11 ml of sodium phosphate buffer (pH 7) and 33 ml of dioxane to give 0.118 g of the desired product after chromatography (C₁₈ reverse phase silica gel plates: 20% acetonitrile/water).

¹H NMR(D₂O):δ 4.3–6.0(m,4H); 4.0–4.2(m,2H); 3.3–3.7 (m,6H); 2.8–2.95(m,1H); 1.95–2.05(m,0.5H); 1.75–1.85(m, 0.5H); 1.4–1.6(m,9H,3Me).

MS(FAB): m/z 371 (M+H); 393 (M+Na); 741 (2M+H).

EXAMPLE 130 cis-(±)-5-[(Ethylamino)methyl]tetrahydro-3-furanol

The title compound is prepared by the procedure of Example 123 using 5.0 g of product from Example 122 Isomer A and 25 ml of 70% aqueous ethylamine to give 4.6 g of the product after chromatography (silica gel: 30% methyl alcohol/chloroform).

EXAMPLE 131 cis-(±)-Ethyl-[(tetrahydro-4-hydroxy-2-furanyl) methyl]carbamic acid (4-nitrophenyl]methyl ester The title compound is prepared by the procedure of Example 124 using 4.6 g of product from Example 130, 4.73 g of 4-nitrobenzyl chloroformate, 2.7 ml of Hunig's base, 25 ml of methylene chloride and 7 ml of tetrahydrofuran to give 2.035 g of the desired product after chromatography (silica gel: 75% ethyl acetate/hexane).

EXAMPLE 132 cis-(±)-Ethyl[[Tetrahydro-4-[(methylsulfonyl)oxy]-2-furanyl]methyl carbamic acid (4-nitrophenyl) methyl ester The title compound is prepared by the procedure of Example 125 using 2.035 g of product from Example 131, 1.31 g of triethylamine, 0.73 g of methanesulfonyl chloride and 14 ml of methylene chloride to give 3.18 g of the desired product after chromatography (silica gel: 75% ethyl acetate/hexane).

EXAMPLE 133 trans-(±)-Ethanethioic acid S-[5-[[ethyl[[(4-nitrophenyl)methoxy]carbonyl]amino] methyltetrahydro-3-furanyl]ester The title compound is prepared by the procedure of Example 126 using 3.1 g of product from Example 132, 1.05 g of potassium thioacetate, 10 ml of dimethylformamide and 10 ml of toluene to give 1.9 g of the desired product after chromatography (silica gel: 75% ethyl acetate/hexane).

$^1$H NMR(CDCl$_3$):δ 8.23(d,2H); 7.52(d,2H); 5.25(s,2H); 4.1–4.32(m,2H); 3.92–4.02(m,1H); 3.18–3.65(m,5H); 2.32 (s,3H,Me); 1.0–2.12(m,2H); 1.18(t,3H,Me).

EXAMPLE 134 trans-(±)-Ethyl[(tetrahydro-4-mercapto-2-furanyl) methyl]carbamic acid (4-nitrophenyl)methyl ester The title compound is prepared by the procedure of Example 127 using 0.573 g of product from Example 133, 0.39 ml of 4N sodium hydroxide, 1.52 ml of 0.968N hydrochloric acid and 3.75 ml of methyl alcohol to give 0.382 g of the desired product after chromatography (silica gel: 50% ethyl acetate/hexane).

$^1$H NMR(CDCl$_3$):δ 8.2(d,2H); 7.49(d,2H); 5.2(s,2H); 4.18–4.30(m,1H); 4.02–4.15(m,1H); 3.1–3.5(m,6H), 1.92–2.1(m,1H); 1.75–1.9(m,1H); 1.69(d,1H,SH); 1.08(t, 3H,Me).

EXAMPLE 135

[4R-[3(3R*,5S* and 3S*,5R*),4α,5β,6β(R*)]]-3-[[5-[[Ethyl[[(4-nitrophenyl)methoxy]carbonyl]amino] methyl]tetrahydro-3-furanyl]thio]-6-(1-hydroxyethyl)-4-methyl-7-oxo-1-azabicyclo[3.2.0] hept-2-ene-2-carboxylic acid (4-nitrophenyl)methyl ester The title compound is prepared by the procedure of Example 17 using 0.382 g of product from Example 134 in 4 ml of acetonitrile, 0.723 g of product from Example 15 in 4 ml of acetonitrile and 170 microliters of Hunig's base to give 0.527 g of the desired product after chromatography (silica gel: 75% ethyl acetate/hexane).

$^1$H NMR(CDCl$_3$):δ 8.2(dd,4H); 7.65(d,2H); 7.52(d,2H); 5.52(d,2H); 5.23(s,4H); 5.22(d,2H); 4.2–4.35(m,4H); 3.2–3.85(m,8H); 1.7–2.2(m,2H+OH); 1.37(dd,3H,Me); 1.27 (dd,3H,Me); 1.15(t,3H,Me of Et).

EXAMPLE 136

[4R-[3(3R*,5R* and 3S*,5S*),4α,5β,6β(R*)]]-3-[(5-[[Ethylamino)methyl]tetrahydro-3-furanyl]thio]-6-(1-hydroxyethyl)-4-methyl-7-oxo-1-azabicyclo [3.2.0]hept-2-ene-2-carboxylic acid The title compound is prepared by the procedure of Example 18 using 0.510 g of product from Example 135, 0.239 g of 10% palladium/carbon, 7.5 ml of sodium phosphate buffer (pH 7) and 22 ml of dioxane to give 0.040 g of the desired product after chromatography (C$_{18}$ reverse phase silica gel plates: 30% acetonitrile/water).

EXAMPLE 137

Ethanethioic Acid S-[3,4-dibromo-1-[(phenylmethoxymethyl)butyl]ester

To a 0° C. solution, under argon, of 1.44 ml of triflic anhydride in 20 ml of methylene chloride is added, sequentially, 0.69 ml of pyridine and 2.51 g of product from Example 3 in 5 ml of methylene chloride. The reaction is stirred for 15 minutes, followed by dilution with diethyl ether. The mixture is filtered and concentrated in vacuo to give the desired triflate.

To the triflate, at 0° C., is added, sequentially, 0.8657 g of thiolacetic acid and 0.61 ml of triethylamine. The reaction is warmed to room temperature and stirred for 6 hours. The reaction mixture is washed with water and extracted with diethyl ether. The diethyl ether extract is washed with sodium bicarbonate, water, dried and concentrated in vacuo. The residue is purified by chromatography (silica gel: 50–100% methylene chloride/hexane) to give 0.638 g of the desired product.

$^1$H NMR(CDCl$_3$):δ 7.35(m,10H); 4.56(m,5H); 4.34–3.82 (m,6H); 3.72–3.51(m,5H).

IR(neat): 2920, 1693, 699 and 629 cm$^{-1}$.

CI-MS: m/z 411(M$^+$+H).

EXAMPLE 138

4-Bromotetrahydro-2-[(phenylmethoxy)methyl] thiophene diastereomers

A 0° C. solution, under argon, of 0.638 g of product from Example 137 in 16 ml of dry methyl alcohol is treated with 0.39 ml of 4.37M sodium methoxide. The reaction is stirred for 2 hours at 0° C. followed by 2 hours at room temperature. The reaction mixture is concentrated i vacuo and the residue is purified by chromatography (silica gel: 0–20% ethyl acetate/hexane) to give 0.413 g of the product as a mixture of diastereomers.

$^1$H NMR(CDCl$_3$):δ 7.34(m,10H); 4.55(m,5H); 4.22(m, 1H); 3.79(m,1H); 3.5(m,6H); 3.35(m,1H); 3.21(m,1H); 3.10 (m,1H); 2.75(m,1H); 2.34(m,2H); 1.90(m,1H).

IR(neat): 2930 cm$^{-1}$.

CI-MS: m/z 287(M+H) and 207(M+H–PhCH$_2$).

EXAMPLE 139

Ethanethioic acid S-[tetrahydro-5-[(phenylmethoxy) methyl]-3-thienyl]ester diastereomers A mixture, under argon, of 0.384 g of product from Example 138, 0.353 g of 18-crown-6, 0.183 g of potassium thioacetate and 2 ml of acetonitrile is heated under reflux temperature for 1.5 hours and stirred at room temperature overnight. The reaction mixture is diluted with water, extracted with ethyl acetate, the organic layer washed with saturated sodium chloride, dried and concentrated in vacuo. The residue is purified by chromatography (silica gel: 5–10% ethyl acetate/hexane) to give 0.0803 g of the product.

$^1$H NMR(CDCl$_3$):δ 7.33(m,5H); 4.55(s,2H); 4.10(m,1H); 3.64(m,1H); 3.50(m,2H); 3.22(m,1H); 2.75(m,1H); 2.30(s, 3H); 2.20(m,1H); 2.05(m,1H).

IR(neat): 2924, 1692 and 1028 cm$^{-1}$.

CI-MS: m/z 283(M$^+$+H).

EXAMPLE 140

Ethanethioic acid S-[tetrahydro-5-(iodomethyl)-3-thienyl]ester

A 0° C. mixture, under argon, of 0.44 g of product from Example 139 in 5 ml of dry chloroform is treated with 0.55 ml of trimethylsilyl iodide. The reaction is stirred, in the dark, for 2 hours. The reaction is quenched with 100 ml of saturated sodium sulfite, extracted with methylene chloride and the layers separated. The organic layer is dried, filtered and concentrated in vacuo. The residue is purified by chromatography (silica gel: 0 –100% methylene chloride/hexane) to give 0.31 g of the product.

$^1$H NMR(CDCl$_3$):δ 4.64(m,1H); 4.10(m,2H); 3.78(m, 1H); 3.40(m,1H); 3.30–3.0(m,6H); 2.85(m,1H); 2.75(m, 1H); 2.60–2.40(m,2H); 2.6(s,2SH); 2.21(m,1H).

IR(neat): 2916 and 1687 cm$^{-1}$.

CI-MS: m/z 303(M$^+$+H) and 175 (M$^+$–I, base).

EXAMPLE 141

Ethanethioic acid S-[5-(azidomethyl)tetrahydro-3-thienyl]ester

A solution, under argon, of 0.183 g of product from Example 140 in 1.0 ml of dry methylene chloride is treated with 0.689 g of tetra-n-butylammonium azide. The reaction mixture is stirred vigorously overnight at room temperature. The reaction is concentrated in vacuo and the residue purified by chromatography (silica gel: 0–10% diethyl ether/hexane) to give 0.061 g of the desired product.

$^1$H NMR(CDCl$_3$):δ 4.35–4.10(m,3H); 3.85(m,1H); 3.6 (m,1H); 3.34(d,2H,J=6.7 Hz); 3.32(dd,1H,J=11.0 and 3.0 Hz); 2.94(dd,1H,J=11.0 and 6.04 Hz); 2.80(m,2H); 2.6(m, 2H).

IR(neat): 2099 and 1690 cm$^{-1}$.

CI-MS: m/z 188(M$^+$–N$_2$–H).

EXAMPLE 142

5-(Azidomethyl)tetrahydro-3-thiophenethiol

A 0° C. solution, under argon, of 0.279 g of product from Example 141 in 3 ml of dry methyl alcohol is treated with 0.35 ml of 4.35M sodium methoxide. After 2 hours, the reaction mixture is concentrated in vacuo and the residue purified by chromatography (silica gel: 0–5% diethyl ether/hexane) to give 0.0465 g of the desired product.

$^1$H NMR(CDCl$_3$):δ 4.05(m,1H); 3.45–3.40(m,4H); 3.27 (m,1H); 3.0–2.78(m,4H); 2.60(m,2H); 2.22–2.0(m,3H); 1.93(d,1H,J=2.5 Hz,SH); 1.85(m,1H).

IR(neat): 2917 and 2104 cm$^{-1}$.

CI-MS: m/z 176(M$^+$+H).

EXAMPLE 143

4-[4R-[4α,5βψ6β(R*)]]-1-Azido-1,2,3,5-tetradeoxy-2,5-epithio-4-S-[6-(1-hydroxyethyl)-4-methyl-2-[[(4-nitrophenyl)methoxy]carbonyl]-7-oxo-1-azabicyclo[3.2.0]hept-2-en-3-yl]-4-thio-D-erythro-pentitol A mixture of 0.070 g of product from Example 142, 0.237 g of product from Example 15 and 1.3 ml of acetonitrile is treated, at 0° C., with 69.6 microliter of Hunig's base. The reaction mixture is stirred at room temperature overnight; followed by concentration in vacuo. The residue is purified by chromatography (silica gel: 0–60% ethyl acetate/hexane) to give 0.034 g of the desired product.

$^1$H NMR(CDCl$_3$):δ 8.23(d,2H,J=3 Hz); 7.66(d,2H,J=3 Hz); 5.51(d,1H,J=13.7 Hz); 5.23(d,1H,J=13.7 Hz); 4.30(m, 2H); 4.19(m,1H); 3.65(m,1H); 3.45(m,1H); 3.32(dd,1H); 2.92(dd,1H); 2.70(m,3H); 2.20(dt,1H); 1.99(br s,1H,OH); 1.72(td,1H); 1.37(d,3H); 1.30(d,3H).

IR(neat): 3468, 2104, 1769 and 1709 cm$^{-1}$.

MS(FAB): m/z 520(M$^+$+H).

EXAMPLE 144

4-[4R-[4α,5βψ6β(R*)]]-1-Azido-4-S-[2-carboxy-6-(1-hydroxyethyl)-4-methyl-7-oxo-1-azabicyclo[3.2.0]hept-2-en-3-yl]-1,2,3,5-tetradeoxy-2,5-epithio-4-thio-D-erythro-pentitol The title compound is prepared by the procedure of Example 18 using 0.030 g of product from Example 143, 0.013 g of 10% palladium/carbon, 10 ml of dioxane and 5 ml of potassium phosphate buffer (pH 7.0) to give 0.012 g of the desired product after chromatography (C$_{18}$ reverse phase silica gel plates: 5% ethyl alcohol/water).

$^1$H NMR(CDCl$_3$):δ 4.18(m,3H); 3.50(m,2H); 3.40(m, 2H); 2.94(dd,1H); 2.70(m,2H); 2.12(dt,1H); 1.73(dd,1H); 1.23(d,3H); 1.16(d,3H).

IR(neat): 3535, 3410, 2104 and 1745 cm$^{-1}$.

MS(FAB): m/z 359(M$^+$+H).

EXAMPLE 145

Ethanethioic acid S-[tetrahydro-5-(hydroxymethyl)-3-thienyl]ester

A 0° C. solution, under argon, of 0.123 g of product from Example 139 in 1.0 ml of dry chloroform is treated with 51.1 microliter of boron trifluoride etherate and 0.193 g of tetra n-butylammonium iodide. the reaction mixture is stirred at room temperature overnight and concentrated in vacuo. The residue is purified by chromatography (silica gel: 0–100% ethyl acetate/hexane) to give 0.079 g of the desired. product.

$^1$H NMR(CDCl$_3$):δ 4.15(m,1H); 3.95(m,1H); 3.80–3.60 (m,4H); 3.30(m,1H); 3.19(m,1H); 2.77(t,1H); 2.48(m,1H); 2.34(s,3H,SAc); 2.27(m,1H); 2.08(m,1H); 1.73(m,1H).

EXAMPLE 146

Tetrahydro-4-mercapto-2-thiophenemethanol

The title compound is prepared by the procedure of Example 138 using 0.079 g of product from Example 146, 0.11 ml of 4.37M sodium methoxide and 1 ml of methyl alcohol to give 0.040 g of the desired product after chromatography (silica gel: 20 –30% ethyl acetate/hexane).

$^1$H NMR(CDCl$_3$):δ 3.83(m,1H); 3.60(m,4H); 3.35(m, 1H); 3.10(m,1H); 2.79(m,1H); 2.50–2.20(m,2H); 1.80(d, 1H); 1.65(m,1H).

EXAMPLE 147

[4R-[4α,5β,6β(R*)]]-6-(1-Hydroxyethyl)-4-methyl-7-oxo-3-[[tetrahydro-5-(hydroxymethyl)-3-thienyl]thio]-1-azabicyclo[3.2.0]hept-2-ene-2-carboxylic acid (4-nitrophenyl)methyl ester The title compound is prepared by the procedure of Example 143 using 0.040 g of product from Example 146, 0.154 g of product from Example 15, 46.4 microliter of Hunig's base and 1 ml of acetonitrile to give 0.071 g of the desired product after chromatography (silica gel: 20–100% ethyl acetate/hexane).

$^1$H NMR(CDCl$_3$):δ 8.25(d,2H,J=8.8 Hz); 7.66(d,2H,J= 8.8 Hz); 5.52(d,1H,J=13.7 Hz); 5.22(d,1H,J=13.7 Hz); 4.28 (m,2H); 3.80–3.6(m,3H); 3.45(m,1H); 3.3(m,1H); 2.87(t, 1H,J=6.7 Hz); 2.5(m,1H); 2.00(br s,1H,OH); 1.78(m,1H).

IR(neat): 3412, 1767 and 1708 cm⁻¹.
MS(FAB): m/z 495 (N⁺+H).

EXAMPLE 148

[4R-[4α,5β,6β(R*)]]-4-S-[2-carboxy-6-(1-hydroxyethyl)-4-methyl-7-oxo-1-azabicyclo[3.2.0]hept-2-en-3-yl]-2,3,5-trideoxy-2,5-epithio-4-thio-D-erythro-pentitol monosodium salt (A) and

[4R-[4α,5β,6β(R*)]]-2-S-[2-carboxy-6-(1-hydroxyethyl)-4-methyl-7-oxo-1-azabicyclo[3.2.0]hept-2-en-3-yl]-1,3,4-trideoxy-1,4-epithio-2-thio-L-threo-pentitol monosodium salt (B)

The title compound is prepared by the procedure of Example 18 using 0.0715 g of product from Example 147, 0.0125 g of sodium bicarbonate, 0.021 g of 10% palladium/carbon, 11.5 ml of 8:2 dioxane:water to give 0.012 g of the trans isomer (A) and 0.016 g of the cis isomer (B) after chromatography (Preparative thin layer silica gel plate: 5% ethyl alcohol).

Isomer B (cis) ¹H NMR(CDCl₃):δ 4.19(m,2H); 3.75–3.36 (m,6H); 3.15(m,1H); 2.80(m,1H); 2.50(m,1H); 1.60(m,1H); 1.25(d,3H),1.15(d,3H).

IR(neat): 3405 and 1742 cm⁻¹.
MS(FAB): m/z 404(M+Na) and 383(M+H).

EXAMPLE 149 trans-(±)-4-Bromotetrahydro-2-furanmethanol

Under anhydrous conditions at −5° C., with an argon flush, 1.05 g of product from Example 4 in 32 ml of dry chloroform is treated, dropwise, with 200.1 ml of trimethylsilyl iodide. The reaction mixture is stirred at −5° C. for 2.5 hours and then stored in a chill room overnight. The reaction is cooled to −5° C. and 630 ml of methyl alcohol is added. The mixture is stirred for 10 minutes and concentrated in vacuo. The residue is purified by chromatography (silica gel: 200 ml aliquots of 15%, 25%, 35% and 50% ethyl acetate/hexane) to give 0.559 g of the desired product.

Calculated for C₅H₉BrO₂: Theory C=33.17, H=5.01, Br=44.14 Found C=33.07, H=5.13, Br=43.80

CI-MS: m/z 278(MH⁺).

EXAMPLE 150

2,5-Anhydro-4-bromo-3,4-dideoxy-D-erythropentonic acid

A 0° C. solution of 6.05 g of product from Example 149 in 120 ml of acetone is treated, dropwise, with 37.5 ml of 0.9M Jones reagent in 50 ml of acetone. The reaction is warmed to room temperature and stirred for 45 additional minutes. The reaction is quenched with isopropyl alcohol and acetone, filtered through diatomaceous earth and concentrated in vacuo to 200 ml volume. The concentrate is mixed with 200 ml of saturated sodium chloride and and reconcentrated in vacuo. The aqueous layer is extracted with 10% isopropyl alcohol/chloroform, dried and concentrated in vacuo to give 5.6 of the acid as a light brown oil.

¹H NMR(CDCl₃):δ 4.84(t,1H,J=7.9 Hz); 4.55(br s,1H); 4.38(dd,1H,J=6.0 and 4.4 Hz); 4.19(dd,1H,J=8.7 and 1.6 Hz); 2.73(m,1H); 2.57(m,1H).

IR(neat): 3084 and 1737 cm⁻¹.
CI-MS: m/z 197(M+H).

EXAMPLE 151

4-(2,5-Anhydro-4-bromo-3,4-dideoxy-D-erythropentonoyl)-1-piperazinecarboxylic acid phenylmethyl ester A mixture of 0.941 g of product from Example 150, 0.652 g of 1-hydroxybenzotriazole, 1.17 g of 1-benzyloxycarbonyl piperazine, 1.39 g of dicyclohexylcarbodiimide and 8 ml of dry methylene chloride is stirred at room temperature for 1 hour. Five ml of dimethylformamide is added and the stirring continued overnight at room temperature. The reaction mixture is diluted with water and extracted with chloroform. The organic layer is dried, concentrated in vacuo and the residue purified by chromatography (silica gel: 10–80% ethyl acetate/hexane) to give 1.1 g of the desired product.

¹H NNR(CDCl₃):δ 7.36(s,5H,Ph); 5.16(s,2H,PhCH₂); 4.92(t,1H,J=7.2 Hz); 4.58(m,1H); 4.23(dd,1H,J=10.4 and 4.3 Hz); 4.14(dd,1H,J=2.1 and 0.5 Hz); 3.76(m,2H); 3.64 (m,2H); 3.44(m,4H); 3.00(m,1H); 2.40(m,1H).

IR(neat): 1702 cm⁻.
CI-MS: m/z 398(M+H).

EXAMPLE 152

4-(4-S-Acetyl-2,5-anhydro-3-deoxy-4-thio-L-threopentonoyl)-1-piperazinecarboxylic acid phenylmethyl ester The title compound is prepared by the procedure of Example 139 using 1.14 g of product from Example 151, 0.393 g of potassium thioacetate, 0.1517 g of 18-crown-6 and 10 ml of acetonitrile to give 0.928 g of the desired product after chromatography (silica gel: 10–60% ethyl acetate/hexane).

¹H NMR(CDCl₃):δ 7.36(s,5H,Ph); 5.15(s,2H,PhCH₂); 4.64(t,1H,J=6.9 Hz); 4.22(t,1H,J=6.8 Hz); 4.03(m,1H); 3.74–3.61(m,5H); 3.60–3.40(m,4H); 2.5(m,2H); 2.32(s,3H).

IR(neat): 1698 and 1653 cm⁻¹.
MS(FAB): m/z 393(M⁺+H).

EXAMPLE 153

4-(2,5-Anhydro-3-deoxy-4-thio-L-threo-pentonoyl)-1-piperazinecarboxylic acid phenylmethyl ester A 0° C. solution, under argon, of 0.20 g of product from Example 152 in 1.5 ml of dry methyl alcohol is treated with 0.25 ml of 4N sodium hydroxide. The reaction is monitored by thin layer chromatography. After 1 hour an additional 0.17 ml of 4N sodium hydroxide is added and the reaction stirred 1 hour. The reaction mixture is quenched with 1.86N hydrochloric acid/isopropyl alcohol, concentrated in vacuo and chromatographed (silica gel: 20–80% ethyl acetate/hexane) to give 0.116 g of the desired product.

¹H NMR(CDCl₃):δ 7.36(s,5H,Ph); 5.5(s,2H,PhCH₂); 4.64(t,1H,J=7.4 Hz); 4.13(dd,1H,J=8.6 and 6.9 Hz); 3.8–3.6 (m,5H); 3.5–3.3(m,4H); 2.55(m,1H); 2.40(m,1H); 1.82(d, 1H,J=8.4 Hz SH).

EXAMPLE 154

[4R-[4α,5β,6β(R*)]]-4-[2,5-Anhydro-3-deoxy-4-S-[6-(1-hydroxyethyl)-4-methyl-2-[[(4-nitrophenyl)methoxy]carbonyl]-7-oxo-1-azabicyclo[3.2.0]hept-2-en-3-yl]-4-thio-L-threo-pentonoyl]-1-piperazinecarboxylic acid phenylmethyl ester The title compound is prepared by the procedure of Example 143 using 0.112 g of product from Example 153, 0.190 g of product from Example 15, 55.7 microliter of Hunigs base and 1.1 ml of acetonitrile to give 0.189 g of the desired product after chromatography (silica gel: 10–100% ethyl acetate/hexane).

¹H NMR(CDCl₃):δ 8.22(dd,2H,J=8.8 and 1.8 Hz); 7.65 (d,2H,J=8.8 Hz); 7.36(s,5H,Ph); 5.48(d,1H,J=13.8 Hz); 5.23

(d,1H,J=13.8 Hz); 5.15(s,2H,PhCH₂); 4.63(m,1H); 4..27(m, 2H); 4.15(m,1H); 3.8–3.60(m,5H); 3.50–3.35(m,4H); 3.27 (dd,1H,J=6.9 and 2.6 Hz); 2.53(m,2H); 1.37(dd,3H,J=6.3 and 1.3 Hz); 1.28(t,3H,J=8.0 Hz).

IR(neat): 1771 and 1702 cm⁻¹.

MS(FAB): m/z 717(M+Na) and 695(M+H).

EXAMPLE 155

[4R-[4α,5β,6β(R*)]]-4-[2,5-Anhydro-4-S-[2-carboxy-6-(1-hydroxyethyl)-4-methyl-7-oxo-1-azabicyclo[3.2.0]hept-2-en-3-yl]-3-deoxy-4-thio-L-threo-pentonoyl]-1-piperazinecarboxylic acid phenylmethyl ester The title compound is prepared by the procedure of Example 18 using 0.170 g of product from Example 154, 0.034 g of 10% palladium/carbon, 15 ml of dioxane and 10 ml of potassium phosphate buffer (pH 7.0) to give after chromatography (C₁₈ reverse phase silica gel plates: 5% ethyl alcohol/water) 0.067 g of the desired product.

¹H NMR(D₂O):δ 7.40(s,5H); 5.16(s,2H,PhCH₂); 4.44(m, 1H); 4.3(m,2H); 4.10(m,1H); 3.7–3.38(m,6H); 3.5–3.30(m, 5H); 3.29(m,1H); 2.50(m,2H); 1.28(d,3H); 1.18(d,3H).

MS(FAB): m/z 581(M⁺+Na).

EXAMPLE 156

1-4-S-Acetyl-2,5-anhydro-3-deoxy-4-thio-L-threo-pentonoyl)piperazine

The title compound is prepared by the procedure of Example 140 using 0.766 g of product from Example 152, 0.430 g of trimethylsilyl iodide and 4 ml of chloroform to give 0.504 g of the desired product after chromatography (silica gel: 15–20% ethyl acetate/hexane).

¹H NMR(MeOH-d₄):δ 4.94(t,1H,J=7.4 Hz); 4.24(dd,1H, J=8.6 and 6.9 Hz); 4.10–3.70(m,5H); 3.40–3.20(m,4H); 2.76(m,1H); 2.34(s,3H,SAc); 2.10(m,1H).

EXAMPLE 157

4-(4-S-Acetyl-2,5-anhydro-3-deoxy-4-thio-L-threo-pentonoyl)-1-piperazinecarboxylic acid (4-nitrophenyl)methyl ester A 0° C. solution, under argon, of 0.300 g of product from Example 156 in 2.3 ml of dry tetrahydrofuran is treated with 0.150 g of Hunigs base and 0.250 g of nitrobenzyl chloroformate. The reaction mixture is stirred at 0° C. and allowed to warm to room temperature (6 hours). The reaction is diluted with water and extracted with ethyl acetate. The organic layer is washed with saturated sodium chloride, dried and concentrated in vacuo to give 0.251 g of the desired product after chromatography (silica gel: 0–100% ethyl acetate/hexane).

¹H NMR(MeOH-d₄):δ 8.23(d,2H,J=8.8 Hz); 7.52(d,2H, J=8.8 Hz); 5.25(s,2H,PhCH₂); 4.64(t,1H,J=7.4 Hz); 4.22(dd, 1H,J=8.9–6 and 6.8 Hz); 4.02(m,1H); 3.90–3.60(m,6H); 3.50–3.40(m,4H); 2.48(m,2H); 2.33(s,3H,SAc).

IR(neat): 1702 cm⁻.

CI-MS: m/z 438(M+H).

EXAMPLE 158

4-(2,5-Anhydro-3-deoxy-4-thio-L-threo-pentonoyl)-1-piperazinecarboxylic acid (4-nitrophenyl)methyl ester The title compound is prepared by the procedure of Example 153 using 0.230 g of product from Example 157, 0.29 ml of 4N sodium hydroxide and 1.7 ml of methyl alcohol to give 0.086 g of the desired product after chromatography (silica gel: 10 –100% ethyl acetate/hexane).

¹H NMR(MeOH-d₄):δ 8.24(d,2H,J=8.8 Hz); 7.52(d,2H, J=8.8 Hz); 5.24(s,2H,PhCH₂); 4.64(t,1H,J=7.3 Hz); 4.13(dd, 1H,J=8.6 and 6.9 Hz); 3.90–3.30(m,10H); 2.55(m,1H); 2.42 (m,1H); 1.82(d,1H,J=8.3 Hz,SH).

EXAMPLE 159

[4R-[4α,5β,6β(R*)]]-4-[2,5-Anhydro-3-deoxy-4-S-[6-(1-hydroxyethyl)-4-methyl-2-[[(4-nitrophenyl)methoxy]carbonyl]-7-oxo-1-azabicyclo[3.2.0]hept-2-en-3-yl]-4-thio-L-threo-pentonoyl]-1-piperazinecarboxylic acid (4-nitrophenyl)methyl ester The title compound is prepared by the procedure of Example 143 using 0.085 g of product from Example 158m 0.128 g of product from Example 15, 37.4 microliter of Hunigs base and 1.0 ml of acetonitrile to give 0.135 g of the desired product after chromatography (silica gel: 20, 40, 80 and 100% ethyl acetate/hexane followed by 2–4% methyl alcohol/ethyl acetate).

¹H NMR(CHCl₃):δ 8.24(d,2H,J=8.8 Hz); 8.23(d,2H,J= 8.8 Hz); 7.65(d,2H,J=8.8 Hz); 7.52(d,2H,J=8.8 Hz); 5.49(d, 1H,J=13.8 Hz); 5.22(d,1H,J=13.8 Hz); 5.25(s,2H); 4.64(m, 1h); 4.25(m,2H); 3.84–3.83(m,6H); 3.52–3.32(m,4H); 3.27 (m,1H); 2.54(m,2H); 1.37(d,3H,J=6.3 Hz); 1.26(d,3H,J=6.4 Hz).

IR(neat): 1772 and 1705 cm⁻¹.

EXAMPLE 160

[4R-[4α,5β,6β(R*)]]-1-[2,5-Anhydro-4-S-[2-carboxy-6-(1-hydroxyethyl)-4-methyl-7-oxo-1-azabicyclo[3.2.0]hept-2-en-3-yl]-3-deoxy-4-thio-threo-pentonoyl]piperazine phenylmethyl ester The title compound is prepared by the procedure of Example 18 using 0.120 g of product from Example 159, 0.030 g of 10% palladium/carbon, 5 ml of dioxane and 1.5 ml of potassium phosphate buffer (pH 7) to give 0.053 g of the desired product after chromatography (preparative silica gel plate: 5% ethyl alcohol/water).

¹H NMR(CHCl₃):δ 4.90(m,1H); 4.30–4.10(m,3H); 4.0–3.60(m,8H); 3.40(m,1H); 3.3(m,3H); 2.80(m,1H); 2.0 (m,1H); 1.28(d,3H); 1.20(t,3H).

IR(KBr): 3545, 3408, 1770 and 1622 cm⁻¹.

MS(FAB): m/z 426(M⁺+H).

EXAMPLE 161

[4R-[3(3R*,5S* and 3S*,5R*),4α,5β,6β(R*)]]-3-[[5-[[[(Dimethylamino)methylene]amino]methyl] tetrahydro-3-furanyl]thio]-6-(1-hydroxyethyl)-4-methyl-7-oxo-1-azabicyclo[3.2.0]hept-2-ene-2-carboxylic acid Three ml of sodium phosphate buffer, pH 7, is cooled to 0° C. and 0.052 g of product from Example 46 is added. To this cooled solution is added, dropwise, 159 μl of N,N-dimethylformamide diisopropyl acetal, while maintaining the pH below 8.5. The reaction mixture is stirred at 0° C. for 35 minutes, pH adjusted to 7.0 and freeze-dried. The residue is purified by chromatography (C₁₈ reverse phase tlc plates: 75% aqueous ethyl alcohol) to give 0.031 g of the desired product.

¹H NMR(D₂O):δ 7.8(s,1H); 4.3(m,1H); 4.19(m,3H); 3.94 (m,1H); 3.75(m,1H); 3.54(m,1H); 3.42(m,3H); 3.21(s,2H, N-Me); 3.01(s,3H,N-Me); 2.08(m,2H,SCCH₂CC); 1.26(d, 2H,Me); 1.18(d,3H,Me).

EXAMPLE 162

2-[4R-[4α,5β,6β(R*)]]-2,5-Anhydro-1,3-dideoxy-1-(dimethylamino)-4-S-[2-carboxy-6-(1-hydroxyethyl)-4-methyl-7-oxo-1-azabicyclo[3.2.0]hept-2-en-3-yl]-4-thio-L-threo-pentitol A mixture of 0.0342 g of product from Example 120, 80 µl of 37% aqueous formaldehyde, 4 ml of water and 0.030 g of platinum oxide is reduced in a Parr apparatus under 40 psi of hydrogen for 4 hours. The reaction mixture is filtered through a pad of diatomaceous earth, washed with a small volume of water and concentrated to a small volume (pH of the filtrate 6.5). The residue is purified by chromatography (C₁₈ reverse phase tlc plate: 95% aqueous ethyl alcohol) to give 0.015 g of the desired product.

¹H NMR(D₂O):δ 4.4(m,1H); 4.00–4.25(m,3H); 3.95–3.80(m,2H); 3.5–3.2(m,4H); 2.88(d,6H,2N-Me); 2.70–2.55(m,1H); 1.8–1.7(m,0.5H); 1.6–1.5(m,0.5H(m, 0.5H); 1.25(d,3H,Me); 1.18(d,3H,Me).

EXAMPLE 163

2,4-Difluoro-alpha-2-propenylbenzenemethanol

Under anhydrous condition at 0° C., a mixture of 18.0 g of freshly distilled 2,4-difluorobenzaldehyde and 120 ml of diethyl ether is treated, dropwise, with 139 ml of 1M allyl magnesium bromide. The reaction is stirred at 0° C. for 1 hour then slowly allowed to warm to room temperature. After 5 hours, thin layer chromatography indicates complete reaction. The mixture is cooled to 0° C. and quenched by the dropwise addition of 100 ml of ice cold saturated ammonium chloride. Two hundred ml of diethyl ether is added and the layers are separated. The aqueous layer is extracted with diethyl ether. The organic layers are combined, washed twice with saturated sodium chloride, dried , filtered and concentrated in vacuo. The residue is purified by Kugelrohr distillation (100° C.) to give 19.9 g of the desired product as a mixture of isomers.

¹H NMR(CDCl₃):δ 7.45(m,1H); 6.88(m,1H); 6.78(m, 1H); 5.82(m,1H); 5.16(dd,2H); 5.03(q,1H); 2.53(m,2H); 1.89(bs,1H).

EXAMPLE 164 alpha-(2,3-Dibromopropyl)-2,4-difluorobenzenemethanol

Under anhydrous condition at 0° C., 3.0 g of product from Example 163 and 12 ml of anhydrous methylene chloride is treated, dropwise over 45 minutes, with a solution of 2.5 g of bromine in 3 ml of methylene chloride. The reaction is quenched with cold saturated sodium sulfite solution and the layers separated. The organic layer is washed with saturated sodium chloride, dried, filtered and concentrated in vacuo. The residue is purified by chromatography (silica gel: 5–10% ethyl acetate/hexane) to give 4.7 g of the desired product as a mixture of isomers.

¹H NMR(CDCl₃):δ 7.53–7.41(m,1H); 6.95–6.77(m,2H); 5.28(m,1H); 4.61–3.63(m,3H); 2.69–1.95(m,3H).

EXAMPLE 165

(cis and trans)-(±)-4-Bromo-2-(2,4-difluorophenyl)tetrahydrofuran

A mixture of 4.5 g of product from Example 164, 1.67 g of calcium hydroxide, 7.5 g of calcium bromide, 25 ml of water and 12 ml of methyl alcohol is stirred and heated at 85° C. overnight. The reaction mixture is cooled, diluted with ethyl acetate and filtered through diatomaceous earth. The layers are separated and the organic layer is washed with saturated sodium chloride, dried, filtered and concentrated in vacuo. The residue is purified by chromatography (silica gel: 3–5% ethyl acetate/hexane) to give 1.96 g of the desired product as a mixture of isomers.

¹H NMR(CDCl₃):δ 7.65–7.57(m,1H); 7.46–7.38(m,1H); 6.93–6.74(m,4H); 5.43(q,1H); 5.16(t,1H); 4.59–4.57(m, 1H); 4.53–4.47(m,2H); 4.25–4.21(m,3H); 3.05(m,1H); 2.89 (q,1H); 2.36–2.18(m,2H).

EXAMPLE 166

(cis and trans)-(±)-Ethanethioic acid S-[5-(2,4-difluorophenyl)tetrahydro-3-furanyl]ester The title compound is prepared by the procedure of Example 5 using 1.9 g of product from Example 165, 0.866 g of potassium thioacetate and 30 ml of acetonitrile to give, after chromatography (silica gel: 5% ethyl acetate/hexane), 1.43 g of the desired product, as a mixture of isomers.

¹H NMR(CDCl₃):δ 7.44(m,2H); 6.87(t,2H); 6.78(t,2H); 5.14(m,2H); 4.50(m,2H); 4.26(m,2H); 4.11(m,2H); 3.90(q, 1H); 3.77(q,1H) 3.04(m,1h); 2.87(m,1H); 2.35(s,3H); 2.32 (s,3H).

EXAMPLE 167

5-(2,4-Difluorophenyl)tetrahydro-3-furanthiol stereoisomers

The title compound is prepared by the procedure of Example 16 using 0.250 g of product from Example 166, 243 µl of 25% sodium methoxide/methyl alcohol, 4.5 ml of tetrahydrofuran and 530 µl of 2N hydrochloric acid/isopropyl alcohol to give, after chromatography (silica gel: 5–10% ethyl acetate/hexane), 0.180 g of the desired product, as a mixture of isomers.

¹H NMR(CDCl₃):δ 7.52(q,1H); 7.41(q,1H); 6.80(m,2H); 6.78(m,2H); 5.32(t,1H); 5.12(q,1H); 4.41(q,1H); 4.24(q, 1H); 3.81(q,1H); 3.72(q,1H); 3.54(m,2H); 2.89(m,1H); 2.29 (m,2H); 1.79(d,1H); 1.73(d,1H); 1.72(m,1H).

EXAMPLE 168

[4R-[4α,5β,6β(R*)]]-3-[[5-(2,4-Difluorophenyl) tetrahydro-3-furanyl]thio]-6-(1-hydroxyethyl)-4-methyl-7-oxo-1-azabicyclo[3.2.1]hept-2-ene-2-carboxylic acid (4-nitrophenyl)methyl ester The title compound is prepared by the procedure of Example 17 using 0.169 g of product from Example 167, 0.300 g of product from Example 15, 87 µl of Hunig's base and 3 ml of acetonitrile to give, after chromatography (preparative silica gel plates: 5% acetone/chloroform), 0.080 g of the desired product, as a mixture of isomers.

¹H NMR(CDCl₃):δ 8.23(d,2H); 7.68(d,2H); 7.41(q,1H); 6.83(,m,2H); 5.53(d,1H); 5.25(d,1H); 4.47(m,1H); 4.27(m, 2H); 3.94(m,1H); 3.8(d,1H); 3.48(m,1H); 3.38(d,1H); 2.44 (m,1H); 2.24(m,1H); 2.17(d,1H); 1.37(d,3H); 1.29(d,3H).

EXAMPLE 169

[4R-[4α,5β,6β(R*)]]-3-[[5-(2,4-Difluorophenyl] tetrahydro-3-furanyl]thio]-6-(1-hydroxyethyl)-4-methyl-7-oxo-1-azabicyclo[3.2.0]hept-2-ene-2-carboxylic acid monosodium salt isomer 1 and

[4R-[4α,5β,6β(R*)]]-3-[[5-(2,4-Difluorophenyl) tetrahydro-3-furanyl]thio]-6-(1-hydroxyethyl)-4-methyl-7-oxo-1-azabicyclo[3.2.0]hept-2-ene-2-carboxylic acid monosodium salt isomer 2

The title compound is prepared by the procedure of Example 18 using 0.80 g of product from Example 168, 0.0117 g of sodium bicarbonate, 2 ml of water, 10 ml of dioxane and 0.030 g of palladium on carbon to give, after chromatography ($C_{18}$ reverse phase plates: 5% ethyl alcohol/water), 0.020 g of isomer 1 and 0.040 g of isomer 2.

Isomer 1:

$^1$H NMR($D_2O$):δ 7.5(m,1H); 6.92(m,2H); 5.2(t,1H); 4.2 (m,2H); 3.95(m,2H); 2.6(m,1H); 3.2(bs,2H); 2.83(m,1H); 2.35(m,1H); 2.0(m,1H); 1.22(d,3H); 1.19(d,3H).

Isomer 2:

$^1$H NMR($D_2O$):δ 7.44(m,1H); 6.9(m,2H); 4.18(m,2H); 3.91(m,2H); 3.6(m,1H); 3.18(m,2H); 2.8(m,1H); 2.37(m,1H); 1.8(m,1H); 1.22(d,3H); 1.19(d,3H).

EXAMPLE 170

1,2-O-(1-Methylethylidene)-alpha-D-xylofuranose bis(4-methylbenzenesulfonate)

Under anhydrous condition, 50.0 g of 1,2-isopropylidene-D-xylofuranose, 250 ml of dry pyridine and 0.200 g of dimethylaminopyridine is cooled to 0° C. To this mixture is added, in portions, 110.26 g of p-toluenesulfonyl chloride. The reaction mixture is stirred and allowed to warm to room temperature overnight. The mixture is cooled to 0° C., quenched with water, extracted with ethyl acetate and the layers are separated. The organic layer is washed with water, saturated sodium chloride, dried, filtered and concentrated in vacuo. The residue is recrystallized from diethyl ether/hexane to give 116.6 g of the desired product.

$^1$H NMR($CHCl_3$):δ 7.79(m,4H); 7.33(m,4H); 5.86(d,1H); 4.72(q,2H); 4.33(m,1H); 4.0(m,2H); 2.48(s,3H); 2.45(s,3H); 1.42(s,3H); 1.27(s,3H).

EXAMPLE 171

2,5-Anhydro-D-xylose dimethyl acetal 3-(4-methylbenzenesulfonate)

Under anhydrous condition at 0° C., hydrogen chloride gas is bubbled through 166 ml of dry methyl alcohol. Five g of product from Example 170 is added and the reaction is stirred for 10 minutes at 0° C.; followed by heating at reflux temperature for 15 hours. The reaction mixture is cooled to 0° C. and neutralized with solid sodium carbonate. The mixture is stirred for 15 minutes, filtered and concentrated in vacuo. The residue is dissolved in 50 ml of acetone, filtered and concentrated in vacuo. The residue is purified by chromatography (silica gel: 40–50% ethyl acetate/hexane) to give 2.89 g of the desired product as a white solid.

$^1$H NMR($CHCl_3$):δ 7.82(d,2H); 7.37(d,2H); 4.81(d,1H); 4.53(m,1H); 4.41(d,1H); 4.22(m,1H); 4.11(m,1H); 3.73(dd, 1H); 3.38(s,3H); 3.11(s,3H); 2.46(s,3H); 2.37(bs,1H).

EXAMPLE 172

2,5-Anhydro-4-deoxy-D-erythro-pentose dimethyl acetal

Under anhydrous conditions at room temperature, 0.90 g of product from Example 171 and 25 ml of dry tetrahydrofuran is treated, via a syringe, with 30 ml of 1M lithium triethylborohydride(Super-Hydride ψ). The reaction is stirred overnight at room temperature. The mixture is cooled to 0° C., quenched carefully with ice, diluted with 75 ml of ethyl acetate and the layers are separated. The organic layer is washed with water, saturated sodium chloride, dried, filtered and concentrated in vacuo. The residue is purified by chromatography (silica gel: 40–60% ethyl acetate/hexane) to give 0.235 g of the desired product.

$^1$H NMR($CHCl_3$):δ 4.34(m,1H); 4.26(m,1H); 3.97(m, 2H); 3.76(m,2H); 3.44(m,6H); 2.72(m,1H); 2.15(m,1H); 1.92(m,1H).

EXAMPLE 173 trans-Tetrahydro-3-hydroxy-2-furanylmethanediol

A mixture of 9.25 g of product from Example 172, 15 ml of water and 1.5 g of DOWEX-50W-X8 (100–200 mesh, hydrogen form) is heated at 95° C. for 4 hours. The reaction mixture is cooled to room temperature, filtered and the residue washed with water. The filtrate is treated with toluene and concentrated in vacuo to give 1.1 g of the desired product as a sticky yellow oil.

$^1$H NMR($D_2O$):δ 4.75(d,1H); 4.27(m,1H); 3.91–3.76(m, 2H); 3.55(m,1H); 2.00(m,1H); 1.78(m,1H).

EXAMPLE 174

[4R-[4α,5β,6β(R*)]]-1-Amino-4-S-[2-carboxy-6-(1-hydroxyethyl)-4-methyl-7-oxo-1-azabicyclo[3.2.0] hept-2-en-2-yl]-1,2,3,4,5-pentadeoxy-2,5-epithio-4-thio-D-erythro-pentitol To a solution of 0.024 g of product from Example 144 in 1 ml of acetonitrile:water (1:1) is added 17 μl of tributylphosphine. The reaction mixture is stirred at room temperature for 24 hours followed by concentration in vacuo. The residue is purified by chromatography ($C_{18}$ reverse phase preparative plates: 5% ethyl alcohol:water) to give 0.014 g of the desired product.

$^1$H NMR($CDCl_3$):δ 4.20(m,2H); 4.05(t,1H); 3.80(m,2H); 3.45–3.20(m,3H); 3.10(dd,1H); 2.89(dd,1H); 2.26(m,1H); 2.01(m,1H); 1.25(d,3H,J=6.2 Hz); 1.15(d,3H,J=7.2 Hz).

IR(KBr): 3400 and 1765 $cm^{-1}$. MS(FAB): m/z 359 ($M^+$+ H).

EXAMPLE 175

4-Bromotetrahydro-2-[(phenylmethoxy)methyl] thiophene 1,1-dioxide

To a 0° C. solution, under argon, of 5.65 g of product from Example 138 in 45 ml of dry methylene chloride is added, slowly, 7.8 g of m-chloroperbenzoic acid. The reaction is stirred at 0° C. for 2 hours, diluted with 100 ml of water and extracted with methylene chloride. The organic layer is washed with saturated sodium bicarbonate, dried, filtered and concentrated in vacuo. The residue is redissolved in methylene chloride, passed through a short column of silica gel, concentrated in vacuo to give 5.87 g of the desired sulfone (60:40 mixture of isomers).

$^1$H NMR($CDCl_3$):δ 7.34(m,5H,Ph); 4.67(m,1H); 4.59(t, 2H,$CH_2$Ph); 4.36(m,1H); 3.77–3.58(m,4H); 3.50(dd,1H); 3.30(dd,1H); 2.90(m,1H); 2.70(m,1H); 2.55(m,1H); 2.33(m, 1H).

IR(neat): 2945,1320,1127,910 and 734 $cm^{-1}$.

CI-MS: m/z 320($M^+$+H).

EXAMPLE 176

4-Bromo-2-thiophenemethanol 1,1-dioxide

To a −78° C. solution, under argon, of 4.23 g of product from Example 175 in 28 ml of dry methylene chloride is added, dropwise, 17.2 ml of 1M boron trichloride. The reaction mixture is warmed to 0° C. and stirred for 1 hour. The reaction is quenched with methyl alcohol, concentrated in vacuo and chromatographed (silica gel: 0–30% ethyl acetate/hexane) to give 2.57 g of the desired product (1:1 mixture of isomers).

mp 56°–57° C.(ethyl acetate and hexane).

$^1$H NMR(CDCl$_3$):δ 4.75(m,1H); 4.42(m,1H); 4.12(m, 2H); 3.94(m,1H); 3.65(m,2H); 3.53(dd,1H); 3.45–3.25(m, 2H); 2.98(br s,1H,OH); 2.90(m,1H); 2.70(m,2H); 2.43(m, 1H).

IR(KBr): 3461, 1314, 1284 and 1123 cm$^{-1}$.

EXAMPLE 177

Tetrahydro4-[[(4-methoxyphenyl)methyl]thio]-2-thiophenemethanol-1,1-dioxide

To a 0° C. slurry, under argon, of 0.502 g of sodium hydride (60% oil dispersion) in 9 ml of dry tetrahydrofuran is added, dropwise over 5 minutes, 1.69 ml of p-methoxy-α-toluenethiol in 9 ml of dry tetrahydrofuran. The reaction is warmed to room temperature for 30 minutes, recooled to 0° C. and a solution of 2.31 g of product from Example 176 in 10 ml of dry tetrahydrofuran is added. The reaction mixture is allowed to warm to room temperature and stirred overnight. The mixture is diluted with 100 ml of water and extracted with diethyl ether. The organic layer is washed with saturated sodium chloride, dried and concentrated in vacuo to give an oil. The oil is purified by chromatography (silica gel: 0–90% ethyl acetate/hexane) to give 3.0 g of the desired product (1:1 mixture of isomers).

$^1$H NMR(CDCl$_3$):δ 7.23(dd,2H,J=1.7 and 8.5 Hz); 6.86 (d,2H,J=8.5 Hz); 4.05(dt,1H); 3.81(s,3H,ArOMe); 3.77(s, 2H,CH$_2$Ar); 3.45(m,1H); 3.24(m,2H); 2.96(dd,1H,J=8.74 and 13.34 Hz); 2.81(t,1H,J=14.6 Hz); 2.58(brs,1H,OH); 2.45(m,2H); 2.22(dt,1H,J=8.78 and 13.82 Hz); 1.97(dt,1H, J=11.09 and 13.34 Hz).

IR(neat): 3503, 1610 and 1512 cm$^{-1}$.

EXAMPLE 178

Tetrahydro-4-[[(4-methoxyphenyl)methyl]thio]-2-thiophenemethanol methanesulfonate 1,1-dioxide A 0° C. solution, under argon, of 2.53 g of product from Example 177 in 27 ml of dry methylene chloride is treated, sequentially, with 1.4 ml of triethylamine and 0.77 ml of methanesulfonyl chloride. The reaction is allowed to warm to room temperature over 1.5 hours. The mixture is diluted with diethyl ether, filtered through a short column of silica gel (diethyl ether and 50% methylene chloride/ethyl acetate) to give 3.087 g of the desired product (mixture of isomers).

$^1$H NMR(CDCl$_3$):δ 7.22(d,2H,J=8.7 Hz); 6.87(d,2H,J= 8.7 Hz); 4.45(m,2H); 3.81(s,3H,ArOMe); 3.77(s,2H, CH$_2$Ar); 3.50–3.20(m,4H); 3.10(s,3H,OSO$_2$Me); 2.85(m, 1H); 2.56(m,1H); 2.27(m,1H); 1.80(m,1H).

IR(neat): 2837, 2107, 1610 and 1584 cm$^{-1}$.

EXAMPLE 179

2-(Azidomethyl)tetrahydro-4-[[(4-methoxyphenyl)methyl]-thio]thiophene 1,1-dioxide A mixture, under argon, of 2.94 g of product from Example 178, 0.757 g of lithium azide and 8 ml of dry dimethylformamide is stirred vigorously at 65° C. for 4 hours. The reaction mixture is diluted with 60 ml of water and extracted with diethyl ether and ethyl acetate. The combined organic layers are washed with saturated sodium chloride, dried and concentrated in vacuo. The residue is purified by chromatography (silica gel: 0–50% ethyl acetate/hexane) to give 1.89 g of the desired product (mixture of isomers).

$^1$H NMR(CDCl$_3$):δ 7.22(dd,2H,J=2.05 and 8.6 Hz); 6.87 (d,2H,J=8.6); 3.81(s,3H,ArOMe); 3.77(d,2H,CH$_2$Ar); 3.58 (dd,1H,J=5.77 and 13.19 Hz); 3.35–3.20(m,2H); 2.88(m, 2H); 2.60(m,2H); 1.75(m,1H).

IR(neat): 2837, 2107, 1610 and 1584 cm$^{-1}$.

EXAMPLE 180

Tetrahydro-4-[[(4-methoxyphenyl)methyl]thio]-2-thio-phenemethanamine 1,1-dioxide (stereoisomers)

A 0° C. solution, under argon, of 1.4 g of product from Example 179 in 14 ml of dry methylene chloride is treated with 1.19 ml of triethylamine. Hydrogen sulfide gas is slowly bubbled through the cold solution for 20 minutes (the excess gas is trapped in a flask containing an aqueous solution of 5.25% sodium hypochlorite). The mixture is stirred at 0° C. for 2 hours, the flask flushed for 20 minutes with argon and the reaction is concentrated in vacuo. The residue is purified by chromatography (silica gel: 10–100% ethyl acetate/hexane, 5% methyl alcohol/ethyl acetate) to give 0.757 g of the desired product (mixture of isomers).

$^1$H NMR(CDCl$_3$):δ 7.22(d,2H,J=8.51 Hz); 6.85(d,2H,J= 8.50 Hz); 4.26(br s,1H); 3.82(s,3H,ArOMe); 3.77(s,2H, CH$_2$Ar); 3.40(m,1H); 3.3–3.10(m,3H); 3.9(dd,1H); 2.50(m, 1H); 2.35(br s,2H,NH$_2$); 2.33(t,1H,J=7.16 Hz); 1.82(m,1H).

CI-MS: m/z 302 (M$^+$+H).

EXAMPLE 181 cis (and trans)-[Tetrahydro-4-[[(4-methoxyphenyl)methyl]thio]-2-thienyl]carbamic acid (4-nitrophenyl)methyl ester S,S-dioxide A 0° C. solution, under argon, of 0.757 g of product from Example 180 in 8 ml of dry methylene chloride is treated with 0.812 g of p-nitrobenzyl chloroformate and 525 µl of triethylamine. The reaction is stirred overnight, diluted with water, extracted with methylene chloride, dried and concentrated in vacuo. The residue is purified by chromatography (silica gel: 10–100% ethyl acetate/hexane) to give 0.756 g of the desired product (mixture of isomers).

$^1$H NMR(CDCl$_3$):δ 8.21(d,2H,J=8.74 Hz); 7.50(d,2H,J= 8.74 Hz); 7.20(d,2H,J=8.63 Hz); 6.86(d,2H,J=8.63 Hz); 5.55(t,1H,NH); 5.19(s,2H,CH$_2$ArNO$_2$); 3.81(s,3H,ArOMe); 3.75(s,2H,CH$_2$ArOMe); 3.69(m,1H); 3.49(m,1H); 3.38–3.15(m,3H); 2.82(m,1H); 2.53(m,1H); 2.20(m,1H); 1.70(m,1H).

IR(KBr): 3389 and 1706 cm$^{-1}$.

EXAMPLE 182

[(Tetrahydro-4-mercapto-2-thienyl)methyl]carbamic acid (4-nitrophenyl)methyl ester thiophene-1,1-dioxide stereoisomers A solution of 0.756 g of product from Example 181 in 31 ml of 80% acetic acid/water is treated with 0.35 ml of anisole and 0.805 g of mercuric trifluoroacetate. The reaction is stirred for 2 hours, diluted with water and hydrogen sulfide gas is bubbled through the solution for 5 minutes. The mixture is filtered, washed with a minimum of water and the filtrate concentrated in vacuo. The black precipitate is washed with ethyl acetate and concentrated in vacuo. The two extracts (water and ethyl acetate) appear to be identical by thin layer chromatography. The extracts are combined and purified by chromatography (silica gel: 15–80% ethyl acetate/hexane) to give 0.44 g of the desired product (3:2 mixture of isomers).

$^1$H NMR(CDCl$_3$):δ 8.23(d,2H,J=8.70 Hz); 7.50(d,2H,J= 8.70 Hz); 5.55(t,1H,NH); 5.21(s,2H, CH$_2$ArNO$_2$); 3.82–3.40(m,5H); 3.11(m,1H); 2.94(dd,1H,J=11.54 and 12.50 Hz); 2.70(m,1H); 2.33(m,1H); 2.10(d,1H,J=7.2 Hz, SH of minor isomer); 1.98(d,1H,J=7.2 Hz, SH of major isomer); 1.78(m,1H).

CI-MS: m/z 361 (M$^+$+H).

EXAMPLE 183

[4R-[4α,5β,6β(R*)]]-6-(1-Hydroxyethyl)-4-methyl-7-oxo-3-[[tetrahydro-5-[[[[(4-nitrophenyl)methoxy]carbonyl]amino]methyl]-3-thienyl]thio]-1-azabicyclo[3.2.0]hept-2-ene-2-carboxylic acid (4-nitrophenyl)methyl ester thiophene-S,S-dioxide The title compound is prepared by the procedure of Example 143 using 0.44 g of product from Example 182, 0.659 g of Example 15, 4 ml of dry acetonitrile and 0.143 g of Hunig's base to give, after chromatography (silica gel:10–100% ethyl acetate/hexane), 0.742 g of the desired product (mixture of isomers and trans isomer pure).

$^1$H NMR(CDCl$_3$):δ 8.22(d,2H,J=8.5 Hz); 8.21(d,2H,J= 8.5 Hz); 7.64(d,2H,J=8.5 Hz); 7.49(d,2H,J=8.5 Hz); 5.66 (brt,1H,NH); 5.49(d,1H,J=13.7 Hz); 5.21(d,1H,J=13.7 Hz); 5.2(d,2H,J=6.31 Hz); 4.28(m,2H); 4.13(m,1H); 3.8–3.45(m, 4H); 3.31(m,1H); 3.13(m,1H); 2.35(t,2H,J=6.5 Hz); 2.00(br s,1H); 1.35(d,3H,J=6.24 Hz); 1.26(d,3H,J=6.2 Hz).

IR(KBr): 3419, 3079, 1772 and 1719 cm$^{-1}$.

MS(FAB): m/z 705(M$^+$+H).

EXAMPLE 184

[4R-[4α,5β,6β(R*)]]-5-Amino-2-S-[2-carboxy-6-(1-hydroxyethyl)-4-methyl-7-oxo-1-azabicyclo[3.2.0]hept-2-en-3-yl]-1,2,3,4,5-pentadeoxy-1,4-epithio-2-thio-L-threo-pentitol S$^1$,S$^1$-dioxide (Cis) [4R-[4α, 5β,6β(R*)]]-1-Amino-4-S-[2-carboxy-6-(1-hydroxyethyl)-4-methyl-7-oxo-1-azabicyclo[3.2.0] hept-2-en-3-yl]-1,2,3,4,5-pentadeoxy-2,5-epithio-4-thio-D-erythro-pentitol S$^2$,S$^2$-dioxide (trans) [4R-[4α,5β,6β(R*)]]-3-[5-(Aminomethyl)tetrahydro-3-thienyl]-6-(1-hydroxyethyl)-4-methyl-7-oxo-1-azabicyclo[3.2.0]hept-2-ene-2-carboxylic acid thiophene-S,S-dioxide (mixture)

The title compound is prepared by the procedure of Example 18 using 0.502 g of product from Example 183, 0.205 g of 10% palladium on carbon, 24 ml of dioxane: 0.1M phosphate buffer (5:2) to give, after chromatography (C$_{18}$ reverse phase chromatography plates: 5% ethyl alcohol/water), 0.014 g of the cis isomer, 0.013 g of the trans isomer and 0.024 g of mixture of cis and trans isomers.
Cis Isomer $^1$H NMR(D$_2$O):δ 4.18(m,2H), 3.95–3.50(m,6H); 3.48–3.20(m,5H); 2.82(m,1H); 1.90(m,1H); 1.23(d,3H,J= 6.2 Hz); 1.16(d,3H,J=6.2 Hz).

IR(KBr): 3538, 3410, 1748 and 1622 cm$^{-1}$.

EXAMPLE 185

3-[[5-(Azidomethyl)tetrahydro-3-furanyl]thio]-4-methyl-6-[1-[[(2-methylpropoxy)carbonyl]oxy]ethyl]-7-oxo-1-azabicyclo[3.2.0]hept-2-ene-2-carboxylic acid (4-nitrophenyl)methyl ester diastereomers Using anhydrous conditions, 1.25 g of product from Example 45 in 27 ml of anhydrous tetrahydrofuran, is cooled to −78° C. under argon. 0.325 ml of isobutyl chloroformate is added, followed by 2.7 ml of lithium bis(trimethylsilyl) amide. The reaction mixture is stirred at −78° C. for 1 hour, followed by stirring at −55° C. for another hour and then concentrated in vacuo. The residue is purified by chromatography (Silica Gel: 50% ethyl acetate/hexane) to give 1.22 g of the desired product.

$^1$H NMR(CDCl$_3$):δ 8.21(d,2H); 7.67(d,2H); 5.50(d,1H); 5.25(d,1H); 5.15(t,1H,HCOCO); 4.27–4.33(m,3H); 3.81–3.95(m,3H); 3.68–3.73(m,1H); 3.31–3.55(m,3H); 3.22–3.31(m,1H); 2.2–2.3(m,1H,CH(CH$_3$)$_2$); 1.41(d,3H, CH$_3$); 1.32(m,3H,CH$_3$); 0.94(d,6H,(CH$_3$)$_2$).

IR(neat): 2101, 1777, 1741 and 1716 cm$^{-1}$.

EXAMPLE 186

3-[[5-(Aminomethyl)tetrahydro-3-furanyl]thio]-4-methyl-6-[1-[[(2-methylpropoxy)carbonyl]oxy]ethyl-7-oxo-1-azabicyclo[3.2.0]hept-2-ene-2-carboxylic acid diastereomers The title compound is prepared by the procedure of Example 18, using 1.22 g of product from Example 185, 0.764 g of 10% palladium on carbon, 21 ml of 0.1M sodium phosphate buffer (pH 7.0) and 78 ml of dioxane to give 0.122 g of the desired product.

EXAMPLE 187

1,4-Anhydro-2-deoxy-D-erythro-pentitol dimethanesulfonate

The title compound is prepared by the procedure of Example 178 using 0.173 g of 1,2-dideoxy-D-ribose prepared by the method of M. Takeshita et al., *J. Bio. Chem.*, (1987), 262(21), 10171, 249 μl of methanesulfonyl chloride and 3 ml of pyridine to give 0.310 g of the desired product after chromatography.

$^1$H NMR(CDCl$_3$):δ 5.18–5.15(m,1H); 4.4–4.31(m,2H); 4.3–4.25(m,1H): 4.15–4.06(m,1H); 4.0–4.9(m,1H); 3.1(s, 3H,CH$_3$); 3.09(s,3H,CH$_3$); 2.3–2.2(m,2H).

EXAMPLE 188

1,4-Anhydro-5-azido-2,5-dideoxy-D-erythro-pentitol 3-methanesulfonate

The title compound is prepared by the procedure of Example 43 using 3.57 g of product from Example 187, 0.726 g of lithium azide and 58 ml of dimethylformamide to give 2.12 g of the desired product after chromatography.

$^1$H NMR(CDCl$_3$):δ 5.08–5.04(m,1H); 4.2–4.09(m,2H); 3.98–3.89(m,1H); 3.56–3.38(dd,2H); 3.06(s,3H,CH$_3$); 2.34–2.22(m,2H).

EXAMPLE 189

2,5-Anhydro-1-azido-1,4-dideoxy-3-thio-D-threo-pentitol 3-acetate

The title compound is prepared by the procedure of Example 5 using 1.57 g of product from Example 188, 0.892 g of potassium thioacetate, 10 ml of dimethylformamide and 10 ml of toluene to give 0.30 g of the desired product after chromatography.

$^1$H NMR(CDCl$_3$):δ 4.28–4.2(m,1H); 4.2–4.1(dd,1H); 4.08–3.98(m,1H); 3.89–3.79(dd,1H); 3.4–3.3(m,2H); 2.5–2.35(m,1H); 2.36(s,3H,Ac); 2.05–1.9(m,1H).

EXAMPLE 190

2,5-Anhydro-1-azido-1,4-dideoxy-3-thio-D-threo-pentitol

The title compound is prepared by the procedure of Example 16 using 0.30 g of product from Example 189, 0.35 ml of sodium methoxide/methyl alcohol (25 wt %) and 5 ml of tetrahydrofuran to give 0.219 g of the desired product after chromatography.

$^1$H NMR(CDCl$_3$):δ 4.1–4.0(m,2H); 3.9–3.8(m,1H); 3.55–3.43(m,3H); 2.55–2.4(m,1H); 2.06–2.94(m,1H); 1.65–1.62(d,1H,SH).

EXAMPLE 191

[4R-[4α,5β,6β(R*)]]-2,5-Anhydro-1-azido-1,4-dideoxy-3-S-[6-(1-hydroxyethyl)-4-methyl-2-[[(4-nitrophenyl) methoxy]carbonyl]-7-oxo-1-azabicyclo[3.2.0]hept-en-3-yl]-3-thio-D-threopentitol The title compound is prepared by the procedure of Example 17 using 0.219 g of product from Example 190 in 3 ml of acetonitrile, 0.818 g of product from Example 15 in 4 ml of acetonitrile, and 186 μl of Hunig's base to give 0.436 g of the desired product after chromatography.

$^1$H NMR(CDCl$_3$):δ 8.20(d,2H); 7.65(d,2H); 5.51(d,1H); 5.21(d,1H); 4.3–4.2(m,3H); 4.17–4.09(m,1H); 3.94–3.8(m, 2H); 3.6–3.4(m,3H); 3.37–3.30(m,1H); 2.67(bs,1H,OH); 2.5–2.4(m,1H); 2.2–2.05(m,1H); 1.35(d,3H,CH$_3$); 1.28(d, 3H,CH$_3$)

EXAMPLE 192

[4R-[4α,5β,6β(R*)]]-1-Amino-2,5-anhydro-3-S-[2-carboxy-6-(1-hydroxyethyl)-4-methyl-7-oxo-1-azabicyclo[3.2.0]hept-2-en-3-yl]-1,4-dideoxy-3-thio-D-threo-pentitol The title compound is prepared by the procedure of Example 18 using 0.436 g of product from Example 191, 0.150 g of palladium on carbon, 9 ml of 0.1M sodium phosphate buffer (pH 7.0) and 13 ml of dioxane to give 0.122 g of the desired product after chromatography.

$^1$H NMR(D$_2$O):δ 4.5–4.3(m,1H); 4.29–4.18(m,2H); 4.12–4.02(m,1H); 4.0–3.85(m,2H); 3.5–3.4(m,2H); 3.35–3.25(m,1H); 3.2–3.1(m,1H); 2.5–2.4(m,1H); 1.27(d, 3H,CH$_3$); 1.17(d,3H,CH$_3$).

EXAMPLE 193

[4R-[4α,5β,6β(R*)]]-2,5-Anhydro-3-S-[2-carboxy-6-(1-hydroxyethyl)-4-methyl 7-oxo-1-azabicyclo [3.2.0]hept-2-en-3-yl]-1,4-dideoxy-1-[(iminomethyl) amino]-3-thio-D-threo-pentitol To 4 ml of a 5° C. phosphate buffer (ph 8.5) solution is added 0.052 g of product from Example 192 and 0.832 g of ethyl formimidate hydrochloride, in portions. The pH is maintained at 8.5 with 1N sodium hydroxide. The solution is stirred at 5° C. and pH 8.5 for 5 minutes, then the pH is adjusted to pH 7.0 with 5% hydrochloric acid and the reaction mixture is concentrated in vacuo with no heat. The residue is purified on a C$_{18}$ reverse phase chromatography plate (5% aqueous ethyl alcohol) to give 0.055 g of the desired product.

$^1$H NMR(D$_2$O):δ 7.75–7.6(t,1H,CH=); 4.5–3.2(m,11H); 2.25(m,1H);1.9(m,1H); 1.1 (d,3H,CH$_3$); 0.99(d,3H,CH$_3$).

EXAMPLE 194

3-[[5-(Azidomethyl)tetrahydro-3-furanyl]thio]-4-methyl-6-[1-[[(2-methylpropoxy)carbonyl]oxy]ethyl]-7-oxo-1-azabicyclo[3.2.0]hept-2-ene-2-carboxylic acid (4-nitrophenyl)methyl ester diastereomers The title compound is prepared by the procedure of Example 185 using 1.00 g of product from Example 63 in 20 ml of tetrahydrofuran, 0.26 ml of isobutyl chloroformate and 2.2 ml of 0.1M lithium bis(trimethylsilyl)amide to give 0.636 g of the desired product after chromatography.

$^1$H NMR(CDCl$_3$):δ 8.23(d,2H); 7.66(d,2H); 5.49(d,1H); 5.26(d,1H); 4.22–4.16(m,3H); 3.93(m,2H); 3.84(m,2H); 3.47–3.36(m,4H); 2.5(m,1H,CHCH$_3$); 1.97(m,1H); 1.7(m, 0.5H); 1.85(m,0.5H); 1.49(d,3H,CH$_3$); 1.29(t,3H,CH$_3$); 0.94 (d,6H,2CH$_3$C).

IR(neat): 2100, 1777, 1741 and 1707 cm$^{-1}$.

EXAMPLE 195

3-[[5-Aminomethyl)tetrahydro-3-furanyl]thio]-4-methyl-6-[1-[[(2-methylpropoxy)carbonyl]oxy] ethyl]-7-oxo-1-azabicyclo[3.2.0]hept-2-ene-2-carboxylic acid diastereomers The title compound is prepared by the procedure of Example 18 using 0.764 g of product from Example 194, 0.478 g of palladium on carbon, 13 ml of sodium phosphate buffer (pH 7.0) and 49 ml of dioxane to give after chromatography 0.0668 g of the desired product.

$^1$H NMR(D$_2$O):δ 4.2(m,2H); 4.1(m,1H); 3.95(d,2H); 3.8 (m,3H); 3.65(m,1H); 3.35(m,1H); 3.13(m,2H); 2.6(m,1H); 1.92(m,1H); 1.6(m,1H); 1.35(d,3H,CH$_3$); 1.18(dd,3H,CH$_3$); 0.88(d,6H,2CH$_3$).

EXAMPLE 196

3,6-Dioxabicyclo[3.1.0]hexane

A 0° C. solution, under argon, of 5 g of 2,5-dihydrofuran in 85 ml of methylene chloride is treated with 13.54 g of 85% m-chloroperbenzoic acid. The reaction mixture is allowed to warm to room temperature overnight. The reaction mixture is filtered and the filtrate stirred for 10 minutes with saturated sodium carbonate and the two layers separated. The organic layer is dried and concentrated in vacuo to give an oil. The oil is distilled under vacuum (water aspirator) to give 3.93 g of the desired epoxide.

$^1$H NMR(CDCl$_3$):δ 4.03(d,2H,J=10.5 Hz); 3.81(s,2H); 3.66(d,2H,J=10.5 Hz).

MS(CI):m/z 87 (M$^+$+H).

EXAMPLE 197 trans-(±)-Tetrahydro-4-hydroxy-3-furancarbonitrile

To 5.0 g of product from Example 196 is added 29 ml of 1M diethylaluminum cyanide at room temperature. The reaction is exothermic. The mixture is stirred for 3 hours, quenched very carefully with ethyl alcohol, as the evolved gas is hydrogen cyanide, cooled to 0° C. and stirred until the reaction warms up to room temperature. The reaction is then flushed with argon for 10 minutes, concentrated in vacuo to about 15 ml, and filtered through a pad of diatomaceous earth. The pad is washed with methyl alcohol and diethyl ether. The combined organic layers are refiltered and concentrated in vacuo to give 0.383 g of the desired product.

$^1$H NMR(CDCl$_3$):δ 4.69(m,1H); 4.22(dd,1H,J=7.3 and 9.12 Hz); 4.05(m,2H); 3.8(dd,1H,J=2.71 and 10.11 Hz); 3.06(m,1H); 2.83(br s,1H.OH).

MS(CI): m/z 114 (M$^+$+H).

EXAMPLE 198

(3R-trans)-Tetrahydro-4-[(methylsulfonyl)oxy]-3-furancarbonitrile

The title compound is prepared by the procedure of Example 178 using 0.367 g of product from Example 197, 0.394 g of triethylamine, and 0.446 g of methanesulfonyl chloride to give 0.554 g of the desired product.

¹H NMR(CDCl₃):δ 5.41(m,1H); 4.24(dd,1H,J=7.16 and 9.13 Hz); 4.18–3.98(m,3H); 3.41(m,1H); 3.19(s,3H, SO₂CH₃).

MS(CI): m/z 192 (M⁺+H).

EXAMPLE 199

(3R-cis)-Tetrahydro-4-[[(4-methoxyphenyl)methyl] thio]-3-furancarbonitrile

A 0° C. slurry, under argon, of 0.14 g of sodium hydride in tetrahydrofuran is treated dropwise with 0.47 ml of 4-methoxytoluenethiol. The reaction mixture is allowed to warm to room temperature over 45 minutes, followed by the dropwise addition of 0.539 g of product from Example 198 in 3 ml of tetrahydrofuran. The reaction is stirred for 45 minutes and then cooled to 0° C. The mixture is diluted, carefully, with water and extracted with diethyl ether. The organic layers are washed with saturated sodium chloride, dried and concentrated in vacuo. The residue is purified by chromatography (Silica gel: 5–40% ethyl acetate/hexane) to give 0.583 g of the desired product as an oil.

¹H NMR(CDCl₃):δ 7.26(d,2H,J=8.7 Hz); 6.87(d,2H,J= 8.7 Hz); 4.05(m,3H); 3.82(s,2H,ArCH₂); 3.81(s,3H, CH₃OAr); 3.46(m,2H); 2.91(m,1H).

MS(CI): m/z 250 (M⁺+H).

EXAMPLE 200 cis-(±)-Tetrahydro-4-[[(4-methoxyphenyl)methyl] thio]-3-furanmethanamine

A room temperature solution, under argon, of 4.22 ml of 1.0M lithium aluminum hydride in tetrahydrofuran is treated, dropwise, with 0.876 g of product from Example 199 in 3 ml of diethyl ether; during which time the reaction refluxes gently. After complete addition, the reaction is stirred at room temperature for 2 hour. The reaction mixture is quenched with 1 ml of water, 10.5 ml of 1.0N sodium hydroxide and 2.0 ml of water. The solid white precipitate formed is collected and washed with large volumes of diethyl ether. The diethyl ether layer is concentrated in vacuo to give 0.889 g of the desired product.

¹H NMR(CDCl₃):δ 7.23(d,2H,J=8.61 Hz); 6.87(d,2H,J= 8.61 Hz); 3.95(m,2H); 3.81(s,3H,OCH₃); 3.73(s,2H, ArCH₂); 3.47(m,2H); 2.82(m,3H); 2.31(m,1H).

MS(CI): m/z 254(M⁺+H).

EXAMPLE 201 cis(±)-Tetrahydro-4-[[(4-methoxyphenyl)methyl] thio]-3-furanyl]methyl]carbamic acid (4-nitrophenyl)methyl ester A 0° C. mixture of 0.889 g of product from Example 200, 0.534 g of potassium carbonate, 0.832 g of p-nitrobenzyl chloroformate and 7 ml of dry tetrahydrofuran is stirred for two hours, while warming to room temperature. The solution is diluted with 50 ml of water and extracted with ethyl acetate. The ethyl acetate layers are washed with saturated sodium chloride, dried and concentrated in vacuo. The residue is purified by chromatography (silica gel: 10–100% ethyl acetate/hexane) to give 0.931 g of the desired product as a colorless oil.

¹H NMR(CDCl₃):δ 8.17(d,2H,J=8.7 Hz); 7.48(d,2H,J= 8.7 Hz); 7.22(d,2H,J=8.6 Hz); 6.83(d,2H,J=8.6 Hz); 5.17(s, 3H,ArCH₂ and NH); 4.02(t,1H,J=7.2 Hz); 3.92(t,1H,J=7.4 Hz); 3.77(s,3H,OCH₃); 3.69(s,2H,ArCH₂); 3.52(m,2H); 3.22(t,2H,J=6.4 Hz); 2.89(m,1H); 2.27(m,1H).

MS(CI): m/z 432(M⁺).

EXAMPLE 202 cis-(±)-[Tetrahydro-4-mercapto-3-furanyl)methyl] carbamic acid (4-nitrophenyl)methyl ester A room temperature solution, under argon, of 0.905 g of product from Example 201 in 30 ml of 80% acetic acid is treated with 0.45 ml of anisole and 1.07 g of mercuric trifluoroacetate. The reaction mixture is stirred for 2.5 hours, diluted with 30 ml of water, hydrogen sulfide gas is bubbled through for 10 minutes and the argon for 10 minutes. The black precipitate is collected, washed with water and ethyl acetate and the combined filtrate is concentrated in vacuo. The residue is purified by chromatography (silica gel: 10–60% ethyl acetate/hexane) to give 0.545 g of the desired product.

¹H NMR(CDCl₃):δ 8.21(d,2H,J=8.7 Hz); 7.51(d,2H,J= 8.7 Hz); 5.21(s,2H,ArCH₂); 5.20(brs,1H,NH); 4.20(dd,1H, J=7.1 and 9.0 Hz); 4.03(dd,1H,J=7.8 and 8.9 Hz); 3.58(m, 2H); 3.37(m,2H); 3.06(m,1H); 2.29(m,1H); 1.73(d,1H,J= 7.74 Hz, SH).

MS(CI): m/z 313(M⁺H).

EXAMPLE 203

[4R-[3(3R*,4R* or 3S*,4S*),4α,5β,6β(R*)]]-6-(1-Hydroxyethyl)-4-methyl-7-oxo-3-[[tetrahydro-4-[[[[(4-nitrophenyl)methoxy]carbonyl]amino]methyl]-3-furanyl]thio-1-azabicyclo[3.2.0]hept-2-ene-2-carboxylic acid (4-nitrophenyl)methyl ester The title compound is prepared by the procedure of Example 17 using 0.49 g of product from Example 202, 0.933 g of product from Example 15, 0.202 g of Hunig's base and 8 ml of acetonitrile to give after chromatography 0.771 g of the desired product.

¹H NMR(CDCl₃):δ 8.21(d,2H,J=8.7 Hz); 8.19(d,2H,J= 8.7 Hz); 7.61(d,2H,J=8.7 Hz); 7.49(d,2H,J=8.7 Hz); 5.49(d, 1H,J=13.8 Hz); 5.24(d,1H,J=13.8 Hz); 5.19(s,3H,NH and ArCH₂); 4.24(m,3H); 4.20(t,1H,J=8.9 Hz); 3.68(m,2H); 3.53(m,1H); 3.39(m,1H); 3.26(m,2H); 2.36(m,1H); 2.0(brs, 2H); 1.35(d,3H,J=6.3 Hz); 1.21(d,3H,J=7.2 Hz).

EXAMPLE 204

[4R-[3(3R*,4R* or 3S*,4S*),4α,5(3,6β(R*)]]-3-[[4-(Aminomethyl)tetrahydro-3-furanyl]thio]-6-(1-hydroxyethyl)-4-methyl-7-oxo-1-azabicyclo[3.2.0]-hept-2-ene-2-carboxylic acid The title compound is prepared by the procedure of Example 18 using 0.136 g of product from Example 203, 0.041 g of 10% palladium on carbon and 8 ml of dioxane: 0.2M phosphate buffer (pH 7) (8:2) to give, after chromatography (C₁₈ reverse phase plates: 5% ethyl alcohol/water), 0.007 g of the desired product.

¹H NMR(D₂O):δ 4.19(m,3H); 3.75(m,1H); 3.58(m,3H); 3.42(m,1H); 3.25(m,2H); 3.10(m,1H); 2.43(m,1H); 1.26(d, 3H,J=5.7 Hz); 1.18(d,3H,J=6.7 Hz).

EXAMPLE 205

Tetrahydro-4-mercapto-2-thiophenemethanol 1,1-dioxide stereoisomers

The title compound is prepared by the procedure of Example 202 using 0.615 g of product from Example 177, 1.04 g of mercuric trifluoroacetate, 0.440 g of anisole and 31 ml of 80% acetic acid to give, after chromatography (Silica gel: 10–100% ethyl acetate/hexane), 0.322 g of the desired product.

$^1$H NMR(CDCl$_3$):δ 4.12(m,2H); 3.90(m,2H); 3.75(m, 1H); 3.50(m,3H); 3.32(m,1H); 3.10(dd,1H,J=8.5 and 13.4 Hz); 2.93(t,1H,J=11.5 Hz); 2.75–2.58(m,2H); 2.38–2.20(m, 3H); 2.10(d,1H,J=7.4 Hz minor isomer SH); 1.98(d,1H,J= 7.4 Hz major isomer SH).

MS(CI): m/z 183 (M$^+$+H).

EXAMPLE 206

[4R-[4α,5β,6β(R*)]]-6-(1-Hydroxyethyl)-4-methyl-7-oxo-3-[[tetrahydro-5-(hydroxymethyl)-3-thienyl]thio]-1-azabicyclo[3.2.0]hept-2-ene-2-carboxylic acid (4-nitrophenyl)methyl ester stereoisomers The title compound is prepared by the procedure of Example 17 using 0.995 g of product from Example 15, 0.305 g of product from Example 205, 0.216 g of Hunig's base and 5 ml of acetonitrile to give, after chromatography (Silica gel: 20–100% ethyl acetate/hexane), 0.789 g of the desired product.

$^1$H NMR(CDCl$_3$):δ 8.22(d,2H,J=8.8 Hz); 7.65(d,2H,J= 8.8 Hz); 5.51(d,1H,J=13.8 Hz); 5.23(d,1H,J=13.8 Hz); 4.08 (m,1H); 3.85(m,2H), 3.6–3.3(m,4H), 3.02(t,1H,J=6.7 Hz); 2.63(m,1H), 2.35(brs,2H); 1.37(d,3H,J=7.2 Hz); 1.29(d,3H, J=7.2 Hz).

MS(CI): m/z 527 (M$^+$H).

EXAMPLE 207

[4R-[4α,5β,6β(R*)]]-6-1-Hydroxyethyl)-4-methyl-7-oxo-3-[[tetrahydro-5-(hydroxymethyl)-3-thienyl]thio]-1-azabicyclo[3.2.0]-hept-2-ene-2-carboxylic acid thiophene-1,1-dioxide stereoisomers The title compound is prepared by the procedure of Example 18 using 0.208 g of product from Example 206, 0.033 g of sodium bicarbonate, 0.066 g of 10% palladium on carbon and 10 ml of dioxane/water (8:2) to give, after chromatography (C$_{18}$ reverse phase plates: 4% ethyl alcohol/water), 0.140 g of the desired product.

$^1$H NMR(CDCl$_3$):δ 4.22(m,2H); 4.07–3.20(m,8H); 2.70 (m,1H); 1.88(m,1H); 1.25(d,3H,J=6.4 Hz), 1.17(brs,3H).

MS(FAB): m/z 414 (M$^+$+Na).

EXAMPLE 208

(R)-1-Phenoxy-5-hexen-2-ol

Under anhydrous conditions at −78° C., 475 ml of 1M solution of allylmagnesium bromide in diethyl ether and 60 ml of triethyl borate in 400 ml of diethyl ether are added simultaneously, but separately, to 400 ml of diethyl ether. The reaction is stirred at −78° C. for 3 hours, warmed to 0° C., 450 ml of 2N hydrochloric acid is added carefully and stirred at room temperature for 2 hours. The layers are separated and the organic layer is dried over magnesium sulfate. The diethyl ether layer is filtered and concentrated in vacuo to 100 ml. The residue is dissolved in 400 ml of diethyl ether and treated with 77.8 g of (−)-diisopropyl D-tartrate. The reaction is stirred overnight at room temperature under argon. Ten grams of magnesium sulfate is added and the mixture stirred for 20 minutes, filtered and concentrated in vacuo. The residue is purified by Kugelrohr distillation (at 0.15 mm Hg. bp 100°–130° C.) to give 72.30 g of the desired borate ester.

Under anhydrous conditions (argon) at −78° C., 20.24 g of (phenylmethoxy)acetaldehyde in 17.35 ml of toluene is added to a mixture of 72.3 g of borate ester in 1000 ml of toluene and 54.22 g of 4A° molecular sieves. The mixture is stirred at −78° C. for 16 hours. The reaction is filtered, the sieves washed with toluene and the filtrate is poured into 800 ml of water. The layers are separated, the organic layer dried and concentrated in vacuo. The residue is redissolved in 725 ml of diethyl ether and treated with 1M potassium hydroxide for 24 hours at room temperature. The layers are separated, the organic layer is washed with saturated sodium bicarbonate, dried and concentrated in vacuo. The residue is purified by Kugelrohr distillation (1–2 mm Hg. bp 100°–110° C.) to give 10.44 g of the desired product. Calcd. C$_{12}$H$_{16}$O$_2$: C: 74.69; H: 8.39 Found: C: 74.69; H: 8.42

[α]$_D^{26}$=−3°±1 in CHCl$_3$

EXAMPLE 209

2,5-Anhydro-1,3-dideoxy-1-iodo-L-threo-pentitol and 1,4-Anhydro-3,5-dideoxy-5-iodo-D-erythro-pentitol To a vigorously stirred 3° C. solution of 10.44 g of product from Example 208 in 200 ml of diethyl ether and 68 ml of water is added 6.76 g of solid sodium bicarbonate, in one portion, followed by 20.33 g of iodine. The reaction mixture is stirred at room temperature for 1½ hours and a saturated sodium sulfite solution is added slowly until the yellow color disappears. The layers are separated, the organic layer is dried and concentrated in vacuo to give 11.8 g of a light yellow oil. The residue is purified by chromatography (Silica gel: 20–50% ethyl acetate/hexane) to give 2.14 g of the cis isomer and 3.6 g of trans isomer.

trans isomer $^1$H NMR(CDCl$_3$):δ 4.59(t,1H); 4.25–4.12(m,1H); 4.41–4.02(m,1H); 3.8(d,1H); 3.2(d,2H); 2.7(s,1H); 2.2–2.1 (m,1H); 1.82–1.75(m,1H).

cis isomer $^1$H NMR(CDCl$_3$):δ 4.5(m,1H); 4.18–4.0(m,1H); 4.0–3.9 (m,1H); 3.82–3.78(m,1H); 3.42–3.3(m,2H); 3.82(bs,1H, OH); 2.4–2.3(m,1H); 1.82–1.75(m,1H).

EXAMPLE 210

1,4-Anhydro-5-azido-3,5-dideoxy-D-erythro-pentitol

A mixture of 3.6 g of the trans isomer from Example 209, 1.54 g of lithium azide and 6 ml of dimethylformamide is heated in a 70° C. oil bath for 3 hours. The reaction mixture is concentrated in vacuo. The residue is purified by chromatography (Silica gel: 75% ethyl acetate/hexane) to give 1.88 g of the desired product.

$^1$H NMR(CDCl$_3$):δ 4.56(m,1H); 4.4(m,1H); 4.1(d,1H); 3.8(m,1H); 3.51(m,1H); 3.25(dd,1H); 2.3(bs,1H,OH); 2.08–1.85(m,2H).

EXAMPLE 211

1,4-Anhydro-5-azido-3,5-dideoxy-D-erythro-pentitol 2-(trifluoromethanesulfonate)

The title compound is prepared by the procedure of Example 22 using 0.716 g of product from Example 210 in 4 ml of methylene chloride, 0.925 ml of trifluoromethanesulfonic anhydride in 7 ml of methylene chloride and 0.445 ml of pyridine to give, after chromatography (Silica gel: 75% ethyl acetate/hexane), 0.985 g of the desired product.

$^1$H NMR(CDCl$_3$):δ 5.57(m,1H); 4.42(m,1H); 4.3–4.1(m, 2H); 3.6(dd,1H); 3.3(dd,1H); 2.4–2.3(m,1H); 2.3–2.18(m, 1H).

EXAMPLE 212

2,5-Anhydro-1-azido-1,3-dideoxy-4-thio-D-threo-pentitol 4-acetate

The title compound is prepared by the procedure of Example 5 using 0.985 g of product from Example 211, 0.450 g of potassium thioacetate and 10 ml of acetonitrile to give, after chromatography (Silica gel: 30% ethyl acetate/hexane), 0.510 g of the desired product.

$^1$H NMR(CDCl$_3$):δ 4.2–4.1(m,2H); 4.08–3.98(m,1H); 3.8–3.7(m,1H); 3.5–3.4(dd,1H); 3.38–3.28(dd,1H); 2.52–2.42(m,1H); 3.34(s,3H,CH$_3$); 1.75–1.65(m,1H).

EXAMPLE 213

2,5-Anhydro-1-azido-1,3-dideoxy-4-thio-D-threo-pentitol

The title compound is prepared by the procedure of Example 16 using 0.510 g of product from Example 212, 0.6 ml of 25wt % sodium methoxide/methyl alcohol and 10 ml of tetrahydrofuran to give, after chromatography (Silica gel: 30% ethyl acetate/hexane), 0.318 g of the desired product.

$^1$H NMR(CDCl$_3$):δ 4.2–4.05(m,2H); 3.65–3.60(m,1H); 3.5–3.25(m,3H); 2.55–2.4(m,1H); 1.8(d,1H,SH); 1.75–1.6 (m,1H).

EXAMPLE 214

2,5-Anhydro-1-azido-1,3-dideoxy-4-S-[6-(1-hydroxyethyl)-4-methyl-2-[[(4-nitrophenyl)methoxy]carbonyl]-g7-oxo-1-azabicyclo[32.0]hept-2-en-3-yl]-4-D-threo-pentitol The title compound is prepared by the procedure of Example 17 using 0.318 g of product from Example 213 in 4 ml of acetonitrile, 1.18 g of product from Example 15 in 6 ml of acetonitrile and 0.27 ml of Hunig's base to give, after chromatography (Silica gel: 75% ethyl acetate/hexane), 0.720 g of the desired product.

$^1$H NMR(CDCl$_3$):δ 8.24(d,2H); 7.67–7.65(d,2H); 5.53–5.48(d,1H); 5.26–5.22(d,1H); 4.29–4.08(m,4H); 3.79–3.74(m,2H); 3.46(3.27(m,4H); 2.52–2.45(m,1H); 1.75–1.6(m,1H +1 OH); 1.37(d,3H); 1.3(d,3H).

EXAMPLE 215

[4R-[4α,5β,6β(R*)]-1-Amino-2,5-anhydro-4-S-[2-carboxy-6-(1-hydroxyethyl)-4-methyl-7-oxo-1-azabicyclo[3.2.0]hept-2-en-3-yl]-1,3-dideoxy-4-thio-D-threo-pentitol The title compound is prepared by the procedure of Example 18 using 0.720 g of product from Example 213, 0.496 g of 10% palladium on carbon, 15 ml of 0.1M sodium-phosphate buffer (pH 7) and 30 ml of dioxane to give, after chromatography (Reverse Phase Plates: 5% aqueous ethyl alcohol), 0.233 g of the desired product.

$^1$H NMR(D$_2$O):δ 4.4–4.12(m,4H); 4.05–3.8(m,2H); 3.58–3.2(m,4H); 2.8–2.65(m,1H); 1.8–1.6(m,1H); 1.35(d, 3H); 1.27(d,3H).

EXAMPLES 216–253

Examples 216 to 253 exemplify compounds of formula I obtained by the methods described hereinabove.

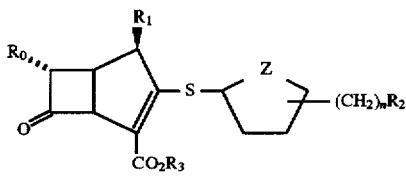

| Example | R$_0$ | R$_1$ | n | Z | R$_2$ | R$_3$ |
|---|---|---|---|---|---|---|
| 216 | CH$_3$CH(OH)— | CH$_3$ | 0 | S | H | Na |
| 217 | CH$_3$CH(OH)— | CH$_3$ | 0 | O | H | Na |
| 218 | CH$_3$CH(OH)— | CH$_3$ | 1 | S | OH | Na |
| 219 | CH$_3$CH(OH)— | CH$_3$ | 1 | O | OH | Na |
| 220 | CH$_3$CH(OH)— | CH$_3$ | 1 | S | OCH$_2$C$_6$H$_5$ | Na |
| 221 | CH$_3$CH(OH)— | CH$_3$ | 1 | O | OCH$_2$C$_6$H$_5$ | Na |
| 222 | CH$_3$CH(OH)— | CH$_3$ | 1 | S | NH$_2$ | H |
| 223 | CH$_3$CH(OH)— | CH$_3$ | 1 | O | NH$_2$ | H |
| 224 | CH$_3$CH(OH)— | CH$_3$ | 1 | S | NHCH$_3$ | H |
| 225 | CH$_3$CH(OH)— | CH$_3$ | 1 | O | NHCH$_3$ | H |
| 226 | CH$_3$CH(OH)— | CH$_3$ | 1 | O | OCH$_3$ | Na |
| 227 | CH$_3$CH(OH)— | CH$_3$ | 1 | S | OCH$_3$ | Na |
| 228 | CH$_3$CH(OH)— | CH$_3$ | 1 | O | OCONH$_2$ | Na |
| 229 | CH$_3$CH(OH)— | CH$_3$ | 1 | S | OCONH$_2$ | Na |
| 230 | CH$_3$CH(OH)— | CH$_3$ | 1 | O | NHCH=NH | H |
| 231 | CH$_3$CH(OH)— | CH$_3$ | 1 | S | NHCH=NH | H |
| 232 | CH$_3$CH(OH)— | CH$_3$ | 1 | O | N=CHN(CH$_3$)$_2$ | H |
| 233 | CH$_3$CH(OH)— | CH$_3$ | 1 | S | N=CHN(CH$_3$)$_2$ | H |
| 234 | CH$_3$CH(OH)— | CH$_3$ | 1 | O | N$^+$(CH$_3$)$_3$ | — |
| 235 | CH$_3$CH(OH)— | CH$_3$ | 1 | S | N$^+$(CH$_3$)$_3$ | — |
| 236 | CH$_3$CH(OH)— | CH$_3$ | 1 | O | CONH$_2$ | Na |
| 237 | CH$_3$CH(OH)— | CH$_3$ | 1 | S | CONH$_2$ | Na |
| 238 | CH$_3$CH(OH)— | CH$_3$ | 1 | O | CON(CH$_3$)$_2$ | Na |
| 239 | CH$_3$CH(OH)— | CH$_3$ | 1 | S | CON(CH$_3$)$_2$ | Na |

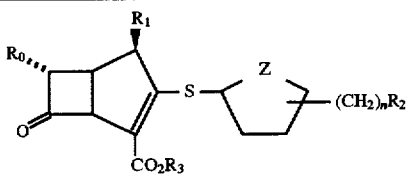

| Example | R₀ | R₁ | n | Z | R₂ | R₃ |
|---------|-----|-----|---|---|-----|-----|
| 240 | CH₃CH(OH)— | CH₃ | 1 | O | 1-Pyridinium | — |
| 241 | CH₃CH(OH)— | CH₃ | 1 | S | 1-Pyridinium | — |
| 242 | CH₃CH(OH)— | CH₃ | 2 | O | NH₂ | H |
| 243 | CH₃CH(OH)— | CH₃ | 2 | S | NH₂ | H |
| 244 | CH₃CH(OH)— | CH₃ | 2 | O | N⁺(CH₃)₃ | — |
| 245 | CH₃CH(OH)— | CH₃ | 2 | S | N⁺(CH₃)₃ | — |
| 246 | CH₃CH(OH)— | CH₃ | 2 | O | NHCH=NH | H |
| 247 | CH₃CH(OH)— | CH₃ | 2 | S | NHCH=NH | H |
| 248 | CH₃CH(OH)— | CH₃ | 2 | O | N=CHN(CH₃)₂ | H |
| 249 | CH₃CH(OH)— | CH₃ | 2 | S | N=CHN(CH₃)₂ | H |
| 250 | CH₃CH(OH)— | CH₃ | 1 | O | [NHC(=O)N(cyclic)-C(=O)-C(=O)NEt] | Na |
| 251 | CH₃CH(OH)— | CH₃ | 1 | O | [NHCN(cyclic with C=O, O)] | Na |
| 252 | CH₃CH(OH)— | CH₃ | 1 | O | [NHCN(cyclic with C=O, NH)] | Na |
| 253 | CH₃CH(OH)— | CH₃ | 1 | O | NHC(=O)N(CH₃)-C₆H₃(OH)₂ | Na |

EXAMPLE 254

Carbonic acid 4-Nitrophenyl (4-Nitrophenyl)methyl Ester

To an ice cooled solution, under argon, of 7.3 g of p-nitrophenol and 7.5 ml of triethylamine in 36 ml of dry tetrahydrofuran, is added, dropwise, a solution of 10.78 g of p-nitrobenzyl chloroformate in 18 ml of dry tetrahydrofuran. The reaction mixture, a suspension, is stirred at room temperature overnight. The formed solid is collected, washed with water and dried to give 5.9 g of the desired product.

$^1$H NMR(CDCl₃):δ 8.3(d,2H,J=3.0 Hz); 8.27(d,2H,J=3.0 Hz); 7.63(d,2H,J=8.7 Hz); 7.40(d,2H,J=9.2); 5.41(s,2H).

EXAMPLE 255

N-[[(4-Nitrophenyl methoxycarbonyl]glycine

One and one half grams of glycine is slurried in 235 ml of a 80/20 mixture of ethyl alcohol/water. To this is added 5.6 ml of triethylamine, solution occurs, followed by 6.36 g of product from Example 254. A precipitate forms and the reaction is stirred overnight at room temperature. The reaction mixture is concentrated in vacuo. The resulting oil is dissolved in water and ethyl alcohol, the pH is adjusted to 1.5 with concentrated hydrochloric acid and the volume is reduced. The reaction mixture is extracted with methylene chloride, the organic layer is washed with water and concentrated in vacuo. The residue is purified by chromatography (Silica gel: ethyl acetate) to give 2.83 g of the desired product.

EXAMPLE 256

[2-[(2,5-Dioxo-1-pyrrolidinyl)oxy]-2-oxoethyl] carbamic acid (4-Nitrophenyl)methyl Ester To a solution of 2.83 g of product from Example 255 in 43 ml of dioxane is added 1.28 g of N-hydroxysuccinimide and 2.30 g of 1,3-dicyclohexylcarbodiimide, hereinafter called DCC, in 13 ml of dioxane. The formed suspension is stirred at room temperature overnight. The urea by-product is collected and the filtrate is concentrated in vacuo to give an oil. The oil is dissolved in methylene chloride, washed with water, the layers are separated and the organic phase is cooled. The formed crystals are collected and dried to give 1.87 g of the desired product.

$^1$H NMR(CDCl₃):δ 8.09(d,2H,J=8.7 Hz); 7.21(d,2H, J=8.7 Hz); 6.8(t,1H,NH); 5.13(s,2H); 4.19(d,2H); 2.74(s, 4H).

EXAMPLE 257

[3-S-[4R-[4α,5β,6β(R*)]]]-1-[(Aminoacetyl)amino]-2,5-anhydro-3-S-[2-carboxy-6-(1-hydroxyethyl)-4-methyl-7-oxo-1-azabicyclo[3.2.0.]hept-2-en-3-yl]-1,4-dideoxy-3-thio-D-threo-pentitol To a 0°–2° C. solution of 5 ml of 0.1M sodium dihydrogen phosphate buffer, pH 7.0, is added 0.171 g of product from Example 192 followed by the adjustment of the pH to 8.5 with 1N sodium hydroxide. A solution of 0.175 g of product from Example 256 in 3.5 ml of dioxane is added while maintaining the pH at 8.5 with 1N sodium hydroxide. After 5 minutes of stirring, a tlc sample shows no starting material present. The pH is adjusted to 7.0 and 0.055 g of 10% palladium on carbon is added. The reaction mixture is reduced in a Parr apparatus, at 44 psi of hydrogen for 3 hours. The mixture is filtered, the filtrate concentrated in vacuo to a small volume, and extracted with ethyl acetate. The aqueous phase is further concentrated and purified by reverse phase chromatography (5% aqueous ethyl alcohol) to give 0.065 g of the desired product.

$^1$H NMR($D_2O$): δ 4.4–4.15(m,3H); 4.15–4.02(m,1H); 4.02–3–65(M,4H); 3.65–3.35(m,4H); 1.30(d,3H,Me, J=6.5 Hz); 1.20(d,3H,Me,J=7.0 Hz).

EXAMPLE 258

N-[[(4-Nitrophenyl)methylcarbonyl]-L-alanine

The title compound is prepared by the procedure of Example 255 using 5.3 g of product from Example 254, 1.48 g of L-alanine, 4.6 ml of triethylamine, and 200 ml of 80/20 ethyl alcohol/water. The resulting oil is purified by chromatography (3×, silica gel: 50% ethyl acetate/hexane) to give 3.39 g of the desired product.

$^1$H NMR($CDCl_3$): δ 11.0(s,1H,COOH); 8.04(d,2H,J=8.6 Hz); 7.4(d,2H,J=8.6 Hz); 5.9(d,1H,NH); 5.1(s,2H); 4.3(t,1H, CH); 1.36(d,3H,Me,J=7.2 Hz).

EXAMPLE 259

(S)-[2-[(2,5-Dioxo-1-pyrrolidinyl)oxy]-1-methyl-2-oxoethyl]carbamic Acid (4-Nitrophenyl)methyl Ester The title compound is prepared by the procedure of Example 256 using 11.85 g of product from Example 258 in 170 ml of dioxane, 5.08 g of N-hydroxysuccinimide and 9.12 g of DCC in 46 ml of dioxane to give 9.8 g of the desired product.

$^1$H NMR($CDCl_3$): δ 8.21(d,2H,J=8.5 Hz); 7.51(d,2H,J= 8.5); 5.55(d,1H); 5.23(s,2H); 4.7((t,1H); 2.86(s,4H); 1.61 (d,3H,J=7.3 Hz).

EXAMPLE 260

[3-S-[4R-[4α,5β,6β(R*)]]]-2,5-Anhydro-3-S-[2-carboxy-6-(1-hydroxyethyl)-4-methyl-7-oxo-1-azabicyclo[3.2.0]hept-2-en-3-yl]-1,4-dideoxy-1-[[2-[[[(4-nitrophenyl)methoxy]carbonyl]amino]-1-oxopropyl]amino]-3-thio-D-threo-pentitol monosodium salt Ten ml of 0.1M, pH 7, sodium dihydrogen phosphate buffer is cooled to 2° C. To the solution is added 0.342 g of product from Example 192 and the pH is adjusted to 8.5 with 1N sodium hydroxide. A solution of 0.401 g of product from Example 259 in 7 ml of dioxane is added while maintaining the pH at 8.5 with 1N sodium hydroxide. The reaction is monitored by tlc. After 5 minutes there is no starting material present. The pH is adjusted to pH 7.0 and the mixture is concentrated in vacuo. The residue is purified by chromatography (Reverse Phase Plates: 20% acetonitrile/water) to give 0.316 g of the desired product.

$^1$H NMR($CDCl_3$): δ 8.26(d,2H); 7.57(d,2H); 5.3(d,2H); 4.20–3.25(m,11H); 2.4(m,1H); 2.05(m,1H); 1.36(d,3H, J=7.0); 1.26(d,3H,J=6.01); 1.09(d,3H,J=7.0).

EXAMPLE 261

[3-S-[4R-[1-(S*),4α,5β,6β(R*)]]]-1-[(2-Amino-1-oxopropyl)amino]-2,5-anhydro-3-S-[2-carboxy-6-(1-hydroxyethyl)-4-methyl-7-oxo-1-azabicyclo[3.2.0] hept-2-en-3-yl]-1,4-dideoxy-3-thio-D-threo-pentitol A mixture of 0.316 g of product from Example 260, 5.2 ml of 0.1M sodium dihydrogen phosphate buffer, 7 ml of dioxane and 0.090 g of 10% palladium on carbon is reduced in a Parr apparatus to give, after chromatography (Reverse Phase Plates: 5% aqueous ethyl alcohol) 0.041 g of the desired product.

$^1$H NMR($CDCl_3$):δ 4.35–4.15(m,3H); 4.10–3.90(m,5H); 3.6–3.35(d,4H); 2.48(m,1H); 2.07(m,1H); 1.49(d,3H, J=6.0); 1.28(d,3H,J=6.0); 1.19(d,3H,J=6.75).

EXAMPLE 262

(S)-4-(Phenylmethyl)-2,5-oxazolidinedione

A mixture of 8.9 g of L-phenylalanine, 4.8 ml of trichloromethylchloroformate (Diphosgene), 70 ml of dry tetrahydrofuran and 0.135 g of activated carbon is heated in an oil bath at 55° C. for 2 hours, until the L-phenylalanine is in solution. The reaction is filtered through diatomaceous earth. The filtrate is concentrated in vacuo, treated with diethyl ether and hexane, and the resulting crystals are collected to give 1.04 g of the desired product.

$^1$H NMR($CDCl_3$): δ 7.19–7.17(m,2H); 7.38–7.31(m,3H); 6.31(s,1H,NH); 4.56–4.52(m,1H,CH); 3.30–3.29(m,1H); 3.04–2.97(m,1H).

EXAMPLE 263

(S)-4-(2-Methylpropyl)-2,5-oxazolidinedione

The title compound is prepared by the procedure of Example 262 using 3.93 g of L-leucine, 2.7 ml of diphosgene, 0.075 g of activated carbon, and 40 ml of dry tetrahydrofuran to give 2.74 g of the desired product.

$^1$H NMR($CDCl_3$):δ 7.1(s,1H,NH); 4.38–4.34(m,1H, CH—N); 1.85–1.72(m,3H,$CH_2$ and C—CH); 0.997(t,6H,2-Me).

EXAMPLE 264

(S)-4-Methyl-2,5-oxazolidinedione

The title compound is prepared by the procedure of Example 262 using 8.91 g of L-alanine, 9.0 ml of diphosgene, 0.250 g of activated carbon, and 150 ml of dry tetrahydrofuran-to give 7.4 g of the desired product.

$^1$H NMR(DMSO): δ 9.0(bs,1H,NH); 4.5(t,1H,CH); 1.33 (d,3H),Me).

EXAMPLE 265

[3-S-[4R-[1-(S*),4α,5β,6β(R*)]]]-1-[(2-Amino-1-oxo-3-phenylpropyl)amino]-2,5-anhydro-3-S-[2-carboxy-6-(1-hydroxyethyl)-4-methyl-7-oxo-1-azabicyclo[3.2.0]-hept-2-en-3-yl]-1,4-dideoxy-3-thio-D-threo-pentitol (A)

To 3 ml of 0.1M, pH 7, sodium dihydrogen phosphate buffer cooled to 2° C. is added 0.308 g of product from Example 192 and the pH is adjusted to 8.5 with 1N sodium hydroxide. A solution of 0.172 g of product from Example 262 in 3 ml of dioxane and 3 ml of sodium dihydrogen phosphate buffer is added while maintaining the pH at 8.5 with 1N sodium hydroxide. The reaction is monitored by tlc. After there is no starting material present, the pH is adjusted to pH 7.0 and the mixture is concentrated in vacuo. The residue is purified by chromatography (Reverse Phase Plates: 20% acetonitrile/water) to give 0.162 g of the product A and 0.073 g of [3-S-[4R-[4α,5β,6β(R*)]]]-2,5-anhydro-3-S-[2-carboxy-6-(1-hydroxyethyl)-4-methyl-7-oxo-1-azabicyclo[3.2.0]-hept-2-en-3-yl]-1,4-dideoxy-1-[(N-L-phenylalanyl-L-phenylalanyl)amino-3-thio-D-threo-pentitol as product B.

Product A $^1$H NMR(D$_2$O):δ 7.4(t,3H); 7.3(d,2H); 4.4–4.2(m,2H); 4.05–3.9(m,2H); 3.9–3.8(m,2H); 4.59–3.0(m,7H); 2.4–2.2(m,1H); 2.02–1.95(m,1H); 1.29(d,3H,Me,J=7.0 Hz); 1.1i(d, 3H,Me,J=7.0 Hz).

Product B $^1$H NMR(D$_2$O):δ 7.4–7.3(m,6H); 7.25–7.15(m,4H); 4.5(t,1H); 4.3–4.3(m,2H); 4.05–3.2(m,5H); 3.45–2.9(m,8H); 2.24–2.2(m,1H); 2.0–1.9(m,1H); 1.29(d,3H,Me,J=7.0 Hz); 1.09(d,3H,Me,J=7.0 Hz).

EXAMPLE 266

[3-S-[4R-[1(S*),4alpha,5beta,6beta(R*)]]]-1-[(2-Amino-4-methyl-1-oxopentyl)amino]-2,5-anhydro-3-S-[2-carboxy 6-(1-hydroxyethyl)-4-methyl-7-oxo-1-azabicyclo[3.2.0]-hept-2-en-3-yl]-1,4-dideoxy-3-thio-D-threo-pentitol (A)

The title compound is prepared by the procedure of Example 265 using 0.308 g of product from Example 192, 0.141 g of product from Example 263, 9 ml of 0.1M sodium dihydrogen phosphate buffer, pH 7.0, and 3 ml of dioxane to give 0.135 g of product A and 0.051 g of [3-S-[4R-[4α,5β,6β(R*)]]]-2,5-anhydro-3-S-[2-carboxy-6-(1-hydroxyethyl)-4-methyl-7-oxo-1-azabicyclo[3.2.0]-hept-2-en-3-yl]-1,4-dideoxy-1-[N-L-leucyl-L-leucyl)amino-3-thio-D-threo-pentitol as product B.

Product A $^1$H NMR(D$_2$O): δ 4.3–4.1(m,3H); 4.1–4.0(q,1H); 3.95–3.8(m,3H); 3.6–3.4(m,4H); 2.5–2.38(m,1H); 2.1–2.0(m,1H); 1.72–1.6(m,3H,CH$_2$CH); 1.27(d,3H,Me,J=7.0).

Product B $^1$H NMR(D$_2$O):δ 4.42–4.3(m,1H); 4.3(m,3H); 4.15–4.0(m,1H); 4.0–3.8(m,3H); 3.6–3.4(m,4H); 2.5–2.4(m,1H); 2.1–2.0(m,1H); 1.8–1.5(m,6H); 1.27(d,3H,Me,J=7.0 Hz); 1.18(d,3H,M3,J=7.0); 1.0–0.8(m,12H,4Me).

An alternative method for making the Product of Example 192, [4R-(4α,5β,6β(R*)]-1-Amino-2,5-anhydro-3-S-[2-carboxy-6-(1-hydroxyethyl)-4-methyl-7-oxo-1-azabicyclo[3.2.0]hept-2-en-3-yl]-1,4-dideoxy-3-thio-D-threo-pentitol is described in Examples 267 to 272.

EXAMPLE 267

2-Deoxy-D-erythro-pentitol

Under anhydrous conditions and an argon purge, 30.0 g of 2-deoxy-D-ribose is dissolved in 1 L of ethyl alcohol. Seven grams of sodium borohydride is added in portions at room temperature. The reaction mixture is stirred for 1–2 hours, until all bubbles disappear. The mixture is acidified with 25 ml of glacial acetic acid and the stirring continued for an additional 30 minutes. The solution is chromatographed using 180 ml of Dowex 50W-X8(H$^+$ form) Resin (50–100 mesh) and ethyl alcohol. The filtrate is concentrated in vacuo to give 40.0 g of a thick oil.

MS(EI):m/z 119(M$^+$ –OH).

EXAMPLE 268

1,4-Anhydro-2-deoxy-D-erythro-pentitol

To 40.0 g of product from Example 267 is added 500 ml of 2N hydrochloric acid. The mixture is heated, in an oil bath, at 95° C. for 72 hours. The reaction is filtered and the filtrate concentrated in vacuo to give 23.4 g of an oil. The oil is purified by Kugelrohr distillation to give 14.05 g (110°–120° C. at 0.4–0.3 mmHg) of the desired product.

$^1$H NMR(CDCl$_3$): δ 4.25(m,1H); 4.0(m,2H); 3.8(m,1H); 3.7(bs,1H,OH); 3.6(m,2H); 3.5(bs,1H,OH); 2.1(m,1H); 1.9(m,1H).

EXAMPLE 269

1,4-Anhydro-2-deoxy-D-erythro-pentitol 5-(Trifluoromethanesulfonate)

To a –20° C. solution, under argon, of 8.4 ml of trifluoromethanesulfonic anhydride in 75 ml of methylene chloride is added, dropwise, a solution of 5.9 g of product from Example 268 and 4.05 ml of pyridine in 25 ml of methylene chloride. The temperature is maintained below –10° C. during the addition. The progress of the reaction is monitored by tlc. The reaction is filtered and the filtrate concentrated in vacuo to an oily residue. The residue is purified by chromatography (silica gel: 50% ethyl acetate/hexane) to give 7.03 g of the desired product.

$^1$H NMR(CDCl$_3$): δ 4.8(bs,1H); 4.48–4.6(m,2H); 4.3–4.4(m,1H); 3.95–4.1(m,3H); 2.1–2.21(m,1H); 1.92–2.02(m,1H).

EXAMPLE 270

1,4-Anhydro-5-azido-2,5-dideoxy-D-erthyro-pentitol

A mixture of 7.0 g of product from Example 269 in 53 ml of methylene chloride and 8.75 g of n-tetrabutylammonium azide is stirred at –20° C., under argon, for 2 hours. The reaction mixture is concentrated in vacuo and purified by chromatography (silica gel: 50% ethyl acetate/hexane) to give 3.22 g of the desired product.

$^1$H NMR(CDCl$_3$):δ 4.22–4.3(m,1H); 3.92–4.1(m,2H); 3.85–3.9(m,1H); 3.3–3.5(m,2H); 2.1–2.25(m,2H); 1.0–2.0(m,1H).

EXAMPLE 271

1,4-Anhydro-5-azido-2,5-dideoxy-D-erythro-pentitol 3-(Trifluoromethanesulfonate)

The title compound is prepared by the procedure of Example 269 using 3.2 g of product from Example 270 dissolved in 28 ml of methylene chloride, 4.14 ml of trifluoromethanesulfonic anhydride dissolved in 57 ml of methylene chloride and 2.0 ml of pyridine to give after chromatography (silica gel: 50% ethyl acetate/hexane) 4.84 g of the desired product.

$^1$H NMR(CDCl$_3$):δ 5.25(m,1H); 4.12–4.20(m,2H); 3.85–3.93(m,1H); 3.40–3.51(m,1H); 3.29–3.4(m,1H); 2.2–2.35(m,2H).

EXAMPLE 272

2,5-Anhydro-1-azido-1,4-dideoxy-3-thio-D-threo-pentitol 3-Acetate

To a 0° C. solution of 4.84 g of product from Example 271 in 120 ml of acetonitrile is added, in one portion, 2.21 g potassium thioacetate. The reaction is stirred at 0° C. for 35 minutes, concentrated in vacuo and purified by chromatography (silica gel: 30% ethyl acetate/hexane) to give 2.63 g of the desired product.

¹H NMR(CDCl₃): δ 4.2–4.3(m,1H); 4.1–4.19(q,1H); 4.0–4.08(m,1H); 3.8–3.88(q,1H); 3.3–3.4(m,2H); 2.35–2.25 (m,1H); 2.36(s,3H,SAc); 1.9–2.05(m,1H).

The procedure for making Example 192, [4R-(4α,5β,6β (R*)]-1-amino-2,5-anhydro-3-S-[2-carboxy-6-(1-hydroxyethyl)-4-methyl-7-oxo-1-azabicyclo[3.2.0]-hept-2-en-3-yl]-1,4-dideoxy-3-thio-D-threo-pentitol from this point on is identical to the experimental described in Examples 190–192.

EXAMPLE 273

[R-(R*,R*)]-5-Hexene-1,2,3-triol

A solution of 11 g of [R-(R*,R*)]-2,2-dimethyl-alpha-2-propenyl-1,3-dioxolane-4-methanol, prepared by the procedure described in *J. Am. Chem. Soc.*, 1985, 107(26), 8186–8190, in 300 ml of 1:1 tetrahydrofuran: 2N hydrochloric acid is heated at the reflux temperature of the solvents for 2 hours. Chloroform is added and the layers are separated. The aqueous layer is re-extracted 2× with chloroform. The aqueous layer is neutralized with potassium carbonate and exhaustively extracted with 80% chloroform/iso-propanol. The combined organic layers are concentrated in vacuo to give 7.51 g of the desired product.

¹H NMR(CDCl₃):δ 5.89(m,1H); 5.18(m,2H); 3.76(m, 3H); 3.60(m,1H); 2.40(m,5H,3(OH)+2H).

EXAMPLE 274

[R-(R*,R*)]-1-[[(1,1-dimethylethyl)diphenylsilyl] oxy]-5-hexene-2,3-diol

A 0° C. solution of 7.33 g of product from Example 273 in 120 ml of 5:1 dry methylene chloride/N,N-dimethylformamide is treated with 5.29 g of imidazole and 16.77 g of t-butyl diphenylsilyl chloride. The reaction mixture is warmed to room temperature and stirred vigorously for 16 hours, diluted with diethyl ether and filtered. The filtrate is concentrated and purified by chromatography (Silica Gel: 0–50% ethyl acetate/hexane) to give 15 g of the desired product.

¹H NMR(CDCl₃):δ 7.67(m,4H); 7.42(m,6H); 5.82(m, 1H); 5.10(m,2H); 3.84–3.70(m,3H); 3.58(m,1H); 2.29(t,1H, J=7.1Hz); 1.07(s,9H, t-bu).

IR(neat): 3430, 3072, 2957, 1650, 1595, 1472, 1428 cm⁻¹.

EXAMPLE 275

2,5-Anhydro-4,6-dideoxy-1-O-[(1,1-dimethylethyl) diphenylsilyl]-6-iodo-D-arabino-hexitol A 0° C. solution of 14.67 g of product from Example 274 in 200 ml of 3:1 diethyl ether/water is treated with 4.99 g of sodium bicarbonate and 15.07 g of iodine. The reaction mixture is stirred vigorously for 24 hours at room temperature, quenched with 15 ml of saturated sodium sulfite, and diluted with 100 ml of water. the reaction mixture is extracted with diethyl ether, dried, concentrated in vacuo, and purified by chromatography (silica gel: 0–10% ethyl acetate/hexane) to give 15.0 g of the desired product.

¹H NMR(CDCl₃):δ 7.74–7.64(m,4H); 7.46–7.36(m,6H); 4.62(t,1H,J=4 Hz); 4.32(m,1H),4.10(m,1H); 3.98(m,2H); 3.29(dd,2H,J=5.7, 1.4 Hz); 2.25(M,1H); 1.83(dt,1H); 1.12 (s,9H,t-Bu).

IR(neat): 3458, 3071, 2956, 1472, 1428 cm⁻¹.

MS(CI): m/z 514(M+NH₄)⁺.

EXAMPLE 276

2,5-Anhydro-6-azido-4,6-dideoxy-1-O-[(1,1-dimethylethyl)diphenylsilyl]-D-arabino-hexitol A solution, under argon, of 5.0 g of product from Example 275 in 10 ml of dry N,N-dimethylformamide is treated with 0.986 g of lithium azide. The mixture is stirred at 80° C. for 1 hour followed by room temperature for 18 hours. The reaction is diluted with water, extracted with diethyl ether, concentrated in vacuo, purified by chromatography (silica gel: 5–50% ethyl acetate/hexane) to give 4.0 g of the desired product.

¹H NMR(CDCl₃): δ 7.70(m,4H); 7.42(m,6H); 4.62(m, 1H); 4.50(m,1H); 4.02(m,3H); 3.80–3.50(m,2H); 3.22(dd, 1H); 2.09(m,1H); 1.94(m,1H); 1.50(s,9H,t-Bu).

IR(neat): 2956, 2101 cm⁻¹.

MS(CI): m/z 429(M+NH₄)⁺.

EXAMPLE 277

2,5-Anhydro-6-azido-4,6-dideoxy-1-O-[(1,1-dimethylethyl)diphenylsilyl]-D-arabino-hexitol 3-Methanesulfonate To a 0° C. solution, under argon, of 3.78 g of product from Example 276 in 20 ml of dry methylene chloride is added, dropwise, 1.02 g of triethylamine and 1.16 g methanesulfonylchloride. The reaction mixture is stirred for 3 hours, diluted with water, extracted with diethyl ether, concentrated in vacuo, and purified by chromatography (silica gel: 0–50% ethyl acetate/hexane) to give 4.30 g of the desired product.

¹H NMR(CDCl₃): δ 7.68(m,4H); 7.41(m,6H); 5.36(m, 1H); 4.43(m,1H); 4.18(m,1H); 3.88(m,2H); 3.54(dd,1HJ= 13.0, 3.5 Hz); 3.19(dd,1HJ=13.0, 4.5 Hz); 2.73(s,3H, OSO₂Me); 2.48(m,1H), 2.18(m,1H); 1.08(s,9H,t-Bu).

IR(neat): 2956, 2101 cm⁻¹.

MS(CI): 430(M⁺+H–N₂).

EXAMPLE 278

2,5-Anhydro-1-azido-1,3-dideoxy-6-O-[(1,1-dimethylethyl)diphenylsilyl]-4-thio-D-arabino-hexitol 4-Acetate A solution of 3.78 g of product from Example 277, 1.76 g of potassium thioacetate, 6.12 g of 18-crown-6 and 25 ml of acetonitrile is heated at the reflux temperature of the solvents for 3 hours. The reaction is diluted with water, extracted with diethyl ether, concentrated in vacuo and purified by chromatography to give 2.209 g of the desired product.

¹H NMR(CDCl₃): δ 7.70(m,4H), 7.40(m,6H); 4.33(m, 1H); 4.13(m,1H); 4.0(m,1H); 3.83–3.70(m,2H), 3.45–3.25 (m,3H); 2.60(m,1H); 2.32(s,3H,SAc); 1.77(m,1H); 1.05(s, 9H,t-Bu).

IR(neat): 2957, 2100, 1696, 1113 cm⁻¹.

MS(CI): m/z 488(M+NH₄)⁺.

EXAMPLE 279

2,5-Anhydro-1-azido-1,3-dideoxy-4-thio-D-arabino hexitol

A 0° C. mixture, under argon, of 2.21 g of product duct from Example 278 in 20 ml of 1:3.3 49% aqueous hydrogen fluoride/acetonitrile is stirred vigorously and allowed to warm slowly to room temperature over 6 hours. The reaction mixture is added slowly to 100 ml of saturated sodium bicarbonate. After the bubbling ceased, ethyl acetate is added and the layers are separated. The organic layer is concentrated in vacuo and purified by chromatography (silica gel: 5–50% ethyl acetate/hexane) to give 0.664 g of the desired product.

$^1$H NMR(CDCl$_3$): δ 4.40(m,1H); 3.92(m,2H); 3.80(m, 1H); 3.62(m,1H); 3.45(m,1H); 3.30(m,1H); 2.50(m,1H); 2.35(s,3H,COCH$_3$); 2.00(br s, 1H, OH); 1.85(m,1H).

IR(neat): 3471, 2925, 2101, 1693 cm$^{-1}$.

MS(CI): 249(M+NH$_4$)$^+$.

EXAMPLE 280

2,5-Anhydro-1-azido-1,3-dideoxy-4-thio-D-arabino-hexitol

To a 0° C. solution, under argon, of 1.1 g of product from Example 279 in 5 ml of dry tetrahydrofuran is added, dropwise, 1.3 ml of 4.37M solution of sodium methoxide. The reaction is stirred for 1 hour, quenched with saturated ammonium chloride and concentrated in vacuo. The residue is purified by chromatography (silica gel: 10–100% ethyl acetate/hexane) to give 0.752 g of the desired product.

$^1$H NMR(CDCl$_3$): δ 4.24(m,1H); 3.90(dd,1H,J=12 and 3 Hz); 3.80–3.70(m,2H); 3.46(dd,1H,J=13, 3.7 Hz); 3.3(m, 2H); 2.52(m,1H); 1.97(br s,1H,OH); 1.80(m,1H); 1.66(d, 1H,SH,J=8.1 Hz).

MS(CI): m/z 207(M+NH$_4$)$^+$.

EXAMPLE 281

4-[4R-[4alpha,5beta,6beta(R*)]]-2,5-Anhydro-1-azido-1,3-dideoxy-4-S-[6-(1-hydroxyethyl)-4-methyl-2-[[(4-nitrophenyl)methoxy]carbonyl]-7-oxo-1-azabicyclo-[3.2.0]hept-2-ene-3-yl]-4-thio-D-arabino-hexitol A 0° C. mixture, under argon, of 0.752 g of product from Example 280, 2.10 g of product from Example 15 and 13 ml of dry acetonitrile is treated, dropwise, with 0.462 g of Hunig's base. The reaction, which is allowed to warm to room temperature, is stirred for 5 hours. The reaction is concentrated in vacuo and purified by chromatography to give 0.752 g of the desired product.

$^1$H NMR(CDCl$_3$):δ 8.25(d,2H,J=8.7 Hz); 7.65(d,2H,J= 8.7 Hz); 5.51(d,1H); 5.22(d,1H); 4.27(m,3H); 4.0–3.70(m, 3H); 3.60(m,1H); 3.45(m,1H); 3.30(m,2H); 2.70(br s,1H); 2.50(m,2H); 2.05(m,1H); 1.85(m,1H); 1.35(d,3H); 1.28(d, 3H).

IR(KBr): 3449, 2971, 2102, 1767, 1709 cm$^{-1}$.

MS(FAB): m/z 534(M$^+$+H).

EXAMPLE 282

4-[4R-[4alpha,5beta,6beta(R*)]]-2,5-Anhydro-1-azido-4-S-[2-carboxy-6-(1-hydroxyethyl)-4-methyl-7-oxo-1-azabicyclo[3.2.0]hept-2-ene-3-yl]-1,3-dideoxy-D-arabino-hexitol A slurry of 0.20 g of product from Example 281 in 10 ml of dioxane: 0.1M sodium dihydrogen phosphate buffer pH 7.0 (8:2) and 0.060 g of 10% palladium on carbon is hydrogenated in a Parr apparatus at 42 psi of hydrogen for 3 hours. The mixture is filtered, concentrated in vacuo and purified by chromatography (Reverse Phase Plates:5% ethyl alcohol/water) to give 0.123 g of the desired product.

$^1$H NMR(D$_2$O): δ 4.35(m,1H); 4.19(m,2H); 3.95(m,1H); 3.70(dd,1H); 3.65–3.50(m,3H); 3.48–3.32(m,2H); 3.15(m, 1H); 2.68(m,1H); 1.74(m,1H); 1.24(d,3H); 1.15(d,3H).

IR(KBr): 3403, 3027, 2969, 2104, 1751, 1598 cm$^{-1}$.

MS (FAB): m/z 373(M$^+$).

EXAMPLE 283

1-Amino-2,5-anhydro-1,3-dideoxy-6-O-[(1,1-dimethylethyl)diphenylsilyl]-D-arabino-hexitol A slurry of 3.78 g of product from Example 276, 0.562 g of 10% palladium on carbon and 50 ml of tetrahydrofuran is hydrogenated under a balloon of hydrogen for 1 hour. The reaction mixture is filtered and the filtrate is concentrated in vacuo to give 3.4 g of the desired product.

$^1$H NMR(CDCl$_3$): δ 7.72(m,4H); 7.45(m,6H); 4.58(br s,1H); 4.27(m,1H); 4.13(m,1H); 3.97(s,2H); 2.82(dd,1H, J=13, 3.7 Hz); 2.64(dd,1H,J=13, 6.8 Hz); 2.05(m,1H); 1.80 (m,1H); 1.08(s,9H,t-Bu).

IR(neat): 3366, 2955, 1589, 1472, 1112 cm$^{-1}$.

MS(CI): m/z 386.6(M$^+$+H).

EXAMPLE 284

2,5-Anhydro-1,3-dideoxy-6-O-[(1,1-dimethylethyl) diphenylsilyl]-1-[[[(4-nitrophenyl)methoxy| carbonyl]-amino]-D-arabino-hexitol A slurry of 3.15 g of product from Example 283 and 1.35 g of potassium carbonate in 15 ml of tetrahydrofuran at 0° C., under argon, is treated with 2.11 g of p-nitrobenzyl chloroformate and the reaction is stirred vigorously at 0° C. for 4 hours. The reaction mixture is diluted with 100 ml of water, extracted with 3×100 ml of ethyl acetate, dried, concentrated in vacuo and purified by chromatography (Silica Gel: 5–50% ethyl acetate/hexane) to give 3.49 g of the desired product.

$^1$H NMR(CDCl$_3$): δ 8.20(d,2H, J=8.7 Hz); 7.68(m,4H); 7.50(d,2H,J=8.7 Hz); 7.42(m,6H); 5.62(br s,1H,NH); 5.20 (s,2H); 4.60(m,1H); 4.15(m,1H); 3.96(m,2H); 3.50(m,1H); 3.30(m,1H); 3.12(m,1H); 2.10(m,1H); 1.80(m,1H); 1.08(s, 9H,t-Bu).

MS(CI): m/z 565(M$^+$+H).

EXAMPLE 285

2,5-Anhydro-1,3-dideoxy-6-O-[(1,1-dimethylethyl) diphenylsilyl]-1-[[[(4-nitrophenyl)methoxy] carbonyl|amino]-D-arabino-hexitol 4-Methanesulfonate The title compound is prepared by the procedure of Example 277 using 3.39 g of product from Example 284, 0.57 ml of methanesulfonyl chloride, 1.03 ml of triethylamine, and 30 ml of methylene chloride to give, after chromatography, 3.0 g of the desired product.

$^1$H NMR(CDCl$_3$): δ 8.21(d,2H,J=8.7 Hz); 7.66(m,4H); 7.50(d,2H,J=8.7 Hz); 7.42((m,6H); 5.32(m,1H); 5.20(s,2H); 5.10(m,1H); 4.33(m,1H); 4.13(m,1H); 3.85(dd,1H,J=6.7, 3.3 Hz); 3.43(m,1H); 3.20(m,1H); 2.93(s,3H,OSO$_2$Me); 2.47(m,1H); 1.95(m,1H); 1.08(s,9H,t-Bu).

IR(neat): 3413, 3342, 2933, 1726, 1522 cm$^{-1}$.

MS(CI): m/z 548(M$^+$+H−SO$_2$Me). Calc'd for C$_{31}$H$_{38}$O$_9$N$_2$SSi: C=57.31; H=5.77; N=4.46; S=5.10 Found: C=57.45; H=5.91; N=4.11; S=4.88

EXAMPLE 286

2,5-Anhydro-1,3-dideoxy-6-O-[(1,1-dimethylethyl) diphenylsilyl]-1-[[[(4-nitrophenyl)methoxy] carbonyl]amino]-4-thio-D-arabino-hexitol 4-Acetate The title compound is prepared by the procedure of Example 278 using 3.0 g of product from Example 285, 1.07 g of potassium thioacetate, 2.5 g of 18-Crown-6 and 15 ml of acetonitrile to give, after chromatography, 2.61 g of the desired product.

$^1$H NMR(CDCl$_3$): δ 8.22 (d,2H,J=8.7 Hz); 7.70(m,4H); 7.50(d,2H,J=8.7Hz); 7.40(m,6H); 5.22(s,2H); 5.17(br s, 1H); 4.19(m,1H); 4.08(m,1H); 3.95(m,1H); 3.75(m,2H); m,2H); 3.45(m,1H); 3.24(m,1H); 2.55(m,1H); 2.41(s,3H, SAc); 1.64(m,1H); 1.06(s,9H,t-Bu).

MS(CI): m/z 566(M$^+$+H−C(CH$_3$)$_3$).

EXAMPLE 287

2,5-Anhydro-1,3-dideoxy-1-[[[(4-nitrophenyl)methoxy]carbonyl]amino]-4-thio-D-arabino-hexitol 4-Acetate The title compound is prepared by the procedure of Example 279 using 2.51 g of product from Example 322, and 20 ml of 3:1 acetonitrile:48% aqueous hydrogen fluoride to give, after chromatography, 1.35 g of the desired product.

$^1$H NMR(CDCl$_3$): δ 8.22(d,2H,J=8.7 Hz); 7.53(d,2H,J=8.7 Hz); 5.30(br t,1H,NH); 5.20(s,2H); 4.22(m,1H); 3.86(m, 2H); 3.76(dd,1H,J=13, 2.5 Hz); 3.60(dd,1H,J=12, 4.0 Hz); 3.46(m,1H), 3.38(m,1H); 3.24(m,1H); 2.50(m,1H); 2.35(s, 3H,SAc); 2.16(br s, 1H,OH); 1.68(m,1H).

IR(KBr): 3340, 2935, 1722, 1696, 1607, 1521 cm$^{-1}$.
MS(CI): m/z 385.5(M$^+$+H).

EXAMPLE 288

2,5-Anhydro-1,3-dideoxy-1-[[[(4-nitrophenyl)methoxy]carbonyl]amino]-4-thio-D-arabino-hexitol The title compound is prepared by the procedure of Example 127 using 0.625 g of product from Example 278, 0.85 ml of 4N sodium hydroxide and 3 ml of tetrahydrofuran to give, after chromatography, 0.440 g of the desired product.

$^1$H NMR(CDCl$_3$): δ 8.21(d,2H,J=8.7 Hz); 7.50(d,2H,J=8.7 Hz); 5.54(br t,1H,NH); 5.20(s,2H); 4.13(m,1H); 3.85 (dd,1H,J=12 and 2 Hz); 3.78−3.65(m,2H); 3.50(m,1H); 3.27 (m,2H); 2.53(p,1H,J=6.0 Hz); 1.63(m,1H); 1.62(d,1H,SH, J=2.0 Hz).

IR(KBr): 3460, 3315, 2922, 2553, 1700, 1607, 1554 cm$^{-1}$.

EXAMPLE 289

[4-[4R-[4alpha,5beta,6beta(R*)]]]-2,5-Anhydro-1,3-dideoxy-4-S-[6-(1-hydroxyethyl)-4-methyl-2-[[(4-nitrophenyl)methoxy]carbonyl]-7-−oxo-1-azabicyclo[3.2.0]hept-2-en-3-yl]-1-[[[(4-nitrophenyl)methoxy]carbonyl]amino]-4-thio-D-arabino-hexitol The title compound is prepared by the procedure of Example 17 using 0.440 g of product from Example 324, 0.764 g of product from Example 15, 0.22 ml of Hunig's base and 4.3 ml of acetonitrile to give, after chromatography, 0.593 g of the desired product.

$^1$H NMR(CDCl$_3$): δ 8.23(d,2H,J=8.7 Hz); 8.22(d,2H,J=8.7 Hz); 7.66(d,2H,J=8.7 Hz); 7.52(d,2H,J=8.7 Hz); 5.52(d, 1H,J=13.8 Hz); 5.22(d,1H,J=13.8 Hz); 5.21(s,2H); 4.25(m, 3H); 3.84(m,2H); 3.67−3.40(m,4H); 3.30−3.20(m,2H); 2.53 (m,1H); 1.7(m,1H); 1.34(d,3H,J=7.3 Hz); 1.25(d,3H,J=7.3 Hz).

MS(FAB): m/z 687(M$^+$+H).

EXAMPLE 290

[4-[4R-[4alpha,5beta,6beta(R*)]]]-1-Amino-2,5-anhydro-4-S-[2-carboxy-6-(1-hydroxyethyl)-4-methyl-7-oxo-1-azabicyclo[3.20]hept-2-en-3-yl]-4-thio-D-arabino-hexitol The title compound is prepared by the procedure of Example 192 using 0.563 g of product from Example 325, 0.140 g of 10% palladium on carbon, and dioxane:0.1M sodium dihydrogen phosphate buffer pH 7.0 (15 ml:5 ml) to give, after chromatography, 0.050 g of the desired product.

$^1$H NMR(D$_2$O): δ 4.36(m,1H); 4.21(m,2H); 3.95(m,1H); 3.78−3.50(m,3H); 3.40(m,2H); 3.18(m,2H); 2.68(m,1H); 1.72(m,1H); 1.24(d,3H,J=6.4 Hz); 1.60(d,3H,J=7.2 Hz).

IR(KBr): 3408, 3347, 2967, 1752, 1622, 1586, 1147 cm$^{-1}$.

MS(FAB):m/z (MB+NaCl) 395(M+Na) and 417(M+2Na−H).

EXAMPLE 291

[3S-[3alpha,3(R*),4alpha]]-[1-Methyl-2-oxo-2-[[[tetrahydro-4-[[(4-methoxyphenyl)methyl]thio]-3-furanyl]methyl]amino]ethyl]carbamic Acid (4-Nitrophenyl)methyl Ester A room temperature mixture, under argon, of 0.455 g of product from Example 200, 0.578 g of product from Example 258, 0.516 g of 1-(3-dimethylaminopropyl)-3-ethylcarbodiimide hydrochloride (EDCI) and 4 ml of methylene chloride is stirred vigorously for 6 hours. The reaction mixture is diluted with water, extracted with methylene chloride, dried, and concentrated in vacuo to give 0.90 g of the desired product.

$^1$H NMR(CDCl$_3$): δ 8.20(d,2H,J=8.7 Hz); 7.50(d,2H,J=8.7 Hz); 7.20(d,2H,J=8.7 Hz); 6.8(d,2H,J=8.7 Hz); 6.45(br s, 1H, NH); 5.60(br s, 1H,NH); 5.25(s,2H,CH$_2$ArNO$_2$): 4.20(m,1H); 4.00(t,1H); 3.90(t,1H); 3.80(s,3H,ArOMe); 3.68(s,2H,CH$_2$ArOMe); 3.50(m,2H); 3.26(m,2H); 2.80(m, 1H); 2.25(m,1H); 1.40(m,3H,CH$_3$).

EXAMPLE 292

[3S-[3alpha,3(R*),4alpha]]-[1-Methyl-2-oxo-2-[[[tetrahydro-4-mercapto-3-furanyl]methyl]amino]ethyl]carbamic Acid (4-Nitrophenyl)methyl Ester The title compound is prepared by the procedure of Example 202 using 0.90 g of product from Example 291, 0.915 g of mercuric trifluoroacetate, 0.386 g of anisole and 27 ml of 80% acetic acid to give 0.60 g of the desired product.

$^1$H NMR(CDCl$_3$): δ 6.38(br s 1H,NH); 5.45(br s,1H,NH); 5.20(s,2H,CH$_2$ArNO$_2$); 4.20(m,2H); 4.00(dd,1H, J=8.8, 7.9 Hz); 3.60−3.40(m,4H); 3.03(t,1H,J=7.4 Hz); 2.28(m,1H); 1.73(d,1H,SH); 1.41(d,3H,J=7.0 Hz).

IR(KBr): 3298, 2975, 2544, 1690, 1651, 1540 cm$^{-1}$.
MS(CI): m/z 384(M$^+$+H).

EXAMPLE 293

[4R-3[3S*,4S*,(S*)],4alpha,5beta,6beta(R*))]]-6-(1-Hydroxyethyl)-4-methyl-7-oxo-3-[[tetrahydro-4-[[[2-[[[(4-nitrophenyl)methoxy]carboxnyl]amino]-1-oxopropyl]amino]methyl-3-furanyl]thio]-1-azabicyclo[3.2.0]hept-2-ene-2-carboxylic Acid (4-Nitrophenyl)methyl Ester The title compound is prepared by the procedure of Example 17 using 0.576 g of product from Example 292, 0.893 g of product from Example 15, 0.194 g of Hunig's base and 5 ml of acetonitrile to give 0.950 g of the desired product.

$^1$H NMR(CDCl$_3$): δ 8.21(d,2H,J=8.7 Hz); 8.20(d,2H, J=8.7 Hz); 7.65(d,2H,J=8.7 Hz); 7.49(d,2H,J=8.7 Hz); 6.55 (br s,1H,NH);6.44(br s,1H,NH); 5.50(dd,1H); 5.22(dd,1H);

5.19(s,4H,CH$_2$ArNO$_2$); 4.35–4.2(m,3H); 3.95(m,1H); 3.70–3.40(m,6H); 3.29(m,1H); 2.42–2.26(m,2H); 1.39(t, 6H,2×CH$_3$); 1.26(d,3H,CH$_3$).

IR(KBr): 2973, 2935, 2873, 1770, 1716, 1670, 1521 cm$^{-1}$.

MS(FAB): m/z (MB+NaCl), 728(M$^+$+H); 750(M$^+$+Na).

EXAMPLE 294

[4R-[3[3S*,4S*(S*)],4alpha,5beta,6beta(R*))]]-3-[[4 [[2-Amino-1-oxopropyl)amino]methyl]tetrahydro-3-furanyl]thio]-6-(1-hydroxyethyl)-4-methyl-7-oxo-1-azabicyclo[3.2.0]hept-2-ene-2-carboxylic Acid (A)

and

[4R-[3[3R*,4E*(S*)],4alpha,5beta,6beta(R*))]]-3-[[4 [[2-Amino-1-oxopropyl)amino]methyl]tetrahydro-3-furanyl]thio]-6-(1-hydroxyethyl)-4-methyl-7-oxo-1-azabicyclo[3.2.0]hept-2-ene-2-carboxylic Acid (B)

The title compounds are prepared by the procedure of Example 192 using 0.90 g of product from Example 293, 0.270 g of 10% palladium on carbon and 30 ml of 4:1 dioxane:0.1M sodium dihydrogen phosphate buffer at 42 psi of hydrogen to give a crude mixture which was purified by chromatography to give 0.074 g of product A and 0.095 g of product B.

Product A $^1$H NMR(D$_2$O): δ 4.24(m,3H); 4.00(m,2H); 3.66(m,1H); 3.60(m,2H); 3.41(m,1H); 3.31(m,3H); 2.40(m,1H); 1.43(d, 3H); 1.25(d,3H); 1.15(d,3H).

IR(KBr): 3350, 3260, 3087, 2965, 1750, 1677, 1584 cm$^{-1}$.

MS(FAB): m/z (MB+NaCl) 414(M$^+$+H); 436(M$^+$+Na).

Product B $^1$H NMR(D$_2$O): δ 4.20(m,3H); 4.10(m,1H); 3.90(m,1H); 3.75(m,1H); 3.55(m,2H); 3.40–3.25(m4H); 2.35(m,1H); 1.46(m,3H); 1.25(d,3H); 1.17(d,3H).

IR(KBr): 3374, 3089, 2967, 1750, 1677, 1583 cm$^{-1}$.

MS(FAB): m/z (MB+NaCl) 414(M$^+$+H); 436(M$^+$+Na).

EXAMPLE 295

N-[[(4-Nitrophenyl)methoxy]carbonyl]-L-valine

The title compound is prepared by the procedure of Example 255 using 14.73 g of product from Example 254, 5.42 g of L-valine, 12.75 ml of triethylamine and 556 ml of 4:1 ethyl alcohol:water to give 4.89 g of the desired product after chromatography.

$^1$H NMR(CDCl$_3$): δ 8.22(d,2H); 7.51(d,2H); 5.32(d,1H); 5.22(d,2H); 4.4–4.3(m,1H); 2.35–2.15(m,1H); 1.02(d,3H, Me); 0.95(d,3H,Me).

Calculated for C$_{13}$H$_{16}$N$_2$O$_6$: C=52.70; H=5.44; N=9.46 Found: C=52.44; H=5.64; N=9.18

EXAMPLE 296

(S)-[1-[[(2,5-Dioxo-1-pyrrolidinyl)oxy]carbonyl-2-methylpropyl]carbamic Acid (4-Nitrophenyl)methyl Ester Using the procedure of Example 256, a room temperature solution, under argon, of 4.89 g of product from Example 295 and 72 ml of dioxane is added 2.09 g of N-hydroxysuccinimide and 3.76 g of 1,3-dicyclohexylcarbodiimide in 19 ml of dioxane. A suspension is formed and the mixture is stirred overnight. The reaction is filtered and the filtrated is concentrated in vacuo to a thick oil. Crystallization from 75% ethyl acetate/hexane gives 4.88 g of the desired product.

$^1$H NMR(CDCl$_3$): δ 8.21(d,2H); 7.52(d,2H); 5.38(d,1H); 5.23(d,2H); 4.7–4.6(m,1H); 2.86(s,4H); 2.4–2.3(m,1H); 1.1 (d,3H,Me); 1.06(d,3H,Me).

Calculated for C$_{17}$H$_{20}$N$_3$O$_8$: C=51.78; H=5.11; N=10.66 Found: C=51.99; N=4.94; N=10.66.

EXAMPLE 297

N-[[(4-Nitrophenyl)methoxy]carbonyl]-L-isoleucine

The title compound is prepared by the procedure of Example 255 using 14.73 g of product from Example 254, 6.07 g of L-isoleucine, 12.73 ml of triethylamine and 556 ml of 4:1 ethyl alcohol:water to give 3.52 g of the desired product.

Calculated for C$_{14}$H$_{18}$N$_2$O$_6$: C=54.19; H=5.85; N=9.03 Found: C=54.27; H=5.85; N=8.81

$^1$H NMR(CDCl$_3$): δ 8.22(d,2H); 7.51(d,2H); 5.31(d,1H); 5.21(d,2H); 4.45–4.35(m,1H); 2.0–1.9(m,1H); 1.55–1.4(m, 1H); 1.3–1.15(m,1H); 0.99(d,3H,Me); 0.95(t,3H,Me).

EXAMPLE 298

[S-(R*,R*)]-[1-[[(2,5-Dioxo-1-pyrrolidinyl)oxy]carbonyl]-2-methylbutyl]carbamic Acid (4-Nitrophenyl)methyl Ester The title compound is prepared by the procedure of Example 256 using 3.52 g of product from Example 297, 1.50 g of N-hydroxysiccinimide, 2.70 g of 1,3-dicyclohexylcarbodiimide and 14 ml of dioxane to give 1.75 g of the desired product.

Calculated for C$_{18}$H$_{21}$N$_3$O$_8$: C=53.07; H=5.20; N=10.31 Found: C=53.66; H=5.26; N=10.20

$^1$H NMR(CDCl$_3$): δ 8.23(d,2H); 7.52(d,2H); 5.4–5.2(m, 3H); 4.74–4.68(m,1H); 2.86(s,4H); 2.1–2.0(m,1H); 1.7–1.5 (m,1H); 1.4–1.2(m,1H); 1.07(d,3H,Me); 0.98(t,3H,Me).

EXAMPLE 299

2,5:3,4-dianhydro-D-ribose Dimethylacetal

A solution of 50.0 g of product from Example 170, 500 ml of anhydrous methyl alcohol, 20 ml of trifluoroacetic acid is heated at reflux temperature for 36 hours. The progress of the reaction is monitored by thin layer chromatography. The reaction mixture is cooled, with stirring, to 5°–10° C. and 50 g of sodium carbonate is added in portions. The reaction is heated at 60° C. for 5 hours, filtered and the filtrate is concentrated in vacuo. The residue is extracted with methylene chloride and concentrated in vacuo to give 14 g of a yellow oil. The oil is purified by distillation (74°–75° C., at 2.5 torr) to give 9.7 g of the desired product.

$^1$H NMR(CDCl$_3$): δ 4.31(d,1H); 4.10(d,1H); 4.0(d,1H); 3.87–3.79(m,3H); 3.48(s,3H); 3.46(s,3H).

EXAMPLE 300

2,5-Anhydro-4-deoxy-D-erythropentose Dimethyl Acetal

To a 0° C. solution of 16.9 g of product from Example 299 in 55 ml of anhydrous tetrahydrofuran is added, dropwise over 30 minutes, 110.0 ml of 1.0M lithium aluminum hydride in tetrahydrofuran. The reaction mixture is heated in an 80° C. oil bath for 1 hour, cooled in an ice bath, and 18.37 g of sodium sulfate decahydrate is added in portions over an hour. The mixture is filtered through diatomaceous earth and the filtrated is concentrated in vacuo to give 13.05 g of the desired product as an oil, which solidified when cooled.

$^1$H NMR(CDCl$_3$): δ 4.32(m,1H); 4.25(d,1H); 3.98(dd, 2H); 3.75(m,1H); 3.44(s,3H,OMe); 3.42(s,3H,OMe); 2.4 (brs,1H,OH); 2.2–2.1(m,1H); 2.0–1.8(m,.1H).

EXAMPLE 301

2,5-Anhydro-4-deoxy-D-erythro-pentitol

To a room temperature mixture of 12.0 g of product from Example 300 in 180 ml of acetonitrile is added, dropwise, a mixture of 12 ml of water and 48 ml of trifluoroacetic acid. The mixture is stirred overnight at room temperature and concentrated in vacuo to about 20 g. Two hundred and forty ml of tetrahydrofuran is added and the reaction mixture is neutralized with sodium bicarbonate solution. The solution is filtered, dried and concentrated to give 20 g of an aldehyde which was used immediately.

The above aldehyde, 12.0 g, is dissolved in 450 ml of ethyl alcohol and the mixture is purged with argon. Sodium borohydride, 2.79 g, is added in portions and the reaction is stirred at room temperature for 2 hours. Five ml of water is added dropwise and the stirring is continued for 1 hour. The reaction mixture is concentrated in vacuo to an oil. The oil is purified by Silica Gel flash column chromatography (10% methyl alcohol/ethyl acetate) to give 3.40 g of the desired product.

$^1$H NMR(CDCl$_3$): δ 4.34–4.29(m,1H); 4.02–3.97(m,2H); 3.84–3.8(m,1H); 3.76–3.6(m,2H); 2.2–2.1(m,1H); 2.0–1.9 (m,1H); 1.86(brs,2H,OH).

EXAMPLE 302

(S)-2-[[[(4-Nitrophenyl)methoxy]carbonyl]amino] butanoic Acid

The title compound is prepared by the procedure of Example 255 using 29.46 g of product from Example 254, 9.5 g of L-2-aminobutyric acid, 25.5 ml of triethylamine and 1112 ml of 4:1 ethyl alcohol/water to give 21.2 g of the desired product after chromatography.

$^1$H NMR(CDCl$_3$): δ 8.22(d,2H, J=8.5 Hz) 7.52(d,2H, J=8.5 Hz); 5.35(d,1H); 5.25(s,2H); 4.7(m,1H); 2.1–2.0(m, 1H); 2.0–1.9(m,1H); 1.1(t,1H,Me).

EXAMPLE 303

(S)-[1[[(2,5-Dioxo-1-pyrrolidinyl)oxycarbonyl] propyl]carbamic Acid (4-Nitrophenyl)methyl Ester The title compound is prepared by the procedure of Example 256 using 21.2 g of product from Example 302 in 314 ml of dioxane, 9.10 g of N-hydroxysuccinimide, 16.3 g of 1,3-dicyclohexylcarbodiimide in 83 ml of dioxane to give 17.5 g of the desired product.

$^1$H NMR(CDCl$_3$): δ 8.2(d,2H,J=8.5 Hz); 7.52(d,2H,J=8.5 Hz); 5.35(d,1H,NH); 5.24(d,2H,J=4.7 Hz); 4.7(m,1H,CH); 2.1–1.9(m,2H); 1.1(t,3H,Me).

EXAMPLE 304

[4R-[3(2S*),4alpha,5beta,6beta(R*)]]-1-[(2-Amino-1-oxobutyl)amino]-2,5-anhydro-3-S-[2-carboxy-6-(1-(hydroxyethyl)-4-methyl-7-oxo-1-azabicyclo [3.2.0]hept-2-en-3-yl]-1,4-dideoxy-3-thio-D-threo-pentitol Using the procedure of Example 257, a solution of 0.342 g of product from Example 192 in 10 ml of pH 7, 0.1M sodium dihydrogen phosphate buffer, is added 1N sodium hydroxide to bring the pH to 8.5. To this mixture is added 0.379 g of product from Example 303 dissolved in dioxane; the pH is maintained at pH 8.5 with 1N sodium hydroxide. The reaction mixture is stirred at room temperature for 1 hour. 0.120 g of 10% palladium on carbon is added and the reaction is reduced in a Parr apparatus at 48 psi of hydrogen for 3 hours. The mixture is filtered and the filtrate concentrated in vacuo to a small volume. The residue is extracted with ethyl acetate and purified by chromatography (Reverse phase plates: 5% aqueous ethyl alcohol) to give 0.109 g of the desired product.

$^1$H NMR(D$_2$O): δ 4.3–4.1(m,3H); 4.15–4.02(m,1H); 4.0–3.7(m,3H); 3.6–3.4(m,4H); 2.55–2.4(m,1H); 2.15–2.0 (m,1H); 1.98–1.8(m,2H); 1.28(d,3H,Me,J=5.95 Hz); 1.19(d, 3H,Me,J=6.94 Hz); 0.96(t,3H,Me,J=7.2 Hz).

EXAMPLE 305

[3-S[4R-[1(S*),4alpha,5beta,6beta(R*)]]]-1-[(2-Amino-3-methyl-1-oxopentyl)amino]-2,5-anhydro-3-S-[2-carboxy-6-(1-hydroxyethyl)-4-methyl-7-oxo-1-azabicyclo[3.2.0]hept-2-en-3-yl]-1,4-dideoxy-3-thio-D-threo-pentitol The title compound is prepared by the procedure of Example 257 using 0.20 g of product from Example 192 in 6 ml of pH 7.0 0.1M sodium dihydrogen phosphate buffer, 0.253 g of product from Example 296 in 6 ml of dioxane and 0.060 g of 10% palladium on carbon. The reaction is cooled to 0°–4° C. and the pH is adjusted to pH 7.4 before the addition of the palladium catalyst. the residue is purified by chromatography (Reverse phase plates: 20% acetonitrile/ water) to give 0.045 g of the desired product.

$^1$H NMR(D$_2$O): δ 4.3–4.2(m,3H); 4.1–4.0(m,1H); 3.95–3.8(m,2H); 3.65(d,1H); 3.58–3.4(m,4H); 2.5–2.4(m, 1H); 2.2–2.0(m,2H); 1.27(d,3H,Me); 1.18(d,3H,Me); 0.99 (d,6H,2Me).

EXAMPLE 306

[3-S[4R-[1(S*,S*),4alpha,5beta,6beta(R*)]]]-1-[2-Amino-3-methyl-1-oxopentyl)amino]-2,5-anhydro-3-S-[2-carboxy-6-(1-hydroxyethyl)-4-methyl-7-oxo-1-azabicyclo[3.2.0]hept-2-en-3-yl]-1,4-dideoxy-3-thio-D-threo-pentitol The title compound is prepared by the procedure of Example 257 using 0.342 g of product from Example 192 in 10 ml of pH 7 0.1M sodium dihydrogen phosphate buffer, 0.407 g of product from Example 299 in 7 ml of dioxane to give after chromatography (Reverse Phase plates: 25% acetonitrile/water) an oil. The oil is mixed with 0.10 g of 10% palladium on carbon, 10 ml of pH 7 0.1M sodium dihydrogen-phosphate buffer and 5 ml of dioxane. The solution is reduced in a Parr apparatus at 47 psi of hydrogen for 3 hours. The reaction mixture is filtered, the filtrate is concentrated in vacuo to a small volume and purified by chromatography (Reverse phase plates: 25% acetonitrile/ water) to give 0.090 g of the desired product.

$^1$H NMR(D$_2$O): δ 4.25(m,3H); 4.08(q,1H); 3.9(m,2H); 3.65(d,1H); 3.6–3.4(m,4H); 3.32(s,1H); 2.45(m,1H); 2.05 (m,1H); 1.88(m,1H); 1.5(m,1H); 1.29(d,3H,Me); 1.18(d,3H, Me); 0.98(d,3H,Me); 0.90(t,3H,Me).

EXAMPLE 307

2,5-Anhydro-4-deoxy-D-erythro-pentitol 1-Trifluoromethanesulfonate

To a –20° C. solution, under argon, of 1.68 ml of trifluoromethanesulfonic anhydride in 15 ml of anhydrous methylene chloride is added, dropwise, a solution of 1.18 g of product from Example 301 in 5 ml of anhydrous methylene chloride and 0.81 ml of pyridine. The temperature is maintained at −20° C. during the addition of the alcohol. No starting material is visible by tlc after the completion of the addition. The mixture is concentrated in vacuo and purified by chromatography (silica gel: 75% ethyl acetate/hexane) to give 0.693 g of the ditriflate and 1.64 g of the desired monotriflate.

$^1$H NMR(CDCl$_3$): δ 4.5(m,2H); 4.3(m,2H); 3.95(m,3H); 2.98(brs,1H,OH); 2.1–2.0(m,1H); 1.95–1.85(m,1H).

EXAMPLE 308

2,5-Anhydro-1-azido-1,4-dideoxy-D-erythro-pentitol

To a 0° C. solution of 1.64 g of product from Example 307 in 12 ml of methylene chloride is added a solution of 2.11 g of tetrabutylammonium azide in 12 ml of methylene chloride. The reaction is stirred overnight at room temperature. The mixture is concentrated in vacuo and purified by chromatography (Silica gel: 50% ethyl acetate/hexane) to give 0.611 g of the desired product.

$^1$H NMR (CDCl$_3$): δ 4.18(m,1H); 4.0–3.85(m,2H); 3.85–3.8(m,1H); 3.75–3.6(brs,1H); 3.4–3.2(m,2H); 2.2–2.05(m,1H); 1.95–1.8.(m,1H).

EXAMPLE 309

2,5-Anhydro-1-azido-1,4-dideoxy-D-erythro-pentitol 3-Trifluoromethanesulfonate

The title compound is prepared by the procedure of Example 307 using 0.6115 g of product from Example 308 in 6 ml of methylene chloride, 0.79 ml plus 0.50 ml for a total of 1.29 ml of trifluoromethanesulfonic anhydride in 11 ml of methylene chloride and 0.38 ml of pyridine to give after chromatography (Silica gel: 50% ethyl acetate/hexane) 0.952 g of the desired product.

$^1$H NMR(CDCl$_3$): δ 5.3(m,1H); 4.3–4.0(m,2H); 4.0–3.8 (m,1H); 3.6–3.15(m,2H); 2.4–2.2(m,2H).

EXAMPLE 310

2,5-Anhydro-1-azido-1,4-dideoxy-3-thio-L-threo-pentitol 3-Acetate

To an ice cooled solution, under argon, of 0.952 g of product from Example 309 in 25 ml of acetonitrile is added 0.435 g of potassium thioacetate. The cooled reaction is stirred for 1 hour, concentrated in vacuo, and purified by chromatography (Silica gel: 30% ethyl acetate/hexane) to give 0.465 g of the desired product.

$^1$H NMR(CDCl$_3$): δ 4.2–4.12(m,1H); 4.1–4.05(m,1H); 4.0–3.9(m,1H); 3.8–3.7(1, 1H); 3.3–3.2(m,2H); 2.45–2.3(m, 1H); 2.29(s,3H,Me); 1.95–1.85(m,1H).

EXAMPLE 311

2,5-Anhydro-1-azido-1,4-dideoxy-3-thio-L-threo-pentitol

The title compound is prepared by the procedure of Example 16 using 0.465 g of product from Example 310, 0.56 ml of 25% (by wt.) sodium methoxide/methyl alcohol and 7 ml of tetrahydrofuran to give after chromatography (Silica gel: ethyl acetate) 0.319 g of the desired product.

$^1$H NMR(CDCl$_3$): δ 4.0(m,2H); 3.78(m,1H); 3.42(m,3H); 2.4(m,1H); 1.95(m,1H); 1.58(d,1H,SH).

EXAMPLE 312

[3-[4R-[4alpha,5beta,6beta(R*)]]]-2,5-Anhydro-1-azido-1,4-dideoxy-3-S-[6-(1-hydroxyethyl)-4-methyl-2-[[(4-nitrophenyl)methoxy]carbonyl]-7-oxo-1-azabicyclo[3.2.0]hept-2-en-3-yl]-3-thio-L-threo-pentitol The title compound is prepared by the procedure of Example 17 using 0.319 g of product from Example 311 in 5 ml of acetonitrile, 0.954 g of product from Example 15 in 10 ml of acetonitrile and 0.3 ml of Hunig's base to give after chromatography (Silica gel: ethyl acetate) 0.486 g of the desired product.

$^1$H NMR(CDCl$_3$): δ 8.12(d,2H,ArH,J=8.7 Hz); 7.57(d, 2H,ArH,J=8.7 Hz); 5.43(d,1H,benzylic H,J=13.7 Hz); 5.14 (d,1H,benzylic H,J=13.7 Hz); 4.25–4.1(m,2H); 4.1–3.95(m, 2H); 3.8–3.7(m,2H); 3.5–3.2(m,4H); 2.78(brs,1H,OH); 2.48–2.35(m,1H); 2.0–1.88(m,1H); 1.26(d,3H,Me,J=6.2 Hz); 1.2(d,3H,Me,J=7.1 Hz).

EXAMPLE 313

[3-[4R-[4alpha,5beta,6beta(R*)]]]-1-Amino-2,5-anhydro-3-S-[2-carboxy-6-(1-hydroxyethyl)-4-methyl-7-oxo-1-azabicyclo[3.2.0]hept-2-em-3-yl]-1,4-dideoxy-3-thio-L-threo-pentitol The title compound is prepared by the procedure of Example 192 using 0.486 g of product from Example 312, 0.167 g of 10% palladium on carbon, 9.8 ml of 0.1M sodium dihydrogen phosphate buffer and 13 ml of dioxane to give after chromatography (Reverse phase plates: 5% aqueous ethyl alcohol) 0.140 g of the desired product.

$^1$H NMR(CDCl$_3$): δ 4.4–4.3(m,1H); 4.3–4.2(m,2H); 4.1–3.9(m,2H); 3.9–3.8(m,1H); 3.5–3.4(m,2H); 3.2–3.1(m, 2H); 2.6–2.4(m,1H); 2.0–1.9(m,1H); 1.28(d,3H,Me,J=7.2 Hz);. 1.22(m,3H,Me,J=7.2 Hz).

EXAMPLE 314

[3-[4R-[1(S*),4alpha,5beta,6beta(R*)]]]-1-[(2-Amino-1-oxopropyl)amino]-2,5-anhydro-3-S-[2-carboxy-6-(1-hydroxyethyl)-4-methyl-7-oxo-1-azabicyclo[3.2.0]hept-2-en-3-yl]-1,4-dideoxy-3-thio-L-threo-pentitol The title compound is prepared by the procedure of Example 257 using 0.330 g of product from Example 313, 0.352 g of product from Example 259, 9.6 ml of 0.1M pH 7.0 sodium dihydrogen phosphate buffer, 7 ml of dioxane and 0.110 g of 10% palladium on carbon to give after chromatography (Reverse phase plates: 5% ethyl alcohol in water, 2×) 0.069 g of the desired product.

$^1$H NMR(D$_2$O): δ 4.3–4.1(m,3H); 4.1–3.9(m,3H); 3.85–3.7(m,1H); 3.6–3.3(m,4H); 2.6–2.4(m,1H); 2.0–1.85 (m,1H); 1.44(d,3H,Me,J=6.8 Hz); 1.27(d,3H,Me,J=6.8 Hz); 1.21(d,3H,Me,J=7.0 Hz).

EXAMPLE 315

1-Chloroethyl Cyclohexyl Carbonate

To twenty grams of cyclohexanol dissolved in 500 ml of anhydrous methylene chloride is added 18.4 ml of pyridine. The solution is cooled to −78° C. under an argon flush. 24.2 ml of 1-chloroethyl chloroformate in 160 ml of anhydrous methylene chloride is added dropwise. After the addition the milky reaction mixture is allowed to warm to room temperature. The now clear solution is stirred at room temperature for two hours, poured into a mixture of 100 ml of ice/100 ml of saturated sodium chloride, the layers are separated and the organic layer is dried and concentrated in vacuo to give 41.03 g of an oily yellow product. The yellow oil is purified by distillation (2.1 mm Hg at 82° C.) to give 38.54 g of a colorless oil.

$^1$HNMR(CDCl$_3$): δ 6.5–6.4(q,1H,Cl—CH); 4.75–4.64 (m,1H, C(=O)—O—CH in ring); 1.83(d,3H,J=5.8,Me); 1.23–2.02 (m,10H).

EXAMPLE 316

1-Bromoethyl Cyclohexyl Carbonate

A mixture of 10.33 g of product from Example 315, 0.20 g of tetrabutylammonium bromide and 7.9 ml of trimethylsilyl bromide is heated in an oil bath for 24 hours at 90° C. The reaction flask is fitted with a 22 cm Vigreux column and the produced trimethylsilyl chloride is distilled and collected at atmospheric pressure as it is formed. After 24 hours, a slight vacuum is applied to remove any residual trimethylsilyl bromide or trimethylsilyl chloride from the reaction. The formed oil is purified by distillation (87° C. at 1.5 mm Hg) to give 9.87 g of the desired product.

$^1$H NMR(CDCl$_3$): δ 6.61(q,1H,BrCH); 4.69(m,1H); 2.03 (d,3H,Me); 2.0–1.2(m,10H).

EXAMPLE 317

1-Chloroethyl p-Nitrophenyl Carbonate

The title compound is prepared by the procedure described in J. Med. Chem., 1988, Vol. 31, No. 2, p.321.

To a ice cooled mixture of 27.8 g of p-nitrophenol, 16.0 g of pyridine and 1 L of chloroform is added, dropwise, 34 g of alpha-chloroethyl chloroformate. After 1 hour, the ice bath is removed and the reaction is stirred for 16 hours at room temperature. The mixture is washed with water, 0.5% sodium hydroxide and water. The organic layer is dried and concentrated in vacuo to give 47.85 g of the desired product.

$^1$H NMR(D$_2$O): δ 8.26(d,2H,ArH); 7.40(d,2H,ArH); 6.53 (q,1H,CHCl); 1.93(d,3H,ArH).

Calculated for C$_9$H$_8$NO$_5$Cl: C=44.00; H=3.30; N=5.70; Cl=14.45 Found: C=44.04; H=3.40; N=5.80; Cl=14.45

EXAMPLE 318

1-Acetoxyethyl p-Nitrophenyl Carbonate

To a solution of 10.0 g of product from Example 317 in 250 ml of acetic acid is added 15.0 g mercuric acetate. The mixture is stirred at room temperature for 22 hours, concentrated in vacuo, and purified by chromatography (Silica gel: methylene chloride –5% methyl alcohol/methylene chloride) to give 7.5 g of the desired product.

$^1$H NMR(D$_2$O): δ 1.62(d,3H,CHMe); 2.13(s,3H,OAc); 6.86(q,1H,CHOAc); 7.41(d,2H,ArH); 8.28(d,2H,ArH).

EXAMPLE 319

[3-[4R-[4alpha,5beta,6beta(R*)]]]-1-[[[1-(Acetyloxy)ethoxy]carbonyl]amino]-2,5-anhydro-3-S-[2-carboxy-6-(1-hydroxyethyl)-4-methyl-7-oxo-1-azabicyclo[3.2.2]hept-2-en-3-yl]-1,4-dideoxy-3-thio-D-threo-pentitol The pH of a solution of 0.342 g of product from Example 192 in 10 ml of 0.1M sodium dihydrogen phosphate buffer, pH 7.0, is adjusted to 8.5. To this is added a solution of 0.269 g of product from Example 318 in 7 ml of dioxane, maintaining the pH at 8.5 with 1N sodium hydroxide. The mixture is stirred at room temperature for 30 minutes, concentrated in vacuo and purified by chromatography (Reverse Phase Plates: 20% acetonitrile/water) to give 0.081 g of the desired product.

$^1$H NMR(D$_2$O): δ 6.76–6.73(m,1H); 4.3–4.2(m,3H); 4.15–4.05(q,1H); 4.0–3.88(m,2H); 3.55–3.35(m,4H); 2.55–2.4(m,1H); 2.15–2.05(m,1H); 2.11(s,3H,Ac); 1.49(d, 3H,Me,J=5.4 Hz); 1.3(d,3H,Me,J=6.2 Hz); 1.21(d,3H,Me, J=5.8 Hz).

EXAMPLE 320

[3-[4R-[4alpha,5beta,6beta(R*)]]]-1-[[[1-(Acetyloxy)ethoxy]carbonyl]amino]-2,5-anhydro-3-S-[2-[[1-[[(cyclohexyloxy)carbonyl]oxy]ethoxy] carbonyl-6-(1-hydroxyethyl)-4-methyl-7-oxo-1-azabicyclo[3.2.0]hept-2-en-3-yl]-1,4-dideoxy-3-thio-D-threo-pentitol A 0° C. solution, under argon, of 0.20 g of product from Example 319 in 10 ml of N,N-dimethylformamide, 0.152 g of product from Example 316 in 5 ml of N,N-dimethylformamide and 0.110 g of sodium bicarbonate is stirred for 3.5 hours. The reaction mixture is concentrated in vacuo, extracted with ethyl acetate and water, and the organic layer is concentrated in vacuo to give after chromatography (Silica gel: ethyl acetate) 0.077 g of the desired product.

$^1$H NMR(D$_2$O): δ 6.8(q,1H,J=5.4 Hz); 6.74(q,1H,J=5.3 Hz); 4.7–4.5(m,1H); 5.3–5.1(m,1H); 4.2–3.15(m,10H); 2.5–1.1(27H) 5Me: 1.17(d), 1.27(d), 1.42(d), 1.53(t), 1.98(s) and 6CH$_2$ in multiplets.

EXAMPLE 321

2,5-Anhydro-4-S-[(4-methoxyphenyl)methyl]-4-thio-L-lyxose Dimethyl Acetal

To 3.5 ml of tetrahydrofuran, at 0° C. under argon, is added 0.168 g of sodium hydride, followed by the dropwise addition of 0.626 g of 4-methoxy-alpha-toluenethiol. The thick mixture is stirred for 55 minutes, during which time the temperature increased to room temperature. The solution is recooled to 0° C. and a solution of 0.50 g of product from Example 299 in 2 ml of tetrahydrofuran is added. The reaction is stirred overnight at room temperature. The mixture is cooled to 0° C., quenched with ice water, and extracted with diethyl ether. The organic layer is washed with water and saturated sodium chloride, dried and concentrated in vacuo to give after chromatography (Silica gel: 25–50% ethyl acetate/hexane) 0.89 g of the desire product.

$^1$H NMR(CDCl$_3$): δ 7.25(d,2H); 6.85(d,2H); 4.38(d,1H); 4.13(m,1H); 4.03(m,1H); 3.79(m,4H); 3.72–3.61(m,2H); 3.46(s,3H); 3.42(s,3H); 3.21–3.12(m,1H); 2.26(d,1H).

EXAMPLE 322

2,5-Anhydro-4-S-[(4-methoxyphenyl)methyl]-4-thio-L-lyxose

To a 0° C. solution of 0.340 g of product from Example 321 in 4 ml of methylene chloride is added a solution of 1 ml of trifluoroacetic acid and 0.266 ml of water. The reaction is stirred at room temperature for 1 hour, concentrated in vacuo, extracted with methylene chloride, neutralized with 1 g of sodium bicarbonate, filtered and concentrated in vacuo

147 to give after chromatography (Silica gel: 50–60% ethyl acetate/hexane) 0.222 g of the desired product.

$^1$H NMR(CDCl$_3$): δ 9.67(d,1H); 7.21(d,2H); 6.86(d,2H); 4.36(t,1H); 4.34–4.28(m,1H); 4.2(d,1H); 3.89–3.84(m,1H); 3.80(s,3H); 3.67(s,2H); 3.12(m,1H); 1.85(brs,1H).

EXAMPLE 323

1,4-Anhydro-2-S-[(4-methoxyphenyl)methyl]-2-thio-L-arabinitol

To a room temperature solution, under argon, of 10.9 g of product from Example 322 in 115 ml of absolute ethyl alcohol is added 1.57 g of sodium borohydride. The reaction is stirred at room temperature for 1 hour. Water is added dropwise with stirring and the mixture is concentrated in vacuo. The residue is extracted with methylene chloride, washed with water, dried and concentrated in vacuo to give after chromatography (Silica gel: 50–75% ethyl acetate/hexane) 7.68 g of the desired product.

$^1$H NMR(CDCl$_3$): δ 7.25(d,2H); 6.86(d,2H); 4.06(m,2H); 3.82–3.65(m,9H); 3.11(m,1H); 2.0(brs,1H); 1.93(brs,1H).

EXAMPLE 324

1,4-Anhydro-2-S-[(4-methoxyphenyl)methyl]-2-thio-L-arabinitol 5-(4-Methylbenzenesulfonate)

To a 0° C. solution, under argon, of 0.580 g of product from Example 323 in 10 ml of pyridine is added 0.430 g of p-toluenesulfonyl chloride. The reaction is stirred at room temperature overnight. The mixture is quenched with water, extracted with diethyl ether, washed with water and saturated sodium chloride, dried and concentrated in vacuo. The residue is purified by chromatography (Silica gel: 50% ethyl acetate/hexane) to give 0.520 g of the desired product.

$^1$H NMR(CDCl$_3$): δ 7.79(d,2H); 7.34(d,2H); 7.20(d,2H); 7.87(d,2H); 4.18(m,2H); 3.98(m,2H); 3.85(m,1H); 3.78(s, 3H); 3.7(s,2H); 3.58(m,1H); 3.1(m,1H); 2.87(brs,1H); 2.43 (s,3H).

EXAMPLE 325

1,4-Anhydro-5-azido-5-deoxy-2-S-[(4-methoxyphenyl)methyl]-2-thio-L-arabinitol

A mixture of 2.0 g of product from Example 324, 0.460 g of lithium azide and 2 ml of N,N-dimethylformamide is stirred at 70° C. for 65 hours. The reaction mixture is concentrated in vacuo. The residue is purified by chromatography (Silica gel: 30% ethyl acetate/hexane), to give 0.454 g of the desired product.

$^1$H NMR(CDCl$_3$): δ 7.25(d,2H); 6.86(d,2H); 4.09–4.03 (m,1H); 3.96(t,1H); 3.83–3.66(m,7H); 3.52–3.33(m,2H); 3.11(1, 1H); 1.7(brs,1H).

EXAMPLE 326

1,4-Anhydro-5-deoxy-2-S-[(4-methoxyphenyl) methyl]-5-[[[(4-nitrophenyl)methoxy]carbonyl] amino]-2-thio-L-arabinitol To a 0° C. solution, under argon, of 0.269 g of product from Example 325 in 4.2 ml of methylene chloride is added 0.171 g of triethylamine followed by 0.308 g of p-nitrobenzylchloroformate. The reaction is stirred at 0° C. for 2 hours, diluted with diethyl ether, filtered and the filtrate is concentrated in vacuo. The residue is purified by chromatography (Silica gel: 50% ethyl acetate/hexane) to give 0.425 g of the desired product.

148

$^1$H NMR(CDCl$_3$): δ 8.21(d,2H); 7.49(d,2H); 7.23(d,2H); 6.85(d,2H); 5.24(m,1H); 5.20(s,2H); 4.06–4.01(q,1H); 3.85–3.79(q,1H); 3.78(s,3H); 3.78–3.62(m,4H); 3.45(m, 1H); 2.05(brs,1H).

EXAMPLE 327

1,4-Anhydro-5-deoxy-5-[[[(4-nitrophenyl)methoxy] carbonyl]amino-2-thio-L-arabinitol The title compound is prepared by the procedure of Example 202 using 0.462 g of product from Example 326, 12 ml of 80% aqueous acetic acid, 0.187 g of anisole, and 0.443 g of mercuric trifluoroacetate to give after chromatography (Silica gel: 50–80% ethyl acetate/hexane) 0.248 g of the desired product.

$^1$H NMR(CDCl$_3$): δ 8.22(d,2H); 7.51(d,2H); 5.29(m,1H); 5.21(s,2H); 4.23(q,1H); 3.83–3.67(m,3H); 3.49(m,2H); 3.31 (m,1H); 2.39(brs,1H); 1.76(d,1H).

EXAMPLE 328

[2-[4R-[4alpha,5beta,6beta(R*)]]-1,4-Anhydro-5-deoxy-2-S-[6-(1-hydroxyethyl)-4-methyl-2-[[(4-nitrophenyl)methoxy]carbonyl]-7-oxo-1-azabicyclo [3.2.0]hept-2-en-3-yl]-5-[[[(4-nitrophenyl)methoxy] carbonyl]amino-2-thio-L-arabinitol The title compound is prepared by the procedure of Example 17 using 0.210 g of product from Example 327, 0.380 g of product from Example 15, 3 ml of acetonitrile, and 0.163 g of Hunig's base to give after chromatography (Silica gel: 5% methyl alcohol/chloroform) 0.249 g of the desired product.

$^1$H NMR(CDCl$_3$): δ 8.24–8.19(m,4H); 7.65(d,2H); 7.49 (d,2H); 5.52–5.18(m,6H); 4.29–4.24(m,2H); 3.95(t,1H); 3.79–3.70(m,4H); 3.49–3.4(m,3H); 3.28(dd,1H); 2.05(brs, 1H); 1.36(d,3H); 1.28–1.22(m,3H).

EXAMPLE 329

[2-[4R-[4alpha,5beta,6beta(R*)]]-5-Amino-1,4-anhydro-2-S-[2-carboxy-6-(1-hydroxyethyl)-4-methyl-7-oxo-1-azabicyclo[3.2.0]hept-2-en-3-yl]-5-deoxy-2-thio-L-arabinitol The title compound is prepared by the procedure of Example 192 using 0.240 g of product from Example 328, 0.072 g of 10% palladium on carbon, 2.5 ml of 0.1M pH 7 sodium dihydrogen phosphate buffer and 7.5 ml of dioxane to give after chromatography (Reverse phase plates: 5% ethyl alcohol/water) 0.028 g of the desire product.

$^1$H NMR(D$_2$O): δ 4.38–4.3(m,1H); 4.25–4.2(m,2H); 4.1 (m,1H); 4.05(m,1H); 3.94(m,1H); 3.75–3.6(m,2H); 3.48–3.4(m,2H); 3.28(d,1H); 1.25(d,3H); 1.19(d,3H).

EXAMPLE 330

(R)-2,2-Dimethyl-1,3-dioxolane-4-carboxaldehyde

A 0° C. mixture, under argon, of 13.7 g of 1,2,5,6-di-O-isopropylidene-D-mannitol, 200 ml of methylene chloride, 72.3 g of potassium carbonate and 24.3 g of lead tetraacetate is stirred for 1½ hours. The suspension is filtered through diatomaceous earth and concentrated in vacuo. The oil is purified by distillation at water aspirator pressure to give 10.0 g (boiling point=62°–66° C.) of the desired product.

$^1$H NMR(CDCl$_3$): δ 9.73(d,1H); 4.4(m,1H); 4.22–4.07 (m,2H); 1.5(s,3H); 1.43(s,3H).

EXAMPLE 331

[R-(R*,R*) and R-(R*),S*)]-2,2-Dimethyl-alpha-2-propenyl-1,3-dioxolane-4-methanol To a stirring -78° C. solution, under argon, of 556 ml of 1M allylmagnesium bromide is added, dropwise over 20 minutes, a solution of 36.4 g of product from Example 330 in 17 ml of tetrahydrofuran. The reaction mixture is stirred at -78° C. for 2 hours. Thin layer chromatography indicates the presence of starting material. An additional 280 ml of 1M allylmagnesium bromide is added and the reaction is stirred overnight at -78° C. The reaction is quenched with dropwise addition of saturated ammonium chloride, filtered through diatomaceous earth and washed with diethyl ether, ethyl acetate and 20% isopropyl alcohol/chloroform. The combined extracts are washed with saturated sodium chloride, dried and concentrated in vacuo to give, after Kugelrohr distillation at 85° C., 38.25 g of the desired product.

$^1$H NMR(CDCl$_3$): δ 5.83(m,1H); 5.15(q,2H); 4.05–3.57 (m,4H); 2.39–2.12(m,3H); 1.43(d,3H); 1.38(d,3H).

EXAMPLE 332

[R-(R*,S*)]-2,2-Dimethyl-4-[1-(phenylmethoxy)-3-butenyl]-1,3-dioxolane (A)

and

[R-(R*,R*)]-2,2-Dimethyl-4-[1-(phenylmethoxy)-3-butenyl]-1,3-dioxolane (B)

Under anhydrous conditions, a flask is charged with 10.7 g of sodium hydride and 35 ml of anhydrous tetrahydrofuran. This slurry is stirred for 10 minutes at 0° C. followed by the dropwise addition of 38.25 g of product from Example 331 in 50 ml of anhydrous tetrahydrofuran. The ice bath is removed and the reaction is stirred for 30 minutes at room temperature. The reaction mixture is recooled to 0° C. and 20 ml of benzyl bromide is added dropwise followed by 0.150 g of tetrabutylammonium iodide. The reaction is allowed to warm to room temperature and the stirring is continued for 60 hours. The mixture is recooled to 0° C., quenched with ice cold saturated ammonium chloride, extracted with diethyl ether and washed with sodium bicarbonate and saturated sodium chloride. The organic layer is dried, concentrated in vacuo to give after chromatography (Silica gel: 5% diethyl ether/hexane) 5.7 g of compound A and 6.1 g of compound B.

Compound A $^1$H NMR(CDCl$_3$): δ 7.34–7.28(m,5H); 5.89(m,1H): 5.18–5.08(m,2H); 4.62(q,2H); 4.11–4.01(m,2H); 3.89(m, 1H); 3.57(q,1H); 2.42–2.39(m,2H); 1.42(s,3H); 1.35(s,3H).

Compound B $^1$H NMR(CDCl$_3$): δ 7.38–7.27(m,5H); 5.89(m,1H); 5.14–5.05(m,2H); 4.69(q,1H); 4.21(q,2H); 3.98(q,1H); 3.71 (t,1H); 3.52(m,1H); 2.37–2.18(m,2H); 1.43(s,3H); 1.37(s, 3H).

EXAMPLE 333

[S-(R*,S*)-3-(Phenylmethoxy)-5-hexene-1,2-diol

A mixture of 26.2 g of product from Example 332, 140 ml of 2N hydrochloric acid and 140 ml of tetrahydrofuran is heated at reflux temperature for 1 hour. The reaction mixture is cooled to 0° C., quenched with solid sodium bicarbonate, and extracted with chloroform. The organic layer is washed with saturated sodium chloride and water, dried and concentrated in vacuo to give 11.0 g of the desired product.

$^1$H NMR(CDCl$_3$): δ 7.36–7.30(m,5H); 5.87(m,1H); 5.19–5.09(m,2H); 4.6(q,2H); 3.79–3.63(m,4H); 2.53–2.37 (m,2H); 2.13(brs,2H).

EXAMPLE 334

2,5-Anhydro-1,3-dideoxy-1-iodo-4-O-(phenylmethyl)-D-ribo-hexitol (A)

and 2,5-Anhydro-1,3-dideoxy-1-iodo-4-O-(phenylmethyl)-D-arabino-hexitol (B)

A 0° C. solution of 4.5 g of product from Example 333 in 77.8 ml of diethyl ether and 25.5 ml of water is treated with 2.58 g of solid sodium bicarbonate followed by 7.6 g of iodine. The reaction is stirred for 3 hours at 0° C. then at room temperature overnight. The mixture is cooled to 0° C. and sodium sulfite is added until the reaction is colorless. The solution is extracted with diethyl ether, dried and concentrated in vacuo to give 7.0 g of an oil. The oil is purified by chromatography (Silica gel: 5% diethyl ether/hexane) to give 2.8 g of Isomer A and 1.86 g of Isomer B.

Isomer A $^1$H NNR(CDCl$_3$): δ 7.37–7.28(m,5H); 4.51(q,2H); 4.12 (m,2H); 3.97(m,1H); 3.68(q,2H); 3.36(m,2H); 2.15(m,2H). 1.78(m,1H).

Isomer B $^1$H NMR(CDCl$_3$): δ 7.36–7.3(m,5H); 4.52(q,2H); 4.31 (m,1H); 4.19–4.07(m,2H); 3.72–3.67(m,1H); 3.58–3.56(m, 1H); 3.35(m,2H); 2.34(m,1H); 2.07(m,1H); 1.96(brs,1H).

EXAMPLE 335

2,5-Anhydro-1,3-dideoxy-4-O-(phenylmethyl)-D-ribo-hexitol

A mixture of 6.0 g of product from Example 334, Isomer A, 34 ml of ethyl alcohol, 17.2 ml of 1N sodium hydroxide and 7.8 g of 10% palladium on carbon is hydrogenated in a Parr apparatus at 45 psi of hydrogen for 15 hours. The reaction mixture is filtered, diluted with ethyl acetate, washed with saturated sodium chloride, dried and concentrated in vacuo to give 2.9 g of the desired product.

$^1$H NMR(CDCl$_3$): δ 7.37–7.27(m,5H); 4.51(q,2H); 4.24 (m,1H); 4.01–3.97(m,2H); 3.77–3.58(m,2H); 2.15–2.08(m, 1H); 1.83(brs,1H); 1.58(brs,1H); 1.58–1.48(m,1H); 1.28(d, 3H).

EXAMPLE 336

2,5-Anhydro-1,3-dideoxy-D-hexitol

A mixture of 1.1 g of product from Example 335 in 44 ml of ethyl alcohol and 22 ml of cyclohexane is treated with 0.250 g of palladium hydroxide on carbon (Pearlman's catalyst). The resulting black suspension is heated at reflux temperature for 3 hours, filtered and concentrated in vacuo. The residue is purified by chromatography (Silica gel: 3% methyl alcohol/chloroform) to give 0.570 g of the desired product.

$^1$H NMR(CDCl$_3$): δ 4.3–4.32(m,2H); 3.8(q,1H); 3.65–3.58(m,2H); 3.57–3.54(m,1H); 3.29(m,1H); 1.99–1.93 (m,1H); 1.65(m,1H); 1.26(d,3H).

EXAMPLE 337

2,5-Anhydro-1,3-dideoxy-D-ribo-hexitol 6-(4-Methylbenzenesulfonate)

The title compound is prepared by the procedure of Example 307 using 0.290 g of product from 336, 0.440 g of p-toluenesulfonyl chloride and 8 ml of pyridine to give after chromatography (Silica gel: 2% methyl alcohol/chloroform) 0.407 g of the desired product.

$^1$H NMR(CDCl$_3$): δ 7.89(d,2H); 7.35(d,2H); 4.31(m,1H); 4.27(m,1H); 4.08(m,1H); 3.94(m,1H); 3.8(m,1H); 2.45(s, 3H); 2.34(brs,1H); 1.93–1.91(m,1H); 1.65(m,1H); 1.20(d, 3H).

EXAMPLE 338

2,5-Anhydro-6-azido-1,3,6-trideoxy-D-ribo-hexitol

A mixture, under argon, of 0.560 g of product from Example 337, 2 ml of N,N-dimethylformamide and 0.250 g of sodium azide is stirred at 75° C. for 12 hours. The reaction mixture is diluted with diethyl ether, washed with water and saturated sodium chloride, dried and concentrated in vacuo to give 0.238 g of the desired product.

$^1$H NMR(CDCl$_3$): δ 4.27(m,2H); 3.9(q,1H); 3.49(m,1H); 3.33–3.27(m,1H); 2.01–1.94(m,1H); 1.74(brs,1H); 1.64(m, 1H); 1.26(d,3H).

EXAMPLE 339

2,5-Anhydro-6-azido-1,3,6-trideoxy-D-ribo-hexitol 4-Methanesulfonate

The title compound is prepared by the procedure of Example 277 using 0.192 g of product from Example 338, 0.316 g of Hunig's base, 0.280 g of methanesulfonyl chloride and. 0.35 ml of methylene chloride to give after chromatography (Silica gel: 30% ethyl acetate/hexane) 0.140 g of the desired product.

$^1$H NMR(CDCl$_3$): δ 5.08–5.05(m,1H); 4.26–4.18(m,2H); 3.6–3.54(m,1H); 3.41–3.35(m,1H); 3.05(s,3H); 2.30–2.27 (m,1H); 1.88–1.78(m,1H); 1.34(d,3H).

EXAMPLE 340

2,5-Anhydro-6-azido-1,3,6-trideoxy-4-thio-D-xylo-hexitol 4-Acetate

A mixture of 0.133 g of product from Example 339, 0.083 g of potassium thioacetate, 500 microliter of dimethylformamide-and 500 microliter of toluene is stirred, under argon, at 70° C. overnight. The progress of the reaction is monitored by tlc. An additional 0.050 g of potassium thioacetate is added and the reaction is stirred at 70° C. for 5 more hours. The mixture is filtered through a thin pad of Silica gel, washed with diethyl ether and the filtrate is concentrated in vacuo. The residue is purified by chromatography (Silica gel: 20% diethyl ether/hexane) to give 0.043 g of the desired product.

$^1$H NMR(CDCl$_3$): δ 4.29–4.21(m,1H); 4.21–4.16(m,1H); 4.08–4.03(m,1H); 3.44–3.39(m,1H); 3.30–3.25(m,1H); 2.46 (m,1H); 2.35(s,3H); 1.59(m,1H); 1.33(d,3H).

EXAMPLE 341

2,5-Anhydro-6-azido-1,3,6-trideoxy-4-thio-D-xylo-hexitol

The title compound is prepared by the procedure of Example 16 using 0.040 g of product from Example 340, 52 microliter of 25% (by wt) sodium methoxide/methyl alcohol and 0.50 ml of tetrahydrofuran to give 0.030 g of the desired product.

$^1$H NMR(CDCl$_3$): δ 4.1–3.96(m,2H); 3.55–3.43(m,3H); 2.61–2.47(m,1H); 1.7(d,1H); 1.48(m,1H); 1.34(d,3H).

EXAMPLE 342

2,5-Anhydro-6-azido-1,3,6-trideoxy-4-S-[6-(1-hydroxyethyl)-4-methyl-2-[[(4-nitrophenyl)methoxy]carbonyl]-7-oxo-1-azabicyclo[3.2.0]hept-2-en-3-yl]-4-thio-D-xylo-hexitol The title compound is prepared by the procedure of Example 17 using 0.030 g of product from Example 341, 0.103 g of product from Example 15, 0.022 g of Hunig's base and 0.50 ml of acetonitrile to give after chromatography (Silica gel: 10% acetone/chloroform) 0.062 g of the desired product.

$^1$H NMR(CDCl$_3$): δ 8.22(d,2H); 7.66(d,2H); 5.52(d,1H); 5.23(d,1H); 4.26(m,2H); 4.06(m,1H); 3.83(q,1H); 3.52(t, 1H); 3.4(m,1H); 3.3(m,1H); 21.5(m,1H); 1.84(brs, 1H); 1.76(m,1H); 1.38–1.25(m,9H); 0.88(m,2H).

EXAMPLE 343

[4-[4R-[4alpha,5beta,6beta(R*)]]]-6-Amino-2,5-anhydro-4-S-[2-carboxy-6-(1-hydroxyethyl)-4-methyl-7-oxo-1-azabicyclo[3.2.0]hept-2-en-3-yl]-1,3,6-trideoxy-4-thio-D-xylo-hexitol The title compound is prepared by the procedure of Example 192 using 0.060 g of product from Example 342, 0.045 g of 10% palladium on carbon, 2.35 ml of 0.1M pH 7 sodium dihydrogen phosphate buffer, and 7.05 ml of dioxane to give after chromatography (Reverse phase plates: 5% ethyl alcohol/water) 0.012 g of the desired product.

$^1$H NMR(D$_2$O): δ 4.04(m,1H); 3.93–3.85(m,3H); 3.69(q, 1H); 3.13–2.97(m,3H); 2.87–2.79(m,1H); 2.33–2.23(m, 1H); 1.44–1.36(m,1H); 1.0–0.95(m,6H); 0.86–0.84(m,3H).

EXAMPLE 344

1,4-Anhydro-2,5-dideoxy-5-(methylamino)-D-erthro-pentitol

To a 0° C. solution of 15 ml of 40% methylamine is added 0.921 g of product from Example 269 in 2 ml of dioxane. The reaction mixture is maintained and stirred at 0° C. for 50 minutes, tlc indicates the absence of starting material. The reaction is concentrated in vacuo and the residue is chromatographed (Silica gel: 30% methyl alcohol/chloroform) 0.749 g of an oil containing the desired product and salts. The sample is redissolved in ethyl acetate; potassium carbonate is added and the mixture is stirred for 2 hours at room temperature. The suspension is filtered, concentrated Ad vacuo and rechromatographed (Silical gel: methyl alcohol) to give 0.102 g of the desired product.

$^1$H NMR(CDCl$_3$): δ 4.0–3.9(m,1H); 3.88–3.75(m,2H); 3.75–3.65(m,1H); 2.6–2.35(m,2H); 2.29(s,3H,N—Me); 2.05–1.92(m,1H); 1.8–1.7(m,1H).

EXAMPLE 345

1,4-Anhydro-2,5-dideoxy-5-[methyl[[(4-nitrophenyl)methoxy]carbonyl]amino]-D-erthro-pentitol A −5° C. mixture, under argon, of 4.35 g of product from Example 344 in 30 ml of methylene chloride is treated with 5.8 ml of Hunig's base followed by dropwise addition of 7.15 ml of p-nitrobenzyl chloroformate in 20 ml of methylene chloride. The reaction mixture is stirred at −5° C. for 2½ hours. The mixture is concentrated in vacuo and the residue is purified by chromatography (Silica gel: 75% ethyl acetate/hexane) to give 6.75 g of the desired product.

¹H NMR(CDCl₃): δ 8.22(d,2H,Arom,J=8.6 Hz); 7.56(d, 2H,Arom,J=8.5 Hz); 5.23(s,2H,benzylic H); 4.16–4.08(q, 2H); 3.97–3.92(t,2H); 3.53(dd,1H); 3.39–3.31(dd,1H); 3.06 (s,3H,NMe); 2.2–2.1(m,1H); 2.0–1.85(m,1H).

EXAMPLE 346

1,4-Anhydro-2,5-dideoxy-5-[methyl[[(4-nitrophenyl) methoxy]carbonyl]amino]-D-erthro-pentitol-3-methanesulfonate The title compound is prepared by the procedure of Example 277 using 0.310 g of product from Example 345, 93 microliters of methanesulfonyl chloride and 167 microliters of triethylamine to give, after chromatography (Silica gel: ethyl acetate), 0.388 g of the desired product.

¹H NMR(CDCl₃): δ 8.1(d,2H,J=8.7 Hz); 7.47(d,2H,J=6.9 Hz); 5.16(s,2H,benzylic H); 5.05(m,1H,S—O—CH); 4.2–4.1(m,1H); 4.05–3.9(m,1H); 3.88–3.78(q,1H); 3.55–3.4 (m,1H); 3.35–3.2(m,1H); 2.97(s,6H,2Me); 2.16–2.12(m, 2H).

EXAMPLE 347

2,5-Anhydro-1,4-dideoxy-1-[methyl [[(4-nitrophenyl) methoxy]carbonyl]amino]-3-thio-D-threo-pentitol 3-Acetate The title compound is prepared by the procedure of Example 278 using 3.9 g of product from Example 346, 1.7 g of potassium thioacetate, 20 ml of dimethylformamide and 20 ml of toluene to give, after chromatography (Silica gel: 50% ethyl acetate/hexane), 2.13 g of the desired product.

¹H NMR(CDCl₃): δ 8.22(d,2H,J=8.0 Hz); 7.53(t,2H); 2.25(s,2H); 4.25–4.0(m,2H); 3.9(m,1H); 3.8(m,1H); 3.6(m, 1H); 3.25(m,1H); 3.03(s,3H,N—Me); 2.5(m,1H); 2.35(s, 3H,SAc); 1.98(m,1H).

EXAMPLE 348

2,5-Anhydro-1,4-dideoxy-1-[methyl [[(4-nitrophenyl) methoxy]carbonyl]amino]-3-thio-D-threo-pentitol To an ice cooled 'solution of 2.13 g of product from Example 347 in 15 ml of methyl alcohol is added, dropwise maintaining the temperature below 5° C., 1.52 ml of 4N sodium hydroxide. The reaction is stirred for 10 minutes. The reaction is monitored by tlc. To the cooled solution is added 2.17 ml of 0.97N hydrochloric acid and the reaction mixture is diluted with ethyl acetate, washed with saturated sodium chloride, and the organic phase is dried. The solution is concentrated in vacuo and the residue is purified by chromatography (Silica gel: 50% ethyl acetate/hexane) to give 1.15 g of the desired product.

¹H NMR(CDCl₃): δ 8.22(d,2H,J=8.0 Hz); 7.5(d,2H,8.0 Hz); 5.21(s,2H); 4.1(m,2H); 3.8(m,2H); 3.5–3.25(m,2H); 3.07(s,3H,N—Me); 2.5(m,1H); 2.0(m,1H); 1.66(SH).

EXAMPLE 349

[3-[4R-[4alpha,5beta,6beta(R*)]]]-2,5-Anhydro-1 4-dideoxy-3-S-[6-(1-hydroxyethyl)-4-methyl-2-[[(4-nitrophenyl)methoxy]carbonyl]-7-oxo-1-azabicyclo [3.2.0]hept-2-en-3-yl]-1-[methyl [[(4-nitrophenyl) methoxy]carbonyl]amino]-3-thio-D-threo-pentitol The title compound is prepared by the procedure of Example 17 using 1.15 g of product from Example 348 in 15 ml of acetonitrile, 1.68 g of product from Example 15 in 15 ml of acetonitrile and 0.54 ml of Hunig's base to give, after chromatography (Silica gel: 80% ethyl acetate/acetone) 1.52 g of the desired product.

¹H NMR(CDCl₃): δ 8.22(d,4H,Arom,J=8.6 Hz); 7.66(d, 2H,Arom,J=8.6 Hz); 7.52(d,2H,Arom,J=8.6); 5.52(d,1H, benzylic H, J=13.8 Hz); 5.23(d,3H,benzylic H,J=10.3 Hz); 4.35–4.2(m,3H); 4.2–4.0(m,1H); 3.95–3.75(m,3H); 3.7–3.1 (m,3H); 3.07(s,3H,N—Me); 2.5–2.35(m,1H); 2.1–2.0(m, 1H); 1.95–1.8(brs,1H,OH); 1.37(d,3H,Me,J=6.2 Hz); 1.28 (d,3H,J=7.3 Hz).

EXAMPLE 350

[3-[4R-[4alpha,5beta,6beta(R*)]]]-2,5-Anhydro-3-S-[2-carboxy-6-(1-hydroxyethyl)-4-methyl-7-oxo-1-azabicyclo[3.2.0]hept-2-en-3-yl]-1,4-dideoxy-1-(methylamino)-3-thio-D-threo-pentitol The title compound is prepared by the procedure of Example 192 using 1.52 g of product from Example 349, 25 ml of 0.1M pH 7.0 sodium dihydrogen phosphate buffer, 0.70 g of 10% palladium on carbon and 70 ml of dioxane to give, after chromatography (Reverse Phase plates: 5% aqueous ethyl alcohol), 0.225 g of the desired product.

¹H NMR(D₂O): δ 4.6–3.8(m,6H); 3.6–3.2(m,4H); 2.76(s, 3H,N—Me); 2.6–2.4(m,1H); 2.2–2.0(m,1H); 1.27(d,3H, Me,J=5.5 Hz); 1.17(d,3H,Me,J=6.3).

EXAMPLE 351

[3-[4R-[3(2S*),4alpha,5beta,6beta(R*)]]]-1-[(2-Amino-1-oxopropyl)methylamino]-2,5-anhydro-3-S-[2-carboxy-6-(1-hydroxyethyl)-4-methyl-7-oxo-1-azabicyclo[3.2.0]hept-2-en-3-yl]-1,4-dideoxy-3-thio-D-threo-pentitol The title compound is prepared by the procedure of Example 304 using 0.173 g of product from Example 350, 0.177 g of product from Example 259, 5 ml of 0.1M pH 7.0 sodium dihydrogen phosphate buffer, 4 ml of dioxane and 0.10 g of 10% palladium on carbon to give, after chromatography (Reverse Phase Plates: 5% aqueous ethyl alcohol) ,0.0386 g of the desired product.

EXAMPLE 352

2-Deoxy-3,5-bis-O-[(1,1-dimethylethyl) dimethylsilyl]-D-erythro-pentonoic Acid gamma-Lactone To a stirring solution, under argon, of 1.18 g of 2-deoxy-D-erythro-pentonoic acid gamma-lactone, prepared by the procedure described in Carbohydrate Research, Vol. 90, 1981, p 17–26, in 11 ml of dimethylformamide containing 3 ml of triethylamine is added dropwise a solution of 2.95 g of tert-butyldimethylsilyl chloride in 9 ml of dimethylformamide. The reaction mixture is stirred overnight at room temperature, poured into a mixture of 110 ml of hexane and 110 ml of water, the layers partitioned. The organic layer is washed with water, dried and concentrated to give 2.64 g of the desired product.

mp 77°–78° C.

¹H NMR(CDCl₃): δ 4.45(m,1H); 4.34(m,1H); 3.78(m, 2H); 2.83(dd,1H); 2.38(d,1H); 0.9(s,18H).

EXAMPLE 353

2-Deoxy-3 5-bis-O-[(1,1-dimethylethyl) dimethylsilyl]-1-thio-D-erythro-pentonoic Acid gamma-Lactone To a solution, under argon, of 1.24 g of product from Example 352 in 16 ml of dry toluene is added 0.973 g of Lawesson's Reagent. The reaction mixture is heated at reflux temperature for 3 hours (the reaction is monitored by thin layer chromatography, tlc). Tlc indicates the presence of starting material. An additional 0.138 g of Lawesson's reagent is added and the reaction is heated at reflux temperature for an additional 1½ hours. The mixture is cooled to room temperature, the solids are collected and washed with toluene. The mother liquor is concentrated to dryness and purified by chromatography (Silica gel: 95% hexane/ ethyl acetate) to give 0.960 g of the desired product.

Calcd for $C_{17}H_{36}O_3SSi_2$: C=54.20; H=9.63; S=8.51 Found: C=53.91; H=9.73; S=8.51.

$^1$H NMR(CDCl$_3$): δ 4.65(m,1H); 4.55(m,1H); 3.85(q, 2H); 3.25(dd,1H); 2.98(d,1H); 0.87(s,18H).

mp 90°–91° C.

EXAMPLE 354

2-Deoxy-3,5-bis-O-[(1,1-dimethylethyl) dimethylsilyl]-1-thio-D-erythro-pentofuranose To a −78° C. solution, under argon, of 0.420 g of product from Example 353 in 8.4 ml of dry tetrahydrofuran is added dropwise 2.8 ml of Super Hydride (1M in tetrahydrofuran). After 1 hour an additional 1.4 ml of Super Hydride is added and the stirring continued at −78° C. for 30 minutes. The reaction is quenched by the addition of 5 ml of 1N hydrochloric acid. Ethyl acetate and water are added and the layers are partitioned. The organic layer is washed with water, saturated sodium chloride, dried and concentrated to give 0.412 g of an oil.

Calcd for $C_{17}H_{38}O_3SSi_2$: C=53.92; H=10.11; S=8.46 Found: C=54.62; H=9.94; S=8.23.

$^1$H NMR(CDCl$_3$): δ 5.5(m,1H); 4.37(m,1H); 4.15(m,1H); 3.74–3.5(m,2H); 2.95(d,1H); 2.54(m,1H); 2.06(m,1H); 0.87 (2s,18H).

EXAMPLE 355

[2S-[2alpha(S*),3beta(S*)]]-1-[1-[1-[(1,1-Dimethylethyl)dimethylsilyl]-3-[1-[[(1,1-dimethylethyl)dimethylsilyl]oxy]ethyl]-4-oxo-2-azatidinyl]ethyl]-3-[(4-nitrophenyl)methoxy-2,3-dioxopropyl 2-deoxy-3,5-bis-O-[(1,1-dimethylethyl) dimethylsilyl]-1-thio-alpha(and beta)-D-erthro-pentofuranoside To a 0° C. solution, under argon, of 0.638 g of product from Example 103 in 5.3 ml of dry tetrahydrofuran is added 0.30 g of product from Example 354 in 4 ml of tetrahydrofuran. 0.133 ml of triethylamine is added and the reaction is stirred for 30 minutes at 0° C. The mixture is allowed to come to room temperature over 30 minutes, diluted with ethyl acetate, washed with saturated sodium bicarbonate, saturated sodium chloride, dried and filtered. The filtrate is purified by chromatography (Silica gel: 98% hexane/ethyl acetate) to give 0.660 g of an impure solid. The solid is rechromatographed (Silica gel: 85% hexane/ethyl acetate) to give 0.294 g of the desired product as a yellow oil.

$^1$H NMR(CDCl$_3$): δ 8.23(d,2H); 7.57(d,2H); 5.36(m,2H); 5.25(m,1H); 4.4–3.25(m,6H); 2.4–1.67(m,2H); 1.22–1.0 (4d,6H).

EXAMPLE 356

[2S-[2alpha(S*),3beta(S*)]]-1-[1-[3-(1-Hydroxyethyl)-4-oxo-2-azetidinyl]ethyl]-3-[(4-nitrophenyl)methoxy]-2,3-dioxopropyl 2-deoxy-1-thio-alpha (and beta)-D-erythro-pentofuranoside To a room temperature solution, under argon, of 0.294 g of product from Example 355 in 3 ml of dry tetrahydrofuran is added 3 ml of triethylammonium trihydrofluoride. After 20 minutes, no starting material was present (by tlc). Stirred in an oil bath at 50° C. for 1 hour and 40 minutes. Only polar spot visible by tlc. The reaction mixture is cooled, cold ethyl acetate is added, the layers are partitioned and the organic layer is washed with cold water, cold sodium bicarbonate, cold saturated sodium chloride, dried and concentrated to give 0.105 g of a glass. The product is used immediately in following Example.

EXAMPLE 357

[4R-[4alpha,5beta,6beta(R*)]]-6-(1-Hydroxyethyl)-4-methyl-2-[[(4-nitrophenyl)methoxy]carbonyl]-7-oxo-1-azabicyclo[3.2.0]hept-2-en-3-yl 2-deoxy-1-thio-alpha (and beta)-L-erythro-pentofuranoside To a room temperature solution, under argon, of 0.105 g of product from Example 356 in 2 ml of dry tetrahydrofuran is added 0.82 ml of titanium tetrachloride (1M in methylene chloride). The reaction is stirred for 10 minutes and poured into a rapidly stirred mixture of ethyl acetate and saturated sodium bicarbonate. The layers are separated, the organic layer is washed with saturated sodium chloride, dried and concentrated to a glass. The glass is purified by chromatography (Silica Gel: 5% methyl alcohol/methylene chloride) to give 0.026 g of the desired product.

$^1$H NMR(acetone-d$_6$): δ 8.25(d,2H); 7.84(d,2H); 5.85(m, 1H); 5.57(d,1H); 5.3(d,1H); 4.5–3.53(m,6H); 3.34(brs,1H); 2.75(m,1H); 2.45–1.93(m,2H); 1.25(brs,6H).

EXAMPLE 358

[4R-[4alpha,5beta,6beta(R*)]]-2-Carboxy-6-(1-hydroxyethyl)-4-methyl-7-oxo-1-aza-bicyclo[3.2.0] hept-2-en-3-yl 2-deoxy-1-thio-alpha (and beta)-D-erythro-pentofuranoside To a solution of 0.026 g of product from Example 357 in 0.3 ml of water (degassed) and 0.3 ml of dioxane is added 0.0053 g of potassium bicarbonate. The mixture is transferred to a Parr apparatus with 0.2 ml of water and 0.2 ml of dioxane. 0.026 g of 10% palladium on carbon is added and the reaction mixture is hydrogenolysed at room temperature, 35 psi, for 1½ hours. The reaction is filtered and washed with water and ethyl acetate. The organic layer is dried and lyophilized to give 0.016 g of the desired product.

$^1$H NMR(D$_2$O): δ 5.8(m,1H); 4.54–3.95(m,4H); 3.9–3.45 (m,6H); 2.78(m,1H); 2.49–2.2(m,1H); 2.05.(m,1H); 1.33(d, 3H); 1.25(d,3H).

EXAMPLE 359

(S)-5-[[[(1,1-Dimethylethyl)dimethylsilyl]oxy] methyl]-dihydro-21(3H)-furanone

The title compound is prepared by the procedure of Example 352 using 0.65 g of S-(+)-dihydro-5-(hydroxymethyl)-2-(3H)-furanone in 9 ml of dimethylformamide, 1.63 g of tert-butyldimethylsilyl chloride, and 1.63 ml of triethylamine to give 0.868 g of the desired product as a colorless oil.

$^1$H NMR(CDCl$_3$): δ 4.6(m,1H); 3.77(ABq,2H); 2.7–2.4 (m,2H); 2.34–2.1(m,2H); 0.9(2s,9H); 0.1(2s,6H).

EXAMPLE 360

(S)-5-[[[(1,1-Dimethylethyl)dimethylsilyl]oxy] methyl]-dihydro-2(3H)-furanthione The title compound is prepared by the procedure of Example 353 using 0.868 g of product from Example 359, 10 ml of toluene and 0.763 g of Lawesson's Reagent to give 0.530 g of the desired product.

$^1$H NMR(CDCl$_3$): δ 4.99(m,1H); 3.86(ABq,2H); 3.27–2.99(m,2H); 2.4–2.18(m,2H); 0.9(s,9H); 0.1(2s,6H).

EXAMPLE 361

(2S-cis) and (2R-trans) 5-[[[(1,1-Dimethylethyl) dimethylsilyl]oxy]methyl]tetrahydro-2(3H)-furanthiol The title compound is prepared by the procedure of Example 354 using 0.0445 g of product from Example 360, 0.9 ml of dry tetrahydrofuran and 0.362 ml of Super Hydride to give a mixture of anomers.

$^1$H NMR(CDCl$_3$): δ 5.64, 5.46(m,1H); 4.31,4.13(2m,1H); 3.8–3.6(m,2H); 2.44–2.75(m,4H); 2.29,2.2(2d,1H); 0.9(2s, 9H); 0.1(2s,6H).

EXAMPLE 362

[2S-[2alpha,2[gammaS*,beta(5R*)]3beta(S*)]]-1 1-[(1,1-Dimethylethyl)dimethylsilyl]-3-[1-[[(1,1-dimethylethyl)dimethylsilyl]oxy]ethyl]-3-[[5-[[[(1,1-dimethylethyl)dimethylsilyl]oxy]methyl]tetrahydro-2-furanyl]thio]-gamma-methyl-alpha,4-dioxo-2-azetidinebutanoic Acid (4-Nitrophenyl)methyl Ester The title compound is prepared by the procedure of Example 355 using 0.334 g of product from Example 103 in 2.8ml of tetrahydrofuran , 0.148 g of product from Example 361 in 2 ml of tetrahydrofuran, and 0.83 ml of triethylamine to give, after chromatography, 0.272 g of the major isomer and 0.128 g of the minor isomer.

Major Isomer
$^1$H NMR(CDCl$_3$): δ 8.25(d,2H); 7.6(d,2H); 5.39(s,2H); 5.18(m,1H); 4.43(d,1H); 4.08(m,1H); 3.98(m,2h); 3.5(d ABq,2H); 2.8(m,1H); 2.5(m,1H); 2.34–1.82(m,4H); 1.25(d, 3H); 1.05(d,3H); 1.0–0.9(4s,3H); 0.25(2s,6H); 0.04(4s, 12H).

Minor Isomer
$^1$H NMR(CDCl$_3$): δ 8.25(d,2H); 7.63(d,2H); 5.37(m,1h); 5.34(ABq,2H); 4.45(d,1H); 4.03(m,2H); 3.68–3.5(m,3H); 3.16(m,1H); 2.65(m,1H); 2.33–1.88(m,4H); 1.3(d,3H); 1.18(d,3H); 0.9(4s,27H); 0.1–0(6s,18H).

EXAMPLE 363

[4R-[3(5S*)4alpha,5beta,6beta(R*)]]-6-(1-Hydroxyethyl)-4-methyl-7-oxo-3-[[tetrahydro-5-(hydroxymethyl)-2-furanyl]thio]-1-azabicyclo-[3.2.0]-hept-2-ene-2-carboxylic Acid(4-Nitrophenyl)methyl Ester The title compound is prepared by the procedure of Example 356 using 0.271 g of product from Example 362 in 0.8 ml of tetrahydrofuran, 0.8 ml of triethylammonium trihydrofluoride to give 0.152 g of [2S-[2alpha,2[gammaS*, beta(5R*)],3beta(S*)]]-3-(1-hydroxyethyl)-gamma-methyl-alpha,4-dioxo-beta-[[tetrahydro-5-(hydroxymethyl)-2-furanyl]thio]-2-azetidinebutanoic. The above recovered product is reacted according to the procedure of Example 356 with 1.2 ml of titanium tetrachloride to give 0.046 g of the desired title product.

$^1$H NMR(CDCl$_3$): δ 8.24(d,2H); 7.67(d,2H); 5.73(m,1H); 5.38(ABq,2H); 4.3(m,3H); 3.84–3.53(m,2H); 3.3(m,1H); 2.43(m,1H); 2.35–1.6(m,4H); 1.38(d,3H); 1.3(d,3H).

EXAMPLE 364

[4R-[3(5S*)4alpha,5beta,6beta(R*)]]-6-(1-Hydroxyethyl)-4-methyl-7-oxo-3-[[tetrahydro-5-(hydroxymethyl)-2-furanyl]thio]-1-azabicyclo[3.2.0] hept-2-ene-2-carboxylic Acid Monopotassium Salt The title compound is prepared by the procedure of Example 358 using 0.046 g of product from Example 363 in 700 microliters of dioxane, 700 microliters water containing 0.0096 g of potassium bicarbonate and 0.046 g of 10% palladium on carbon, at 38 psi, to give 0.009 g of the desired product.

$^1$H NMR(D$_2$O): δ 5.73(m,1H); 4.25(m,1H); 3.88–3.35(m, 5H); 2.39(m,1H); 2.22–1.73(m,4H); 1.33(d,3H); 1.24(d, 3H).

EXAMPLE 365

3,5-Bis-O-[(1,1-Dimethylethyl)dimethylsilyl]-D-ribonic Acid gamma-Lactone

To three grams of gamma-lactone D-(+)-ribonic acid in 25 ml of dry dimethylformamide, under argon and cooled in an ice bath, is added, dropwise over 20 minutes, 7.0 g of tert-butyldimethylsilyl chloride and 8.47 ml of triethylamine in 5 ml of dimethylformamide. The reaction mixture is allowed to stir at room temperature for 2 hours then is diluted with diethyl ether. The mixture is washed with saturated sodium bicarbonate, water, and saturated sodium chloride; dried, filtered and concentrated in vacuo. The crystalline residue is purified by chromatography (Silica gel: 10% ethyl acetate/hexane) to give 5.74 g of a mixture of products.

$^1$H NMR(CDCl$_3$): δ 4.59(d,1H); 4.27(br s,2H); 3.82(q, 2H); 0.9(3s,18H).

EXAMPLE 366

2,5-Bis-O-[(1,1-Dimethylethyl]dimethylsilyl]-D-ribonic Acid gamma-Lactone Methanesulfonate (A)
3,5-Bis-O-[(1,1-Dimethylethyl]dimethylsilyl]-D-ribonic Acid gamma-Lactone Methanesulfonate (B)

To an ice cooled, under argon, solution of 2.0 g of product from Example 365 in 12 ml of pyridine is added 1.65 ml of methanesulfonyl chloride. The reaction is stirred at room temperature for 1 hour and then stored in a refrigerator for 2 days. The mixture is poured into cold water, extracted with diethyl ether and the layers are separated. The organic layer is washed with 1N hydrochloric acid, saturated sodium bicarbonate, saturated copper sulfate and water; dried and concentrated in vacuo. The crystalline residue is purified by chromatography (Silica gel: 10% ethyl acetate/hexane) to give 1.46 g of the desired product (A) and 0.79 g of product (B).

Product A
$^1$H NMR(CDCl$_3$): δ 5.17(m,1H); 4.75(m,1H); 4.59(br s, 1H); 3.85(br s,2H); 3.05(s,3H); 0.91(s,9H); 0.84(s,9H).

EXAMPLE 367

(S)-3-[[(1,1-Dimethylethyl)dimethylsilyl]oxy-5-[[[(1,1-dimethylethyl)dimethyldilyl]oxy]methyl]-2(5H)-furanone To 0.73 g of product from Example 366 in 8 ml of dry methylene chloride is added, dropwise, 0.288 ml of 1,8-dizabicyclo[5.4.0]undec-7-ene. After 30 minutes the reaction is diluted with diethyl ether, washed with 1N hydrochloric acid followed by saturated sodium chloride, dried and concentrated in vacuo to give 0.535 g of the desired product.

$^1$H NMR(CDCl$_3$): δ 6.16(s,11H); 4.84(m,1H); 3.74(m, 2H); 0.91(s,9H); 0.83(s,9H).

EXAMPLE 368

3-Deoxy-2,5-bis-O-[(1,1-dimethylethyl) dimethylsilyl]-D-threo-pentonic Acid gamma-Lactone To 0.535 g of product from Example 367 in 5 ml of ethyl alcohol is added 0.50 g of 10% palladium on carbon. The mixture is hydrogenated in a Parr apparatus at 34 psi of hydrogen. The reaction mixture is filtered, rinsed with ethyl acetate and concentrated in vacuo to give 0.417 g of the desired product.

$^1$H NMR(CDCl$_3$): δ 4.51(m,1H); 4.3(m,1H); 3.93–3.65 (m,2H); 2.49(m,1H); 2.1(m,1H); 0.93(s,9H); 0.84(s,9H).

EXAMPLE 369

3-Deoxy-2,5-bis-O-[) 1,1-dimethylethyl) dimethylsilyl]-1-thio-D-threo-pentonic Acid gamma-Lactone To 0.416 g of product from Example 368 in 7.4 ml of toluene is added 0.562 g of Lawesson's reagent. The reaction is heated at reflux temperature for 3.5 hours, while monotoring by tlc. An additional 0.20 g of Lawesson's reagent is added and the reaction is refluxed and additional 1½ hours. The solution is cooled overnight, concentrated in vacuo, and purified by chromaotgraphy (Silica gel: 10% ethyl acetate/hexane) to give 0.184 g of the desired product.

$^1$H NMR(CDCl$_3$): δ 4.73(m,1H); 4.57(dd,1H); 3.86(m, 2H); 2.52(m,1H); 2.1(m,1H); 0.93(s,9H); 0.90(s,9H).

EXAMPLE 370

3-Deoxy-2,5-bis-O-[(1,1-dimethylethyl) dimethylsilyl]-1-thio-alpha (and beta)-D-threo-pentofuranose To a −78° C. solution, under argon, of 0.39 g of product from Example 369 in 5.17 ml of dry tetrahydrofuran is added, dropwise, 2.07 ml of Super Hydride. After 30 minutes, an additional 1 ml of Super Hydride is added. The reaction is stirred for 30 minutes, quenched with 3.5 ml of 1N hydrochloric acid, and diluted with ethyl acetate and water. The layers are separated, the organic layer is washed with water and saturated sodium chloride, dried and concentrated in vacuo to give 0.377 g of the desired product.

$^1$H NMR(CDCl$_3$): δ 5.27(m,1H); 4.34(m,1H); 4.05(m, 1H); 3.83(dd,1H); 3.65(dd,1H); 2.25(d,1H); 2.2(m,1H); 1.93(m,1H); 0.93(s,9H); 0.89(s,9H).

EXAMPLE 371

[2S-[2alpha(S*),3beta(S*)]]-1-[-[-[(1,1-Dimethylethyldimethylsilyl]-3-[1-[[1,1-dimethylethyl)dimethylsilyl]oxy]ethyl-4-oxo-2-azetidinyl]ethyl]-3-[(4-(nitrophenyl)methoxy]-2,3-dioxopropyl 3-deoxy-2,5-bis-O-[(1,1-dimethylethyl) dimethylsilyl]-1-thio-alpha (and beta)-D-threo-pentofuranoside To an ice cold solution, under argon, of 0.377 g of product from Example 370 in 3.3 ml of dry tetrahydrofuran is added 0.558 g of product from Example 103 in 4.7 ml of dry tetrahydrofuran. To this mixture is added, dropwise, 0.139 ml of triethylamine and the reaction is stirred cold for 30 minutes. The cold bath is removed and the reaction is allowed to reach room temperature. The reaction is diluted with ethyl acetate, washed with saturated sodium bicarbonate and saturated sodium chloride, dried and concentrated in vacuo. The residue is purified by chromatography (Silica gel: 20% ethyl acetate/hexane) to give 0.450 g of a major isome[(A) and 0.118 g of a minor isomer (B).

Major Isomer (A) $^1$H NMR(CDCl$_3$): δ 8.25(d,2H); 7.59(d, 2H); 5.38(s,2H); 5.03(s,1H); 4.3(m,1H); 4.2–3.96(m,3H); 3.79–3.59(m,3H); 3.03(m,1H); 2.67(m,1H); 2.26(m,2H); 1.21(d,3H); 1.06(d,3H).

Minor Isomer (B)
$^1$H NMR(CDCL$_3$): δ 8.24(d,2H); 7.6(d,2H); 5.36(ABq, 2H); 5.03(d,1H); 4.4(d,1H); 4.37(m,1H); 4.14(m,2H); 3.93 (m,1H); 3.56(dd,1H); 3.54(dd,1H); 2.78(m,1H); 2.45(m, 1H); 2.15(m,1H); 1.9(m,1H); 1.21(d,3H); 1.06(d,3H).

EXAMPLE 372

[2S-[2alpha,(S*),3beta(S*)]]-1-[1-[3-(1-Hydroxyethyl)-4-oxo-2-azetidinyl]ethyl-3-[(4-nitrophenyl)methoxy]-2,3-dioxopropyl 3-deoxy-1-thio-alpha (and beta)-threo-pentofuranoside The title compound is prepared by the procedure of Example 356 using 0.450 g of the major isomer (A) from Example 371, 1.3 ml of tetrahydrofuran and 1.3 ml of triethylammonium trihydrogenfluoride to give 0.186 g of the desired product. The product is used immediately in following Example.

EXAMPLE 373

[4R-[4alpha,5beta,6beta(R*)]]-6-(1-Hydroxyethyl)-4-methyl-2-[[(4-nitrophenyl)methoxy|carbonyl[-7-oxo-1-azabicyclo[3.2.0]hept-2-en-3-yl 3-deoxy-1-thio-alpha (and beta)-threo-pentofuranoside The title compound is prepared by the procedure of Example 357 using 0.186 g of product from Example 372. 2.3 ml of dry tetrahydrofuran, 1.45 ml of 1M titanium tetrachloride solution (methylene chloride) to give, after chromatography, 0.90 g of the desired product.

$^1$H NMR(CDCL$_3$): δ 8.23(d,2H); 7.65(d,2H); 5.57(s,1H); 5.5(d,1H); 5.24(d,1H); 4.53(br d,1H); 4.35(d,1H); 4.26(m, 2H) 3.94(br d,1H); 3.65(br d,1H); 3.3(m,1H); 2.55(m,1H); 2.17–1.52(m,4H); 1.37(d,3H); 1.3(d,3H).

EXAMPLE 374

{4R-[4alpha,5beta,6beta(R*)]]-2-Carboxy-6-(1-hydroxyethyl)-4-methyl-7-oxo-1-azabicylo[3.2.0] hept-2-en-3-yl 3-deoxy-1-thio-alpha (and beta)-threo-pentofuranoside Potassium Salt The title compound is prepared by the procedure of Example 358 using 0.90 g product from Example 373, 1.4 ml of dioxane, 1.4 ml of water containing 0.0182 g of of potassium bicarbonate, and 0.90 g of 10% palladium on carbon at 36 psi of hydrogen to give 0.053 g of the desired product.

$^1$H NMR(D$_2$O): δ 5.53(s,1H); 4.38–3.44(m,8H); 2.56(m, 1H); 1.75(m,1H); 1.35(d,3H); 1.28(d,3H).

EXAMPLE 375

[4S-[3(2S* or 2R*,5R*),4alpha,5beta,6beta(R*)]]-6-(1-Hydroxyethyl)-4-methyl-7-oxo-3-[[tetrahydro-5-hydroxymethyl)-2-thienyl]thio]-1-azabicyclo[3.2.0] hept-2-ene-2-carboxylic Acid (4-Nitrophenyl)methyl Ester A solution containing 0.396 g of [4R[4alpha, 5beta,6beta (R*)]]-6-(1-hydroxyethyl)-3-mercapto-4-methyl-7-oxo-1-azabicyclo[3.2.0]hept-2-ene-2-carboxylic acid (4-nitrophenyl)methyl ester monosilver(+1)salt (prepared by the procedure of European Patent Appl.

EP0481511A2), 0.41 g of 1-O-acetyl-5-O(tert-butyldiphanylsilyl)-2,3-dideoxy-4-thioribofuranose (prepared by the procedure of J. A. Secrist et al., J. Med.

Chem., 1992, 32, 533), and 16 ml of acetonitrile is stirred at 0° C. under argon. To this is added, dropwise, 0.98 mmol of a 1M solution in hexane of diethylaluminum chloride.

After ½ hour the reaction is poured into saturated sodium bicarbonate and methylene chloride. The aqueous portion is washed with additional methylene chloride. The organic layers are combined, dried and concentrated in vacuo. The residue is purified by chromatography (Silica gel: 40–60% ethyl acetate/hexane gradient) to give 0.98 g of product as a mixture of 2 isomers.

The above 0.98 g of product is dissolved in 4 ml of tetrahydrofuran and 0.15 ml of acetic acid. To this is added 1.6 mmol of tetrabutylammonium fluoride as a 1M tetrahydrofuran solution. The resulting solution is stirred for 6 hours at 20° C. Water and ethyl acetate are added and the reaction is given an aqueous workup. Purification by chromatography gives 0.033 g of a major isomer and 0.008 g of a minor isomer.

Major Isomer $^1$H NMR(CDCl$_3$): δ 8.2(d,2H,Ar); 7.65(d,2H,Ar); 5.38 (dd,2H,CH$_2$Ar); 4.82(t,1H,CHS$_2$); 4.3(m,2H,CH$_2$O); 3.75 (m,H$_5$); 3.6(m,2H); 3.45(m,1H); 3.3(dd,1H,H$_6$); 2.4(m,2H, CH$_2$); 2.1(m,2H,CH$_2$); 1.38(d,3H,CH$_3$); 1.28(d,2H,CH$_3$).

Minor Isomer $^1$H NMR(CDCl$_3$): δ 8.2(d,2H,Ar); 7.63(d,2H,Ar); 5.18 (dd,2H,CH$_2$Ar); 4.92(dd,CHS$_2$); 4.3(m,2H,CH$_2$O); 3.7(m, 3H); 3.5.(p,CHO); 3.42(t,1H); 3.28(dd,1H,H$_6$); 2.4(m,1H); 2.2(m,3H); 1.38(d,3H,CH$_3$); 1.24(d,3H,CH$_3$).

EXAMPLE 376

[4S-[3(2R* or 2S*,5R*), 4alpha,5beta,6beta(R*)]]-6-(1-Hydroxyethyl)-4-methyl-7-oxo-3-[[tetrahydro-5-hydroxymethyl)-2-thienyl]thio]-1-azabicyclo [3.2.0]hept-2-ene-2-carboxylic Acid Monopotassium Salt The title compound is prepared by the procedure of Example 18 using 0.014 g of the major isomer from Example 375, 5 ml of 1:1 ethyl acetate:water, 0.0033 g of potassium bicarbonate and 0.015 g of 10% palladium on carbon to give, after purification, 0.008 g of the desired compound.

$^1$H NMR(D$_2$O): δ 4.95(dd,1H,CHS$_2$); 4.2(dd,2H,CH$_2$OH); 3.8–3.2(m,3H,CHOH,H$_5$ and CHS);3.4(m,2H,H$_6$ and allylic CH); 2.38(m,1H); 2.18(m,2H); 2.0(m,1H); 1.25 (d,3H,CH$_3$); 1.18(d,3H,CH$_3$)

EXAMPLE 377

[4S-[3(2R* or 2S*,5R*),4alpha,5beta,6beta(R*)]]-6-(1-Hydroxyethyl)-4-methyl-7-oxo-3-[[tetrahydro-5-hydroxymethyl)-2-thienyl]thio]-1-azabicyclo[3.2.0] hept-2-ene-2-carboxylic Acid Monosodium Salt The title compound is prepared by the procedure of Example 18 using 0.043 g of the minor isomer from Example 375, 6 ml of 1:1 ethyl acetate:water, 0.008 g of sodium bicarbonate and 0.043 g of 10% palladium on carbon to give, after purification, 0.025 g of the desired product.

$^1$H NMR(D$_2$O): δ 4.88(t,CHS$_2$); 4.2(m,2H, CH$_2$OH); 3.68(m,H$_5$); 3.6(m,1H,CHOH); 3.42(m,3H,H$_6$,CHS and allylic CH); 2.3(m,2H); 2.1(m,1H); 1.95(m,1H); 1.25(d,3H, CH$_3$); 1.2(d,3H,CH$_3$).

EXAMPLE 378

1-S-Acetyl-5-O-(tert-butyldiphenylsilyl)-2,3-dideoxy-4-thioribofuranose

Two grams of 5-O-(tert-butyldiphenylsilyl)-2,3-dideoxy-4-thioribofuranose (prepared according to J. A. Secrist et al.,
J. Med. Chem., 1992,35,533) is stirred with 0.456 g of thioacetic acid in 25 ml of methylene chloride and 0.0.025 g of toluenesulfonic acid for 68 hours. On workup the reaction is adsorbed onto magnesium silicate and then flash chromatographed on silica gel to give 1.5 g of the desired product.

$^1$H NMR(CDCl$_3$): δ 7.65(m,4H,Ar); 7.4(m,6H,Ar); 5.0(t, 1H,CHS$_2$); 3.63(m,3H,CH$_2$OH,CHS); 2.3(d,3H,CH$_3$); 2.4–2.2(m,4H,2CH$_2$); 1.03(s,9H,3CH$_3$).

EXAMPLE 379

Ethanethioic Acid S-[5-[[(Aminocarbonyl)oxy]methyl]tetrahydro-2-thienyl]Ester

A solution containing 0.817 g of product from Example 378, 15 ml of tetrahydrofuran, 1 ml of acetic acid and 8.5 mmol of n-tetrabutylammonium fluoride 1M solution is stirred for 2 hours. The reaction progress is monitored by tlc. Following an aqueous workup (ethyl acetate, 0.5M potassium phosphate, saturated sodium chloride) and silica gel chromatography 0.252 g of the desired alcohol is isolated.

$^1$H NMR(CDCl$_3$): δ 5.2(t,1H,CHS$_2$); 3.7(m,3H,CH$_2$O and CHS); 2.4(s,3H,CH$_3$); 2.5–1.8(m,4H,2CH$_2$).

The alcohol, 0.247 g, prepared above, 0.67 g of trichloroacetyl isocyanate and 17 ml of methylene chloride are reacted at –20° C. as described in Example 7. The intermediate thus formed is hydrolyzed with 650 microliters of acetic acid, 5.5 mmol of 1M n-tetrabutylammonium fluoride and 1 ml of water as also described in Example 7 to yield, after workup and purification, 0.276 g of the desired product.

Anal. Calcd for C$_8$H$_3$NO$_3$S$_2$: C=40.83; H=5.57; N=5.95 Found: C=40.88; H=5.33; N=5.72.

EXAMPLE 380

[4R-[4alpha,5beta,6beta(R*)]]-3-[[5-[[(Aminocarbonyl)oxy]methyl]tetrahydro-2-thienyl]-thio]-6-(1-hydroxyethyl)-4-methyl-7-oxo-1-azabicyclo[3.2.0]hept-2-ene-2-carboxylic Acid (4-Nitrophenyl)methyl Ester (A)

and

[4R-[4alpha,5beta,6beta(R*)]]-3-[[5-[[(Aminocarbonyl)oxy]methyl]tetrahydro-2-thienyl] thio]-6-(1-hydroxyethyl)-4-methyl-7-oxo-1-azabicyclo[3.2.0]hept-2-ene-2-carboxylic Acid (4-Nitrophenyl)methyl Ester (B)

The product, 0.256 g, from Example 379 and 1.2 mmol of sodium methoxide (as a 4.4M solution in methyl alcohol) is hydrolyzed in 8 ml of tetrahydrofuran as described in Example 16. The thiol product obtained in this reaction is immediately reacted with 0.476 g of product from Example 15, 0.155 g of diisopropylethyl amine, in 7 ml of acetonitrile at 0° C. under argon for a total of 18 hours as described in Example 17. The standard workup and purification yields two diastereomeric products. The least polar product carbapenem (A), 0.156 g, has a tlc R$_f$=0.36 and the more polar product carbapenem (B), 0.142 g, has a tlc R$_f$=0.28.

EXAMPLE 381

[4R-[3(5R*),4alpha,5beta,6beta(R*)]]3-[[5-[[(Aminocarbonyl)oxy]methyl]tetrahydro-2-thienyl] thio-6-(1-hydroxyethyl)-4-methyl-7-oxo-1-azabicyclo[3.2.0]hept-2-ene-2-carboxylic Acid Monopotassium Salt The title compound is prepared by the procedure of Example 18 using 0.116 g of product (A) from Example 380, 20 ml of 1:1 dioxane:water, 0.030 g of potassium bicarbonate and 0.045 g of 10% palladium on carbon to give, after chromatography, 0.026 g of the desired product.

$^1$H NMR(CDCl$_3$): δ 5.0(t,1H,CHS$_2$); 4.2(m,3H,CH$_2$OCO and CHS); 4.0(m,1H,CHOH); 3.8(m,1H,H$_5$); 3.4(m,2H,H$_6$ and allylic CH); 2.5–1.8(m,4H2CH$_2$); 1.22(d,3H,CH$_3$); 1.18 (d,3H,CH$_3$).

EXAMPLE 382

[4R-[4alpha,5beta,6beta(R*)]]-3-[[5-[[(Aminocarbonyl)oxy[methyl]tetrahydro-2-thienyl]thio]-6-(1-hydroxyethyl)-4-methyl-7-oxo-1-azabicyclo[3.2.0]hept-2-ene-2-carboxylic Acid Monopotassium Salt The title compound is prepared by the procedure of Example 18 using 0.137 g of product (B) from Example 380, 15 ml of ethyl acetate, 9 ml of water, 0.029 g of potassium bicarbonate and 0.085 g of 10% palladium on carbon to give, after chromatography, 0.031 g of the desired product.

IR(KBr): 4371, 33,97, 2963, 1713, 1613 cm$^{-1}$.

EXAMPLE 383

Ethanethioic Acid S-(Tetrahydro-5-(hydroxymethyl)-2-thienyl) Ester

A solution containing 2.19 g of product from Example 378, 20 ml of tetrahydrofuran, 5.3 g of acetic acid and 25 mmol of 1M solution of n-tetrabutylammonium fluoride is stirred for 18 hours or until all starting material is consumed by tlc. The reaction is diluted with ethyl acetate, washed with aqueous 0.5M potassium dihydrogen phosphate and saturated sodium chloride, dried and concentrated in vacuo. The residue is purified by chromatography to give 0.876 g of the desired product.

$^1$H NMR(CDCl$_3$): δ 5.08(t,1H,CHS$_2$); 3.8–3.5(m,3H, CH$_2$O and CHS); 2.3(s,3H,CH$_3$); 2.5–2.8(m,4H,2CH$_2$).

EXAMPLE 384

(5R)-Ethanethioic Acid S-[5-[(Ethoxymethoxy)methyl]tetrahydro-2-thienyl]Ester

To a 0° C. mixture of 0.165 g of product from Example 383 in 4 ml of tetrahydrofuran and 0.222 g of diisopropylethyl amine is added 0.122 g of chloromethylethyl ether. The reaction is stirred for 45 minutes at 0° C. and then 23 hours at 20° C. The mixture is given an aqueous workup (ethyl acetate, 0.5M potassium dihydrogen phosphate, saturated sodium chloride) and the purified by chromatography to give 0.100 g of the desired product.

$^1$H NMR(CDCl$_3$): δ 5.08(t,1H,CHS$_2$); 4.7(d,2H,CH$_2$O$_2$); 3.8–3.4(m,5H,2CH$_2$O, CHS); 2.3(s,3H,CH$_3$); 2.5–1.75(m, 4H,2CH$_2$); 1.2(t,3H,CH$_3$).

EXAMPLE 385

[4R-[3(5R*),4alpha,5beta,6beta(R*)]]-3-[[5-(Ethoxymethoxy)methyl]tetrahydro-2-thienyl]thio]-6-(1-hydroxyethyl)-4-methyl-7-oxo-1-azabicyclo[3.2.0]hept-2-ene-2-carboxylic acid (4-Nitrophenyl) methyl Ester The product, 0.096 g, of Example 384 is dissolved in 4 ml of tetrahydrofuran and is hydrolyzed and worked up in a similar fashion to that described in Example 16 using 0.35 mmol of a 4.4M sodium methoxide solution to give the crude thiolproduct. The thiol product is reacted directly with 0.185 g of product from Example 15, 0.074 g of diisopropylethyl amine and 3 ml of acetonitrile as described in Example 17. The product of this reaction is a mixture of two diastereomers. The more polar of the two, 0.070 g, is isolated and characterized.

$^1$H NMR(CDCl$_3$): δ 8.22(d,2H,Ar); 7.65(d,2H,Ar); 5.38 (ABq,2H,CH$_2$Ar); 4.85(t,1H,CHS$_2$); 5.18(s,2H,CH$_2$O$_2$); 4.25(m,2H,CH$_2$O); 3.78(m,1H,H$_5$); 3.6(q,2H,CH$_2$O); 3.55–3.4(m,2H,allylic H and CHS); 3.28(dd,1H,H$_6$); 2.4–1.9(m,4H,2CH$_2$); 1.48(d,3H,CH$_3$); 1.3(d,3H,CH$_3$); 1.22 (t,3H,CH$_3$).

EXAMPLE 386

[4R-[3(5R*),4alpha,5beta,6beta(R*)]]-3-[[5-(Ethoxymethoxy)methyl]tetrahydro-2-thienyl]thio]-6-(1-hydroxyethyl)-4-methyl-7-oxo-1-azabicyclo[3.2.0]hept-2-ene-2-carboxylic acid Monopotassium Salt The title compound is prepared by the procedure of Example 18 using 0.065 g of product from Example 385, 10 ml of 1:1 dioxane:water, 0.017 g potassium carbonate, and 0.033 g of 10% palladium on carbon to give, after purification, 0.019 g of the desired product.

$^1$H NMR(D$_2$O): δ 4.85(m,1H,CHS$_2$); 4.7(s,2H,CH$_2$O$_2$); 4.2(m,2H); 3.8(m,2H); 3.64(m,4H); 3.45(m,2H,CHS, allylic CH); 3.4(dd,1H,H$_6$); 2.35–1.85(m,4H,2CH$_2$); 1.25(d,3H, CH$_3$); 1.15(t,6H,2CH$_3$).

EXAMPLE 387

(2R)-5-(Acetyloxy)tetrahydro-2-thiophenemethanol

To a mixture of 0.54 g of 1-O-acetyl-5-O-(tert-butyldiphenylsilyl)-2,3-dideoxy-4thioribofuranose (prepared by the procedure of J. A. Secrist et al., J. Med. Chem.,1992, 35, 533) in 8 ml of tetrahydrofuran and 0.6 g of acetic acid is added 4 mmol of 1M n-tetrabutylamnonium fluoride solution. The reaction is stirred for 5 hours and then another portion of 0.10 g of acetic acid and 1 mmol of n-tetrabutylammonium fluoride is added and the reaction is stirred for 1 hour. Cold potassium dihydrogen phosphate and ethyl acetate are added to the reaction mixture, followed by an aqueous workup. Purification by chromatography gives 0.164 g of the desired product.

$^1$H NMR(D$_2$O): δ 6.15(t,1H,CHS(OAc)); 3.68(m,2H, CH$_2$O); 3.58(dd,1H,CHS); 2.2(m,5H,2CH$_2$,OH); 2.0(s,3H, CH$_3$).

EXAMPLE 388

(5R)-5-Azidomethyl tetrahydro-2-thiopheneol Acetate (ester)

To a 0° C. solution of 5 ml of methylene chloride and 0.439 g of product from Example 387 is added 0.303 g of triethylamine followed by 0.341 g of methanesulfonyl chloride. The reaction is warmed to 20° C. with stirring for 2 hours. The reaction is concentrated in vacuo and the residue is purified by chromatography to give 0.150 g of material which is dissolved in 1 ml of dimethylformamide. To this solution is added 0.338 g of n-tetrabutylammonium azide and the reaction solution is stirred at 20° C. for 4 hours. The azido product is isolated following an aqueous workup and purification by chromatography to give 0.082 g of pure azide.

$^1$H NMR(D$_2$O): δ 6.18(t,1H,CH(OAC)S); 3.7–3.2(m,3H, CH$_2$N$_3$, CHS); 2.4–2.07(m,4H,2CH$_2$); 2.05(s,3H,CH$_3$).

EXAMPLE 389

[4R-[3(5R*),4alpha,5beta,6beta(R*)]]-3-[[5-Azidomethyl)tetrahydro-2-thienyl]thio]-6-(1-hydroxyethyl)-4-methyl-7-oxo-1-azabicyclo[3.2.0]hept-2-ene-2-carboxylic acid (4-Nitrophenyl)methyl Ester To a solution, under argon, of 0.080 g of product from Example 388, 4 ml of acetonitrile and [4R[4alpha,5beta,6beta(R*)]]-6-(1-hydroxyethyl)-3-mercapto-4-methyl-7-oxo-1-azabicyclo[3.2.0]hept-2-ene-2-carboxylic acid (4-nitrophenyl)methyl ester mono silver(+)salt (prepared by the procedure of European Patent Appl. EP0481511A2) is added 0.6 mmol of 1M diethylaluminum chloride. The reaction is stirred for an hour followed by aqueous workup and chromatography to give 0.016 g of the desired product.

$^1$H NMR(CDCl$_3$): δ 8.2(d,2H,Ar); 7.65(d,2H,Ar); 5.35(q, 2H,CH$_2$Ar);4.9(t,1H,CHS$_2$); 4.28(m,1H,CHO); 4.23(d,H$_5$); 3.73(t,1H,allylic H); 3.35(d,2H,CH$_2$N$_3$); 3.3(dd,H$_6$); 2.38 (m,2H,CH$_2$); 2.25(m,1H); 1.95(d,3H,CH$_3$); 1.3(d,3H,CH$_3$).

EXAMPLE 390

[4R-[4alpha,5beta,6beta(R*)]]-3-[[5-(Aminomethyl) tetrahydro-2-thienyl]thio]-6-(1-hydroxyethyl)-4-methyl-7-oxo-1-azabicyclo[3.2.0]-hept-2-ene-2-carboxylic Acid The title compound is prepared by the procedure of Example 192 using 0.010 g of Example 389, 3 ml of dioxane and 0.1M pH 7.0 sodium dihydrogen phosphate buffer and 0.010 g of 10% palladium on carbon to give, after chromatography, 0.006 g of the desired product.

$^1$H NMR(D$_2$O): δ 4.9(m,CHS$_2$); 3.9(m,2H,CH$_2$N); 3.55 (m,1H,CHOH); 3.45(m,1H,H$_5$); 3.4-3.15(m,3H,H$_6$CHS, allylic H); 2.9-2.7(m,2H); 2.2(m,1H); 1.7(m,1H); 1.22(d, 3H,CH$_3$); 1.18(d,3H,CH$_3$).

EXAMPLE 391

[3-S-[4R-[4alpha,5beta,6beta(R*)]]]-1-[(N-L-Alanyl-L-alanyl)amino]-2,5-anhydro-3-S-[2-carboxy-6-(1-hydroxyethyl)-4-methyl-7-oxo-1-azabicycle-[3.2.0]hept-2-en-3-yl]-1,4-dideoxy-3-thio-D-threo-pentitol The title compound is prepared by the procedure of Example 257 using 0.494 g of product from Example 261, 0.437 g of product from Example 259, 6 ml of 0.1M pH 7.0 sodium dihydrogen phosphate buffer, 12 ml of dioxane and 0.13 g of 10% palladium on carbon to give, after chromatography (C$_{18}$-Reverse Phase Plates: 5% ethyl alcohol/water), 0.12 g of the desired product.

$^1$H NMR(D$_2$O): δ 4.25(m,4H); 4.05(m,2H); 3.9(m,2H); 3.6-3.4(m,4H); 2.5-2.4(m,1H); 2.1-2.0(m,1H); 1.50(d,3H, Me, J=7 Hz); 1.38(d,3H,Me, J=7.1 Hz); 1.27(d,3H,Me, J=6.3 Hz); 1.19(d,3H,Me, J=7.1 Hz).

EXAMPLE 392

1,4-Dioxa-8-thiaspiro[4.5]decane

A mixture of 5.0 g of tetrahydrothiopyran-4-one, 2.5 ml of ethylene glycol, 0.230 g of p-toluenesulfonic acid and 125 ml of benzene is stirred at reflux temperature for 2.5 hours. The water formed is removed using a Dean-Stark trap. The reaction is treated with saturated sodium bicarbonate, water, saturated sodium chloride, dried and concentrated in vacuo to give 6.52 g of the desired product as an oil.

EXAMPLE 393

1,4-Dioxa-8-thiaspiro[4.5]decane 8-oxide

A room temperature mixture of 13.8 g of product from Example 392 dissolved in 100 ml of acetic acid is treated, dropwise over 20 minutes, with 9.0 ml of 30% hydrogen peroxide. The reaction mixture is stirred at room temperature for 1 hour, concentrated in vacuo at 50° C., and extracted with ethyl acetate. The organic layer is washed 2× with saturated sodium bicarbonate, water and saturated sodium chloride, dried and concentrated in vacuo. The aqueous washes are combined and concentrated in vacuo to about 25 ml. The residue is saturated with solid potassium carbonate and extracted 2× with 200 ml of ethyl acetate. The organic phase is concentrated in vacuo to a solid which is triturated with hexane and collected to give 13.1 g of the desired product.

EXAMPLE 394

1,4-Dioxa-8-thiaspiro[4.5]decan-7-ol

A mixture of 0.88 g of product from Example 393, 5.0 ml of acetic anhydride and 2.0 ml of lutidine is heated at 110°-115° C. for 2.5 hours, followed by increasing the temperature to 150° C. and then heated for 3 hours. The reaction mixture is diluted with ethyl acetate, washed 2× with 1N hydrochloric acid, water, saturated sodium chloride, dried and concentrated in vacuo. The residue is dissolved in methylene chloride, filtered through a pad of hydrous magnesium silicate and reconcentrated in vacuo to give 0.569 g of the desired product.

EXAMPLE 395

Ethanethioic Acid S-(1,4-Dioxa-8-thiaspiro[4.5] decan-7-yl) Ester

A mixture of 0.545 g of product from Example 394, 0.23 ml of thioacetic acid, 0.16 g of p-toluenesulfonic acid and 8 ml of carbon tetrachloride is stirred at room temperature for 1 hour. After work up concentration in vacuo gives 0.556 g of the desired product.

EXAMPLE 396

1,4-Dioxa-8-thiaspiro[4.5]decane-7-thiol

A mixture of 0.56 g of product from Example 395, 0.60 ml of 4.37M sodium methoxide and 10 ml of tetrahydrofuran is stirred in an ice bath for 20 minutes. Ethyl acetate is added followed by 0.5M potassium phosphate monobasic. The organic layer is dried and concentrated in vacuo to give 0.37 g of the desired product as a yellow oil.

EXAMPLE 397

[4R-[4alpha,5beta,6beta(R*)]]-3-1,4-Dioxa-8-thiaspiro[4.5]dec-7-ylthio)6-(1-hydroxyethyl)-4-methyl-7-oxo-1-azabicyclo[3.2.0]hept-2-ene-2-carboxylic Acid (4-Nitrophenyl)methyl Ester The title compound is prepared by the procedure Example 17 using 0.335 g of product from Example 15, 0.121 g of product from Example 396, 0.11 ml of diisopropylethylamine and 5 ml of acetonitrile to give 0.080 g of the desired product after chromatography.

EXAMPLE 398

[4R-[4alpha,5beta,6beta(R*)]]-3-1,4-Dioxa-8-thiaspiro[-4.5]dec-7-oxo)6-(1-hydroxyethyl)-4-methyl-7-oxo-1-azabicyclo[3.2.0]hept-2-ene-2-carboxylic Acid Monosodium Salt The title compound is prepared by the procedure of Example 18 using 0.80 g of product from Example 397, 0.0125 g of sodium bicarbonate, 0.080 g of 10% palladium on carbon, 4 ml of ethyl acetate and 2 ml of water to give 0.032 g of the desired product after chromatography.

EXAMPLE 399

[3-[4R-[4alpha,5beta,6beta,(R*)]]]-2,6-Anhydro-4,5-dideoxy-3-S-6-(hydroxyethyl)-4-methyl-2-[[(4-nitrophenyl)methoxy]carbonyl]-7-oxo-1-azabicyclo[3.2.0]hept-2-en-3-yl]-1-O-(methoxymethyl)-3-thio-D-threo-hexitol The title compound is prepared by the procedure of Example 17 using 0.375 g of (2R,3R)-2-methoxymethoxymethyl tetrahydropyran-3-thiol (prepared according to the procedure of Miyazaki, H. et al. in *Chem. Pharm. Bull.*, Vol 37, pp 2391–2397(1989)) in 5 ml of acetonitrile, 0.954 g of product from Example 15 in 10 ml of acetonitrile and 0.3 ml of diisopropylethyl amine to give, after chromatography (Silica gel), the desired compound.

EXAMPLE 400

[3-[4R-[4alpha,5beta,6beta(R*)]]]-2,6-Anhydro-3-S-[2-carboxy-6-(1-hydroxyethyl)-4-methyl-7-oxo-1-azabicyclo[3.2.0]hept-2-en-3-yl]-4,5-dideoxy-1O-(methoxymethyl)-3-thio-D-threo-hexitol Monosodium Salt The title compound is prepared by the procedure of Example 192 using 0.243 g of product from Example 399, 0.084 g of 10% palladium on carbon, 5 ml of 0.1M pH 7.0 sodium dihydrogen phosphate buffer and 7 ml of dioxane to give, after chromatography (Reverse Phase Plates: 5% aqueous ethyl alcohol), to give the desired product.

EXAMPLE 401

2,4-Anhydro-D-lyxonic Acid Methyl Ester

A slurry of 1.01 g of 2,4-anhydro-3,5-bis-O-(phenylmethyl)-D-lyxonic acid methyl ester (prepared by the procedure in Tetrahedron Letters, Vol 31, No. 33, p4787, 1990), 0.253 g of palladium hydroxide on carbon, and 30 ml of methyl alcohol is hydrogenated under a balloon of hydrogen (1 atm.) for 2.5 hours. The mixture is filtered through diatomaceous earth, washed with ethyl acetate and ethyl alcohol, and concentrated in vacuo to give 0.460 g of the desired product.

$^1$H NMR(CDCl$_3$): δ 5.07(d,1H, J=4.9 Hz); 4.85(m,2H); 4.28(br d,1H); 4.10(m,2H); 3.83(s,3H,OMe); 2.65(br s, 1H).
IR(neat): 3400, 2957, 1739, 1441, 1226, 1020 cm$^{-1}$.
MS(CI):m/z 163(M$^+$+H).

EXAMPLE 402

2,4-Anhydro-D-lyxonic acid Methyl Ester 5-(4-Methylbenzenesulfonate)

To a 0° C. solution, under argon, of 0.435 g of product from Example 401 in 9 ml of pyridine is added 0.614 g of p-toluenesulfonyl chloride and the reaction is stirred overnight. The reaction mixture is diluted with 50 ml of 10% hydrochloric acid and extracted with diethyl ether and ethyl acetate. The organic layers are combined, dried and purified by chromatography to give 0.517 g of the desired product.

$^1$H NMR(CDCl$_3$): δ 7.81(d,2H,J=8.3 Hz); 7.36(d,2H,J=8.3 Hz); 4.93(m,3H); 4.54(dd,1H,J=11.3 and 4.9 Hz); 4.30 (dd,1H,J=dd,1H,J=11.3 and 3.75 Hz); 3.81(s,3H,OMe); 2.92 (d,1H,J=6.0 Hz); 2.46(s,3H,SO$_2$ArMe).

IR(KBr): 3361, 2936, 1749, 1355, 1174 cm$^{-1}$.
MS(CI):m/z 317(M$^+$+H).

EXAMPLE 403

2,4-Anhydro-3-thio-D-arabinonic Acid Methyl Ester 3-Acetate 5-(4-Methylbenzenesulfonate)

A 0° C. solution, under argon, of 0.111 g of product from Example 402 in 3 ml of dry methylene chloride is treated, sequentially, with 0.03 ml of pyridine and 0.07 ml of triflic anhydride. After the addition, the reaction is stirred for 30–45 minutes, until consumption of the starting material. The mixture is diluted with diethyl ether, filtered to remove salts, and the filtrate is concentrated in vacuo.

The residue, under argon at room temperature, is dissolved in 1.0 ml of dry acetonitrile, treated with 2 equivalents of potassium thioacetate and stirred for 2 hours. The mixture is diluted with water, extracted with ethyl acetate, dried, concentrated and purified by chromatography to give 0.092 g of the desired product.

$^1$H NMR(CDCl$_3$): δ 7.83(d,2H,J=8.3 Hz); 7.35(d,2H,J=8.3 Hz); 5.17(d,1H,J=8.17 Hz); 4.90(m,2H); 4.27(m,2H); 3.80(s,3H,Ome); 2.45(s,3H,SO$_2$ArMe); 2.31(s,3H,SAc).
IR(neat): 2851, 1755, 1703, 1598, 1438, 1362, 1129 cm$^{-1}$.
MS(CI):m/z 375(M$^+$+H).

EXAMPLE 404

2,4-Anhydro-3-thio-D-arabinonic Acid Methyl Ester 5-(4-Methylbenzenesulfonate)

To a 0° C. solution, under argon, of 0.618 g of product from Example 403 in 4 ml of dry tetrahydrofuran is added, dropwise, 0.45 ml of 4.37M sodium methoxide. The reaction is stirred at 0° C. for 45 minutes, quenched with 1–2 ml of 10% hydrochloric acid and the mixture is concentrated in vacuo. The residue is purified by chromatography (Silica gel: 5–50% ethyl acetate/hexane) to give 0.285 g of the desired product as a colorless oil.

$^1$H NMR(CDCl$_3$): δ 7.82(d,2H,J=8.3 Hz); 7.36(d,2H,J=8.3 Hz); 5.13(d,1H,J=8.6); 4.78(m,1H); 4.21(d,2H,J=2.4 Hz); 3.85(s,3H,OMe); 2.45(s,3H,ArCH$_3$); 1.97(d,1H,J=9 Hz,SH).
IR(neat): 2850, 2566, 1751, 1598, 1438, 1361, 1178 cm$^{-1}$.
MS(CI):m/z 161(M$^+$+H−oTs).

EXAMPLE 405

[3-[4R-[4alpha,5beta,6beta(R*)]]]-2,4-Anhydro-3-S-[6-(1-hydroxyethyl)-4-methyl-2-[[(4-nitrophenyl)methoxy]carbonyl]-7-oxo-1-azabicyclo-[3.2.0]hept-2-en-3-yl]-3-thio-D-arabinonic Acid Methyl Ester 5-(4-Methylbenzenesulfonate)

To a 0° C. solution, under argon, of 0.273 g of product from Example 404, 0.439 g of product from Example 15, in 3.8 ml of acetonitrile is added, dropwise, 0.13 ml of Hunig's base. After addition the reaction is warmed to room temperature for 2 hours. The mixture is concentrated in vacuo and purified by chromatography (Silica gel: 10–100% ethyl acetate/hexane) to give 0.49 g of the desired product.

$^1$H NMR(CDCl$_3$): δ 8.23(d,2H,J=8.7 Hz); 7.8(d,2H,J=8.3 Hz); 7.65(d,2H,J 8.7 Hz); 7.37(d,2H,J=8.3 Hz); 5.49(d,1H, J=13.8 Hz); 5.24(d,1H,J=13.8 Hz); 5.20(d,1H,J=8.5 Hz); 4.96(m,1H); 4.79(dd,1H); 4.35–4.10(m,4H); 3.83(s,3H, CO$_2$Me); 3.5(m,1H); 3.31(dd,2H); 2.46(S,4,3H,ArOMe); 1.37(d,3H,J=6.3 Hz); 1.22(d,3H,J=7.4 Hz).

IR(KBr): 3527, 3112, 2877, 1772, 1522, 1347, 1212, 1177, 1140 cm⁻¹.
MS(FAB):m/z 677(M⁺+H).

EXAMPLE 406

[3-[4R-[4alpha,5beta,6beta(R*)]]]-2,4-Anhydro-3-S-[2-carboxy-6-(1-hydroxyethyl)-4-methyl-7-oxo-1-azabicyclo[3.2.0]hept-2-en-3-yl]-3-thio-D-arabinonic Acid 1-Methyl Ester 5-(4-Methylbenzenesulfonate Monosodium Salt The title compound is prepared by the procedure of Example 192 using 0.150 g of product from Example 405, 0.046 g of 10% palladium on carbon, 0.028 g of sodium bicarbonate, 7.25 ml of dioxane:sodium dihydrogen phosphate buffer, pH 7.0 in a Parr apparatus to give after chromatography 0.011 g of the desired product.

¹H NMR(CDCl₃): δ 7.87(d,2H,J=8.3 Hz); 7.51(d,2H,J 8.3 Hz); 4.5–4.3(m,5H); 3.34(s,3H,CO₂Me); 3.3–3.1(m,4H); 2.48(s,3H,ArMe); 1.13(d,3H); 1.1(d,3H).
IR(KBr): 3538, 3409, 2923, 1745, 1624, 1141, 1119 cm⁻¹.

EXAMPLE 407

[3-[4R-[4alpha,5beta,6beta(R*)]]]-1-[[[1-(Acetyloxy)ethoxy]carbonyl]amino]-2,5-anhydro-1,4-dideoxy-3-S-[2-[[(2,2-dimethyl-1-oxopropoxy)methoxy]carbonyl]-6-(1-hydroxyethyl)-4-methyl-7-oxo-1-azabicyclo[3.2.0]hept-2-en-3-yl]-thio-D-threo-pentitol A 0° C. mixture of 0.557 g of product from Example 319, 0.24 ml of chloromethyl pivalate, 0.189 g of sodium bicarbonate and 0.252 g of sodium iodide is stirred for 5 hours. The reaction is monitored by tlc. The solution is concentrated in vacuo, the residue is slurried with ethyl acetate, filtered, concentrated in vacuo and purified by chromatography (Silica Gel: ethyl acetate) to give 0.249 g of the desired product.

¹H NMR(CDCl₃): δ 6.7(m,1H,CH); 5.82(ABq,2H, OCH₂O); 5.36(m,1H,NH); 4.3–4.1(m,3H); 4.0–3.9(m,1H); 3.78(m,2H); 3.55(m,1H); 3.38(m,1H); 3.21(m,3H); 2.45–2.3(m,1H); 1.99(s,3H,Ac); 2.05–1.9(m,1H); 1.38(d, 3H,Me,J=5.1 Hz); 1.25(d,3H,Me,J=6.1 Hz); 1.19(d,3H,Me, J=7.0 Hz); 1.49(s,9H,3Me,t-Bu).

EXAMPLE 408

[4R-[3(3R*,5R* and 3S*,5S*),4alpha,5beta,6beta (R*)]]-3-[[5-[[(Aminocarbonyl)oxy]methyl]tetrahydro-3-furanyl]thio]-6-(1-hydroxyethy)-4-methyl-7-oxo-1-azabicyclo[3.2.0]hept-2-ene-2-carboxylic acid (2,2-Dimethyl-1-oxopropoxy) methyl Ester The title compound is prepared by the procedure of Example 407 using 0.460 g of product from Example 18, 0.24 ml of chloromethyl pivalate, 0.189 of sodium bicarbonate and 0.252 g of sodium iodide to give after chromatography 0.3 g of the desired product.

EXAMPLE 409

[4R-[3(3R*,5S* and 3S*,5R*),4alpha,5beta,6beta (R*)]]-3-[[5-[[(Aminocarbonyl)oxy]methyl]tetrahydro-3-furanyl]thio]-6-(1-hydroxyethy)-4-methyl-7-oxo-1-azabicyclo[3.2.0]hept-2-ene-2-carboxylic acid (2,2-Dimethyl-1-oxopropoxy) methyl Ester The title compound is prepared by the procedure of Example 407 using 0.460 g of product from Example 21, 0.24 ml of chloromethyl pivalate, 0.189 g of sodium bicarbonate and 0.252 g of sodium iodide to give after chromatograph 0.32 g of the desired product.

We claim:

1. A compound of the formula:

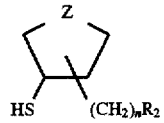

wherein:
Z is oxygen;
n is an integer from 0–4;
R₂ is selected from:
(i) fluorine, chlorine, bromine, iodine, —OCOCH₃, —OCOCF₃, —OSO₂CH₃, —OSO₂Phenyl, and azido;
(ii) a moiety of the formula:

wherein n" is an integer from 0–2; and Rᵃ is
(a) hydrogen or an
(b) organic group bonded via a carbon atom selected from substituted or unsubstituted (C₁–C₄)alkyl, substituted or unsubstituted (C₃–C₆)cycloalkyl, substituted or unsubstituted (C₂–C₄)alkenyl, substituted or unsubstituted (C₂–C₄)alkynyl, substituted or unsubstituted aryl, and substituted or unsubstituted aryl (C₁–C₆)alkyl wherein said substitution is selected from (C₁–C₄)alkyl, hydroxy, (C₁–C₄)alkoxy, phenyl, amino, amidino, guanidino, carboxamido, carbamoyl, and quaternary ammonio associated with a physiologically acceptable anion;
(iii) hydroxy, —ORᵃ, —OC(O)Rᵃ, —OC(O)ORᵃ, —OC(O)NRᵃRᵃ,

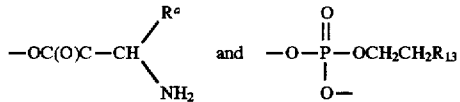

wherein Rᵃ is independently selected and is as hereinabove defined, and
wherein R₁₃ is selected from a moiety of the formula:

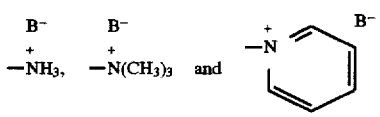

where B⁻ is a physiologically acceptable anion;
(iv) an organic residue bonded via a nitrogen atom, selected from:
(a) NO, NO₂, NO₃, NC, NCO, NHCN and NRʰR^J wherein Rʰ and R^J are independently selected from hydrogen, amino, substituted or unsubstituted amino, substituted or unsubstituted (C₁–C₄) alkyl, (C₃–C₆)cycloalkyl(C₁–C₄)alkyl, aryl, and aralkyl wherein the substituents for the aforementioned substituted alkyl and amino moieties are selected from amino, mono-, di- and tri(C₁–C₄) alkylamino, hydroxyl, oxo, carboxyl, alkoxyl, chloro, fluoro, bromo, nitro, —SO₂NH₂, phenyl, benzyl, acyloxy, alkoxylcarbonyl, alkoxycarbonyloxy, cycloalkoxycarbonyloxy and carboxamido;

(b) hydroxylamino, hydazinyl, iminyl and a hydroxamic acid derivative selected from:

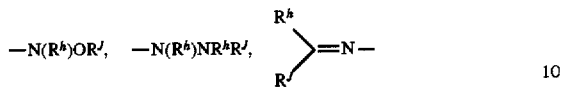

and 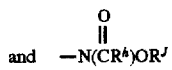

wherein $R^h$ and $R^J$ are as hereinbefore defined;

(c) moieties of the formulae:

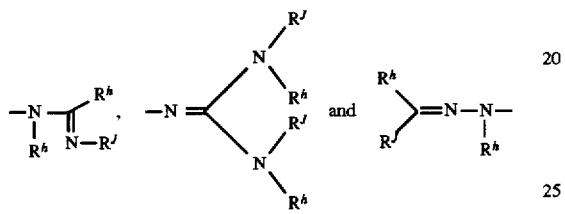

wherein $R^h$ and $R^J$ are as hereinabove defined;

(d) acylamino moieties of the formulae:

wherein $R^h$ and $R^J$ are as hereinabove defined;

(e) moieties of the formulae:

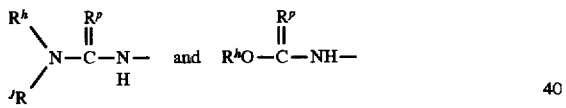

wherein $R^h$ and $R^J$ are as hereinabove defined and $R^p$ is selected from oxygen and sulfur;

(f) moieties of the formula:

wherein $R^k$ is hydrogen, substituted or unsubstituted $(C_1-C_3)$alkyl, $(C_2-C_4)$alkenyl, $(C_2-C_4)$ alkynyl, heterocyclyl and heteroaryl wherein said substituents consist of amino, mono-, di- and tri$(C_1-C_4)$alkylamino, hydroxyl, oxo, carboxyl, alkoxyl, chloro, fluoro, bromo, nitro, —SO₂NH₂, phenyl, benzyl, acyloxy, alkoxylcarbonyl, alkoxycarbonyloxy, cycloalkoxycarbonyloxy and carboxamido; and wherein the heteroatom and heteroatoms are selected from 1–4 oxygen, nitrogen or sulfur atoms and the cyclic portion has 5 or 6 ring atoms;

(g) moieties of the formula:

wherein n' and $R^a$ are as hereinabove defined;

(h) moieties of the formulae:

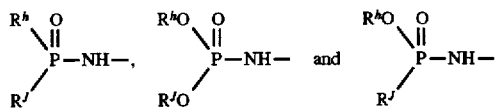

wherein $R^h$ and $R^J$ are as hereinabove defined;

(i) an amino moiety which is an acyl residue of an amino acid or peptide represented by the formula:

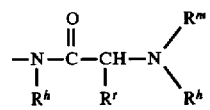

wherein $R^h$ is as hereinabove defined; $R^m$ is hydrogen or an acyl residue of an amino add or peptide said amino acid selected from the group consisting of alanine, glycine, arginine, cysteine, isoleucine, leucine, lysine, methionine, phenylalanine, proline, aminopimelic acid and threonine; and $R^r$ is hydrogen, benzyl, and straight or branched $(C_1-C_6)$alkyl optionally substituted with halo, hydroxy, amino, guanidinyl, carboxy, phenyl, aminocarbonyl, alkylthio, hydroxyphenyl or heterocyclyl as defined hereabove;

(j) an acyclic quaternary ammonio moiety of the formula:

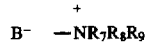

wherein $R_7$, $R_8$ and $R^9$ are the same or different and are selected from hydrogen, a straight or branched $(C_1-C_4)$alkyl, $(C_2-C_4)$alkenyl and substituted $(C_1-C_4)$alkyl, wherein the substitution is selected from hydroxy, $(C_1-C_4)$alkyl, $(C_1-C_4)$ alkoxy, azido, amino, $(C_1-C_4)$alkylamino, di$(C_1-C_4)$alkylamino, guanidino, nitrile, carboxy, formimidoyl and phenyl; alternatively, $R_7$ and $R_8$ taken together are —$(CH_2)_2X(CH_2)_2$—, wherein X is $(CH_2)_w$ oxygen, sulfur, NH, $NR^h$, NOH or $NOR^h$ where W is an integer from 0 to 2, $R^h$ is hereinbefore defined and $B^-$ is a physiologically acceptable anion;

(v) a moiety bonded via a carbon atom selected from the following groups;

(a) a nitrile moiety, an acetylenic group, or a moiety of the formulae:

wherein $R^a$ is as hereinabove defined;

(b) a moiety selected from those of the formulae:

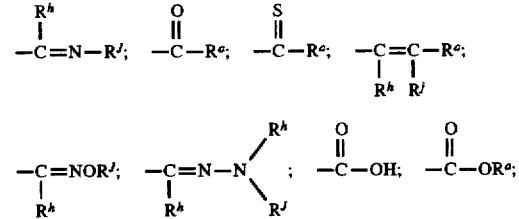

173

-continued

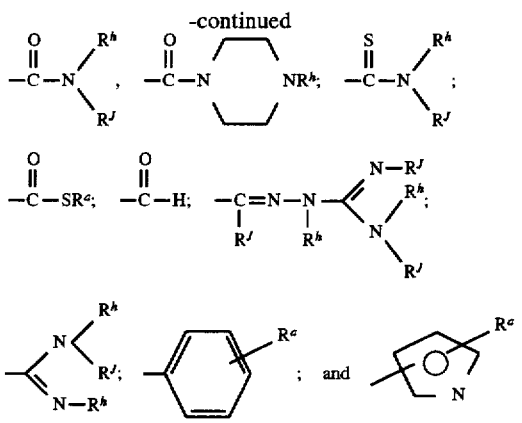

wherein $R^a$, $R^h$ and $R^J$ are as hereinabove defined; and (c) a moiety selected from —$CHF_2$, $CF_3$, —$CF_2CF_3$, —$CH(OCH_3)_2$, and —$CHCl_2$, provided that when $R^2$ is hydroxy, then n cannot be 0.

2. The compound according to claim 1 wherein:

$R_2$ is selected from:
(i) fluorine, chlorine, bromine, iodine, —$OCOCH_3$, —$OCOCF_3$, —$OSO_2CH_3$, —$OSO_2Ph$, azido;
(ii) a moiety of the formula:

wherein n" is an integer from 0–2; and $R^a$ is
(a) hydrogen or an
(b) organic group bonded via a carbon atom selected from substituted or unsubstituted ($C_1$–$C_4$)alkyl, substituted or unsubstituted phenyl; wherein said substitution is selected from ($C_1$–$C_4$)alkyl, hydroxy, ($C_1$–$C_4$)alkoxy, phenyl, amino, amidino, guanidino, carboxamido, carbamoyl, and quaternary ammonio associated with a physiologically acceptable anion;
(iii) hydroxy, —$OR^a$, —$OC(O)NR^aR^a$,

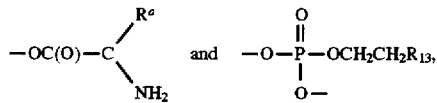

wherein $R^a$ is independently selected and is as hereinabove defined;
wherein $R_{13}$ is selected from a moiety of the formula:

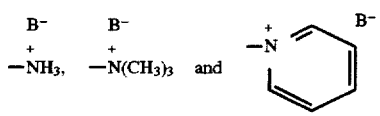

where B⁻ is a physiologically acceptable anion;
(iv) moieties of the formulae —$NR^hR^J$,

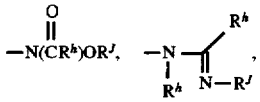

174

-continued

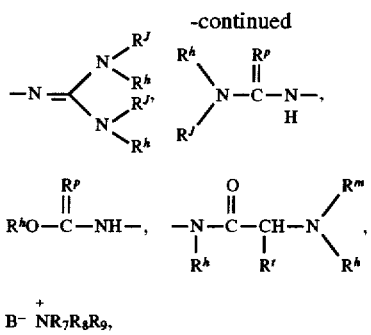

B⁻ $\overset{+}{N}R_7R_8R_9$, wherein $R^h$ and $R^J$ are independently selected from hydrogen, substituted or unsubstituted ($C_1$–$C_4$)alkyl, ($C_3$–$C_6$)cycloalkyl($C_1$–$C_4$)alkyl, and phenyl, wherein the substituents consist of amino, mono-, di- and tri($C_1$–$C_4$)alkylamino, hydroxy, oxo, carboxyl, alkoxyl, chloro, fluoro, bromo, nitro, —$SO_2NH_2$, phenyl, benzyl, acyloxy, alkoxylcarbonyloxy, cycloalkoxycarbonyloxy and carboxamido; $R^P$ is oxygen or sulfur; $R^m$ is hydrogen or an acyl residue of an amino acid or peptide said amino acid selected from the group consisting of alanine, glycine, arginine, cysteine, isoleucine, leucine, lysine, methionine, phenylalanine, proline, aminopimelic acid and threonine; $R^r$ is hydrogen or ($C_1$–$C_4$)alkyl and $R_7$, $R_8$, and $R_9$ are the same or different and are selected from hydrogen, a straight or branched ($C_1$–$C_4$)alkyl, ($C_2$–$C_4$)alkenyl and substituted ($C_1$–$C_4$)alkyl, wherein the substitution is selected from hydroxy, $C_1$–$C_4$)alkoxy, azido, amino, ($C_1$–$C_4$) alkylamino, di($C_1$–$C_4$)alkylamino, guanidino, nitrile, carboxy, formimidoyl, and phenyl; alternatively, $R_7$ and $R_8$ taken together are —($CH_2$)$_2$X($CH_2$)$_2$—, wherein X is ($CH_2$)$_w$, oxygen, sulfur, NH, $NR^h$, NOH or $NOR^h$ where W is an integer from 0 to 2. $R^h$ is hereinabove defined and B⁻ is a physiologically acceptable anion;

(v) a nitrile group, a moiety of the formulae:

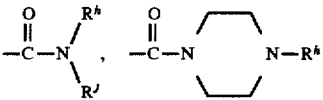

—$CHF_2$, $CF_3$, —$CF_2CF_3$, —$CH(OCH_3)_2$, and —$CHCl_2$.

3. The compound according to claim 1, cis-(±)-Tetrahydro-4-mercapto-2-furanmethanol-2-carbamate.

4. The compound according to claim 1, trans-(±)-Tetrahydro-4-mercapto-2-furanmethanol-2-carbamate.

5. The compound according to claim 1, trans-(±)-Tetrahydro-5-(phenoxymethyl)-3-furanthiol.

6. The compound according to claim 1, trans-(±)-Tetrahydro-4-mercapto-2-furanmethanol.

7. The compound according to claim 1, cis-(±)-Tetrahydro-4-mercapto-2-furanmethanol.

8. The compound according to claim 1, cis-(±)-5-(Azidomethyl)-tetrahydro-3-furanthiol.

9. The compound according to claim 1, trans-(±)-5-(Azidomethyl)tetrahydro-3-furanthiol.

10. The compound according to claim 1, trans-(±)-Tetrahydro-5-[(2-naphthalenyloxy)methyl]-3-furanthiol.

11. The compound according to claim 1, trans-(±)-N-[(Tetrahydro-4-mercapto-2-furanyl)-methyl]-N-(phenylmethoxy)acetamide.

12. The compound according to claim 1, cis(±)-Tetrahydro-5-[(phenylmethoxy)methyl-3-furanthiol.

13. The compound according to claim 1, 1,4-Anhydro-3-deoxy-2-thio-L-threo-pentitol 5-ester with N,N,N-trimethyl-2-phosphonooxy)-ethanaminium hydroxide inner salt (cis).

14. The compound according to claim 1, 2,5-Anhydro-3-deoxy-4-thio-D-erythro-pentitol 1-ester with 1-[2-phosphonooxy)ethyl]pyridinium hydroxide inner salt (trans).

15. The compound according to claim 1, 2,5-Anhydro-1-azido-1,3-dideoxy-4-thio-L-threo-pentitol.

16. The compound according to claim 1, 1,4-Anhydro-5-azido-3,5-dideoxy-2-thio-D-erythro-pentitol.

17. The compound according to claim 1, 2,5-Anhydro-1-azido-1,3-dideoxy-4-thio-D-threo-pentitol.

18. The compound according to claim 1, 2,5-Anhydro-1-azido-1,4-dideoxy-3-thio-D-threo-pentitol.

19. A compound selected from:
trans-(±)-5-[[(4-Fluoro-phenyl)sulfonyl]methyl]-tetrahydro-3-furanthiol;
5-[(4-Fluorophenoxy)methyl]-tetrahydro-3-furanthiol;
trans-(±)-5-[[4-(Fluorophenyl)thio]methyl]tetrahydro-3-furanethiol];
trans(±)-tetrahydro-2-methyl-3[[(tetrahydro-4-mercapto-2-furanyl)methyl]thio]-1,2,4-triazine-5,6-dione;
cis-(±)-Ethyl[(tetrahydro-4-mercapto-2-furanyl)-methyl]carbamic acid (4-nitrophenyl)methyl ester;
trans-(±)-Ethyl[(tetrahydro-4-mercapto-2-furanyl)-methyl]carbamic acid (4-nitrophenyl)methyl ester;
5-(2,4-Difluorophenyl)-tetrahydro-3-furanthiol;
4-(2,5-Anhydro-3-deoxy-4-thio-L-threo-pentonoyl)-1-piperazinecarboxylic acid phenylmethyl ester;
4-(2,5-Anhydro-3-deoxy-4-thio-L-threo-pentonoyl)-1-piperazinecarboxylic acid (4-nitrophenyl)methyl ester; and
cis-(±)-[Tetrahydro-4-mercapto-3-furanyl)methyl]-carbamic acid (4-nitrophenyl)methyl ester.

20. The compound according to claim 19, trans-(±)-5-[[(4-Fluoro-phenyl)sulfonyl]methyl]-tetrahydro-3-furanthiol.

21. The compound according to claim 19, 5-[(4-Fluorophenoxy)methyl]-tetrahydro-3-furanthiol.

22. The compound according to claim 19, trans-(±)-5-[[4-(Fluorophenyl)thio]methyl]tetrahydro-3-furanethiol.

23. The compound according to claim 19, trans-(±)-tetrahydro-2-methyl-3[[(tetrahydro-4-mercapto-2-furanyl)methyl]thio]-1,2,4-triazine-5,6-dione.

24. The compound according to claim 19, cis-(±)-Ethyl-[(tetrahydro-4-mercapto-2-furanyl)-methyl]carbamic acid (4-nitrophenyl)methyl ester.

25. The compound according to claim 19, trans-(±)-Ethyl [(tetrahydro-4-mercapto-2-furanyl)-methyl]carbamic acid (4-nitrophenyl)methyl ester.

26. The compound according to claim 19, 5-(2,4-Difluorophenyl)-tetrahydro-3-furanthiol.

27. The compound according to claim 19, 4-(2,5-Anhydro-3-deoxy-4-thio-L-threo-pentonoyl)-1-piperazinecarboxylic acid phenylmethyl ester.

28. The compound according to claim 19, 4-(2,5-Anhydro-3-deoxy-4-thio-L-threo-pentonoyl)-1-piperazinecarboxylic acid (4-nitrophenyl)methyl ester.

29. The compound according to claim 19, cis-(±)-[Tetrahydro-4-mercapto-3-furanyl)methyl]-carbamic acid (4-nitrophenyl)methyl ester.

* * * * *